United States Patent
Oberboersch et al.

(10) Patent No.: US 8,318,769 B2
(45) Date of Patent: Nov. 27, 2012

(54) SUBSTITUTED SULFONAMIDE COMPOUNDS

(75) Inventors: Stefan Oberboersch, Aachen (DE); Melanie Reich, Aachen (DE); Stefan Schunk, Aachen (DE); Michael Franz-Martin Engels, Turnhout (DE); Ruth Jostock, Stolberg (DE); Tieno Germann, Aachen (DE); Jean De Vry, Stolberg (DE); Klaus Schiene, Juechen (DE); Sabine Hees, Aachen (DE)

(73) Assignee: Gruenethal GmbH, Aachen (DE)

( * ) Notice: Subject to any disclaimer, the term of this patent is extended or adjusted under 35 U.S.C. 154(b) by 329 days.

(21) Appl. No.: 12/420,488

(22) Filed: Apr. 8, 2009

(65) Prior Publication Data

US 2009/0264400 A1    Oct. 22, 2009

Related U.S. Application Data

(60) Provisional application No. 61/043,249, filed on Apr. 8, 2008.

(30) Foreign Application Priority Data

Apr. 8, 2008    (EP) ..................... 08006957

(51) Int. Cl.
| | |
|---|---|
| C07D 215/58 | (2006.01) |
| C07D 401/14 | (2006.01) |
| C07D 213/30 | (2006.01) |
| C07D 401/12 | (2006.01) |
| C07D 265/36 | (2006.01) |
| A61K 31/4709 | (2006.01) |
| A61K 31/4465 | (2006.01) |
| A61K 31/497 | (2006.01) |
| A61K 31/55 | (2006.01) |
| A61K 31/45 | (2006.01) |
| A61K 31/536 | (2006.01) |
| A61P 29/00 | (2006.01) |
| A61P 37/08 | (2006.01) |
| A61P 27/14 | (2006.01) |
| A61P 25/28 | (2006.01) |
| A61P 17/00 | (2006.01) |
| A61P 17/06 | (2006.01) |
| A61P 31/04 | (2006.01) |

(52) U.S. Cl. ... 514/312; 514/316; 514/318; 514/253.12; 514/230.5; 514/253.07; 514/217.08; 514/326; 546/153; 546/187; 546/194; 546/208; 544/364; 544/363; 544/105; 540/597

(58) Field of Classification Search .................. 540/480, 540/481; 544/23, 298, 408; 546/193, 207, 546/209; 514/210.19, 210.2, 217.04, 217.03, 514/217.05, 217.06, 252.01, 252.02, 255.05, 514/269

See application file for complete search history.

(56) References Cited

U.S. PATENT DOCUMENTS

| | | |
|---|---|---|
| 2005/0234044 A1 | 10/2005 | Groneberg et al. |
| 2006/0178360 A1 | 8/2006 | Barth et al. |
| 2010/0197655 A1* | 8/2010 | Beaudoin et al. ........ 514/210.18 |

FOREIGN PATENT DOCUMENTS

| | | |
|---|---|---|
| DE | 10 2006 039 003 A1 | 2/2008 |
| WO | WO 2004/087700 A1 | 10/2004 |
| WO | WO 2004/092116 A1 | 10/2004 |
| WO | WO 2007/140383 A2 | 12/2007 |
| WO | WO 2008/024692 A1 | 2/2008 |

OTHER PUBLICATIONS

R. Hayashi et al., "Bradykinin Stimulates IL-6 and IL-8 Production by Human Lung Fibroblasts Through ERK-and p38 MAPK-dependent Mechanisms", European Respiratory Journal, 2000, pp. 452-458, vol. 16, ISSN: 0903-1936.

Bichoy H. Gabra et al., "The Kinin System Mediates Hyperalgesia through the Inducible Bradykinin B1 Receptor Subtype: Evidence in Various Experimental Animal Models of Type 1 and Type 2 Diabetic Neuropathy", Biol. Chem., Feb. 2006, pp. 127-143, vol. 387.

Joao B. Calixto et al., "Kinin $B_1$ Receptors: Key G-protein-coupled Receptors and their Role in Inflammatory and Painful Processes", British Journal of Pharmacology, 2004, pp. 803-818, vol. 143, 2004 Nature Publishing Group. Sara H. Bengtson et al., "Kinin Receptor Expression During *Staphylococcus aureus* Infection", Blood, Sep. 15, 2006, pp. 2055-2063, vol. 108, No. 6, The American Society of Hematology.

Antoni Stadnicki et al., "Immunolocalization and Expression of Kinin $B_1R$ and $B_2R$ Receptors in Human Inflammatory Bowel Disease", Am. J. Physiol. Gastrointest. Liver Physiol, Mar. 31, 2005, pp. G361-G366, vol. 289, American Physiological Society.

(Continued)

*Primary Examiner* — James O Wilson
*Assistant Examiner* — Cecilia M Jaisle
(74) *Attorney, Agent, or Firm* — Crowell & Moring LLP

(57) ABSTRACT

Substituted sulfonamide compounds corresponding to formula I:

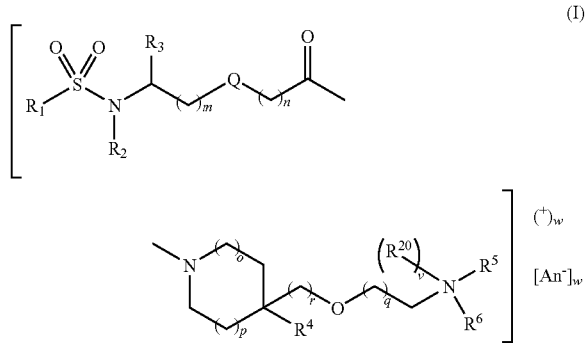

processes for the preparation thereof, pharmaceutical compositions containing these compounds, and the use of such substituted sulfonamide compounds in pharmaceutical compositions for the treatment and/or inhibition of pain and other conditions at least partly mediated by the bradykinin 1 receptor.

17 Claims, No Drawings

OTHER PUBLICATIONS

Joao B. Pesquero et al., "Genetically Altered Animal Models in the Kallikrein-Kinin System", Biol. Chem., Feb. 2006, pp. 119-126, vol. 387.

A. Prat et al., "Bradykinin $B_1$ Receptor Expression and Function on T Lymphocytes in Active Multiple Sclerosis", Neurology, Dec. 10, 1999, pp. 2087-2092, vol. 53, No. 9, 1999 American Academy of Neurology, ISSN: 0028-3878.

J. Fred Hess et al., "Generation and characterization of a humanized bradykinin B1 receptor mouse", Biol. Chem., vol. 387, pp. 195-201, Feb. 2006.

"Eine neue Variante der Mannich-Reaktion", Angew. Chem. vol. 88, Jan. 1976, No. 8, pp. 261 & 262.

L.M. Fredrik Leeb-Lundberg et al., "International Union of Pharmacology. XLV. Classification of the Kinin Receptor Family: from Molecular Mechanisms to Pathophysiological Consequences", Pharmacological Reviews, 2005, pp. 27-77, vol. 57, No. 1, The American Society for Pharmacology and Experimental Therapeutics, USA.

Joao B. Pesquero et al., "Hypoalgesia and Altered Inflammatory Responses in Mice Lacking Kinin B1 Receptors", PNAS, Jul. 5, 2000, pp. 8140-8145, vol. 97, No. 14.

Giselle F. Passos, et al., "Kinin $B_1$ Receptor Up-Regulation after Lipopolysaccharide Administration: Role of Proinflammatory Cytokines and Neutrophil Influx[1]", The Journal of Immunology, 2004, pp. 1839-1847.

International Search Report with partial translation dated Sep. 18, 2009 (Ten (10) pages).

European Search Report with partial translation dated Dec. 1, 2008 (Six (6) pages).

PCT/ISA/220 (Three (3) pages), Jan. 12, 2005.

\* cited by examiner

SUBSTITUTED SULFONAMIDE COMPOUNDS

CROSS REFERENCE TO RELATED APPLICATIONS

This application claims priority from U.S. provisional patent application No. 61/043,249 and European patent application no. EP 08006957.8, both filed Apr. 8, 2008, the entire disclosures of which are incorporated herein by reference.

BACKGROUND OF THE INVENTION

The present invention relates to substituted sulfonamide compounds, processes for the preparation thereof, pharmaceutical compositions containing these compounds and the use of substituted sulfonamide compounds for the preparation of pharmaceutical compositions.

In contrast to the constitutive expression of the bradykinin 2 receptor (B2R), in most tissues the bradykinin 1 receptor (B1R) is not expressed or is expressed only weakly. Nevertheless, expression of B1R can be induced on various cells. For example, in the course of inflammation reactions a rapid and pronounced induction of B1R takes place on neuronal cells, but also various peripheral cells, such as fibroblasts, endothelial cells, granulocytes, macrophages and lymphocytes. In the course of inflammation reactions, a switch from a B2R to a B1R dominance thus occurs on the cells involved. The cytokines interleukin-1 (IL-1) and tumour necrosis factor alpha (TNFα) are involved to a considerable degree in this upwards regulation of B1R (Passos et al. J. Immunol. 2004, 172, 1839-1847). After activation with specific ligands, B1R-expressing cells then themselves can secrete inflammation-promoting cytokines such as IL-6 and IL-8 (Hayashi et al., Eur. Respir. J. 2000, 16, 452-458). This leads to inwards migration of further inflammation cells, e.g. neutrophilic granulocytes (Pesquero et al., PNAS 2000, 97, 8140-8145). The bradykinin B1R system can contribute towards chronification of diseases via these mechanisms. This is demonstrated by a large number of animal studies (overviews in Leeb-Lundberg et al., Pharmacol. Rev. 2005, 57, 27-77 und Pesquero et al., Biol. Chem. 2006, 387, 119-126). On humans too, an enhanced expression of B1R, e.g. on enterocytes and macrophages in the affected tissue of patients with inflammatory intestinal diseases (Stadnicki et al., Am. J. Physiol. Gastrointest. Liver Physiol. 2005, 289, G361-366) or on T lymphocytes of patients with multiple sclerosis (Prat et al., Neurology. 1999; 53, 2087-2092) or an activation of the bradykinin B2R-B1R system in the course of infections with *Staphylococcus aureus* (Bengtson et al., Blood 2006, 108, 2055-2063) is found. Infections with *Staphylococcus aureus* are responsible for syndromes such as superficial infections of the skin up to septic shock.

Based on the described pathophysiological relationships, there is a great therapeutic potential for the use of B1R antagonists on acute and, in particular, chronically inflammatory diseases. These include diseases of the respiratory tract (bronchial asthma, allergies, COPD/chronic obstructive pulmonary disease, cystic fibrosis etc.), inflammatory intestinal diseases (ulcerative colitis, CD/Crohn's disease etc.), neurological diseases (multiple sclerosis, neurodegeneration etc.), inflammations of the skin (atopic dermatitis, psoriasis, bacterial infections etc.) and mucous membranes (Behcet's disease, pelvitis, prostatitis etc.), rheumatic diseases (rheumatoid arthritis, osteoarthritis etc.), septic shock and reperfusion syndrome (following cardiac infarction, stroke).

The bradykinin (receptor) system is moreover also involved in regulation of angiogenesis (potential as an angiogenesis inhibitor in cancer cases and macular degeneration on the eye), and B1R knockout mice are protected from induction of obesity by a particularly fat-rich diet (Pesquero et al., Biol. Chem. 2006, 387, 119-126). B1R antagonists are therefore also suitable for treatment of obesity.

B1R antagonists are suitable in particular for treatment of pain, in particular inflammation pain and neuropathic pain (Calixto et al., Br. J. Pharmacol. 2004, 1-16), and here in particular diabetic neuropathy (Gabra et al., Biol. Chem. 2006, 387, 127-143). They are furthermore suitable for treatment of migraine.

In the development of B1R modulators, however, there is the problem that the human and the rat B1R receptor differ so widely that many compounds which are good B1R modulators on the human receptor have only a poor or no affinity for the rat receptor. This makes pharmacological studies on animals considerably difficult, since many studies are usually conducted on the rat. However, if no activity exists on the rat receptor, neither the action nor side effects can be investigated on the rat. This has already led to transgenic animals with human B1 receptors being produced for pharmacological studies on animals (Hess et al., Biol. Chem. 2006; 387(2): 195-201). Working with transgenic animals, however, is more expensive than working with the unmodified animals. Since in the development of pharmaceutical compositions, however, precisely long-term toxicity studies on the rat belong to the standard studies, but this is inappropriate in the event of an absence of activity on the receptor, an important established instrument for checking safety is lacking for the development of such compounds. There is therefore a need for novel B1R modulators, B1R modulators which bind both to the rat receptor and to the human receptor offering particular advantages.

SUMMARY OF THE INVENTION

It was therefore an object of the present invention to provide new compounds which are suitable in particular as pharmacological active compounds in pharmaceutical compositions.

A particular object of the invention was to provide new pharmaceutically active compounds and pharmaceutical compositions for treatment of disorders or diseases which are at least partly mediated by B1R receptors.

These and other objects have been achieved by the substituted sulfonamide compounds according to the invention described and claimed hereinafter.

The invention provides substituted sulfonamide compounds corresponding to formula I

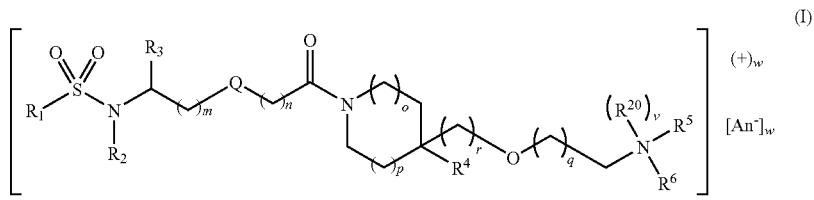

wherein m represents 0, 1 or 2;
n represents 1 or 2;
represents 0, 1 or 2;
p represents 0, 1 or 2;
q represents 0, 1, 2 or 3;
r represents 0, 1 or 2, with the proviso that q+r is not greater than 3;
v represents 0 or 1;
w represents 0 or 1;
with the proviso that if v represents 0, w represents 0;
An⁻ represents a halide anion
Q represents a single bond, —O— or —CH$_2$—;
$R^1$ represents aryl or heteroaryl or denotes an aryl or heteroaryl bonded via a $C_{1-3}$-alkylene group;
$R^2$ and $R^3$ are defined as described under (i) or (ii):
(i) $R^2$ represents H, $C_{1-6}$-alkyl, $C_{3-8}$-cycloalkyl, bicyclic 8- to 12-membered carbocyclyl, aryl or heteroaryl; or denotes a $C_{3-8}$-cycloalkyl, bicyclic 8- to 12-membered carbocyclyl, CH(aryl)$_2$, aryl or heteroaryl bonded via a $C_{1-6}$-alkylene group, $C_{2-6}$-alkenylene group or $C_{2-6}$-alkynylene group;
$R^3$ represents H, $C_{1-6}$-alkyl, aryl or heteroaryl; or denotes an aryl or heteroaryl bonded via a $C_{1-6}$-alkylene group, $C_{2-6}$-alkenylene group or $C_{2-6}$-alkynylene group;
or
(ii) $R^2$ and $R^3$ together with the —N—(CH—)— group joining them form a heterocyclic ring, which can be fused with an aryl or heteroaryl group,
wherein the heterocyclic ring is saturated or at least monounsaturated, but not aromatic, is 4-, 5-, 6- or 7-membered, can contain, in addition to the N hetero atom to which $R^2$ is bonded, at least one further hetero atom or a hetero atom group chosen from the group consisting of N, NR$^7$, O, S, S=O or S(=O)$_2$;
wherein $R^7$ represents H, $C_{1-6}$-alkyl, —C(=O)—$R^8$, $C_{3-8}$-cycloalkyl, aryl, heteroaryl or a $C_{3-8}$-cycloalkyl, aryl or heteroaryl bonded via a $C_{1-3}$-alkylene group, and $R^8$ denotes $C_{1-6}$-alkyl, $C_{3-8}$-cycloalkyl, aryl, heteroaryl or a $C_{3-8}$-cycloalkyl, aryl or heteroaryl bonded via a $C_{1-3}$-alkylene group,
$R^4$ denotes aryl, heteroaryl or an aryl or heteroaryl bonded via a $C_{1-6}$-alkylene group;
$R^5$ and $R^6$ each independently represent H, $C_{1-6}$-alkyl, $C_{3-8}$-cycloalkyl or a $C_{3-8}$-cycloalkyl bonded via a $C_{1-3}$-alkylene group, wherein $R^5$ and $R^6$ do not simultaneously represent H; or $R^5$ and $R^6$ together represent a substituted or unsubstituted 5- or 6-membered heteroaryl which can also contain, in addition to the N atom to which $R^5$ and $R^6$ are bonded, at least one further hetero atom from the group N, O or S; or $R^5$ and $R^6$ together represent a group chosen from —(CH$_2$)$_d$— or —(CH$_2$)$_e$—X—(CH$_2$)$_f$—, wherein d denotes 2, 3, 4, 5 or 6 and e and f independently of one another denote 1, 2 or 3, with the proviso that e+f is not greater than 5; and X denotes NR$^{12}$, CF$_2$, O, S, S=O or S(=O)$_2$, and wherein $R^{12}$ denotes H, $C_{1-6}$-alkyl, $C_{3-8}$-cycloalkyl, aryl, heteroaryl or a $C_{3-8}$-cycloalkyl, aryl or heteroaryl bonded via a $C_{1-3}$-alkylene group;
$R^{20}$ represents $C_{1-6}$-alkyl, cyclopropyl, a $C_{3-8}$-cycloalkyl, aryl or heteroaryl bonded via a $C_{1-3}$-alkylene group, or =O; with the proviso that if $R^{20}$ represents =O, w represents 0; and
wherein the abovementioned groups $C_{1-6}$-alkyl, $C_{1-6}$-alkylene, $C_{2-6}$-alkenylene, $C_{2-6}$-alkynylene, $C_{3-8}$-cycloalkyl, $C_{3-8}$-heterocycloalkyl, bicyclic 8- to 12-membered carbocyclyl, aryl and heteroaryl can in each case be unsubstituted or substituted once or several times by identical or different groups and the above-mentioned groups $C_{1-6}$-alkyl, $C_{1-6}$-alkylene, $C_{2-6}$-alkenylene and $C_{2-6}$-alkynylene can in each case be branched or unbranched;
in the form of an individual enantiomer or of an individual diastereomer, of the racemate, of the enantiomers, of the diastereomers, mixtures of the enantiomers and/or diastereomers, and in each case in the form of their bases and/or physiologically acceptable salts.

In the context of the present invention, the term "halogen" preferably represents the groups F, Cl, Br and I, particularly preferably the groups F, Cl and Br. The term "halide anion" correspondingly represents fluoride, chloride, bromide and iodide.

In the context of this invention, the expression "$C_{1-6}$-alkyl" includes acyclic saturated hydrocarbon groups having 1, 2, 3, 4, 5 or 6 C atoms, which can be branched- or straight-chain (unbranched) and unsubstituted or substituted once or several times, for example 2, 3, 4 or 5 times, by identical or different groups. The alkyl groups can preferably be chosen from the group consisting of methyl, ethyl, n-propyl, iso-propyl, n-butyl, iso-butyl, sec-butyl, tert-butyl, n-pentyl, iso-pentyl, neopentyl and hexyl. Particularly preferred alkyl groups can be chosen from the group consisting of methyl, ethyl, n-propyl, iso-propyl, n-butyl, sec-butyl, iso-butyl and tert-butyl.

In the context of this invention, the expression "$C_{2-6}$-alkenyl" includes acyclic unsaturated hydrocarbon groups having 2, 3, 4, 5 or 6 C atoms, which can be branched or straight-chain (unbranched) and unsubstituted or substituted once or several times, for example 2, 3, 4 or 5 times, by identical or different groups. In this context, the alkenyl groups contain at least one C=C double bond. Alkenyl groups can preferably be chosen from the group consisting of vinyl, prop-1-enyl, allyl, 2-methylprop-1-enyl, but-1-enyl, but-2-enyl, but-3-enyl, but-1,3-dienyl, 2-methylprop-1-enyl, but-2-en-2-yl, but-1-en-2-yl, pentenyl and hexenyl. Particularly preferred alkenyl groups can be chosen from the group consisting of vinyl, prop-1-enyl, allyl, 2-methylprop-1-enyl, but-1-enyl, but-2-enyl, but-3-enyl, but-1,3-dienyl, 2-methylprop-1-enyl, but-2-en-2-yl and but-1-en-2-yl.

In the context of this invention, the expression "$C_{3-8}$-cycloalkyl" denotes cyclic saturated hydrocarbons having 3, 4, 5, 6, 7 or 8 carbon atoms, which can be unsubstituted or substituted once or several times, for example by 2, 3, 4 or 5 identical or different groups, on one or more ring members. $C_{3-8}$-Cycloalkyl can preferably be chosen from the group consisting of cyclopropyl, cyclobutyl, cyclopentyl, cyclohexyl, cycloheptyl and cyclooctyl.

In the context of this invention, the expression "aryl" denotes aromatic hydrocarbons, in particular phenyls and naphthyls. The aryl groups can also be condensed with further saturated, (partially) unsaturated or aromatic ring systems. Each aryl group can be unsubstituted or substituted once or several times, for example 2, 3, 4 or 5 times, wherein the substituents on the aryl can be identical or different and can be in any desired and possible position of the aryl. Aryl can advantageously be chosen from the group consisting of phenyl, 1-naphthyl and 2-naphthyl, which can in each case be unsubstituted or substituted once or several times, for example by 2, 3, 4 or 5 groups.

In the context of the present invention, the expression "heteroaryl" represents a 5-, 6- or 7-membered cyclic aromatic group which contains at least 1, if appropriate also 2, 3, 4 or 5 hetero atoms, wherein the hetero atoms can be identical or different and the heteroaryl can be unsubstituted or substituted once or several times, for example 2, 3, 4 or 5 times, by identical or different groups. The substituents can be bonded in any desired and possible position of the heteroaryl. The heterocyclic ring can also be part of a bi- or polycyclic, in particular a mono-, bi- or tricyclic system, which can then be more than 7-membered in total, preferably up to 14-membered. Preferred hetero atoms are chosen from the group consisting of N, O and S. The heteroaryl group can preferably be chosen from the group consisting of pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, benzoxazolyl, benzoxadiazolyl, imidazothiazolyl, dibenzofuranyl, dibenzothienyl, phthalazinyl, pyrazolyl, imidazolyl, thiazolyl, oxadiazolyl, isoxazoyl, pyridinyl, pyridazinyl, pyrimidinyl, pyrazinyl, pyranyl, indazolyl, purinyl, indolizinyl, quinolinyl, isoquinolinyl, quinazolinyl, quinoxalinyl, carbazolyl, phenazinyl, phenothiazinyl and oxadiazolyl, wherein bonding to the general structure I can be via any desired and possible ring member of the heteroaryl group. The heteroaryl group can be particularly preferably chosen from the group consisting of furyl, thienyl and pyridinyl.

In the context of the present invention, the expression "bicyclic 8- to 12-membered carbocyclyl" represents cyclic hydrocarbon compounds which comprise two condensed ring systems, wherein the two ring systems together contain 8-12 ring members and no hetero atoms. In this context the two ring systems can have different ring sizes and different degrees of saturation, i.e. the two rings can each in itself be either aromatic, saturated or partly unsaturated. In particular, bicyclic 8- to 12-membered carbocyclyls are understood as meaning compounds which comprise an aromatic ring system with a fused-on saturated ring system. In this context bonding to the general structure I can be via any desired and possible ring member of the carbocyclyl group, but preferably via a ring member of an unsaturated ring. The bicyclic 8- to 12-membered carbocyclyl can be particularly preferably chosen from the group consisting of 2,3-dihydro-1H-indenyl or 1,2,3,4-tetrahydronaphthyl.

In the context of the present invention, the expression "$C_{1-6}$-alkylene group" includes acyclic saturated hydrocarbon groups having 1, 2, 3, 4, 5 or 6 C atoms, which can be branched- or straight-chain (unbranched) and unsubstituted or substituted once or several times, for example 2, 3, 4 or 5 times, by identical or different groups and which link a corresponding group to the main general structure. The alkylene groups can preferably be chosen from the group consisting of —$CH_2$—, —$CH_2$—$CH_2$—, —$CH(CH_3)$—, —$CH_2$—$CH_2$—, —$CH(CH_3)$—$CH_2$—, —$CH(CH_2CH_3)$—, —$CH_2$—$(CH_2)_2$—$CH_2$—, —$CH(CH_3)$—$CH_2$—$CH_2$—, —$CH_2$—$CH(CH_3)$—$CH_2$—, —$CH(CH_3)$—$CH(CH_3)$—, —$CH(CH_2CH_3)$—$CH_2$—, —$C(CH_3)_2$—$CH_2$—, —$CH(CH_2CH_2CH_3)$—, —$C(CH_3)(CH_2CH_3)$—, —$CH_2$—$(CH_2)_3$—$CH_2$—, —$CH(CH_3)$—$CH_2$—$CH_2$—$CH_2$—, —$CH_2$—$CH(CH_3)$—$CH_2$—$CH_2$—, —$CH(CH_3)$—$CH_2$—$CH(CH_3)$—, —$CH(CH_3)$—$CH(CH_3)$—$CH_2$—, —$C(CH_3)_2$—$CH_2$—$CH_2$—, —$CH_2$—$C(CH_3)_2$—$CH_2$—, —$CH(CH_2CH_3)$—$CH_2$—$CH_2$—, —$CH_2$—$CH(CH_2CH_3)$—$CH_2$—, —$C(CH_3)_2$—$CH(CH_3)$—, —$CH(CH_2CH_3)$—$CH(CH_3)$—, —$C(CH_3)(CH_2CH_3)$—$CH_2$—, —$CH(CH_2CH_3)$—$CH(CH_3)$—, —$CH(CH_2CH_3)$—$CH_2$—$CH_2$—, —$C(CH_2CH_3)$—$CH_2$—$CH_2$—, —$CH(CH_2CH_2CH_2CH_3)$—, —$C(CH_3)(CH_2CH_2CH_3)$—, —$C(CH_2CH_3)_2$— and —$CH_2$—$(CH_2)_4$—$CH_2$—. The alkylene groups can be particularly preferably chosen from the group consisting of —$CH_2$—, —$CH_2$—$CH_2$— and —$CH_2$—$CH_2$—$CH_2$—.

In the context of the present invention, the expression "$C_{2-6}$-alkenylene group" includes acyclic hydrocarbon groups having 2, 3, 4, 5 or 6 C atoms, which are unsaturated once or several times, for example 2, 3 or 4 times, and can be branched- or straight-chain (unbranched) and unsubstituted or substituted once or several times, for example 2, 3, 4 or 5 times, by identical or different groups and which link a corresponding group to the main general structure. In this context the alkenylene groups contain at least one C=C double bond. The alkenylene groups can preferably be chosen from the group consisting of —CH=CH—, —CH=CH—$CH_2$—, —$C(CH_3)$=$CH_2$—, —CH=CH—$CH_2$—$CH_2$—, —$CH_2$—CH=CH—$CH_2$—, —CH=CH—CH=CH—, —$C(CH_3)$=CH—$CH_2$—, —CH=$C(CH_3)$—$CH_2$—, —$C(CH_3)$=$C(CH_3)$—, —$C(CH_2CH_3)$=CH—, —CH=CH—$CH_2$—$CH_2$—$CH_2$—, —$CH_2$—CH=$CH_2$—$CH_2$—$CH_2$—, —CH=CH=CH—$CH_2$—$CH_2$— and —CH=$CH_2$—CH—CH=$CH_2$—.

In the context of the invention, the expression "$C_{2-6}$-alkynylene group" includes acyclic hydrocarbon groups having 2, 3, 4, 5 or 6 C atoms, which are unsaturated once or several times, for example 2, 3 or 4 times, and can be branched- or straight-chain (unbranched) and unsubstituted or substituted once or several times, for example 2, 3, 4 or 5 times, by identical or different groups and which link a corresponding group to the main general structure. In this context the alkynylene groups contain at least one C≡C triple bond. The alkynylene groups can preferably be chosen from the group consisting of —C≡C—, —C≡C—$CH_2$—, —C≡C—$CH_2$—$CH_2$—, —$CH_2$—C≡C—$CH(CH_3)$—, —$CH_2$—C≡C—$CH_2$—, —C≡C—C≡C—, —C≡C—$C(CH_3)_2$—, —C≡$CH_2$—$CH_2$—$CH_2$—, —$CH_2$—C≡C—$CH_2$—$CH_2$—, —C≡C—C≡C—$CH_2$— and —C≡C—$CH_2$—C≡C—.

In the context of the present invention, the expression "aryl or heteroaryl bonded via a $C_{1-6}$-alkylene group, $C_{2-6}$-alkenylene group or $C_{2-6}$-alkynylene group" means that the $C_{1-6}$-alkylene groups, $C_{2-6}$-alkenylene groups, $C_{2-6}$-alkynylene groups and aryl or heteroaryl have the meanings defined above and the aryl or heteroaryl is bonded to the main general structure via a $C_{1-6}$-alkylene group, $C_{2-6}$-alkenylene group or $C_{2-6}$-alkynylene group. There may be mentioned by way of example benzyl, phenethyl and phenylpropyl.

In the context of the present invention, the expression "$C_{3-8}$-cycloalkyl and heterocyclyl bonded via a $C_{1-6}$-alkylene group, $C_{2-6}$-alkenylene group or $C_{2-6}$-alkynylene group" means that the $C_{1-6}$-alkylene group, $C_{2-6}$-alkenylene group, $C_{2-6}$-alkynylene group, $C_{3-8}$-cycloalkyl and heterocyclyl have the meanings defined above and $C_{3-8}$-cycloalkyl and heterocyclyl are bonded to the main general structure via a $C_{1-6}$-alkylene group, $C_{2-6}$-alkenylene group or $C_{2-6}$-alkynylene group.

In connection with "alkyl", "alkenyl", "alkylene", "alkenylene", "alkynylene" and "cycloalkyl", in the context of this invention the term "substituted" is understood as meaning replacement of a hydrogen by F, Cl, Br, I, CN, $NH_2$, NH—$C_{1-6}$-alkyl, NH—$C_{1-6}$-alkylene-OH, $C_{1-6}$-alkyl, N($C_{1-6}$-alkyl)$_2$, N($C_{1-6}$-alkylene-OH)$_2$, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$-alkyl, $CO_2$H, $CO_2$—$C_{1-6}$-alkyl or benzyl, wherein groups substituted several times are to be understood as meaning those groups which are substituted several times, for example two or three times, either on different or on the same atoms, for example three times on the same C atom, as in the case of $CF_3$ or —$CH_2CF_3$, or at different places, as in the case of CH(Cl)—CH=CH—$CHCl_2$. Substitution several times can be by identical or different substituents, such as, for example, in the case of CH(OH)—CH=CH—$CHCl_2$.

With respect to "aryl" and "heteroaryl", in the context of this invention "substituted" is understood as meaning replacement once or several times, for example 2, 3, 4 or 5 times, of one or more hydrogen atoms of the corresponding ring system by F, Cl, Br, I, CN, $NH_2$, $NH-C_{1-6}$-alkyl, $NH-C_{1-6}$-alkylene-OH, $N(C_{1-6}$-alkyl$)_2$, $N(C_{1-6}$-alkylene-OH$)_2$, $NH$-aryl$^1$, $N($aryl$^1)_2$, $N(C_{1-6}$-alkyl)aryl$^1$, pyrrolinyl, piperazinyl, morpholinyl, $NO_2$, SH, $S-C_{1-6}$-alkyl, OH, $O-C_{1-6}$-alkyl, $O-C_{1-6}$-alkyl-OH, $C(=O)C_{1-6}$-alkyl, $NHSO_2C_{1-6}$-alkyl, $NHCOC_{1-6}$-alkyl, $CO_2H$, $CH_2SO_2$-phenyl, $CO_2-C_{1-6}$-alkyl, $OCF_3$, $CF_3$, $-O-CH_2-O-$, $-O-CH_2-CH_2-O-$, $-O-C(CH_3)_2-CH_2-$, unsubstituted $C_{1-6}$-alkyl, pyrrolidinyl, imidazolyl, piperidinyl, benzyloxy, phenoxy, phenyl, naphthyl, pyridinyl, $-C_{1-3}$-alkylene-aryl$^1$, benzyl, thienyl, furyl, wherein aryl$^1$ represents phenyl, furyl, thienyl or pyridinyl, on one or various atoms, wherein the above-mentioned substituents—unless stated otherwise—can optionally be substituted in their turn by the substituents mentioned. Substitution of aryl and heteroaryl several times can be by identical or different substituents. Preferred substituents for aryl and heteroaryl can be chosen from the group consisting of $-O-C_{1-3}$-alkyl, unsubstituted $C_{1-6}$-alkyl, F, Cl, Br, I, $CF_3$, $OCF_3$, OH, SH, phenyl, naphthyl, furyl, thienyl and pyridinyl, in particular from the group consisting of F, Cl, Br, $CF_3$, $CH_3$ and $OCH_3$.

With respect to "bicyclic 8- to 12-membered carbocyclyl", in the context of this invention "substituted" is understood as meaning replacement once or several times of hydrogen atoms of the corresponding ring systems of the bicyclic carbocyclyl. In this context the substituents bonded to a saturated or partly unsaturated ring system of the carbocyclyl are chosen independently of one another from the group of substituents for cycloalkyl defined above, that is to say from F, Cl, Br, I, CN, $NH_2$, $NH-C_{1-6}$-alkyl, $NH-C_{1-6}$-alkylene-OH, $C_{1-6}$-alkyl, $N(C_{1-6}$-alkyl$)_2$, $N(C_{1-6}$-alkylene-OH$)_2$, $NO_2$, SH, $S-C_{1-6}$-alkyl, S-benzyl, $O-C_{1-6}$-alkyl, OH, $O-C_{1-6}$-alkylene-OH, $=O$, O-benzyl, $C(=O)C_{1-6}$-alkyl, $CO_2H$, $CO_2-C_{1-6}$-alkyl, or benzyl, wherein in the case of replacement several times several hydrogen atoms of one ring member and/or one hydrogen atom on several ring members are replaced. Substituents which are bonded to an aromatic ring system of the carbocyclyl are chosen independently of one another from the group of substituents for aryl or heteroaryl defined above, that is to say from F, Cl, Br, I, CN, $NH_2$, $NH-C_{1-6}$-alkyl, $NH-C_{1-6}$-alkylene-OH, $N(C_{1-6}$-alkyl$)_2$, $N(C_{1-6}$-alkylene-OH$)_2$, $NH$-aryl$^1$, $N($aryl$^1)_2$, $N(C_{1-6}$-alkyl)aryl$^1$, pyrrolinyl, piperazinyl, morpholinyl, $NO_2$, SH, $S-C_{1-6}$-alkyl, OH, $O-C_{1-6}$-alkyl, $O-C_{1-6}$-alkyl-OH, $C(=O)C_{1-6}$-alkyl, $NHSO_2C_{1-6}$-alkyl, $NHCOC_{1-6}$-alkyl, $CO_2H$, $CH_2SO_2$-phenyl, $CO_2-C_{1-6}$-alkyl, $OCF_3$, $CF_3$, $-O-CH_2-O-$, $-O-CH_2-CH_2-O-$, $-O-C(CH_3)_2-CH_2-$, unsubstituted $C_{1-6}$-alkyl, pyrrolidinyl, imidazolyl, piperidinyl, benzyloxy, phenoxy, phenyl, naphthyl, pyridinyl, $-C_{1-3}$-alkylene-aryl$^1$, benzyl, thienyl, furyl, wherein aryl$^1$ represents phenyl, furyl, thienyl or pyridinyl. Preferred substituents for aromatic ring members of the bicyclic 8- to 12-membered carbocyclyl can be chosen from the group consisting of $-O-C_{1-3}$-alkyl, unsubstituted $C_{1-6}$-alkyl, F, Cl, Br, I, $CF_3$, $OCF_3$, OH, SH, phenyl, naphthyl, furyl, thienyl and pyridinyl, in particular from the group consisting of F, Cl, Br, $CF_3$, $CH_3$ and $OCH_3$.

In the context of the present description, the symbol

used in formulas designates a linking of a corresponding group to the particular main general structure.

In the context of this invention, the term "physiologically acceptable salt" is understood as meaning preferably salts of the compounds according to the invention with inorganic or organic acids, which are physiologically acceptable—in particular when used on humans and/or mammals. Examples of suitable acids are hydrochloric acid, hydrobromic acid, sulfuric acid, methanesulfonic acid, formic acid, acetic acid, oxalic acid, succinic acid, tartaric acid, mandelic acid, fumaric acid, maleic acid, lactic acid, citric acid, glutamic acid, 1,1-dioxo-1,2-dihydro1$\lambda^6$-benzo[d]isothiazol-3-one (saccharic acid), monomethylsebacic acid, 5-oxo-proline, hexane-1-sulfonic acid, nicotinic acid, 2-, 3- or 4-aminobenzoic acid, 2,4,6-trimethylbenzoic acid, α-liponic acid, acetylglycine, hippuric acid, phosphoric acid and/or aspartic acid. The salts of hydrochloric acid (hydrochlorides) and of citric acid (citrates) are particularly preferred.

In preferred embodiments of the compounds according to the invention, in the general formula I v and w and r represent 0; i.e. these compounds are represented by the following formula I$^1$:

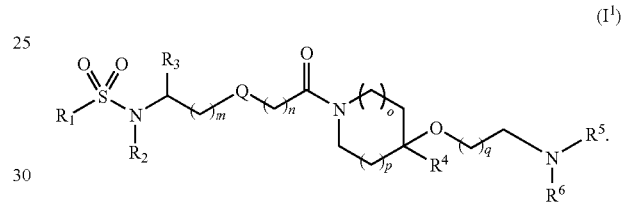

(I$^1$)

In a similarly preferred embodiment of the present invention, in the substituted sulfonamide compounds according to the invention R$^1$ represents phenyl, naphthyl, Indolyl, benzofuranyl, benzothiophenyl (benzothienyl); benzoxazolyl, benzoxadiazolyl, pyrrolyl, furanyl, thienyl, pyridinyl, pyridazinyl, pyrimidinyl, pyrazinyl, imidazothiazolyl, carbazolyl, dibenzofuranyl or dibenzothiophenyl (dibenzothienyl), benzyl or phenethyl, preferably phenyl, naphthyl, benzothiophenyl, benzoxadiazolyl, thiophenyl, pyridinyl, imidazothiazolyl or dibenzofuranyl, particularly preferably phenyl or naphthyl, in each case unsubstituted or substituted once or several times by identical or different substituents, the substituents preferably being chosen from the group consisting of $-O-C_{1-3}$-alkyl, $C_{1-6}$-alkyl, F, Cl, Br, I, $CF_3$, $OCF_3$, OH, SH, phenyl, naphthyl, furyl, thienyl and pyridinyl.

In a further preferred embodiment of the present invention, in the substituted sulfonamide compounds according to the invention R$^1$ represents phenyl or naphthyl, wherein the phenyl or naphthyl is unsubstituted or substituted once or several times, for example 2, 3, 4 or 5 times, by identical or different groups chosen from the group consisting of methyl, methoxy, $CF_3$, $OCF_3$, F, Cl and Br.

In a further preferred embodiment, R$^1$ in the sulfonamide compounds according to the invention is chosen from the group consisting of 4-methoxy-2,3,6-trimethylphenyl, 4-methoxy-2,6-dimethylphenyl, 4-methoxy-2,3,5-trimethylphenyl, 2,4,6-trimethylphenyl, 2-chloro-6-methylphenyl, 2,4,6-trichlorophenyl, 2-chloro-6-(trifluoromethyl)phenyl, 2,6-dichloro-4-methoxyphenyl, 2-methylnaphthyl, 2-chloronaphthyl, 2-fluoronaphthyl, 2-chloro-4-(trifluoromethoxy) phenyl, 4-chloro-2,5-dimethylphenyl, 2,3-dichlorophenyl, 3,4-dichlorophenyl, 2,4-dichlorophenyl, 2-(trifluoromethyl) phenyl, 3-(trifluoromethyl)phenyl, 4-(trifluoromethyl)phenyl, 1-naphthyl and 2-naphthyl.

In a further preferred embodiment, in the sulfonamide compounds according to the general formula I according to the invention p and o represent 1, p represents 1 and o represents 0, or p represents 2 and o represents 1.

In a further preferred embodiment, in the sulfonamide compounds according to the general formula I according to the invention Q represents a single bond, m represents 0 or 1 and n represents 1 or 2; or Q represents —O—, m represents 1 or 2 and n represents 1.

In a further preferred embodiment of the sulfonamide compounds according to the general formula I according to the invention, $R^4$ denotes phenyl, a phenyl bonded via a $C_{1-3}$-alkylene group; 2-, 3- or 4-pyridinyl or a 2-, 3- or 4-pyridinyl bonded via a $C_{1-3}$-alkylene group, wherein the phenyl can in each case be substituted once or several times by F, Cl or $CF_3$. In particular, the phenyl can be substituted once in the 3- or 4-position, in particular by F.

In a further preferred embodiment of the sulfonamide compounds according to the general formula I according to the invention q denotes 1 or 2.

In a further preferred embodiment of the sulfonamide compounds according to the general formula I according to the invention, $R^5$ and $R^6$ each independently represent $C_{1-6}$-alkyl which is unsubstituted or substituted once or several times; or $R^5$ and $R^6$ together represent a group chosen from —N=CH—CH=CH—, —CH=CH—N=CH—, —CH$_2$—CH$_2$—CH$_2$—; —CH$_2$—CH$_2$—CH$_2$—CH$_2$—, —CH$_2$—CH$_2$—CH$_2$—CH$_2$—CH$_2$— or —CH$_2$—CH$_2$—NR$^9$—CH$_2$—CH$_2$—, wherein $R^9$ represents H or a $C_{1-6}$-alkyl. In particular, $R^5$ and $R^6$, with inclusion of the N atom to which they are bonded, can represent a group selected from

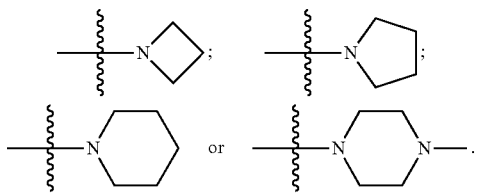

In a further preferred embodiment of the compounds according to the invention, $R^5$ and $R^6$ together with the N atom to which they are bonded form a heteroaryl group chosen from imidazolyl, in particular 1H-imidazol-1-yl, triazolyl, in particular 1H-[1,2,4]triazol-1-yl], tetrazolyl, pyrazolyl, benzimidazolyl, pyrrolyl or indolyl, wherein all these heteroaryl groups can in each case be unsubstituted, or substituted once or several times by identical or different groups, which in particular can be chosen from the group consisting of F, Cl, Br, $CF_3$, $CH_3$ and $OCH_3$. In certain embodiments of the invention, the heteroaryl group formed by $R^5$ and $R^6$ is chosen from the group consisting of imidazolyl, in particular 1H-imidazol-1-yl, and triazolyl, in particular 1H-[1,2,4]triazol-1-yl].

In a further preferred embodiment of the sulfonamide compounds according to the general formula I according to the invention, $R^2$ represents H, $C_{1-6}$-alkyl, $C_{3-6}$-cycloalkyl, 8- to 10-membered benzo-fused cycloalkyl, CH(phenyl)$_2$, aryl or heteroaryl; or $R^2$ represents a $C_{3-6}$-cycloalkyl, CH(phenyl)$_2$, aryl or heteroaryl bonded via a $C_{1-6}$-alkylene group, $C_{2-6}$-alkenylene group or $C_{2-6}$-alkynylene group, wherein the groups $C_{1-6}$-alkyl, $C_{3-6}$-cycloalkyl, $C_{2-6}$-alkylene, $C_{2-6}$-alkenylene, $C_{2-6}$-alkynylene, 8- to 10-membered benzo-fused cycloalkyl, aryl and heteroaryl in each case be unsubstituted or substituted, aryl and heteroaryl in particular can be substituted once or several times by identical or different groups chosen from the group consisting of $C_{1-6}$-alkyl, $C_{1-6}$-alkyl-O—, F, Cl, Br, I, $CF_3$, $OCF_3$, OH and SH.

In a further preferred embodiment of the sulfonamide compounds according to the general formula I according to the invention, $R^2$ represents H, substituted or unsubstituted $C_{1-6}$-alkyl, 2,3-dihydro-1H-indenyl or cyclopropyl; or $R^2$ represents CH(phenyl)$_2$, phenyl, pyridinyl or a phenyl or pyridinyl bonded via a $C_{1-6}$-alkylene group, wherein the phenyl or pyridinyl is in each case unsubstituted or substituted once or several times by identical or different groups, wherein the groups are chosen from the group consisting of methyl, ethyl, n-propyl, iso-propyl, n-butyl, iso-butyl, sec-butyl, tert-butyl, methoxy, F, Cl, Br, I $CF_3$, $OCF_3$ and OH.

In a further variant of the compounds according to the general formula I according to the invention, $R^3$ represents H, $C_{1-6}$-alkyl or aryl; or $R^3$ represents an aryl bonded via a $C_{1-6}$-alkylene group, $C_{2-6}$-alkenylene group or $C_{2-6}$-alkynylene group, wherein the groups $C_{1-6}$-alkyl, $C_{3-6}$-cycloalkyl, $C_{2-6}$-alkylene, $C_{2-6}$-alkenylene, $C_{2-6}$-alkynylene or aryl can in each case be unsubstituted or substituted, the aryl in particular can be substituted once or several times by identical or different groups chosen from the group consisting of $C_{1-6}$-alkyl, $C_{1-6}$-alkyl-O—, F, Cl, Br, I, $CF_3$, $OCF_3$, OH and SH. In particular, $R^3$ can represent H or phenyl, wherein the phenyl is in each case unsubstituted or substituted once or several times by identical or different groups, wherein the substituents are chosen from the group consisting of methyl, ethyl, n-propyl, iso-propyl, n-butyl, iso-butyl, sec-butyl, tert-butyl, methoxy, F, Cl, Br, I, $CF_3$, $OCF_3$ and OH.

In a further preferred embodiment of the compounds according to the general formula I according to the invention, the groups $R^2$ and $R^3$ together with the —N—(CH—)— group joining them form a heterocyclic ring according to the general formula (II):

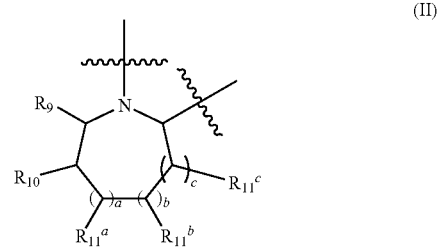

(II)

wherein
a, b and c each independently represent 0 or 1; and
$R^9$, $R^{10}$, $R^{11a}$, $R^{11b}$ and $R^{11c}$ each independently represent H or two vicinal groups from $R^9$, $R^{10}$, $R^{11a}$, $R^{11b}$ and $R^{11c}$ form a 5- or 6-membered fused-on aryl or heteroaryl group, which can be unsubstituted or substituted once or several times by identical or different groups. In particular, the heterocyclic ring (II) can be chosen from

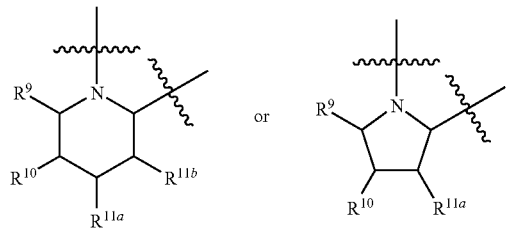

In particular, the groups $R^9$ and $R^{10}$ together can form a fused-on benzo group.

Persons skilled in the art will understand that the partial structure of the general formula (I) represented by the heterocyclic ring (II)

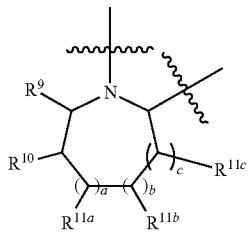
(II)

can assume the following forms for the particular values 0 and 1 of the indices a, b and c:

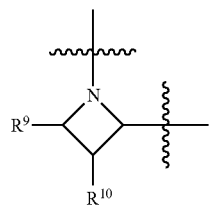 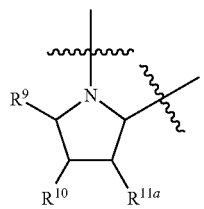

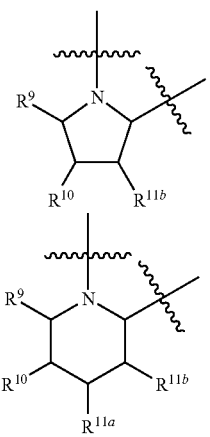 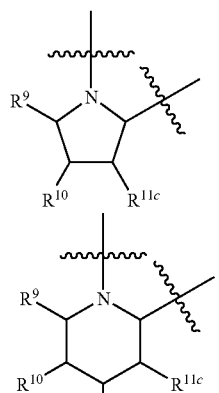

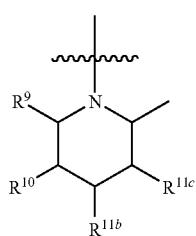 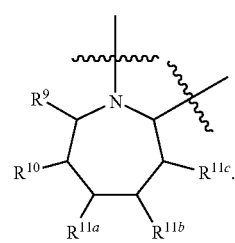

Persons skilled in the art furthermore will understand that if two vicinal (adjacent) groups from $R^9$, $R^{10}$, $R^{11a}$, $R^{11b}$ and $R^{11c}$ form a (fused-on) ring which is aromatic or is unsaturated on one or both of the carbon atoms linked with the vicinal groups, this/these carbon atom(s) can no longer have a hydrogen. For example, the following form thus results for a heterocyclic ring according to (II) in which one of the indices a, b or c=0 and the other two are each=1 and the adjacent groups $R^9$ and $R^{10}$ form a fused-on benzene ring:

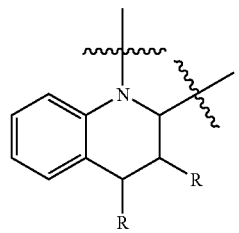

wherein R represents the corresponding group from $R^{11a}$, $R^{11b}$ and $R^{11c}$.

The following form results for a heterocyclic ring according to (II) in which one of the indices a, b or c=0 and the other two are each=1 and the adjacent groups $R^{10}$ and $R^{11a}$ or $R^{11b}$ form a fused-on benzene ring:

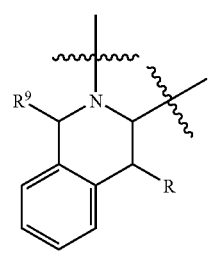

wherein R represents the corresponding group from $R^{11b}$ or $R^{11c}$.

The following form results for a heterocyclic ring (II) in which one of the indices a, b or c=0 and the other two are each=1 and two adjacent groups from $R^{11a}$, $R^{11b}$ and/or $R^{11c}$ form a fused-on benzene ring:

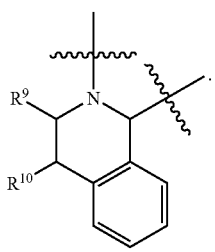

If the ring size of the heterocyclic rings according to (II) described above allows, i.e. for compounds in which a+b+c=2 or 3, in each case two pairs of adjacent groups can also form a fused-on ring, for example:

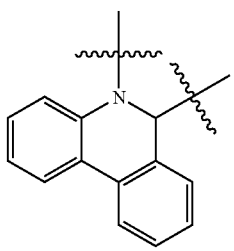

In a further preferred embodiment of the compounds according to the general formula I according to the invention, v and w represent 1 and $R^{20}$ represents $C_{1-6}$-alkyl. In particular, $R^{20}$ is chosen from methyl, ethyl, n-propyl, i-propyl, n-butyl, sec-butyl, i-butyl or tert-butyl. In this context it is particularly preferable for $An^-$ to represent iodide.

In a further preferred embodiment of the compounds according to the general formula I according to the invention, v represents 1, w represents 0 and $R^{20}$ represents =O. The person skilled in the art understands that in this case the representation of the oxo group "=O" with a double bond is only a simplified formalism for the description of the linkage between the N and O atom, since he knows that a five-valent N is not possible here. This representation—which can be seen by the person skilled in the art—is thus an alternative style of writing for an N-oxide, which as a rule is represented as the -ylide group, as shown below:

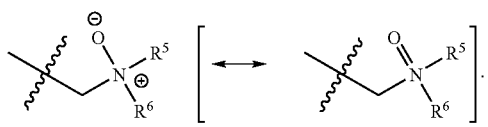

In a further preferred embodiment, the substituted sulfonamide compounds according to the invention are compounds having the general formula Ia

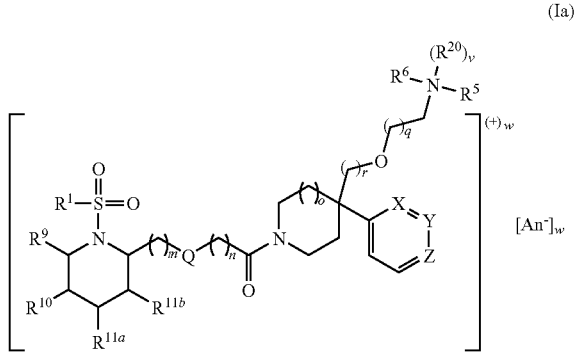

(Ia)

wherein X, Y or Z represents N, C—H; C—F, C—Cl or C—CF$_3$, with the proviso that always only one of X, Y or Z represents something other than CH, wherein X, Y and Z preferably do not simultaneously represent C—H, and the groups $An^-$, Q, $R^1$, $R^5$ and $R^6$, $R^9$, $R^{10}$, $R^{11a}$, $R^{11b}$ and $R^{20}$ and the variables b, m, n, o, q, r, v and w can assume the particular meanings as in the embodiments according to the invention which are described above. Preferably, v, w and r in each case represent 0. In another preferred embodiment, v and w represent 0 and r represents 1.

In another preferred embodiment, the substituted sulfonamide compounds according to the invention are compounds having the general formula Ib

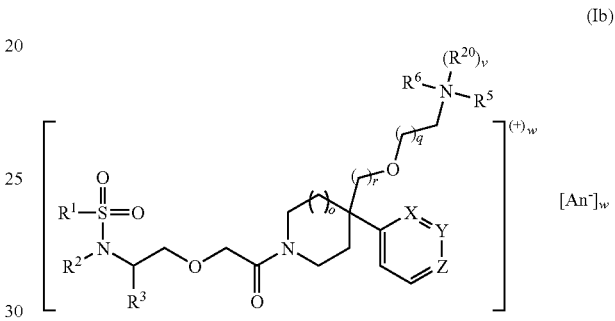

(Ib)

wherein X, Y or Z represents N, C—H; C—F, C—Cl or C—CF$_3$, with the proviso that always only one of X, Y or Z represents something other than CH, wherein X, Y and Z preferably do not simultaneously represent C—H, and the groups $An^-$, Q, $R^1$, $R^5$ and $R^6$, $R^9$, $R^{10}$, $R^{11a}$, $R^{11b}$ and $R^{20}$ and the variables o, q, v and w can assume the particular meanings as in the embodiments according to the invention which are described above. In preferred embodiments, v, w and r represent 0. In another preferred embodiment, v and w represent 0 and r represents 1.

In a further preferred embodiment, the substituted sulfonamide compounds according to the invention are compounds having the general formulas Ic, Id, Ie, If, Ig and Ih

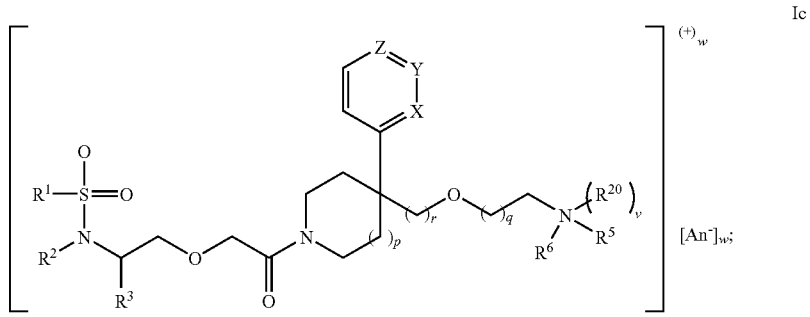

Ic

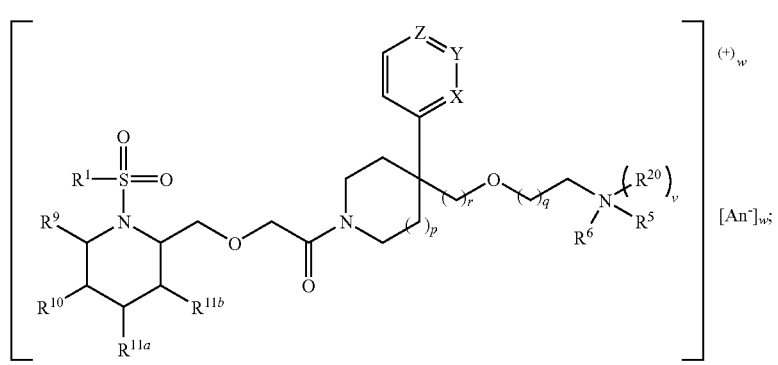
Id

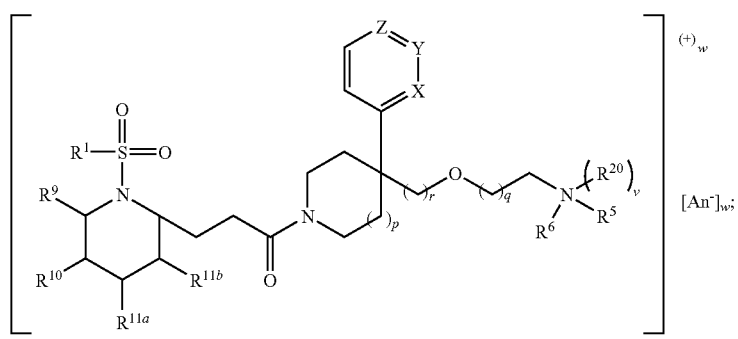
Ie

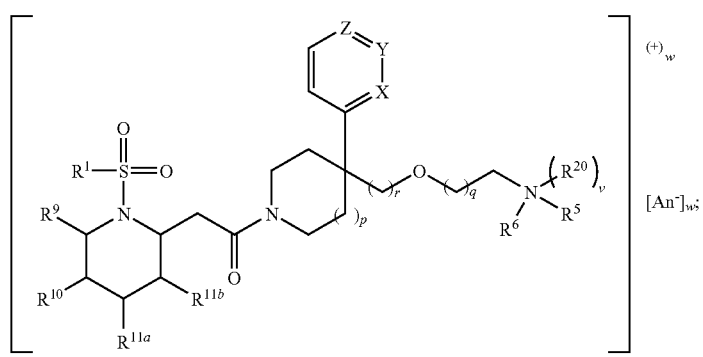
If

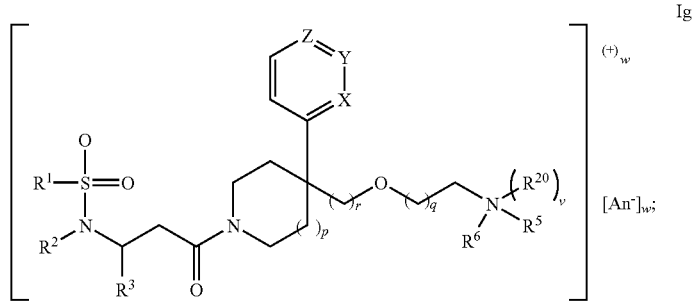
Ig wherein in the compounds according to the general formulas Ic to Ig, X, Y and Z are chosen independently of one another from the group consisting of CH, N, C—F, C—Cl and C—$CF_3$, under the condition that always only one of X, Y or Z represents something other than CH and X, Y and Z do not simultaneously represent C—H; and wherein the groups $An^-$, $R^1$, $R^2$, $R^3$, $R^5$, $R^6$, $R^9$, $R^{10}$, $R^{11a}$ and $R^{11b}$ and the variables p, q, r, v and w can assume the particular meanings described in the embodiments described above. In this context, in the compounds according to the general formulas Ic to Ig, p preferably represents 0 or 1, in particular 1, q preferably represents 1 or 2, X and Z preferably represent CH and Y represents N or C—F, preferably N. Furthermore, in the compounds according to the general formulas Ic to Ig, v and w in each case represent 0; or v represents 1, w represents 0 and $R^{20}$ represents =O; or v and w in each case represent 1, $An^-$ represents a halide anion, preferably iodide, and $R^{20}$ is chosen from methyl, ethyl, n-propyl, s-propyl, i-propyl, n-butyl, s-butyl, i-butyl or t-butyl. In the compounds according to the general formulas Ic to Ig, r preferably represents 0 or 1. In a particular embodiment of the compounds according to the general formulas Ic to Ig according to the invention, v represents 0, w represents 0, r represents 1 and q represents 1. Furthermore, in the compounds according to the general formulas Ic to Ig, $R^1$ preferably represents phenyl or naphthyl, wherein the phenyl or naphthyl is unsubstituted or substituted once or several times, for example 2, 3, 4 or 5 times, by identical or different groups chosen from the group consisting of methyl, methoxy, $CF_3$, $OCF_3$, F, Cl and Br; in particular, $R^1$ represents 4-methoxy-2,6-dimethylphenyl, 4-chloro-2,5-dimethylphenyl, 2,3-dichlorophenyl, 2,4-dichlorophenyl, 3,4-dichlorophenyl, 2-chloro-6-methylphenyl, 2-methyl-4-chlorophenyl, 2-(trifluoromethyl)phenyl, 3-(trifluoromethyl)phenyl, 1-naphthyl or 2-naphthyl. In the compounds according to the general formulas Ic to Ig, $R^2$ is preferably chosen from H, methyl, cyclopropyl, —CH(Ph)$_2$, (pyridin-3-yl)methyl and 2,3-dihydro-1H-inden-1-yl; in this context, the benzo group or the phenyl groups in $R^2$ can be unsubstituted or substituted, preferably by a substituent chosen from methyl, methoxy, $CF_3$, F, Cl and Br. In the compounds according to the general formula Ic to Ig, $R^3$ is preferably chosen from H or phenyl, wherein the phenyl group can be unsubstituted or substituted, preferably by a substituent chosen from methyl, methoxy, $CF_3$, F, Cl and Br. In the compounds according to the general formulas Ic to Ig, $R^5$ and $R^6$ preferably each independently represent $C_{1-6}$-alkyl, in particular methyl, ethyl, n-propyl, iso-propyl, n-butyl, iso-butyl, sec-butyl or tert-butyl, which is unsubstituted or substituted once or several times; or $R^5$ und $R^6$ together form a group chosen from —N=CH—CH=CH—, —CH=CH—N=CH—, —CH$_2$—CH$_2$—CH$_2$—; —CH$_2$—CH$_2$—CH$_2$—CH$_2$—, —CH$_2$—CH$_2$—CH$_2$—CH$_2$—CH$_2$— or —CH$_2$—CH$_2$—NR$^9$—CH$_2$—CH$_2$—, wherein $R^9$ represents an H or a $C_{1-6}$-alkyl, in particular methyl, ethyl, n-propyl, iso-propyl, n-butyl, iso-butyl, sec-butyl or tert-butyl; or $R^5$ and $R^6$ together with the N atom to which they are bonded form a 5- or 6-membered heteroaryl groups chosen from imidazolyl, in particular 1H-imidazol-1-yl, triazolyl, in particular 1H-[1,2,4]triazol-1-yl], wherein all these heteroaryl groups can in each case be unsubstituted or substituted once or several times by identical or different groups, which in particular can be chosen from the group consisting of F, Cl, Br, $CF_3$, $CH_3$ and $OCH_3$.

In the compounds according to the general formula Ic to Ig, $R^9$, $R^{10}$, $R^{11a}$ and $R^{11b}$ each independently represent H or two vicinal groups from $R^9$, $R^{10}$, $R^{11a}$ and $R^{11b}$, preferably $R^9$ and $R^{10}$, form a fused-on benzo group, which can be unsubstituted or substituted once or several times by identical or different groups, preferably by groups which are chosen independently of one another from the group consisting of methyl, methoxy, $CF_3$, F, Cl and Br.

In further preferred embodiments of the substituted sulfonamide compounds according to the invention, the part structure A* from the general formula I

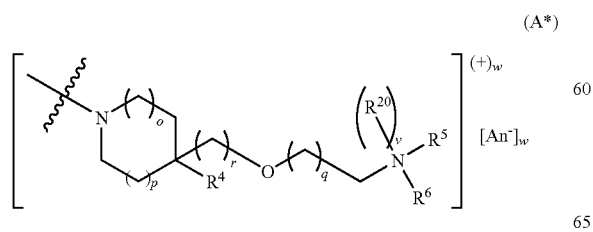

(A*)

represents a group chosen from

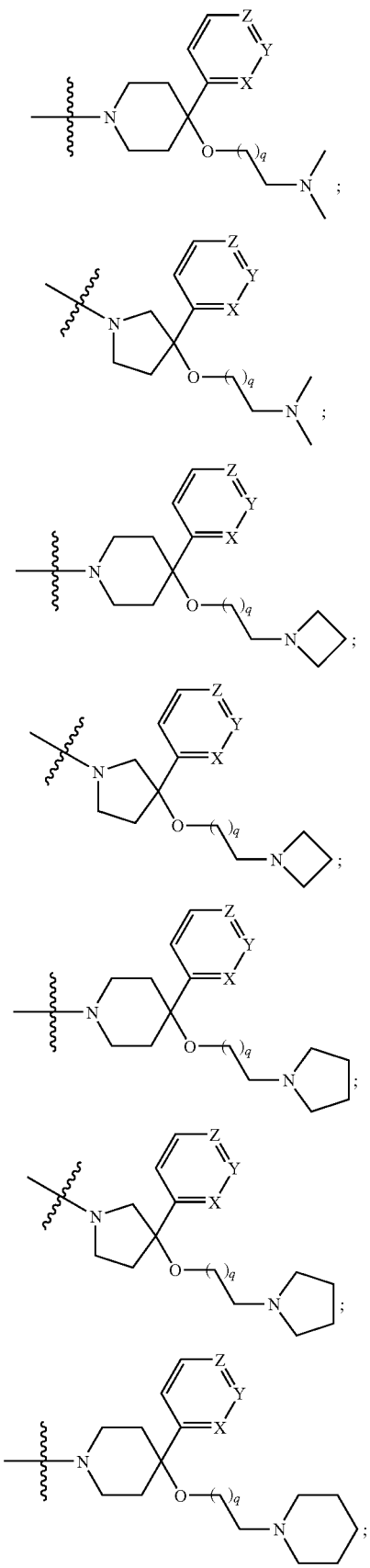

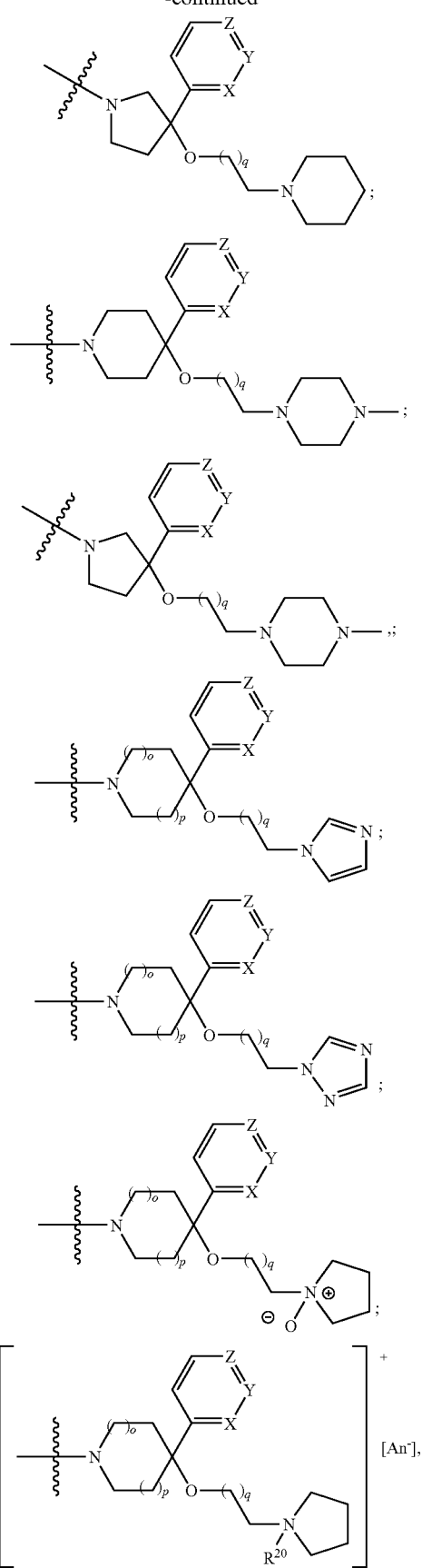

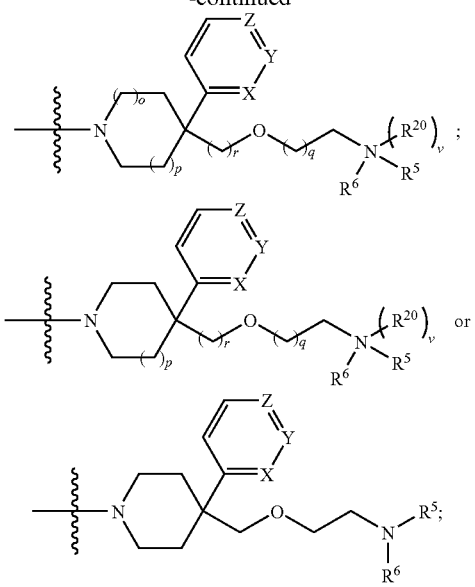

wherein o denotes 0, 1 or 2 and p denotes 0 or 1, q denotes 0, 1 or 2, preferably 1 or 2, and X, Y and Z represent N, C—H; C—F, C—Cl or C—$CF_3$, with the proviso that always only one of X, Y or Z represents something other than CH, wherein X, Y and Z preferably do not simultaneously represent C—H. It is particularly preferable for Y or Z, in particular Z, to represent N or CF. In a preferred embodiment, Y represents N and X and Z correspondingly represent CH. Furthermore, in the formulas shown above, $R^{20}$ represents methyl, ethyl, n-propyl, s-propyl, i-propyl, n-butyl, s-butyl, i-butyl or t-butyl, in particular methyl; and $An^−$ represents a halide anion, in particular iodide.

In further preferred embodiments of the substituted sulfonamide compounds according to the invention, the part structure S* from the general formula I

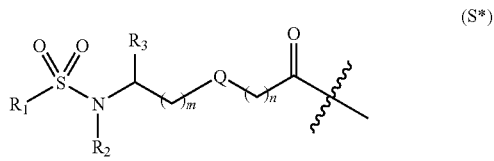

(S*)

is chosen from the group consisting of:

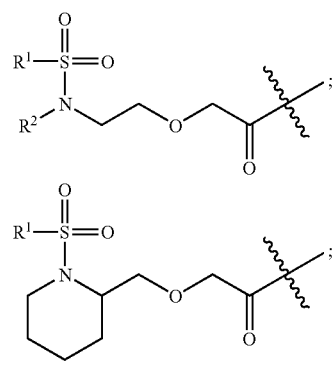

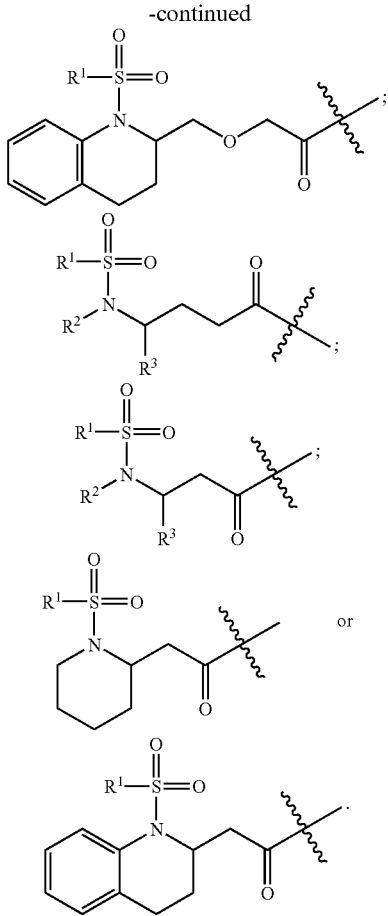

In this context, the groups $R^1$, $R^2$ and $R^3$ can assume the particular meanings as in the embodiments according to the invention which are described above.

In further preferred embodiments of the substituted sulfonamides according to the invention, the part structure S* shown above is chosen from the group consisting of

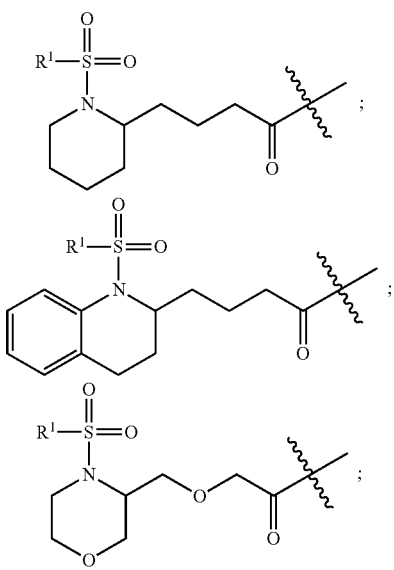

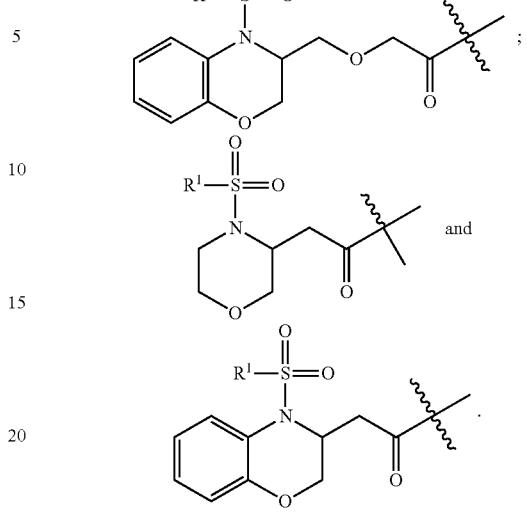

In this context $R^1$ can assume the particular meanings as in the embodiments according to the invention which are described above and the fused-on benzo group can be unsubstituted or substituted as explained above in connection with the term "aryl".

In a further preferred embodiment of the present invention, the sulfonamide compounds according to the invention are chosen from the group consisting of:

(1) (S)-2-((1-(4-methoxy-2,6-dimethylphenylsulfonyl)-1,2,3,4-tetrahydroquinolin-2-yl)methoxy)-1-(4-(pyridin-3-yl)-4-(2-(pyrrolidin-1-yl)ethoxy)piperidin-1-yl)ethanone;

(2) 4-(1-(4-methoxy-2,6-dimethylphenylsulfonyl)piperidin-2-yl)-1-(4-(pyridin-3-yl)-4-(2-(pyrrolidin-1-yl)ethoxy)piperidin-1-yl)butan-1-one;

(3) N-cyclopropyl-4-methoxy-2,6-dimethyl-N-(2-(2-oxo-2-(4-(pyridin-3-yl)-4-(2-(pyrrolidin-1-yl)ethoxy)piperidin-1-yl)ethoxy)ethyl)benzenesulfonamide;

(4) N-benzhydryl-2,4-dichloro-N-(2-(2-oxo-2-(4-(pyridin-3-yl)-4-(2-(pyrrolidin-1-yl)ethoxy)piperidin-1-yl)ethoxy)ethyl)benzenesulfonamide;

(5) 4-methoxy-2,6-dimethyl-N-(2-(2-oxo-2-(4-(pyridin-3-yl)-4-(2-(pyrrolidin-1-yl)ethoxy)piperidin-1-yl)ethoxy)ethyl)-N-(pyridin-3-ylmethyl)benzenesulfonamide;

(6) N-benzhydryl-4-methoxy-2,6-dimethyl-N-(2-(2-oxo-2-(4-(pyridin-3-yl)-4-(2-(pyrrolidin-1-yl)ethoxy)piperidin-1-yl)ethoxy)ethyl)benzenesulfonamide;

(7) 2,4-dichloro-N-(2,3-dihydro-1H-inden-1-yl)-N-(2-(2-oxo-2-(4-(pyridin-3-yl)-4-(2-(pyrrolidin-1-yl)ethoxy)piperidin-1-yl)ethoxy)ethyl)benzenesulfonamide;

(8) 1-(4-(pyridin-3-yl)-4-(2-(pyrrolidin-1-yl)ethoxy)piperidin-1-yl)-4-(1-(2-(trifluoromethyl)phenylsulfonyl)piperidin-2-yl)butan-1-one;

(9) 4-(1-(2-chloro-6-methylphenylsulfonyl)piperidin-2-yl)-1-(4-(pyridin-3-yl)-4-(2-(pyrrolidin-1-yl)ethoxy)piperidin-1-yl)butan-1-one;

(10) 1-(4-(2-(piperidin-1-yl)ethoxy)-4-(pyridin-3-yl)piperidin-1-yl)-2-(1-(3-(trifluoromethyl)phenylsulfonyl)piperidin-2-yl)ethanone;

(11) N-(3-oxo-1-phenyl-3-(4-(2-(piperidin-1-yl)ethoxy)-4-(pyridin-3-yl)piperidin-1-yl)propyl)naphthalene-2-sulfonamide;

(12) 3-(1-(4-chloro-2,5-dimethylphenylsulfonyl)piperidin-2-yl)-1-(4-(3-(piperidin-1-yl)propoxy)-4-(pyridin-3-yl)piperidin-1-yl)propan-1-one;

(13) 3-(1-(4-chloro-2,5-dimethylphenylsulfonyl)piperidin-2-yl)-1-(4-(2-(piperidin-1-yl)ethoxy)-4-(pyridin-3-yl)piperidin-1-yl)propan-1-one;

(14) 2-((1-(4-methoxy-2,6-dimethylphenylsulfonyl)piperidin-2-yl)methoxy)-1-(4-(2-(piperidin-1-yl)ethoxy)-4-(pyridin-3-yl)piperidin-1-yl)ethanone;

(15) 4-methoxy-N,2,6-trimethyl-N-(2-(2-oxo-2-(4-(2-(piperidin-1-yl)ethoxy)-4-(pyridin-3-yl)piperidin-1-yl)ethoxy)ethyl)-benzenesulfonamide;

(16) 2-((1-(3,4-dichlorophenylsulfonyl)-1,2,3,4-tetrahydroquinolin-2-yl)methoxy)-1-(4-(2-(piperidin-1-yl)ethoxy)-4-(pyridin-3-yl)piperidin-1-yl)ethanone;

(17) 2-((1-(4-methoxy-2,6-dimethylphenylsulfonyl)piperidin-2-yl)methoxy)-1-(4-(3-(piperidin-1-yl)propoxy)-4-(pyridin-3-yl)piperidin-1-yl)ethanone;

(18) 4-methoxy-N,2,6-trimethyl-N-(2-(2-oxo-2-(4-(3-(piperidin-1-yl)propoxy)-4-(pyridin-3-yl)piperidin-1-yl)ethoxy)ethyl)benzenesulfonamide;

(19) 2-((1-(3,4-dichlorophenylsulfonyl)-1,2,3,4-tetrahydroquinolin-2-yl)methoxy)-1-(4-(3-(piperidin-1-yl)propoxy)-4-(pyridin-3-yl)piperidin-1-yl)ethanone;

(20) 2-((1-(4-methoxy-2,6-dimethylphenylsulfonyl)piperidin-2-yl)methoxy)-1-(4-(pyridin-3-yl)-4-(2-(pyrrolidin-1-yl)ethoxy)piperidin-1-yl)ethanone;

(21) 4-methoxy-N,2,6-trimethyl-N-(2-(2-oxo-2-(4-(pyridin-3-yl)-4-(2-(pyrrolidin-1-yl)ethoxy)piperidin-1-yl)ethoxy)ethyl)benzenesulfonamide;

(22) 1-(4-(pyridin-3-yl)-4-(2-(pyrrolidin-1-yl)ethoxy)piperidin-1-yl)-2-(1-(3-(trifluoromethyl)phenylsulfonyl)piperidin-2-yl)ethanone;

(23) 1-(4-(3-(piperidin-1-yl)propoxy)-4-(pyridin-3-yl)piperidin-1-yl)-2-(1-(3-(trifluoromethyl)phenylsulfonyl)piperidin-2-yl)ethanone;

(24) 2-((1-(3,4-dichlorophenylsulfonyl)-1,2,3,4-tetrahydroquinolin-2-yl)methoxy)-1-(4-(pyridin-3-yl)-4-(2-(pyrrolidin-1-yl)ethoxy)piperidin-1-yl)ethanone;

(25) 3-(1-(4-chloro-2,5-dimethylphenylsulfonyl)piperidin-2-yl)-1-(4-(pyridin-3-yl)-4-(2-(pyrrolidin-1-yl)ethoxy)piperidin-1-yl)propan-1-one;

(26) N-(3-oxo-1-phenyl-3-(4-(pyridin-3-yl)-4-(2-(pyrrolidin-1-yl)ethoxy)piperidin-1-yl)propyl)naphthalene-2-sulfonamide;

(27) N-(3-oxo-1-phenyl-3-(4-(3-(piperidin-1-yl)propoxy)-4-(pyridin-3-yl)piperidin-1-yl)propyl)naphthalene-2-sulfonamide;

(28) 2-((1-(4-methoxy-2,6-dimethylphenylsulfonyl)piperidin-2-yl)methoxy)-1-(4-(2-(4-methylpiperazin-1-yl)ethoxy)-4-(pyridin-3-yl)piperidin-1-yl)ethanone;

(29) 4-methoxy-N,2,6-trimethyl-N-(2-(2-(4-(2-(4-methylpiperazin-1-yl)ethoxy)-4-(pyridin-3-yl)piperidin-1-yl)-2-oxoethoxy)ethyl)benzenesulfonamide;

(30) 1-(4-(2-(4-methylpiperazin-1-yl)ethoxy)-4-(pyridin-3-yl)piperidin-1-yl)-2-(1-(3-(trifluoromethyl)phenylsulfonyl)piperidin-2-yl)ethanone;

(31) 3-(1-(4-chloro-2,5-dimethylphenylsulfonyl)piperidin-2-yl)-1-(4-(2-(4-methylpiperazin-1-yl)ethoxy)-4-(pyridin-3-yl)piperidin-1-yl)propan-1-one;

(32) N-(3-(4-(2-(4-methylpiperazin-1-yl)ethoxy)-4-(pyridin-3-yl)piperidin-1-yl)-3-oxo-1-phenylpropyl)naphthalene-2-sulfonamide;

(33) 2-((1-(4-methoxy-2,6-dimethylphenylsulfonyl)piperidin-2-yl)methoxy)-1-(4-(3-(4-methylpiperazin-1-yl)propoxy)-4-(pyridin-3-yl)piperidin-1-yl)ethanone;

(34) 4-methoxy-N,2,6-trimethyl-N-(2-(2-(4-(3-(4-methylpiperazin-1-yl)propoxy)-4-(pyridin-3-yl)piperidin-1-yl)-2-oxoethoxy)ethyl)benzenesulfonamide;

(35) 1-(4-(3-(4-methylpiperazin-1-yl)propoxy)-4-(pyridin-3-yl)piperidin-1-yl)-2-(1-(3-(trifluoromethyl)phenylsulfonyl)piperidin-2-yl)ethanone;

(36) 3-(1-(4-chloro-2,5-dimethylphenylsulfonyl)piperidin-2-yl)-1-(4-(3-(4-methylpiperazin-1-yl)propoxy)-4-(pyridin-3-yl)piperidin-1-yl)propan-1-one;

(37) 2-((1-(3,4-dichlorophenylsulfonyl)-1,2,3,4-tetrahydroquinolin-2-yl)methoxy)-1-(4-(3-(4-methylpiperazin-1-yl)propoxy)-4-(pyridin-3-yl)piperidin-1-yl)ethanone;

(38) 2-((1-(3,4-dichlorophenylsulfonyl)-1,2,3,4-tetrahydroquinolin-2-yl)methoxy)-1-(4-(2-(4-methylpiperazin-1-yl)ethoxy)-4-(pyridin-3-yl)piperidin-1-yl)ethanone;

(39) N-(3-(4-(3-(4-methylpiperazin-1-yl)propoxy)-4-(pyridin-3-yl)piperidin-1-yl)-3-oxo-1-phenylpropyl)naphthalene-2-sulfonamide;

(40) 2-((1-(4-methoxy-2,6-dimethylphenylsulfonyl)piperidin-2-yl)methoxy)-1-(4-(pyridin-3-yl)-4-(3-(pyrrolidin-1-yl)propoxy)piperidin-1-yl)ethanone;

(41) 4-methoxy-N,2,6-trimethyl-N-(2-(2-oxo-2-(4-(pyridin-3-yl)-4-(3-(pyrrolidin-1-yl)propoxy)piperidin-1-yl)ethoxy)ethyl)benzenesulfonamide;

(42) 1-(4-(pyridin-3-yl)-4-(3-(pyrrolidin-1-yl)propoxy)piperidin-1-yl)-2-(1-(3-(trifluoromethyl)phenylsulfonyl)piperidin-2-yl)ethanone;

(43) 3-(1-(4-chloro-2,5-dimethylphenylsulfonyl)piperidin-2-yl)-1-(4-(pyridin-3-yl)-4-(3-(pyrrolidin-1-yl)propoxy)piperidin-1-yl)propan-1-one;

(44) N-(3-oxo-1-phenyl-3-(4-(pyridin-3-yl)-4-(3-(pyrrolidin-1-yl)propoxy)piperidin-1-yl)propyl)naphthalene-2-sulfonamide;

(45) 2-((1-(3,4-dichlorophenylsulfonyl)-1,2,3,4-tetrahydroquinolin-2-yl)methoxy)-1-(4-(pyridin-3-yl)-4-(3-(pyrrolidin-1-yl)propoxy)piperidin-1-yl)ethanone;

(46) (S)-2-((1-(4-methoxy-2,6-dimethylphenylsulfonyl)piperidin-2-yl)methoxy)-1-(4-(pyridin-3-yl)-4-(2-(pyrrolidin-1-yl)ethoxy)piperidin-1-yl)ethanone hydrochloride;

(47) (S)-1-(4-(pyridin-3-yl)-4-(2-(pyrrolidin-1-yl)ethoxy)piperidin-1-yl)-2-((1-(2-(trifluoromethyl)phenylsulfonyl)piperidin-2-yl)methoxy)ethanone;

(48) (S)-2-((1-(2-chloro-6-methylphenylsulfonyl)piperidin-2-yl)methoxy)-1-(4-(pyridin-3-yl)-4-(2-(pyrrolidin-1-yl)ethoxy)piperidin-1-yl)ethanone;

(49) (S)-2-((1-(4-methoxy-2,6-dimethylphenylsulfonyl)piperidin-2-yl)methoxy)-1-(4-(pyridin-3-yl)-4-((2-(pyrrolidin-1-yl)ethoxy)methyl)piperidin-1-yl)ethanone;

(50) 2-(((S)-1-(4-methoxy-2,6-dimethylphenylsulfonyl)piperidin-2-yl)methoxy)-1-(3-(pyridin-3-yl)-3-(2-(pyrrolidin-1-yl)ethoxy)pyrrolidin-1-yl)ethanone;

(51) (S)-1-(4-(3-fluorophenyl)-4-(2-(pyrrolidin-1-yl)ethoxy)piperidin-1-yl)-2-((1-(4-methoxy-2,6-dimethylphenylsulfonyl)piperidin-2-yl)methoxy)ethanone;

(53) 2-chloro-N-cyclopropyl-N-[2-[2-[4-(3-fluorophenyl)-4-[2-(1-oxido-pyrrolidin-1-ium-1-yl)-ethoxy]-piperidin-1-yl]-2-oxo-ethoxy]-ethyl]-6-methyl-benzenesulfonic acid amide;

(54) 2-[[(2S)-1-[(4-methoxy-2,6-dimethyl-phenyl)sulfonyl]-piperidin-2-yl]-methoxy]-1-[4-(2-pyrrolidin-1-yl-ethoxy)-4-[3-(trifluoromethyl)phenyl]-piperidin-1-yl]-ethanone;

(55) 2-[[(2S)-1-[(4-methoxy-2,6-dimethyl-phenyl)sulfonyl]-piperidin-2-yl]-methoxy]-1-[4-pyridin-3-yl-4-(2-pyrrolidin-1-yl-ethoxy)-azepan-1-yl]-ethanone;

(56) 1-[4-(3-chlorophenyl)-4-(2-pyrrolidin-1-yl-ethoxy)-piperidin-1-yl]-2-[[(2S)-1-[(4-methoxy-2,6-dimethyl-phenyl)sulfonyl]-piperidin-2-yl]-methoxy]-ethanone;

(57) 2-[[(2S)-1-[(4-methoxy-2,6-dimethyl-phenyl)sulfonyl]-piperidin-2-yl]-methoxy]-1-[4-pyridin-4-yl-4-(2-pyrrolidin-1-yl-ethoxy)-piperidin-1-yl]-ethanone;

(58) N-cyclopropyl-4-methoxy-2,6-dimethyl-N-[2-[2-[4-[2-(1-methyl-pyrrolidin-1-ium-1-yl)-ethoxy]-4-pyridin-3-yl-piperidin-1-yl]-2-oxo-ethoxy]-ethyl]-benzenesulfonic acid amide iodide;

(59) 2-[[(2S)-1-[(4-methoxy-2,6-dimethyl-phenyl)sulfonyl]-piperidin-2-yl]-methoxy]-1-[4-pyridin-3-yl-4-[2-(1H-[1,2,4]triazol-1-yl)-ethoxy]-piperidin-1-yl]-ethanone;

(60) 1-[4-[2-(1H-imidazol-1-yl)-ethoxy]-4-pyridin-3-yl-piperidin-1-yl]-2-[[(2S)-1-[(4-methoxy-2,6-dimethyl-phenyl)sulfonyl]-piperidin-2-yl]-methoxy]-ethanone;

(61) 1-[4-[2-(azetidin-1-yl)-ethoxy]-4-pyridin-3-yl-piperidin-1-yl]-2-[[(2S)-1-[(4-methoxy-2,6-dimethyl-phenyl)sulfonyl]-piperidin-2-yl]-methoxy]-ethanone;

(62) 2-chloro-N-cyclopropyl-N-[2-[2-[4-(3-fluorophenyl)-4-(2-pyrrolidin-1-yl-ethoxy)-piperidin-1-yl]-2-oxo-ethoxy]-ethyl]-6-methyl-benzenesulfonic acid amide;

(64) 1-[4-(4-fluorophenyl)-4-(2-pyrrolidin-1-yl-ethoxy)-piperidin-1-yl]-2-[[1-[(4-methoxy-2,6-dimethyl-phenyl)sulfonyl]-piperidin-2-yl]-methoxy]-ethanone;

(65) 2-[[1-[(4-methoxy-2,6-dimethyl-phenyl)sulfonyl]-piperidin-2-yl]-methoxy]-1-[4-(2-pyrrolidin-1-yl-ethoxy)-4-[4-(trifluoromethyl)-phenyl]-piperidin-1-yl]-ethanone;

(66) N-cyclopropyl-N-[2-[2-[4-(4-fluorophenyl)-4-(2-pyrrolidin-1-yl-ethoxy)-piperidin-1-yl]-2-oxo-ethoxy]-ethyl]-4-methoxy-2,6-dimethyl-benzenesulfonic acid amide;

(67) N-cyclopropyl-4-methoxy-2,6-dimethyl-N-[2-[2-oxo-2-[4-(2-pyrrolidin-1-yl-ethoxy)-4-[4-(trifluoromethyl)-phenyl]-piperidin-1-yl]-ethoxy]-ethyl]-benzenesulfonic acid amide;

(68) 2-[[1-[(2-chloro-6-methyl-phenyl)sulfonyl]-piperidin-2-yl]-methoxy]-1-[4-(4-fluorophenyl)-4-(2-pyrrolidin-1-yl-ethoxy)-piperidin-1-yl]-ethanone;

(69) 2-[[1-[(2-chloro-6-methyl-phenyl)sulfonyl]-piperidin-2-yl]-methoxy]-1-[4-(2-pyrrolidin-1-yl-ethoxy)-4-[4-(trifluoromethyl)-phenyl]-piperidin-1-yl]-ethanone;

(70) 2-chloro-N-cyclopropyl-N-[2-[2-[4-(4-fluorophenyl)-4-(2-pyrrolidin-1-yl-ethoxy)-piperidin-1-yl]-2-oxo-ethoxy]-ethyl]-6-methyl-benzenesulfonic acid amide;

(71) 2-chloro-N-cyclopropyl-6-methyl-N-[2-[2-oxo-2-[4-(2-pyrrolidin-1-yl-ethoxy)-4-[4-(trifluoromethyl)-phenyl]-piperidin-1-yl]-ethoxy]-ethyl]-benzenesulfonic acid amide;

(72) 1-[4-(4-fluorophenyl)-4-(2-pyrrolidin-1-yl-ethoxy)-piperidin-1-yl]-2-[1-[[3-(trifluoromethyl)phenyl]sulfonyl]-piperidin-2-yl]-ethanone;

(73) 1-[4-(2-pyrrolidin-1-yl-ethoxy)-4-[4-(trifluoromethyl)-phenyl]-piperidin-1-yl]-2-[1-[[3-(trifluoromethyl)phenyl]sulfonyl]-piperidin-2-yl]-ethanone;

(74) 3-[1-[(4-chloro-2,5-dimethyl-phenyl)sulfonyl]-piperidin-2-yl]-1-[4-(4-fluorophenyl)-4-(2-pyrrolidin-1-yl-ethoxy)-piperidin-1-yl]-propan-1-one;

(75) 3-[1-[(4-chloro-2,5-dimethyl-phenyl)sulfonyl]-piperidin-2-yl]-1-[4-(2-pyrrolidin-1-yl-ethoxy)-4-[4-(trifluoromethyl)-phenyl]-piperidin-1-yl]-propan-1-one;

(76) N-[3-[4-(4-fluorophenyl)-4-(2-pyrrolidin-1-yl-ethoxy)-piperidin-1-yl]-3-oxo-1-phenyl-propyl]-naphthalene-2-sulfonic acid amide;

(77) N-[3-oxo-1-phenyl-3-[4-(2-pyrrolidin-1-yl-ethoxy)-4-[4-(trifluoromethyl)-phenyl]-piperidin-1-yl]-propyl]-naphthalene-2-sulfonic acid amide;

(78) 1-[4-(4-fluorophenyl)-4-(2-pyrrolidin-1-yl-ethoxy)-piperidin-1-yl]-4-[1-[(4-methoxy-2,6-dimethyl-phenyl)sulfonyl]-piperidin-2-yl]-butan-1-one;

(79) 4-[1-[(4-methoxy-2,6-dimethyl-phenyl)sulfonyl]-piperidin-2-yl]-1-[4-(2-pyrrolidin-1-yl-ethoxy)-4-[4-(trifluoromethyl)-phenyl]-piperidin-1-yl]-butan-1-one;

(80) 4-methoxy-N,2,6-trimethyl-N-[2-[2-oxo-2-[4-pyridin-3-yl-4-(2-pyrrolidin-1-yl-ethoxy)-piperidin-1-yl]-ethoxy]-ethyl]-benzenesulfonic acid amide;

(81) N-[2-[2-[4-(3-fluorophenyl)-4-(2-pyrrolidin-1-yl-ethoxy)-piperidin-1-yl]-2-oxo-ethoxy]-ethyl]-4-methoxy-N,2,6-trimethyl-benzenesulfonic acid amide;

(82) 2-[[1-[(4-methoxy-2,6-dimethyl-phenyl)sulfonyl]-piperidin-2-yl]-methoxy]-1-[4-pyridin-3-yl-4-(2-pyrrolidin-1-yl-ethoxy)-piperidin-1-yl]-ethanone;

(83) 1-[4-(3-fluorophenyl)-4-(2-pyrrolidin-1-yl-ethoxy)-piperidin-1-yl]-2-[[1-[(4-methoxy-2,6-dimethyl-phenyl)sulfonyl]-piperidin-2-yl]-methoxy]-ethanone;

(84) 2-[[1-[(4-methoxy-2,6-dimethyl-phenyl)sulfonyl]-piperidin-2-yl]-methoxy]-1-[4-pyridin-4-yl-4-(2-pyrrolidin-1-yl-ethoxy)-piperidin-1-yl]-ethanone;

(85) 4-[1-[(2-chloro-6-methyl-phenyl)sulfonyl]-piperidin-2-yl]-1-[4-(3-fluorophenyl)-4-(2-pyrrolidin-1-yl-ethoxy)-piperidin-1-yl]-butan-1-one;

(86) 1-[4-(3-fluorophenyl)-4-(2-pyrrolidin-1-yl-ethoxy)-piperidin-1-yl]-4-[1-[[2-(trifluoromethyl)-phenyl]sulfonyl]-piperidin-2-yl]-butan-1-one;

(87) 4-[1-[(4-methoxy-2,6-dimethyl-phenyl)sulfonyl]-piperidin-2-yl]-1-[4-pyridin-3-yl-4-(2-pyrrolidin-1-yl-ethoxy)-piperidin-1-yl]-butan-1-one;

(88) 4-[1-[(4-methoxy-2,6-dimethyl-phenyl)sulfonyl]-piperidin-2-yl]-1-[4-pyridin-3-yl-4-(2-pyrrolidin-1-yl-ethoxy)-piperidin-1-yl]-butan-1-one;

(89) 1-[4-(3-fluorophenyl)-4-(2-pyrrolidin-1-yl-ethoxy)-piperidin-1-yl]-4-[1-[(4-methoxy-2,6-dimethyl-phenyl)sulfonyl]-piperidin-2-yl]-butan-1-one;

(90) 4-[1-[(4-methoxy-2,6-dimethyl-phenyl)sulfonyl]-piperidin-2-yl]-1-[4-pyridin-4-yl-4-(2-pyrrolidin-1-yl-ethoxy)-piperidin-1-yl]-butan-1-one;

(91) 4-[1-[(4-methoxy-2,6-dimethyl-phenyl)sulfonyl]-piperidin-2-yl]-1-[4-pyridin-4-yl-4-(2-pyrrolidin-1-yl-ethoxy)-piperidin-1-yl]-butan-1-one;

(92) 4-[1-(naphthalen-1-ylsulfonyl)-piperidin-2-yl]-1-[4-pyridin-3-yl-4-(2-pyrrolidin-1-yl-ethoxy)-piperidin-1-yl]-butan-1-one;

(93) 1-[4-(3-fluorophenyl)-4-(2-pyrrolidin-1-yl-ethoxy)-piperidin-1-yl]-4-[1-(naphthalen-1-ylsulfonyl)-piperidin-2-yl]-butan-1-one;

(94) 4-[1-(naphthalen-1-ylsulfonyl)-piperidin-2-yl]-1-[4-pyridin-4-yl-4-(2-pyrrolidin-1-yl-ethoxy)-piperidin-1-yl]-butan-1-one;

(95) 4-[1-(naphthalen-2-ylsulfonyl)-piperidin-2-yl]-1-[4-pyridin-3-yl-4-(2-pyrrolidin-1-yl-ethoxy)-piperidin-1-yl]-butan-1-one;

(96) 1-[4-(3-fluorophenyl)-4-(2-pyrrolidin-1-yl-ethoxy)-piperidin-1-yl]-4-[1-(naphthalen-2-ylsulfonyl)-piperidin-2-yl]-butan-1-one;

(98) 4-methoxy-2,6-dimethyl-N-[2-[2-oxo-2-[4-pyridin-3-yl-4-(2-pyrrolidin-1-yl-ethoxy)-piperidin-1-yl]-ethoxy]-ethyl]-N-phenyl-benzenesulfonic acid amide;

(99) N-[2-[2-[4-(3-fluorophenyl)-4-(2-pyrrolidin-1-yl-ethoxy)-piperidin-1-yl]-2-oxo-ethoxy]-ethyl]-4-methoxy-2,6-dimethyl-N-phenyl-benzenesulfonic acid amide;

(100) 4-methoxy-2,6-dimethyl-N-[2-[2-oxo-2-[4-pyridin-4-yl-4-(2-pyrrolidin-1-yl-ethoxy)-piperidin-1-yl]-ethoxy]-ethyl]-N-phenyl-benzenesulfonic acid amide;

(101) 2-[[1-[(4-methoxy-2,6-dimethyl-phenyl)sulfonyl]-1,2,3,4-tetrahydro-quinolin-2-yl]-methoxy]-1-[4-pyridin-3-yl-4-(2-pyrrolidin-1-yl-ethoxy)-piperidin-1-yl]-ethanone;

(102) 1-[4-(3-fluorophenyl)-4-(2-pyrrolidin-1-yl-ethoxy)-piperidin-1-yl]-2-[[1-[(4-methoxy-2,6-dimethyl-phenyl)sulfonyl]-1,2,3,4-tetrahydro-quinolin-2-yl]-methoxy]-ethanone;

(103) 2-[[1-[(4-methoxy-2,6-dimethyl-phenyl)sulfonyl]-1,2,3,4-tetrahydro-quinolin-2-yl]-methoxy]-1-[4-pyridin-4-yl-4-(2-pyrrolidin-1-yl-ethoxy)-piperidin-1-yl]-ethanone;

(104) N-benzhydryl-N-[2-[2-oxo-2-[4-pyridin-3-yl-4-(2-pyrrolidin-1-yl-ethoxy)-piperidin-1-yl]-ethoxy]-ethyl]-methanesulfonic acid amide;

(105) N-benzhydryl-N-[2-[2-[4-(3-fluorophenyl)-4-(2-pyrrolidin-1-yl-ethoxy)-piperidin-1-yl]-2-oxo-ethoxy]-ethyl]-methanesulfonic acid amide;

(106) 2-[[4-[(4-methoxy-2,6-dimethyl-phenyl)sulfonyl]-3,4-dihydro-2H-[1,4]benzoxazin-3-yl]-methoxy]-1-[4-pyridin-3-yl-4-(2-pyrrolidin-1-yl-ethoxy)-piperidin-1-yl]-ethanone;

(107) 1-[4-(3-fluorophenyl)-4-(2-pyrrolidin-1-yl-ethoxy)-piperidin-1-yl]-2-[[4-[(4-methoxy-2,6-dimethyl-phenyl)sulfonyl]-3,4-dihydro-2H-[1,4]benzoxazin-3-yl]-methoxy]-ethanone;

(108) 2-[[4-[(4-methoxy-2,6-dimethyl-phenyl)sulfonyl]-3,4-dihydro-2H-[1,4]benzoxazin-3-yl]-methoxy]-1-[4-pyridin-4-yl-4-(2-pyrrolidin-1-yl-ethoxy)-piperidin-1-yl]-ethanone;

(109) 2-[[4-[(2-chloro-6-methyl-phenyl)sulfonyl]-3,4-dihydro-2H-[1,4]benzoxazin-3-yl]-methoxy]-1-[4-(3-fluorophenyl)-4-(2-pyrrolidin-1-yl-ethoxy)-piperidin-1-yl]-ethanone;

(110) 1-[4-pyridin-3-yl-4-(2-pyrrolidin-1-yl-ethoxy)-piperidin-1-yl]-2-[[4-[[2-(trifluoromethyl)-phenyl]sulfonyl]-3,4-dihydro-2H-[1,4]benzoxazin-3-yl]-methoxy]-ethanone;

(111) 1-[4-(3-fluorophenyl)-4-(2-pyrrolidin-1-yl-ethoxy)-piperidin-1-yl]-2-[[4-[[2-(trifluoromethyl)-phenyl]sulfonyl]-3,4-dihydro-2H-[1,4]benzoxazin-3-yl]-methoxy]-ethanone;

(112) 1-[4-pyridin-4-yl-4-(2-pyrrolidin-1-yl-ethoxy)-piperidin-1-yl]-2-[[4-[[2-(trifluoromethyl)-phenyl]sulfonyl]-3,4-dihydro-2H-[1,4]benzoxazin-3-yl]-methoxy]-ethanone;

(113) 4-methoxy-N,2,3,6-tetramethyl-N-[2-[2-oxo-2-[4-pyridin-3-yl-4-(2-pyrrolidin-1-yl-ethoxy)-piperidin-1-yl]-ethoxy]-ethyl]-benzenesulfonic acid amide;

(114) N-[2-[2-[4-(3-fluorophenyl)-4-(2-pyrrolidin-1-yl-ethoxy)-piperidin-1-yl]-2-oxo-ethoxy]-ethyl]-4-methoxy-N,2,3,6-tetramethyl-benzenesulfonic acid amide;

(115) 4-methoxy-N,2,3,6-tetramethyl-N-[2-[2-oxo-2-[4-pyridin-4-yl-4-(2-pyrrolidin-1-yl-ethoxy)-piperidin-1-yl]-ethoxy]-ethyl]-benzenesulfonic acid amide;

(116) 1-[4-pyridin-3-yl-4-(2-pyrrolidin-1-yl-ethoxy)-piperidin-1-yl]-2-[[1-[[2-(trifluoromethyl)-phenyl]sulfonyl]-piperidin-2-yl]-methoxy]-ethanone;

(117) 1-[4-pyridin-3-yl-4-(2-pyrrolidin-1-yl-ethoxy)-piperidin-1-yl]-2-[[1-[[2-(trifluoromethyl)-phenyl]sulfonyl]-piperidin-2-yl]-methoxy]-ethanone;

(118) 1-[4-(3-fluorophenyl)-4-(2-pyrrolidin-1-yl-ethoxy)-piperidin-1-yl]-2-[[1-[[2-(trifluoromethyl)-phenyl]sulfonyl]-piperidin-2-yl]-methoxy]-ethanone;

(119) 3-[[1-[(4-methoxy-2,6-dimethyl-phenyl)sulfonyl]-piperidin-2-yl]-methoxy]-1-[4-pyridin-3-yl-4-(2-pyrrolidin-1-yl-ethoxy)-piperidin-1-yl]-propan-1-one;

(120) 3-[[1-[(4-methoxy-2,6-dimethyl-phenyl)sulfonyl]-piperidin-2-yl]-methoxy]-1-[4-pyridin-3-yl-4-(2-pyrrolidin-1-yl-ethoxy)-piperidin-1-yl]-propan-1-one;

(121) 1-[4-(3-fluorophenyl)-4-(2-pyrrolidin-1-yl-ethoxy)-piperidin-1-yl]-3-[[1-[(4-methoxy-2,6-dimethyl-phenyl)sulfonyl]-piperidin-2-yl]-methoxy]-propan-1-one;

(122) 1-[4-(3-fluorophenyl)-4-(2-pyrrolidin-1-yl-ethoxy)-piperidin-1-yl]-3-[[1-[(4-methoxy-2,6-dimethyl-phenyl)sulfonyl]-piperidin-2-yl]-methoxy]-propan-1-one;

(123) 2-[2-[1-[(4-methoxy-2,6-dimethyl-phenyl)sulfonyl]-piperidin-2-yl]-ethoxy]-1-[4-pyridin-3-yl-4-(2-pyrrolidin-1-yl-ethoxy)-piperidin-1-yl]-ethanone;

(124) 2-[2-[1-[(4-methoxy-2,6-dimethyl-phenyl)sulfonyl]-piperidin-2-yl]-ethoxy]-1-[4-pyridin-3-yl-4-(2-pyrrolidin-1-yl-ethoxy)-piperidin-1-yl]-ethanone;

(125) 1-[4-(3-fluorophenyl)-4-(2-pyrrolidin-1-yl-ethoxy)-piperidin-1-yl]-2-[2-[1-[(4-methoxy-2,6-dimethyl-phenyl)sulfonyl]-piperidin-2-yl]-ethoxy]-ethanone;

(126) 1-[4-(3-fluorophenyl)-4-(2-pyrrolidin-1-yl-ethoxy)-piperidin-1-yl]-2-[2-[1-[(4-methoxy-2,6-dimethyl-phenyl)sulfonyl]-piperidin-2-yl]-ethoxy]-ethanone;

(127) N-[4-[4-(3-fluorophenyl)-4-(2-pyrrolidin-1-yl-ethoxy)-piperidin-1-yl]-4-oxo-butyl]-N-methyl-3-(trifluoromethyl)-benzenesulfonic acid amide;

(128) 2-[4-[(2,4-dichlorophenyl)sulfonyl]-3,4-dihydro-2H-[1,4]benzoxazin-3-yl]-1-[4-(3-fluorophenyl)-4-(2-pyrrolidin-1-yl-ethoxy)-piperidin-1-yl]-ethanone;

(129) 2-[[1-(naphthalen-2-ylsulfonyl)-1,2,3,4-tetrahydro-quinolin-2-yl]-methoxy]-1-[4-pyridin-3-yl-4-(2-pyrrolidin-1-yl-ethoxy)-piperidin-1-yl]-ethanone;

(130) 2-[[1-(naphthalen-2-ylsulfonyl)-1,2,3,4-tetrahydro-quinolin-2-yl]-methoxy]-1-[4-pyridin-3-yl-4-(2-pyrrolidin-1-yl-ethoxy)-piperidin-1-yl]-ethanone; and (131) 1-[4-(3-fluorophenyl)-4-(2-pyrrolidin-1-yl-ethoxy)-piperidin-1-yl]-2-[[1-(naphthalen-2-ylsulfonyl)-1,2,3,4-tetrahydro-quinolin-2-yl]-methoxy]-ethanone;

The numbering of the individual embodiments of the compounds according to the invention used above is retained in the following explanations of the present invention, in particular in the description of the examples.

The compounds according to the invention preferably have an antagonistic action on the human B1R receptor or the B1R receptor of the rat. In a preferred embodiment of the invention, the compounds according to the invention have an antagonistic action both on the human B1R receptor (hB1R) and on the B1R receptor of the rat (rB1R).

Compounds which show an inhibition of at least 15%, 25%, 50%. 70%, 80% or 90% on the human B1R receptor and/or on the B1R receptor of the rat in the FLIPR assay at a concentration of 10 μm are particularly preferred. Compounds which show an inhibition on the human B1R receptor and on the B1R receptor of the rat of at least 70%, in particular of at least 80% and particularly preferably of at least 90% at a concentration of 10 μm are very particularly preferred.

The agonistic or antagonistic action of substances can be quantified on the bradykinin 1 receptor (B1R) of the human and rat species with ectopically expressing cell lines (CHO K1 cells) and with the aid of a $Ca^{2+}$-sensitive dyestuff (Fluo-4) in a fluorescent imaging plate reader (FLIPR). The figure in % activation is based on the $Ca^{2+}$ signal after addition of Lys-Des-$Arg^9$-bradykinin (0.5 nM) or Des-$Arg^9$-bradykinin (100 nM). Antagonists lead to a suppression of the $Ca^{2+}$ inflow after addition of the agonist. % inhibition compared with the maximum achievable inhibition is stated.

The substances according to the invention can act, for example, on the B1R relevant in connection with various diseases, so that they are suitable as a pharmaceutical active compound in pharmaceutical compositions. The invention therefore also provides pharmaceutical compositions containing at least one substituted sulfonamide compound according to the invention and optionally suitable additives and/or auxiliary substances and/or optionally further active compounds.

The pharmaceutical compositions according to the invention optionally contain, in addition to at least one substituted sulfonamide compound according to the invention, suitable additives and/or auxiliary substances, that is to say also carrier materials, fillers, solvents, diluents, dyestuffs and/or binders, and can be administered as liquid pharmaceutical composition forms in the form of injection solutions, drops or juices or as semi-solid pharmaceutical composition forms in the form of granules, tablets, pellets, patches, capsules, plasters/spray-on plasters or aerosols. The choice of auxiliary substances etc. and the amounts thereof to be employed depend on whether the pharmaceutical composition is to be administered orally, perorally, parenterally, intravenously, intraperitoneally, intradermally, intramuscularly, nasally, buccally, rectally or topically, for example to the skin, the mucous membranes or into the eyes. Formulations in the form of tablets, coated tablets, capsules, granules, drops, juices and syrups are suitable for oral administration, and solutions, suspensions, easily reconstitutable dry formulations and sprays are suitable for parenteral, topical and inhalatory administration. Sulfonamide compounds according to the invention in a depot, in dissolved form or in a plaster, optionally with the addition of agents which promote penetration through the skin, are suitable formulations for percutaneous administration. Formulation forms which can be used orally or percutaneously can release the substituted sulfonamide compounds according to the invention in a delayed manner. The substituted sulfonamide compounds according to the invention can also be used in parenteral long-term depot forms, such as e.g. implants or implanted pumps. In principle, other further active compounds known to the person skilled in the art can be added to the pharmaceutical compositions according to the invention.

The amount of active compound to be administered to patients varies as a function of the weight of the patient, of the mode of administration, the indication and the severity of the disease. 0.00005 to 50 mg/kg, preferably 0.01 to 5 mg/kg of at least one substituted sulfonamide compound according to the invention are conventionally administered.

In a preferred form of the pharmaceutical composition, a substituted sulfonamide compound according to the invention contained therein is present as the pure diastereomer and/or enantiomer, as a racemate or as a non-equimolar or equimolar mixture of the diastereomers and/or enantiomers.

B1R is involved in particular in the pain event. The substituted sulfonamide compounds according to the invention can accordingly be used for treatment and/or preparation of a pharmaceutical composition for treatment of pain, in particular acute, visceral, neuropathic, chronic pain or inflammation pain.

The invention therefore also provides the use of a substituted sulfonamide compound according to the invention for treatment and/or preparation of a pharmaceutical composition for treatment of pain, in particular acute, visceral, neuropathic, chronic pain or inflammation pain.

The invention also provide the use of a substituted sulfonamide compound according to the invention for treatment and/or preparation of a pharmaceutical composition for treatment of diabetes, diseases of the respiratory tract, for example bronchial asthma, allergies, COPD/chronic obstructive pulmonary disease or cystic fibrosis; inflammatory intestinal diseases, for example ulcerative colitis or CD/Crohn's disease; neurological diseases, for example multiple sclerosis or neurodegeneration; inflammations of the skin, for example atopic dermatitis, psoriasis or bacterial infections; rheumatic diseases, for example rheumatoid arthritis or osteoarthritis; septic shock; reperfusion syndrome, for example following cardiac infarction or stroke, obesity; and as an angiogenesis inhibitor.

In this context, in one of the above uses it may be preferable for a substituted sulfonamide compound which is used to be present as the pure diastereomer and/or enantiomer, as a racemate or as a non-equimolar or equimolar mixture of the diastereomers and/or enantiomers.

The invention also provides a method for the treatment, in particular in one of the abovementioned indications, of a non-human mammal or a human requiring treatment of pain, in particular chronic pain, by administration of a therapeutically active dose of a substituted sulfonamide compound according to the invention, or of a pharmaceutical composition according to the invention.

The invention also provides a process for the preparation of the substituted sulfonamide compounds according to the invention as described in the following description, examples and claims.

In one aspect of the present invention, the substituted sulfonamide compounds according to the invention are prepared by the process described in the following, wherein step 2 of the process shown in the following is required only for synthesis of the N-oxide or alkyl- or arylammonium compounds:

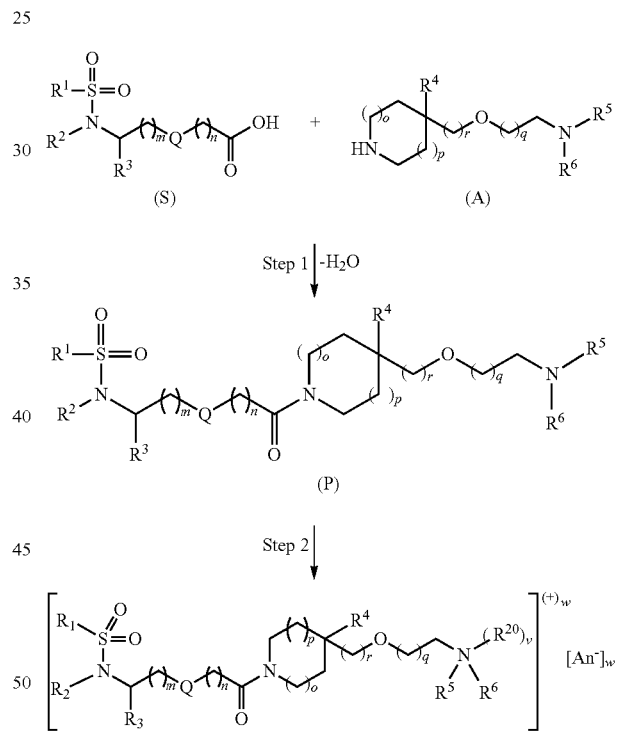

The free amines (AM) and the carboxylic acids (AC) are reacted in an amide formation in the presence at least of a dehydrating agent and an organic base in an organic solvent to give the compounds (P) according to the invention.

Dehydrating agents which can be used are, for example, sodium sulfate or magnesium sulfate, phosphorus oxide or reagents such as, for example, CDI, DCC (optionally polymer-bonded), TBTU, EDCl, PyBOP or PFPTFA, also in the presence of HOAt or HOBt. Organic bases which can be used are, for example, triethylamine, DIPEA or pyridine, and organic solvents which can be used are THF, methylene chloride, diethyl ether, dioxane, DMF or acetonitrile. The temperature in the amide formation step (1) is preferably between 0 and 50° C.

In one variant of the process, the PG-protected compounds (GP-AM)

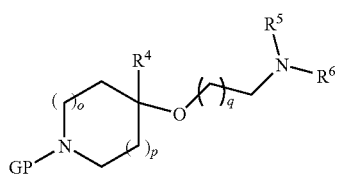

of the amine units (AM) can be deprotected in a prior step under conditions known to the person skilled in the art and added to the acid, and the reaction can then be carried out as described above to give the end products (P).

The compounds (P) obtained in this way by step 1 can be converted into ammonium salts or N-oxides according to the invention in step 2 by alkylation with alkyl halides, for example methyl iodide, or oxidation with m-chloroperbenzoic acid, $H_2O_2$, dimethyldioxirane, Oxone or perhydrol.

General Synthesis Process for the Preparation of the Acyclic Acid Units ylene chloride or tetrahydrofuran, and at a temperature of from 0° C. to the reflux temperature, to give the sulfonylated amino alcohols B.

The sulfonylated amino alcohols B are reacted in an alkylation reaction with halogenated ester compounds using tetrabutylammonium chloride or bromide or tetrabutylammonium hydrogen sulfate in a phase transfer reaction using an organic solvent, such as THF, toluene, benzene or xylene, and an inorganic base, such as potassium hydroxide, sodium hydroxide, sodium carbonate, sodium bicarbonate, potassium carbonate, or in the presence of an organic or inorganic base, conventional inorganic bases are metal alcoholates, such as sodium methanolate, sodium ethanolate, potassium tert-butylate, lithium bases or sodium bases, such as lithium diisopropylamide, butyllithium, tert-butyllithium, sodium methylate, or metal hydrides, such as potassium hydride, lithium hydride, sodium hydride, conventional organic bases are diisopropylethylamine, triethylamine, in an organic solvent, such as methylene chloride, THF or diethyl ether, at 0° C. to the reflux temperature, to give the products of the general structure C.

In Method II, the racemic (R and S configuration) or enantiomerically polyurethane (R or S configuration) amino alco-

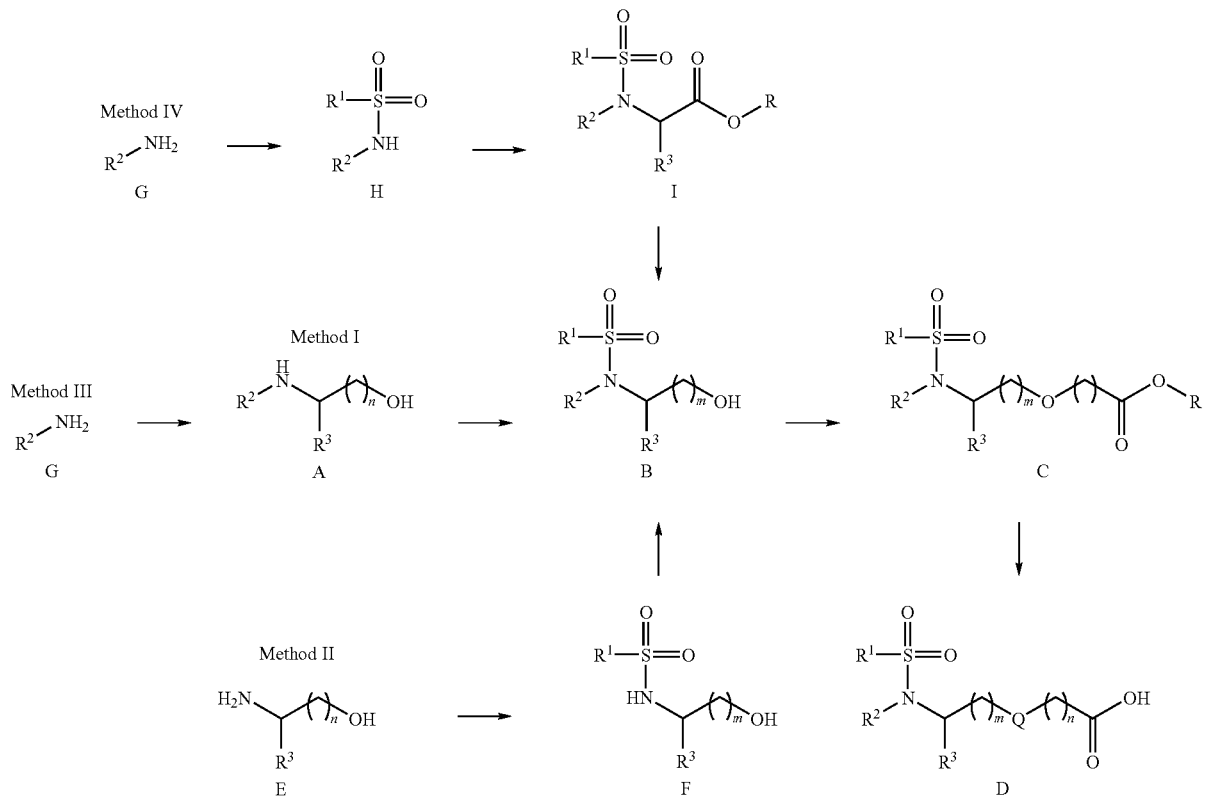

In Method 1, the racemic (R and S configuration) or enantiomerically pure (R or S configuration) amino alcohols A are reacted in a sulfonylation with sulfonyl chlorides, bromides or pentafluorophenolate $R_3SO_2X$ (X=Cl, Br, OPFP), optionally in the presence of an organic or inorganic base, for example potassium carbonate, sodium carbonate, sodium bicarbonate, diusopropylethylamine, triethylamine, pyridine, dimethylaminopyridine, diethylamine or DBU, preferably in an organic solvent, for example acetone, acetonitrile, methhols E are reacted in a sulfonylation with sulfonyl chlorides, bromides or pentafluorophenolate $R_3SO_2X$ (X=Cl, Br, OPFP), optionally in the presence of an organic or inorganic base, for example potassium carbonate, sodium bicarbonate, diisopropylethylamine, triethylamine, pyridine, dimethylaminopyridine, diethylamine or DBU, preferably in an organic solvent, for example acetone, acetonitrile, methylene chloride or tetrahydrofuran, and at a temperature of from 0° C. to the reflux temperature, to give the sulfonylated amino alcohols F. The sulfonylated amino alcohols F are then reacted in an alkylation reaction with alkyl halides (RX, X=I, Br, Cl), mesylates or alternative alkylating reagents, optionally in the presence of an organic or inorganic base, for example sodium hydroxide, potassium carbonate, caesium carbonate, DBU or DIPEA, preferably in an organic solvent, for example dimethylformamide, acetone, THF, acetonitrile, dioxane or these solvents as mixtures, at a temperature of from 0° C. to the reflux temperature, to give the sulfonylated amino alcohols B.

In Methods I-III, the ester compounds C are reacted in an ester cleavage using organic acids, such as trifluoroacetic acid, or aqueous inorganic acids, such as hydrochloric acid, or using aqueous inorganic bases, such as lithium hydroxide, potassium hydroxide, sodium hydroxide, sodium carbonate, sodium bicarbonate, potassium carbonate, in organic solvents, such as methanol, dioxane, methylene chloride, THF, diethyl ether or these solvents as mixtures, at 0° C. to room temperature, to give the acid stages of the general formula D.

In Method III, commercial amines or amines accessible to the person skilled in the art are alkylated with 2-bromoethanol or compounds in organic solvents, such as ethanol, methanol, ether, THF or methylene chloride, at a temperature of from 0° C. to the reflux temperature for up to 20 h. The further process proceeds analogously to the other methods.

In Method IV, the amines are reacted in a sulfonylation with sulfonyl chlorides, bromides or pentafluorophenolate $R_3SO_2X$ (X=Cl, Br, OPFP), optionally in the presence of an organic or inorganic base, for example potassium carbonate, sodium carbonate, sodium bicarbonate, diisopropylethylamine, triethylamine, pyridine, dimethylaminopyridine, diethylamine or DBU, preferably in an organic solvent, for example acetone, acetonitrile, methylene chloride or tetrahydrofuran, and at a temperature of from 0° C. to the reflux temperature, to give the sulfonylated compounds H.

The sulfonylated amines are then reacted in an alkylation reaction with methyl 2-bromoacetate or compounds H, optionally in the presence of an organic or inorganic base, for example sodium hydride, potassium carbonate, caesium carbonate, DBU or DIPEA, preferably in an organic solvent, for example dimethylformamide, acetone, THF, acetonitrile, dioxane or these solvents as mixtures, to give the sulfonylated amino esters I.

The sulfonylated amino esters I are reacted in a reduction reaction to give a sulfonylated amino alcohol B using metal hydrides as reducing agents, such as, for example, $LiAlH_4$, $BH_3{\times}DMS$ or $NaBH_4$, in an organic solvent, such as THF or diethyl ether. The further process of Method IV corresponds to the other methods.

General Synthesis Process for the Preparation of the Cyclic Acid Units

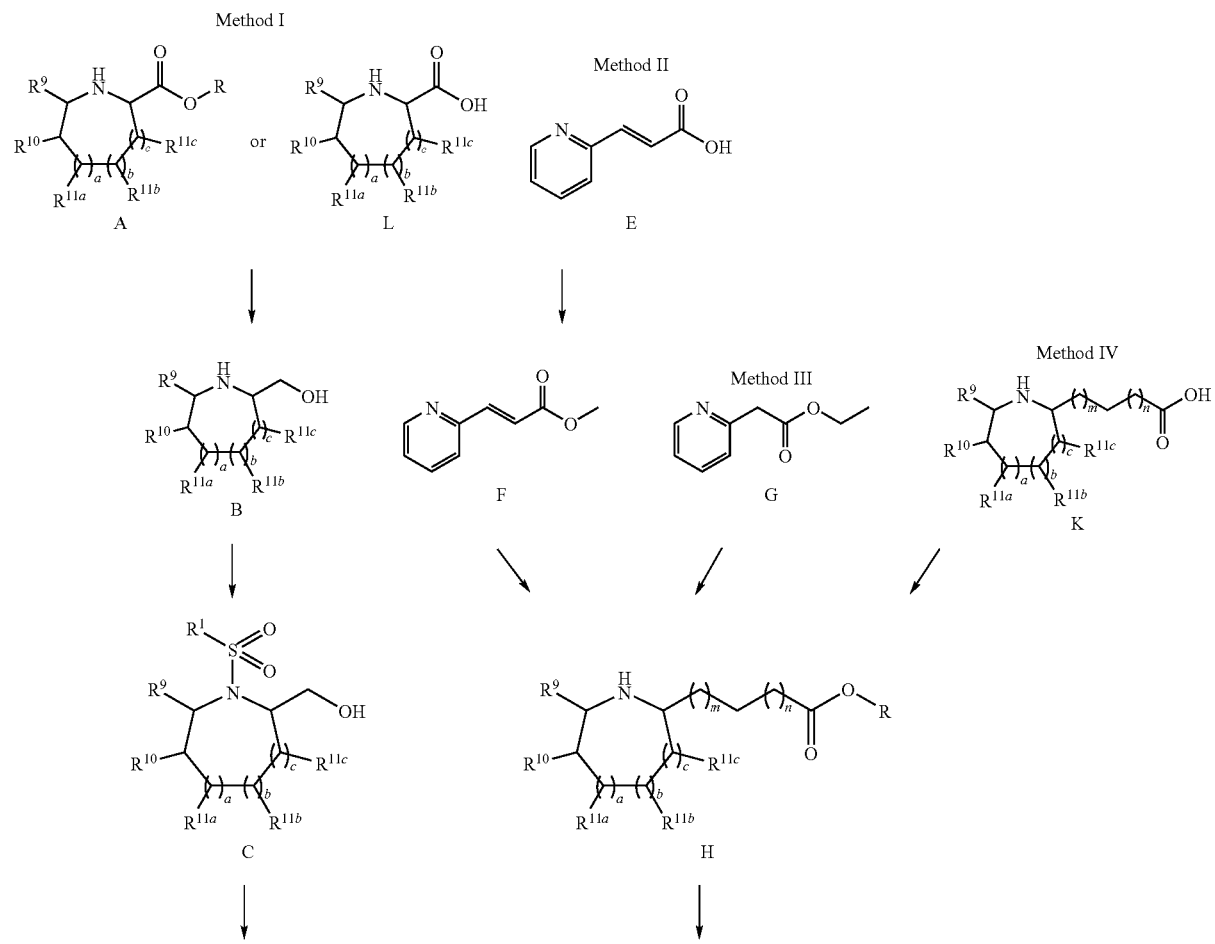

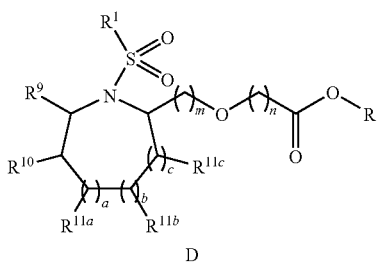

D

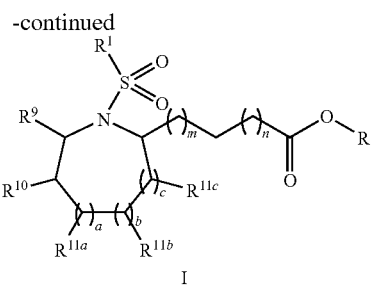

I

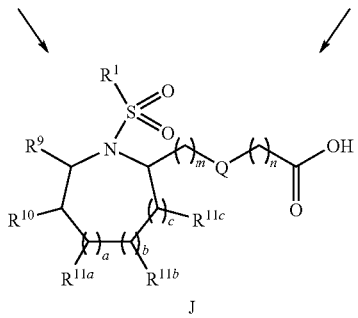

J

In Method 1, the racemic (R and S configuration) or enantiomerically pure (R or S configuration) amino acid esters A or amino acids L are reacted by a reduction to give an amino alcohol B using metal hydrides as reducing agents, such as, for example, $LiAlH_4$, $BF_3$ etherate, $BH_3 \times DMS$ or $NaBH_4$, in an organic solvent, such as THF or diethyl ether, at temperatures of from 0° C. to the reflux temperature. The amino alcohols B are reacted further in a sulfonylation with sulfonyl chlorides, bromides or pentafluorophenolate $R_3SO_2X$ (X=Cl, Br, OPFP), optionally in the presence of an organic or inorganic base, for example potassium carbonate, sodium bicarbonate, diisopropylethylamine, triethylamine, pyridine, dimethylaminopyridine, diethylamine or DBU, preferably in an organic solvent, for example acetone, acetonitrile, methylene chloride or tetrahydrofuran, and at a temperature of from 0° C. to the reflux temperature, to give the sulfonylated amino alcohols C.

The sulfonylated amino alcohols C are reacted in an alkylation reaction with halogenated ester compounds using tetrabutylammonium chloride or bromide or tetrabutylammonium hydrogen sulfate in a phase transfer reaction using an organic solvent, such as THF, toluene, benzene or xylene, and an inorganic base, such as potassium hydroxide, sodium hydroxide, sodium carbonate, sodium bicarbonate, potassium carbonate, or in the presence of an organic or inorganic base, conventional inorganic bases are metal alcoholates, such as sodium methanolate, sodium ethanolate, potassium tert-butylate, lithium bases or sodium bases, such as lithium diisopropylamide, butyllithium, tert-butyllithium, sodium methylate, or metal hydrides, such as potassium hydride, lithium hydride, sodium hydride, conventional organic bases are diisopropylethylamine, triethylamine, in an organic solvent, such as methylene chloride, THF or diethyl ether, at 0° C. to the reflux temperature, to give the products of the general structure D.

In Method II, 3-(pyridin-2-yl)acrylic acid E is esterified using dehydrating reagents, for example inorganic acids, such as $H_2SO_4$ or phosphorus oxides, or organic reagents, such as thionyl chloride, in organic solvents, such as THF, diethyl ether, methanol, ethanol or methylene chloride, to give stage F, at temperatures of from room temperature to the reflux temperature.

In Methods II and III, the ester stages F and G are hydrogenated in a hydrogenation under conditions known to the person skilled in the art in organic solvents, such as THF, chloroform, and in the presence of catalysts, such as platinum oxides, with hydrogen under normal pressure or increased pressure to give the intermediates H.

In Methods II-III, stage H is reacted further in a sulfonylation with sulfonyl chlorides, bromides or pentafluorophenolate $R_3SO_2X$ (X=Cl, Br, OPFP), optionally in the presence of an organic or inorganic base, for example potassium carbonate, sodium bicarbonate, diisopropylethylamine, triethylamine, pyridine, diethylamine or DBU, preferably in an organic solvent, for example acetonitrile, methylene chloride or tetrahydrofuran, at 0° C. to the reflux temperature, to give the sulfonylated amino esters I.

In Methods I-III, the ester compounds D and I are reacted in an ester cleavage using organic acids, such as trifluoroacetic acid, or aqueous inorganic acids, such as hydrochloric acid, or using aqueous inorganic bases, such as lithium hydroxide, potassium hydroxide, sodium hydroxide, sodium carbonate, sodium bicarbonate, potassium carbonate, in organic solvents, such as methanol, dioxane, methylene chloride, THF, diethyl ether or these solvents as mixtures, at 0° C. to room temperature, to give the acid stages of the general formula J.

In Method IV, the racemic (R and S configuration) or enantiomerically pure (R or S configuration) amino acids K are esterified using dehydrating reagents, for example inorganic acids, such as $H_2SO_4$ or phosphorus oxides, or organic reagents, such as thionyl chloride, in organic solvents, such as THF, diethyl ether, methanol, ethanol or methylene chloride, to give the amino esters H. The further course of the general process corresponds to Methods II-III.

General Process for the Synthesis of the Amine Units
Method 1

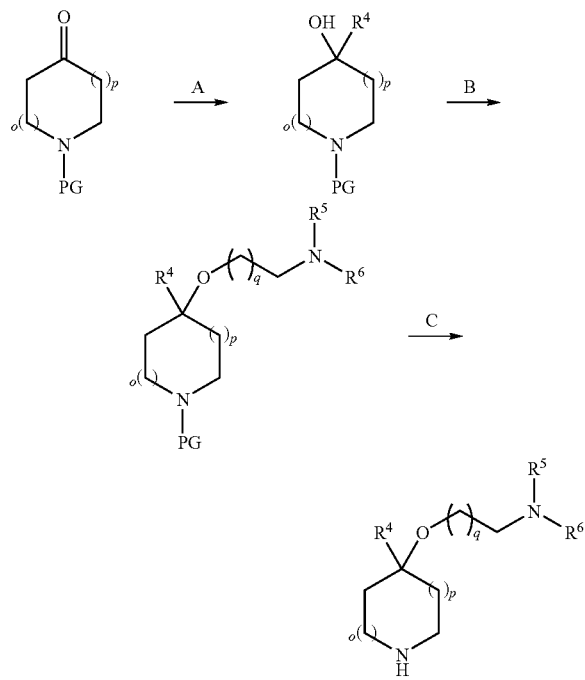

A: In the first step, the carbonyl compound is reacted with metal organyls, typically Li or Mg organyls (Grignard), in solvents, such as, for example, toluene, benzene, hexane, pentane, THF or diethyl ether, optionally with the addition of, for example, CeCl$_3$ to give the tertiary alcohol.

B: In a substitution reaction, the tertiary alcohol is dissolved in a suitable solvent, such as, for example, ethanol, methanol, 2-butanone, DMSO, diethyl ether, water, benzene, toluene, THF, MC, acetonitrile, acetone, DMF or pentane or a mixture of these solvents, and a suitable base is added, such as, for example, potassium hydroxide, sodium hydroxide, optionally in aqueous or alcoholic solution, potassium carbonate, potassium hexamethyldisilazane, sodium hydride, potassium hydride, sodium methanolate, sodium ethanolate, sodium tert-butylate or diisopropylethylamine, optionally with the addition of an auxiliary substance, such as, for example, 18-crown-6,15-crown-5, tetrabutylammonium bromide or sulfate, benzyltriethylammonium chloride, 1-n-butyl-3-methylimidazolium tetrafluoroborate or DMAP. Reaction with the corresponding iodide, bromide or chloride compound is then carried out.

C: The method for splitting off of the protective group depends on the nature of the protective group used. Suitable protective groups are, for example, the Boc, Cbz, Fmoc or benzyl protective group.

BOC protective groups can be split off, for example, by reaction with HCl in organic solvents, such as, for example, dioxane, methanol, ethanol, acetonitrile or ethyl acetate, or by reaction with TFA or methanesulfonic acid in methylene chloride or THF at a temperature of from 0° C. to 110° C. over a reaction time of 0.5-20 h. The Cbz protective group can be split off, for example, under acidic conditions. This acidic splitting off can be carried out, for example, by reaction with an HBr/glacial acetic acid mixture, a mixture of TFA in dioxane/water or HCl in methanol or ethanol. However, reagents such as, for example, Me$_3$SiI, in solvents, such as, for example, MC, chloroform or acetonitrile, BF$_3$ etherate with the addition of ethanethiol or Me$_2$S in solvents, such as, for example, MC, a mixture of aluminium chloride/anisole in a mixture of MC and nitromethane or triethylsilane/PdCl$_2$ in methanol with the addition of triethylamine, are also suitable. A further method is the hydrogenolytic splitting off of the protective group under increased pressure or normal pressure with the aid of catalysts, such as, for example, Pd on charcoal, Pd(OH)$_2$, PdCl$_2$, Raney nickel or PtO$_2$, in solvents, such as, for example, methanol, ethanol, 2-propanol, THF, acetic acid, ethyl acetate, chloroform, optionally with the addition of HCl, formic acid or TFA.

The Fmoc protective group is as a rule split off under basic conditions in solvents, such as, for example, acetonitrile, DMF, THF, diethyl ether, methanol, ethanol, 1-octanethiol, MC or chloroform. Suitable bases are, for example, diethylamine, piperidine, 4-aminomethylpiperidine, pyrrolidine, DBU, NaOH or LiOH. However, reagents such as, for example, Ag$_2$O/MeI can also be used.

A benzylic protective group can be split off, for example, by catalytic hydrogenation. Suitable catalysts are, for example, Pd on charcoal, PtO$_2$ or Pd(OH)$_2$. The reaction can be carried out in solvents, such as, for example, ethanol, methanol, 2-propanol, acetic acid, THF or DMF, optionally with the addition of acids, such as, for example, ammonium formate, maleic acid or formic acid, or in mixtures of the solvents.

Method 2

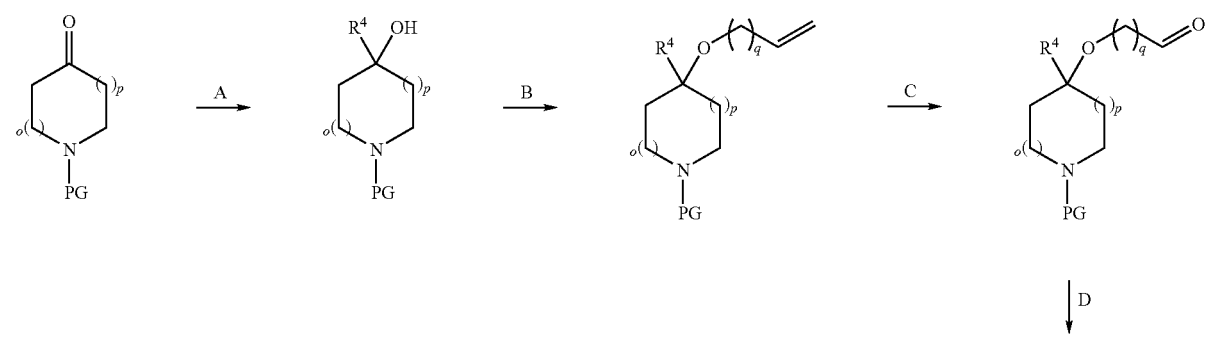

-continued

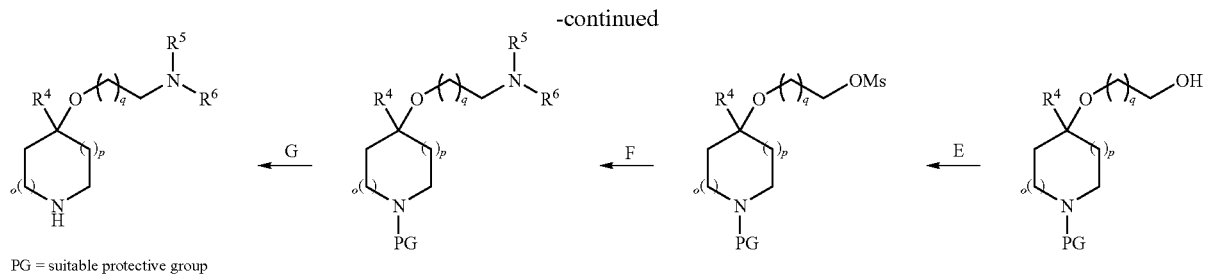

PG = suitable protective group

A: The carbonyl compound is reacted with metal organyls, typically Li or Mg organyls (Grignard), in solvents, such as, for example, toluene, benzene, hexane, pentane, THF or diethyl ether, optionally with the addition of, for example, $CeCl_3$ to give the tertiary alcohol.

B: In a substitution reaction, the tertiary alcohol is reacted with an allyl halide, preferably allyl bromide, in a suitable solvent, such as, for example, ethanol, methanol, 2-butanone, DMSO, diethyl ether, water, benzene, toluene, THF, MC, acetonitrile, acetone, DMF or pentane or a mixture of these solvents, in the presence of a suitable base, such as, for example, potassium hydroxide, sodium hydroxide, potassium carbonate, potassium hexamethyldisilazane, sodium hydride, potassium hydride, sodium methanolate, sodium ethanolate, sodium tert-butylate or diisopropylethylamine, optionally with the addition of an auxiliary substance, such as, for example, 18-crown-6,15-crown-5, tetrabutylammonium bromide or sulfate, benzyltriethylammonium chloride, 1-n-butyl-3-methylimidazolium tetrafluoroborate or DMAP.

C: The alkene is converted into the aldehyde under ozonolysis conditions known to the person skilled in the art.

D: The aldehyde is reacted with at least one suitable reducing agent, preferably sodium borohydride or lithium aluminium hydride, in at least one solvent, preferably chosen from the group consisting of THF, diethyl ether, toluene, methanol, ethanol or MC, to give the alcohol. Alternatively, the reaction can also be achieved by hydrogenolysis in the presence of a suitable catalyst. Catalysts which can be used are, for example, Pt on charcoal, palladium on charcoal, Raney nickel or $Pt_2O$. The hydrogenolysis takes place in solvents, such as, for example, acetic acid, methanol, ethanol, ethyl acetate, hexane, chloroform or mixtures of these solvents.

E: The alcohol is reacted with methylsulfonyl chloride in at least one solvent, preferably chosen from the group consisting of methylene chloride, dioxane, diethyl ether, tetrahydrofuran, acetonitrile and dimethylformamide, in the presence of at least one base, preferably chosen from the group consisting of caesium carbonate, calcium carbonate, potassium carbonate, triethylamine, diisopropylethylamine and pyridine, to give the methylsulfonate.

F: The methylsulfonate is reacted with a suitable amine in at least one solvent, preferably chosen from the group consisting of methylene chloride, dioxane, diethyl ether, tetrahydrofuran, acetonitrile, toluene and dimethylformamide, in the presence of a base, preferably chosen from the group consisting of caesium carbonate, calcium carbonate, potassium carbonate, potassium bicarbonate, sodium bicarbonate, triethylamine, diisopropylethylamine and pyridine.

G: The method for splitting off of the protective group depends on the nature of the protective group used. Suitable protective groups are, for example, the Boc, Cbz, Fmoc or benzyl protective group.

Protective groups can be introduced and split off by literature methods known to the person skilled in the art, as described, for example, in (a) Philip J. Kocienski, Protecting Groups, 3rd edition, Georg Thieme Verlag, 2005 (ISBN 3-13-135603-0) [in particular pages 487-643].

(b) Peter G. M. Wuts, Theodora W. Greene, Greene's Protective Groups in Organic Synthesis, 4th edition, Wiley-Interscience, 2007 (ISBN-13: 978-0-471-69754-1) [in particular pages 696-932].

Method 3

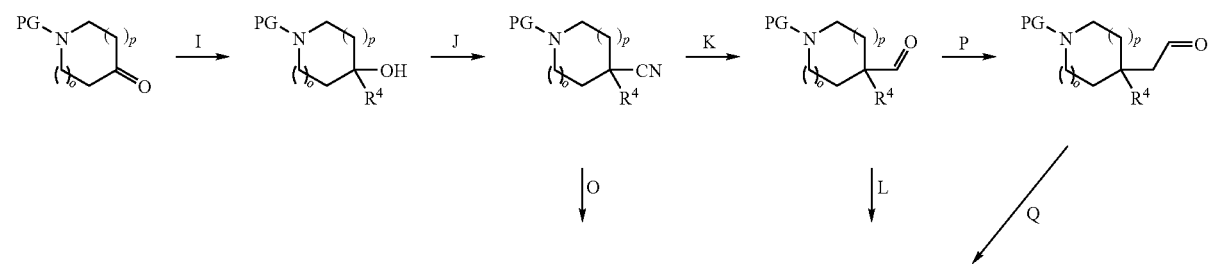

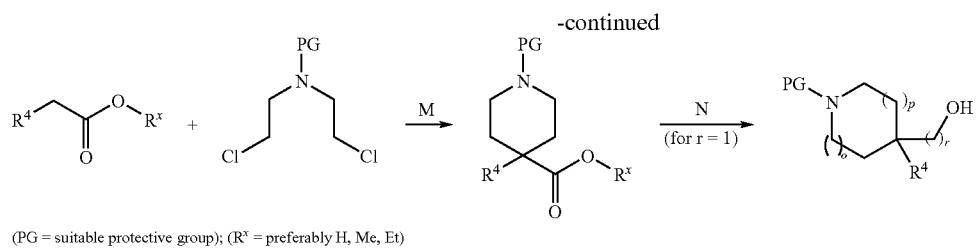

(PG = suitable protective group); (R$^x$ = preferably H, Me, Et)

I: The carbonyl compound is reacted with metal organyls, typically Li or Mg organyls (Grignard), in solvents, such as, for example, toluene, benzene, hexane, pentane, THF or diethyl ether, optionally with the addition of, for example, CeCl$_3$ to give the tertiary alcohol.

J: The alcohol is reacted to give the nitrile using trimethylchlorosilane/sodium iodide, trimethylsilyl cyanide/BF$_3$ etherate or DMF in organic solvents, such as THF, ether, MC, chloroform or acetonitrile.

K: The reduction of the nitrile to give the aldehyde is carried out using reducing agents, such as, for example, diisobutylaluminium hydride, in organic solvents, such as THF, ether, toluene or benzene.

L/Q: The aldehyde is reacted with at least one suitable reducing agent, preferably sodium borohydride or lithium aluminium hydride, in at least one solvent, preferably chosen from the group consisting of THF, diethyl ether, toluene, methanol, ethanol or MC, to give the alcohol. Alternatively, the reaction can also be achieved by hydrogenolysis in the presence of a suitable catalyst. Catalysts which can be used are, for example, Pt on charcoal, palladium on charcoal, Raney nickel or Pt$_2$O. The hydrogenolysis takes place in solvents, such as, for example, acetic acid, methanol, ethanol, ethyl acetate, hexane, chloroform or mixtures of these solvents.

M: The substitution reaction of a CH-acid compound to give the piperidine compound can be carried out in solvents, such as, for example, methanol, ethanol, i-propanol, t-butanol, acetone, acetonitrile, DMF, DME, DMSO, toluene, benzene, THF or liquid NH$_3$, with the addition of bases, such as, for example, potassium hydroxide, sodium hydroxide, sodium or potassium methanolate, ethanolate, i-propylate or t-butylate, lithium or sodium amide, lithium diisopropylamide, potassium carbonate, pyridine or elemental sodium, and optionally with the addition of sodium iodide or potassium iodide, HMPA, 1-butyl-3-methylimidazolinium hexafluorophosphate or 18-crown-6.

N: The reduction of the carboxylic acid or of the carboxylic acid ester to give the alcohol can be carried out with the aid of various reducing agents. Suitable reducing agents are, for example, LiBH$_4$ or NaBH$_4$ in solvents, such as, for example, diethyl ether, toluene, THF, water, methanol, ethanol or mixtures of these solvents, optionally with the addition of auxiliary reagents, such as, for example, boric acid esters. However, Zn(BH$_4$)$_2$ in, for example, DME can also be used as a further borohydride. The reduction can also be carried out, however, with BH$_3$-Me$_2$S complex in solvents, such as, for example, THF or MC. In addition to the boron compounds, the complex aluminium hydrides, such as, for example, DIBAH or LAH, in solvents, such as, for example, diethyl ether, benzene, toluene, THF, MC, DME, hexane or mixtures of these solvents, are also suitable for reduction of the ester function to the alcohol.

O: The nitrile can be hydrolyzed to give the corresponding carboxylic acid or the corresponding carboxylic acid ester by methods known to the person skilled in the art in the presence of a suitable acid, for example HCl, HBr, p-toluenesulfonic acid, trimethylsilyl chloride or H$_2$SO$_4$, in a suitable solvent, for example water, methanol, ethanol or mixtures of these solvents. Depending on the amine-protecting group used, it may be necessary to introduce this again by methods known to the person skilled in the art.

P: The aldehyde can be reacted by methods known to the person skilled in the art in a Wittig reaction with the corresponding phosphonium compound, for example (methoxymethyl)triphenyl-phosphonium chloride, and a strong base, for example potassium tert-butylate, n-butyllithium, s-butyllithium, phenyllithium, lithium diisopropylamide or lithium hexamethyldisilazide, in organic solvents, for example THF, diethyl ether, cyclohexane, toluene or appropriate mixtures.

The further general process for synthesis of the amine units is carried out analogously to Method 1 (stages B and C) or Method 2 (stages C, D, E, F and G) starting from the alcohols which are obtained in stage L, N or Q of Method 3.

The invention is explained in further detail hereinafter with reference to illustrative examples, without limiting the scope of the general inventive idea.

EXAMPLES

The chemicals and solvents employed were obtained commercially from the conventional suppliers (e.g. Acros, Avocado, Aldrich, Bachem, Fluka, Lancaster, Maybridge, Merck, Sigma, TCI etc.) or synthesized by the methods known to the person skilled in the art. Commercially obtainable materials, for example Al$_2$O$_3$ or silica gel [for example from E. Merck, Darmstadt, Germany] were employed as the stationary phase for the column chromatography. The thin layer chromatography investigations were carried out with commercially obtainable HPTLC precoated plates (for example silica gel 60 F 254 from E. Merck, Darmstadt). The mixing ratios of solvents, mobile phases or for chromatography investigations are, unless indicated otherwise, always stated in volume/volume. Unless stated otherwise, the analytical studies were carried out by mass spectroscopy (ESI-MS).

ABBREVIATIONS eq. equivalent(s)
MC methylene chloride
min minute(s)
RT room temperature.
TFA trifluoroacetic acid
i. vac. in vacuo
KOtBu potassium tert-butylate
sat. saturated
LAH lithium aluminium hydride
EDCI N-(3-dimethylaminopropyl)-N'-ethyl-carbodiimide HOBt 1-hydroxy-1H-benzotriazole
DIPEA diisopropylethylamine
OPFP O-pentafluorophenyl
THF tetrahydrofuran
DMS dimethyl sulfide
LAH lithium aluminium hydride
DMAP dimethylaminopyridine
h—hour(s)
d—day(s)
eq.—equivalent(s)

sat.—saturated
aq.—aqueous
conc.—concentrated
DMF—N,N-dimethylformamide
MsCl—methanesulfonyl chloride
HATU—O-(7-azabenzotriazol-1-yl)-N,N,N',N'-tetramethyluronium hexafluorophosphate Synthesis of Acid Units for the Parallel Synthesis The acid units AC1-AC33 used in the parallel synthesis described below were prepared as follows:

| No. | Product | Name |
|---|---|---|
| AC-01 | | 2-(1-(3-(trifluoromethyl)phenylsulfonyl)piperidin-2-yl)acetic acid |
| AC-02 | | 3-(1-(4-chloro-2,5-dimethylphenylsulfonyl)piperidin-2-yl)propionic acid |
| AC-03 | | 2-((1-(4-methoxy-2,6-dimethylphenylsulfonyl)piperidin-2-yl)methoxy)-acetic acid |
| AC-04 | | 2-((1-(3,4-dichlorophenylsulfonyl)-1,2,3,4-tetrahydroquinolin-2-yl)methoxy)acetic acid |

-continued

| No. | Product | Name |
|---|---|---|
| AC-05 | | 2-(2-(4-methoxy-N,2,6-trimethylphenylsulfonamido)-ethoxy)acetic acid |
| AC-06 | | 3-(naphthalene-2-sulfonamido)-3-phenylpropionic acid |
| AC-07 | | 2-[2-[[(4-methoxy-2,3,6-trimethyl-phenyl)sulfonyl]-methyl-amino]-ethoxy]-acetic acid (AC-07) |
| AC-10 | | 2-[[1-[[2-(trifluoromethyl)-phenyl]sulfonyl]-piperidin-2-yl]-methoxy]-acetic acid (AC-10) |
| AC-11 | | 3-[[1-[(4-methoxy-2,6-dimethyl-phenyl)sulfonyl]-piperidin-2-yl]-methoxy]-propionic acid (AC-11) |
| AC-12 | | 2-[2-[1-[(4-methoxy-2,6-dimethyl-phenyl)sulfonyl]-piperidin-2-yl]-ethoxy]-acetic acid (AC-12) |

-continued

| No. | Product | Name |
|---|---|---|
| AC-13 | | 4-[methyl-[[3-(trifluoromethyl)phenyl]sulfonyl]-amino]-butyric acid (AC-13) |
| AC-14 | | 2-[4-[(2,4-dichlorophenyl)sulfonyl]-3,4-dihydro-2H-[1,4]benzoxazin-3-yl]-acetic acid (AC-14) |
| AC-15 | | 2-[2-(N-[(4-methoxy-2,6-dimethyl-phenyl)sulfonyl]-anilino)-ethoxy]-acetic acid (AC-15) |
| AC-16 | | 2-[[1-(naphthalen-2-ylsulfonyl)-1,2,3,4-tetrahydro-quinolin-2-yl]-methoxy]-acetic acid (AC-16) |
| AC-17 | | 2-[[1-[(4-methoxy-2,6-dimethyl-phenyl)sulfonyl]-1,2,3,4-tetrahydro-quinolin-2-yl]-methoxy]-acetic acid (AC-17) |
| AC-18 | | 4-[1-[(2-chloro-6-methyl-phenyl)sulfonyl]-piperidin-2-yl]-butyric acid (AC-18) |

| No. | Product | Name |
|---|---|---|
| AC-19 | 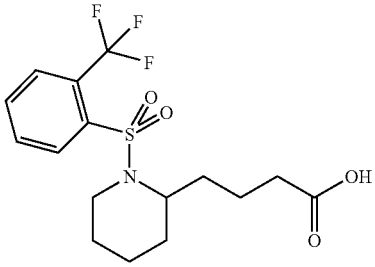 | 4-[1-[[2-(trifluoromethyl)-phenyl]sulfonyl]-piperidin-2-yl]-butyric acid (AC-19) |
| AC-20 | 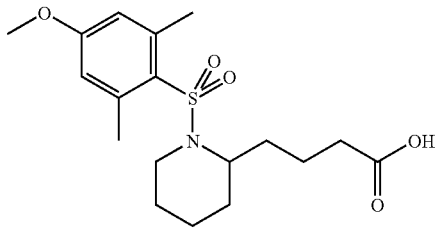 | 4-[1-[(4-methoxy-2,6-dimethyl-phenyl)sulfonyl]-piperidin-2-yl]-butyric acid (AC-20) |
| AC-21 | 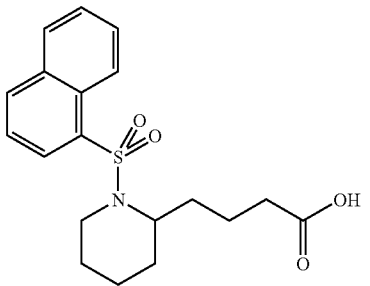 | 4-[1-(naphthalen-1-ylsulfonyl)-piperidin-2-yl]-butyric acid (AC-21) |
| AC-22 | 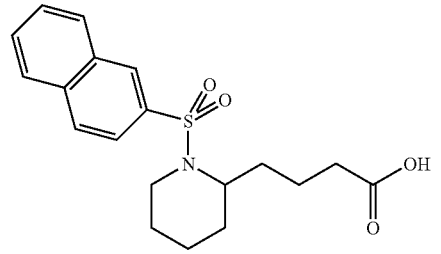 | 4-[1-(naphthalen-2-ylsulfonyl)-piperidin-2-yl]-butyric acid (AC-22) |
| AC-23 | 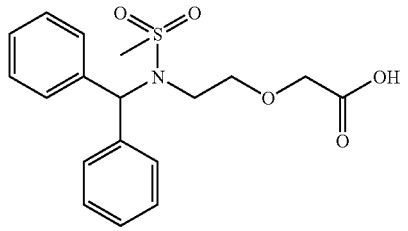 | 2-[2-(benzhydryl-methylsulfonyl-amino)-ethoxy]-acetic acid (AC-23) |
| AC-24 | 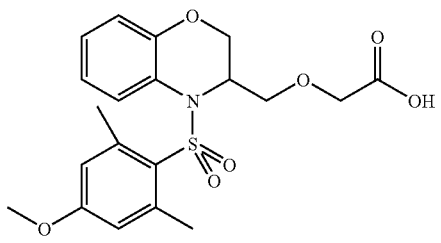 | 2-[[4-[(4-methoxy-2,6-dimethyl-phenyl)sulfonyl]-3,4-dihydro-2H-[1,4]benzoxazin-3-yl]-methoxy]-acetic acid (AC-24) |

| No. | Name |
|---|---|
| AC-26 | 2-[[4-[(2-chloro-6-methyl-phenyl)sulfonyl]-3,4-dihydro-2H-[1,4]benzoxazin-3-yl]-methoxy]-acetic acid (AC-26) |
| AC-27 | 2-[[4-[[2-(trifluoromethyl)-phenyl]sulfonyl]-3,4-dihydro-2H-[1,4]benzoxazin-3-yl]-methoxy]-acetic acid (AC-27) |
| AC-28 | 2-[2-[cyclopropyl-[(4-methoxy-2,6-dimethyl-phenyl)sulfonyl]-amino]-ethoxy]-acetic acid (AC-28) |
| AC-29 | 2-[[1-[(2-chloro-6-methyl-phenyl)sulfonyl]-piperidin-2-yl]-methoxy]-acetic acid (AC-29) |
| AC-30 | 2-[2-[[(2-chloro-6-methyl-phenyl)sulfonyl]-cyclopropyl-amino]-ethoxy]-acetic acid (AC-30) |
| AC-31 | 2-[1-[[3-(trifluoromethyl)phenyl]sulfonyl]-piperidin-2-yl]-acetic acid (AC-31) |

-continued

| No. | Product | Name |
|---|---|---|
| AC-32 | 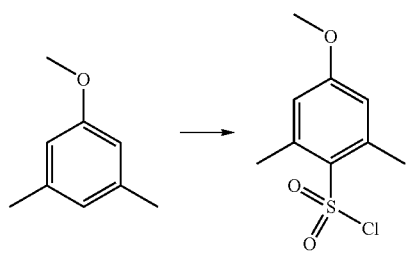 | 3-[1-[(4-chloro-2,5-dimethyl-phenyl)sulfonyl]-piperidin-2-yl]-propionic acid (AC-32) |
| AC-33 | 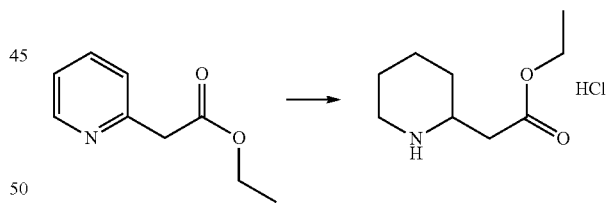 | 3-[(naphthalen-2-ylsulfonyl)amino]-3-phenyl-propionic acid (AC-33) |

4-Methoxy-2,6-dimethylbenzene-1-sulfonyl Chloride

A solution of 3,5-dimethylanisole (102.5 g, 753 mmol) in MC (1,000 ml) was cooled to 0° C. A solution of chlorosulfonic acid (251 ml, 3.763 mmol) in MC (250 ml) was added dropwise to this solution. After a reaction time of 10 min, the reaction solution was introduced into an ice bath (1,000 ml), the phases were separated and extraction was carried out once more with MC (250 ml). The combined organic phases were washed with water (1,000 ml) and saturated sodium chloride solution (1,000 ml), dried over Na₂SO₄ and concentrated. The product was purified by column chromatography over silica gel (heptane/MC 5:1). Yield: 63.5 g, 36%

Synthesis of the Amino Alcohols (1,2,3,4-Tetrahydroquinolin-2-yl)methanol

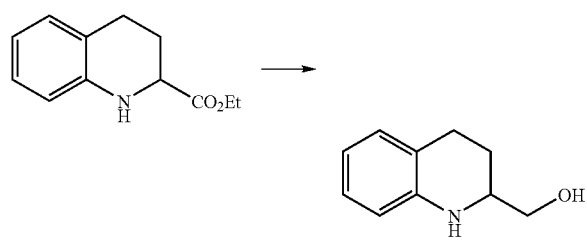

1,2,3,4-Tetrahydroquinoline-2-carboxylic acid ethyl ester (4.75 g 25 mmol) in THF (5 ml/mmol) was added dropwise to a suspension of LAH (2 eq.) in THF (50 ml) at 0° C. The reaction mixture was stirred at RT for 1 h and then heated under reflux for 4 h. After addition of aqueous saturated Na₂SO₄ solution, the mixture was filtered and the organic solvent was removed in vacuo. The product was purified by column chromatography (silica gel, ethyl acetate/hexane 3:7). Yield: 50%

Synthesis of the Amino Acid Esters

Ethyl 2-(piperidin-2-yl)acetate Hydrochloride

Ethyl 2-(pyridin-2-yl)acetate (24.51 g, 148.4 mmol) was dissolved in ethanol (130 ml), and PtO₂ (3.37 g, 14.84 mmol, 0.1 eq.) and chloroform (20 ml) were added. The suspension was stirred under an H₂ atmosphere (8 bar) at 40° C. overnight. According to TLC control (silica gel, MC/methanol 95:5), the reaction was not complete, so that further chloroform (15 ml) was added and the mixture was stirred under an H₂ atmosphere (8 bar) at 40° C. for a further 2 d (TLC control). After cooling, the catalyst was first removed by filtering over filtering earth and the filtrate was concentrated to dryness in vacuo. The ethyl 2-(piperidin-2-yl)acetate hydrochloride was employed in the next stage without further purification.

Yield: 31.51 g, >100%

Methyl 3-(piperidin-2-yl)propionate Hydrochloride

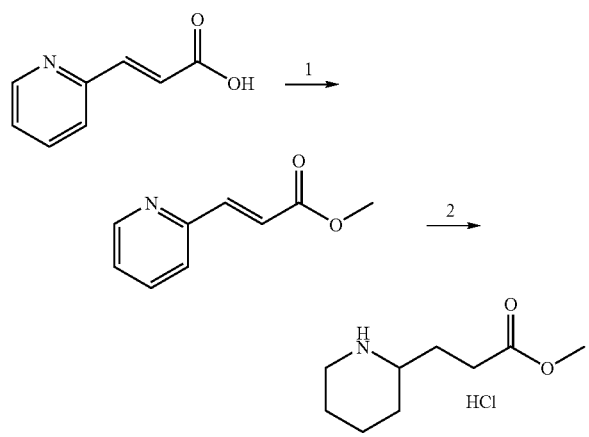

Stage 1. H$_2$SO$_4$ (12.8 ml, 240 mmol) was added to a solution of 3-(2-pyridyl)-acrylic acid (23.88 g, 160 mmol) in methanol (750 ml). The reaction mixture was heated under reflux overnight and, after cooling to RT, was poured into saturated aqueous NaHCO$_3$ solution (1,000 ml). The methanol was stripped off on a rotary evaporator and the aqueous phase was extracted twice with ethyl acetate (400 ml). The organic phase was washed with saturated NaCl solution (500 ml), dried over Na$_2$SO$_4$ and concentrated. The crude product of the methyl 3-(pyridin-2-yl)acrylate was employed in the next stage without further purification. Yield: 22.19 g, 85%.

Stage 2. Methyl 3-(pyridin-2-yl)acetate (22.15 g, 136 mmol) was dissolved in THF (300 ml) and chloroform (10.9 ml), and PtO$_2$ (3.08 g, 13.6 mmol, 0.1 eq.) was added under a nitrogen atmosphere. The solution was first flushed with nitrogen for 10 min and then stirred under an H$_2$ atmosphere (8 bar) overnight. After cooling, the mixture was first flushed again with nitrogen, the catalyst was removed by filtering over filtering earth and rinsed with MC and the filtrate was concentrated to dryness in vacuo. The methyl 3-(piperidin-2-yl)propionate hydrochloride was employed in the next stage without further purification. Yield: 27.95 g, 99%

Methyl 3-amino-3-phenylpropionate

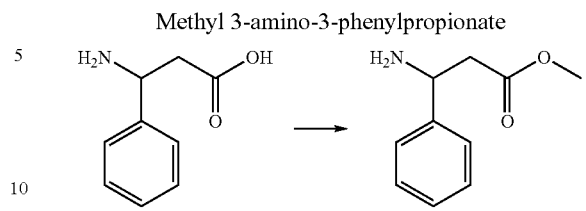

Thionyl chloride (19.1 g, 162 mmol) was added dropwise to a solution, cooled to 0° C., of 3-amino-3-phenylpropionic acid (8.9 g, 54 mmol) in methanol (150 ml). The reaction mixture was then heated under reflux for 12 h (TLC control). The solvent was removed completely and the residue was dried in vacuo. The crude product was employed in the next stage without further purification.

Sulfonylation of the Amino Alcohols and Amino Acid Esters
Method A

The corresponding amino alcohol or amino acid ester (1.1 eq.) was dissolved in MC (4 ml/mmol) and triethylamine (2.2 eq.) was added. The solution was cooled to 0° C., a solution of the corresponding sulfonic acid chloride (1 eq.), dissolved in MC (2.3 ml/mmoi), was added dropwise and the mixture was stirred at RT for 1.5 h. When the reaction had ended, HCl (0.5 M, 2.3 ml/mmol) was added, the phases were separated and the product phase was washed with water, dried over Na$_2$SO$_4$ and concentrated. The crude product was purified by column chromatography.

Method B

Pyridine (5 eq.), DMAP (0.5 eq.) and 3,4-dichlorobenzenesulfonyl chloride (1.2 eq.), dissolved in MC (2.6 ml/mmol of sulfonic acid chloride), were added to a suspension, cooled to 0° C., of the alcohol (1 eq.) in MC (5 ml/mmol). After stirring at 0° C. for 5 h, MC was added and the mixture was washed with aqueous copper sulfate solution, water and saturated NaCl solution. After drying over Na$_2$SO$_4$ and filtration, the solvent was removed in vacuo. The crude product was purified by column chromatography.

| Sulfonic acid chloride | Amino alcohol/ amino acid ester | Method | Product | Purification |
|---|---|---|---|---|
| 3-trifluoro-methylbenzene-sulfonyl chloride | ethyl 2-(piperidin-2-yl)acetate hydrochloride | A | ethyl 2-(1-(3-(trifluoromethyl)-phenylsulfonyl)-piperidin-2-yl)acetate | silica gel, MC |

-continued

| Sulfonic acid chloride | Amino alcohol/ amino acid ester | Method | Product | Purification |
|---|---|---|---|---|
| 4-chloro-2,5-dimethyl-benzenesulfonyl chloride | methyl 3-(piperidin-2-yl)-propionate hydrochloride | A | 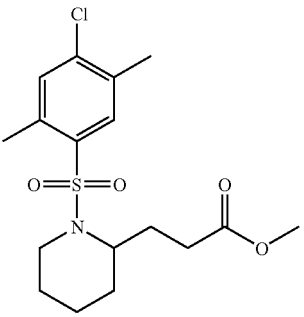<br>methyl 3-(1-(4-chloro-2,5-dimethylphenyl-sulfonyl)-piperidin-2-yl)propionate | silica gel, hetane/ethyl acetate, 6:1 → 3:1 |
| 4-methoxy-2,6-dimethyl-benzene-1-sulfonyl chloride | 2-piperidine-methanol | A | 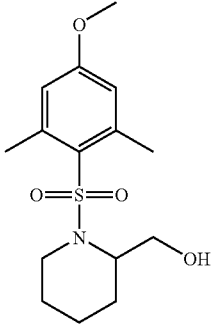<br>(1-(4-methoxy-2,6-dimethylphenylsulfonyl)-piperidin-2-yl)methanol | — |
| 3,4-dichloro-benzenesulfonyl chloride | (1,2,3,4-tetrahydroquinolin-2-yl)methanol | B | 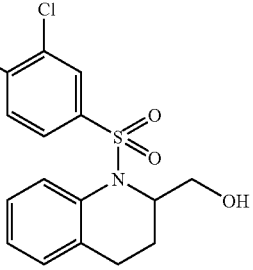<br>(1-(3,4-dichlorophenyl-sulfonyl)-1,2,3,4-tetrahydroquinolin-2-yl)methanol | silica gel, MC/methanol, 95:5 |

| Sulfonic acid chloride | Amino alcohol/ amino acid ester | Method | Product | Purification |
|---|---|---|---|---|
| 4-methoxy-2,6-dimethyl-benzene-1-sulfonyl chloride | 2-(methylamino)-ethanol | A | 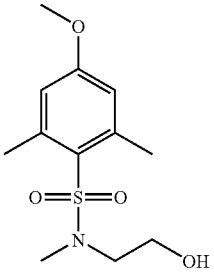<br>N-(2-hydroxyethyl)-4-methoxy-N,2,6-trimethylbenzene-sulfonamide | — |
| naphthalene-2-sulfonyl chloride | methyl 3-amino-3-phenylpropionate | A | 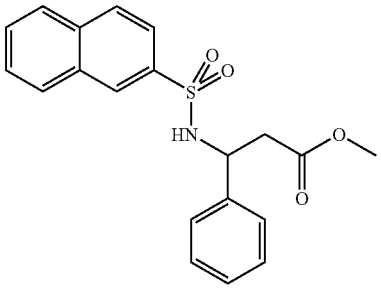<br>methyl 3-(naphthalene-2-sulfonamido)-3-phenylpropionate | silica gel, ethyl acetate/ hexane, 3:7 |

Synthesis of the tert-butyl methoxyacetates

Method A n-Bu$_4$NCl (0.33 eq.) was added to a solution of the corresponding sulfonylated amino alcohol (1 eq.) in toluene (6 ml/mmol). The reaction solution was cooled to 0° C. and an NaOH solution (35%, 6 ml/mmol of amino alcohol) was added. tert-Butyl bromoacetate (1.5 eq.) was added dropwise to this solution and the mixture was then stirred at RT for 3 h. The organic phase was separated and washed three times with water (7 ml/mmol), dried over Na$_2$SO$_4$ and concentrated. The crude product was purified by column chromatography.

Method B

A solution of the sulfonamide (1 eq.) dissolved in THF (6.3 ml/mmol) was added dropwise to a suspension, cooled to 0° C., of NaH (2 eq.) in THF (10 ml/mmol), while stirring. After stirring for 45 min at this temperature, a solution of tert-butyl bromoacetate (1.5 eq.) in THF (2 ml/mmol) was added. The reaction mixture was heated at 50° C. for 20 h. It was then cooled to 0° C., ice was added and the mixture was extracted with ethyl acetate. The organic phase was washed with aqueous saturated NaCl solution and dried over Na$_2$SO$_4$. After filtration, the solvent was removed in vacuo. The crude product was purified by column chromatography.

| Sulfonylated amino alcohol | Method | Product | Purification |
|---|---|---|---|
| (1-(4-methoxy-2,6-dimethylphenylsulfonyl)-piperidin-2-yl)methanol | A | tert-butyl 2-((1-(4-methoxy-2,6-dimethylphenylsulfonyl)-piperidin-2-yl)methoxy)acetate | silica gel, heptane/ethyl acetate, 3:1 |
| (1-(3,4-dichlorophenyl-sulfonyl)-1,2,3,4-tetrahydro-quinolin-2-yl)methanol | B | tert-butyl 2-((1-(3,4-dichlorophenylsulfonyl)-1,2,3,4-tetrahydroquinolin-2-yl)methoxy)acetate | silica gel, hexane/ethyl acetate, 9:1 |
| N-(2-hydroxyethyl)-4-methoxy-N,2,6-trimethylbenzene-sulfonamide | A | tert-butyl 2-(2-(4-methoxy-N,2,6-trimethylphenyl-sulfonamido)ethoxy)acetate | |

Hydrolysis of the Esters

Method A

The corresponding tert-butyl methoxyacetate was stirred in a solution of TFA (0.7 ml/mmol) and MC (4.7 ml/mmol) at RT for 2 h. When the reaction had ended, the solvent was removed on a rotary evaporator, the residue was taken up in toluene and the mixture was concentrated again.

Method B

The corresponding ester (1 eq.) was dissolved in a mixture of methanol (5.5 ml/mmol), dioxane (1.5 ml/mmol) and aqueous NaOH solution (4 M, 6 eq.) and the solution was stirred overnight When the reaction had ended (TLC control), the solution was concentrated. The crude product was taken up in ethyl acetate (22 ml/mmol) and the mixture was with $KHSO_4$ solution (0.5 M, 22 ml/mmol). The aqueous phase was extracted once more with ethyl acetate and the combined organic phases were washed with saturated NaCl solution (500 ml), dried over $Na_2SO_4$ and concentrated.

Method C

Aqueous NaOH solution (6 M, 3 ml/mmol) was added to a solution of the corresponding ester (1 eq.) in THF (3 ml/mmol). After a reaction time of 1 h, the solvent was removed on a rotary evaporator and the residue was cooled to 0° C. HCl (6 M, 3 ml/mmol) was added and the mixture was extracted with ethyl acetate. The organic phase was dried over $Na_2SO_4$ and concentrated.

Method D

First triethylsilane (1.55 eq.) and then TFA (0.8 ml/mmol) were added to a solution of the acetic acid tert-butyl ester compound (1 eq.) in MC (8 ml/mmol) and the mixture was stirred at RT for 5 h. The mixture was then concentrated I. vac., the residue was taken up repeatedly in toluene and the mixture was in each case concentrated again. The crude produce was dissolved in ethyl acetate and the solution was extracted with 5% NaHCO$_3$ solution. The combined aqueous phases were adjusted to pH 1 with conc. hydrochloric acid and extracted again with ethyl acetate. The combined organic phases were dried with Na$_2$SO$_4$ and concentrated i. vac.

Method E

LiOH*H$_2$O (2 eq.) was added to a solution of the ester (1 eq.) in a methanol/water:mixture (3:1, 10 ml/mmol) at a reaction temperature of 0° C. The reaction mixture was stirred at RT for 16 h. The solvent was stripped off under reduced pressure, the residue was taken up in water and the mixture was washed with MC. The aqueous phase was then cautiously acidified with HCl (1 N) and extracted with ethyl acetate. The organic phase was washed with water and sat. NaCl solution and dried over Na$_2$SO$_4$. After removal of the solvent, the product was obtained in an adequate purity.

| Ester | Method | Product |
|---|---|---|
| 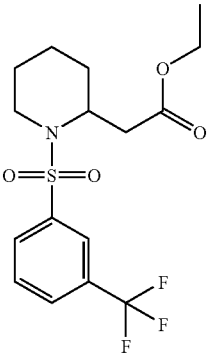<br>ethyl 2-(1-(3-(trifluoromethyl)phenyl-sulfonyl)-piperidin-2-yl)acetate | B | 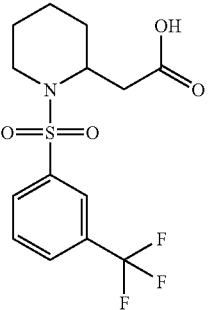<br>2-(1-(3-(trifluoromethyl)-phenylsulfonyl)piperidin-2-yl)acetic acid (AC1) |
| 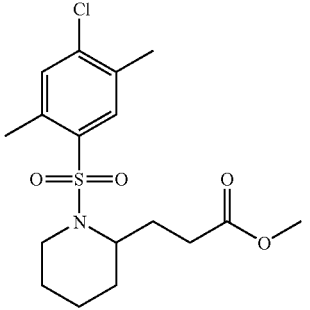<br>methyl 3-(1-(4-chloro-2,5-dimethylphenylsulfonyl)piperidin-2-yl)propionate | C | 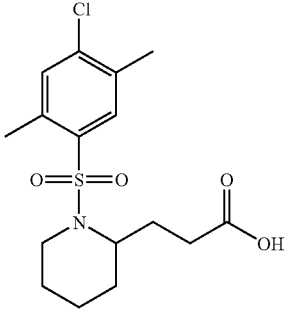<br>3-(1-(4-chloro-2,5-dimethylphenylsulfonyl)-piperidin-2-yl)propionic acid (AC2) |
| 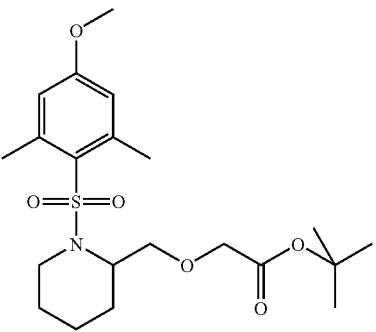<br>tert-butyl 2-((1-(4-methoxy-2,6-dimethylphenylsulfonyl)piperidin-2-yl)methoxy)acetate | A | 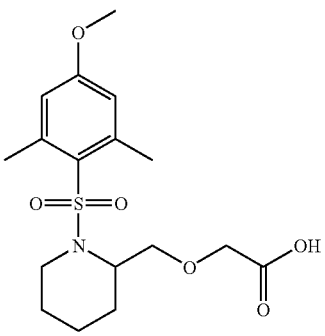<br>2-((1-(4-methoxy-2,6-dimethylphenylsulfonyl)-piperidin-2-yl)methoxy)-acetic acid (AC3) |

| Ester | Method | Product |
|---|---|---|
| 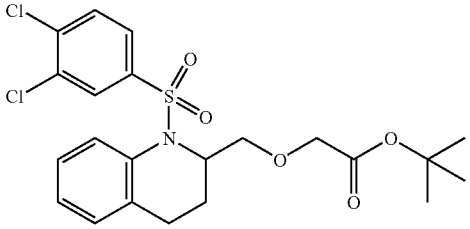 tert-butyl 2-((1-(3,4-dichlorophenylsulfonyl)-1,2,3,4-tetrahydroquinolin-2-yl)methoxy)-acetate | A | 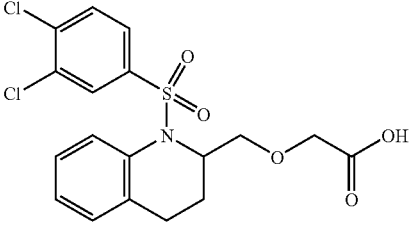 2-((1-(3,4-dichlorophenylsulfonyl)-1,2,3,4-tetrahydroquinolin-2-yl)methoxy)acetic acid (AC4) |
| 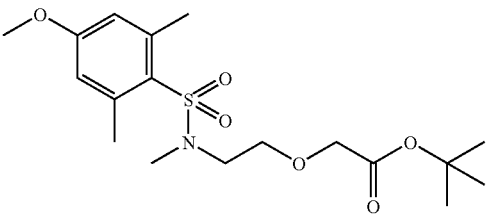 tert-butyl 2-(2-(4-methoxy-N,2,6-trimethylphenyl-sulfonamido)ethoxy)acetate | D | 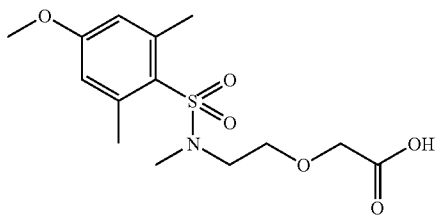 2-(2-(4-methoxy-N,2,6-trimethylphenylsulfonamido)-ethoxy)acetic acid (AC5) |
| 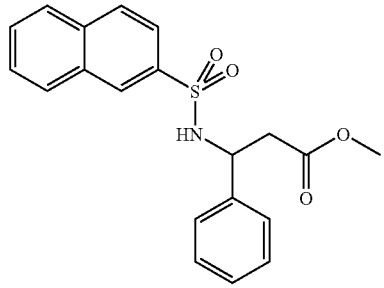 methyl 3-(naphthalene-2-sulfonamido)-3-phenylpropionate | E | 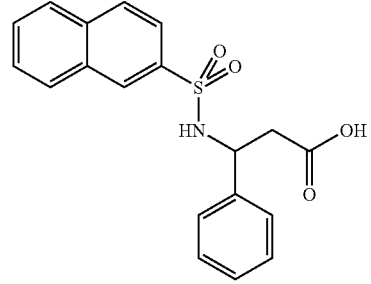 3-(naphthalene-2-sulfonamido)-3-phenylpropionic acid (AC6) |

Synthesis of the Acid Unit AC-07: 2-[2-[[(4-Methoxy-2,3,6-trimethylphenyl)sulfonyl]-methyl-amino]-ethoxy]-acetic Acid (AC-07)

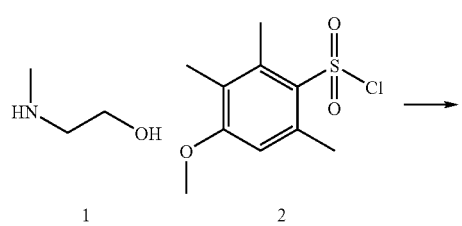

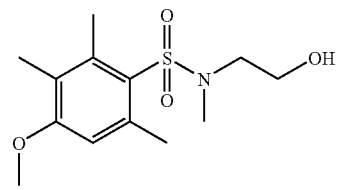

Stage-1: 2-Methylaminoethanol 1 (1 eq. 79.9 mmol) was dissolved in 500 ml of methylene chloride, and triethylamine (1.2 eq., 95.9 mmol) and the sulfonyl chloride 2 (1.2 eq., 95.9 mmol), dissolved in 60 ml of methylene chloride, were then added in succession. The mixture was stirred at room temperature for 4 h (TLC control). H₂O (100 ml) and sat. NaHCO₃ solution (100 ml) were then added to the reaction mixture. After separation of the phases, the aqueous phase was extracted 3× with methylene chloride (250 ml). The combined organic phases were dried over Na₂SO₄, filtered and concentrated. The residue was purified by column chromatography (silica, diethyl ether/hexane 8:2→9:1) to obtain the alcohol 3 (66.3 mmol, 83% yield).

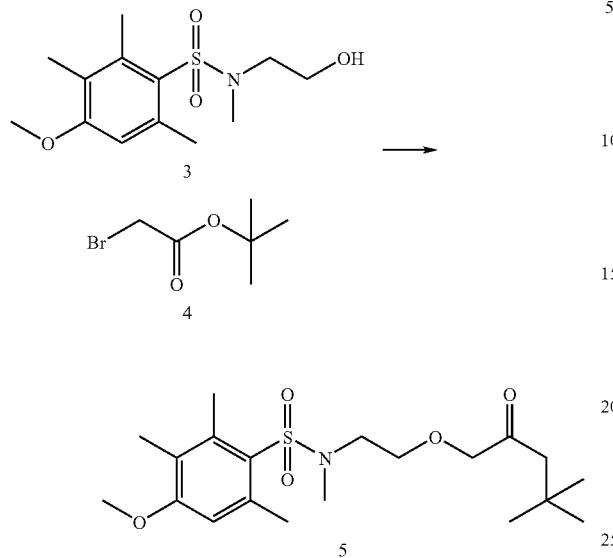

Stage-2: A mixture of alcohol 3 (1 eq., 74.8 mmol), tert-butyl bromoacetate (2.1 eq., 157 mmol), tetrabutylammonium hydrogen sulfate (0.1 eq., 7.48 mmol), aqueous 50% NaOH solution and toluene was vigorously mixed thoroughly at room temperature for 3.5 h (TLC control). The two phases were separated and the aqueous phase was extracted 2× with 450 ml of diethyl ether. The combined organic phases were dried over $Na_2SO_4$ and concentrated. The product 5 was obtained (67.3 mmol, 90%) and was employed in the next stage without further purification.

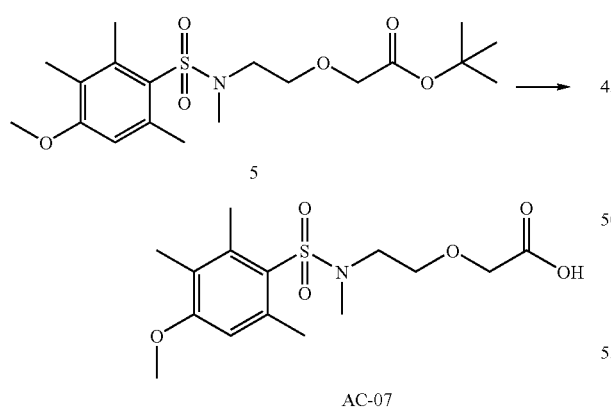

Stage-3: 5 (1 eq., 67.3 mmol) was dissolved in methylene chloride (110 eq., 7,400 mmol), and TFA (20 eq., 1,345 mmol) was then added. The mixture was stirred at RT for 4 h (TLC control). The reaction mixture was dried over magnesium sulfate, filtered and concentrated to dryness. The residue was co-evaporated 2× with toluene (300 ml). The residue was then washed 3× with diisopropyl ether, the diisopropyl ether being decanted off during this procedure. The residue was taken up in methylene chloride and the mixture was concentrated to dryness to obtain product AC-07 (101.9 mmol, 151%).

Synthesis of the Acid Unit AC-10: 2-[[1-[[2-(Trifluoromethyl)-phenyl]sulfonyl]-piperidin-2-yl]-methoxy]-acetic Acid (AC-10)

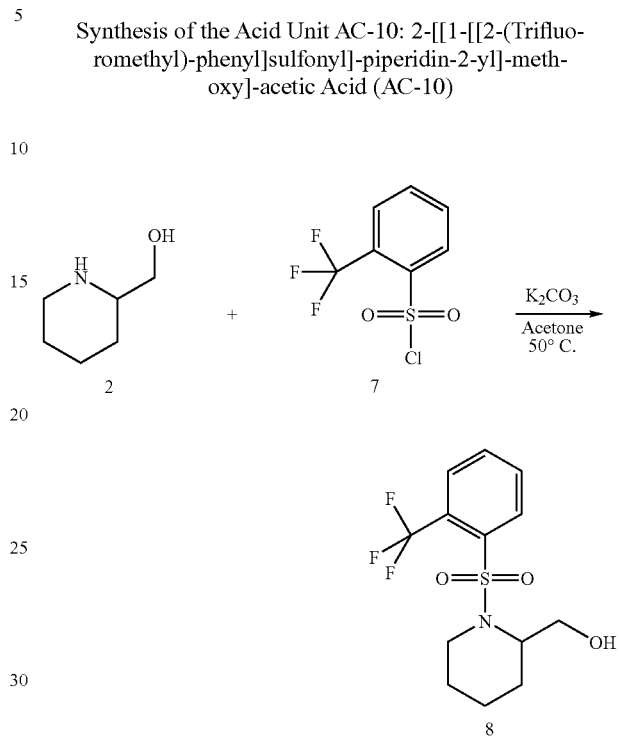

The alcohol 2 (4.3 g, 37.2 mmol) was suspended in acetone (150 ml). $K_2CO_3$ (10.27 g, 74.3 mmol) and 2-(trifluoromethyl)benzenesulfonyl chloride (7, 10 g, 40.9 mmol) were then added. The mixture was stirred at 50° C. overnight. After cooling to room temperature, the reaction mixture was filtered and the filtrate was concentrated to dryness under reduced pressure. The crude product was purified by column chromatography (silica, heptane/ethyl acetate 2:1) to obtain 8.95 g (75%) of the alcohol 8.

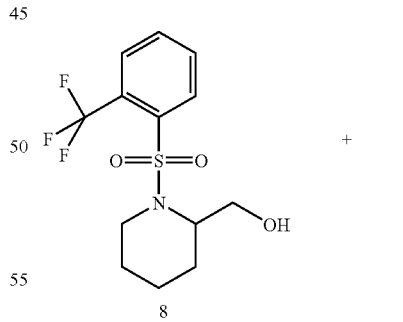

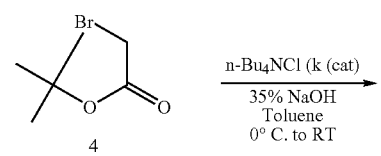

-continued

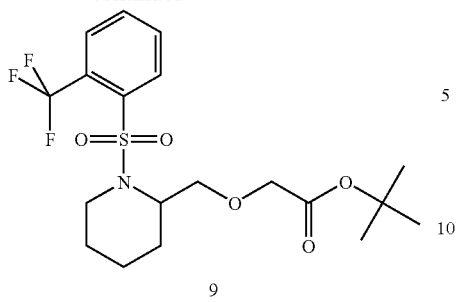

9 n-Bu$_4$NCl (2.54 g, 9.1 mmol) was added to a solution of the alcohol 8 (8.95 g, 27.7 mmol) in toluene (100 ml). After the mixture had been cooled to 0° C., an aqueous 35% NaOH solution (100 ml) was added, followed by tert-butyl bromoacetate (4, 6.05 ml, 41.5 mmol). After stirring at room temperature for 3 h, the reaction was complete. The organic phase was separated and washed with water (4×200 ml) and sat. NaCl solution (200 ml) until this was neutral, dried over Na$_2$SO$_4$ and concentrated under reduced pressure. Purification by column chromatography (silica, heptane/ethyl acetate 4:1) gave 11.57 g (96%) of the ester 9.

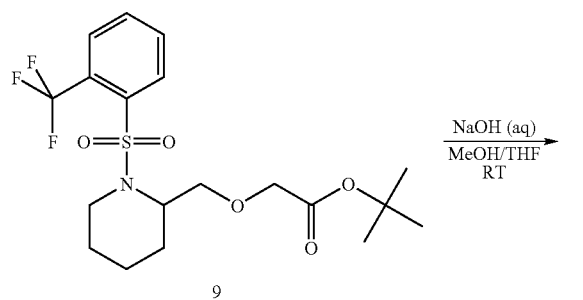

Ester 9 (11.57 g, 26.4 mmol) was stirred in aqueous 6 M NaOH (88 ml, 528 mmol), MeOH (85 ml) and THF (85 ml) at room temperature for 30 min. According to TLC (silica, heptane/ethyl acetate 2:1) the reaction was complete. The solution was then concentrated under reduced pressure. The suspension obtained was acidified with aqueous 6 M HCl (120 ml) at 0° C. CH$_2$Cl$_2$ (300 ml) was added, and after separation of the phases the aqueous phase was extracted with CH$_2$Cl$_2$ (100 ml). The combined organic phases were dried (Na$_2$SO$_4$) and concentrated to dryness under reduced pressure to obtain 9.89 g (98%) of the acid AC-10.

Synthesis of the Acid Unit AC-11: 3-[[1-[(4-Methoxy-2,6-dimethyl-phenyl)sulfonyl]-piperidin-2-yl]-methoxy]-propionic Acid (AC-11)

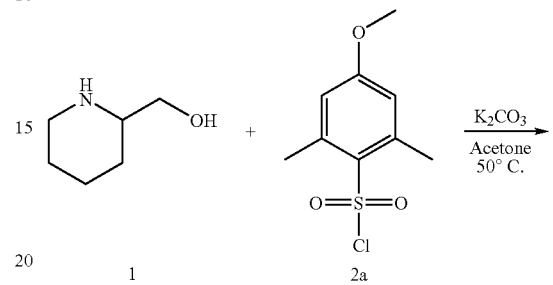

2-Piperidinemethanol (1, 8.1 g, 70.11 mmol) was suspended in acetone (350 ml). K$_2$CO$_3$ (19.4 g, 140.22 mmol) was added, followed by sulfonyl chloride 2a (18.1 g, 77.12 mmol). The mixture was stirred at 50° C. overnight. After cooling to room temperature, the reaction mixture was filtered and the filtrate was concentrated to dryness under reduced pressure. Purification by column chromatography (silica, heptane/ethyl acetate 2:1) gave 3 (12.9 g, 59%) as a white solid.

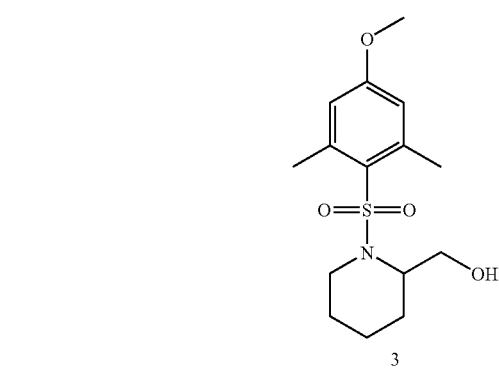

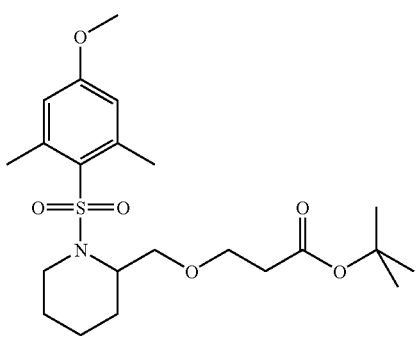

5

Bu₄NCl (3.7 g, 13.48 mmol) was added to a solution of the alcohol 3 (12.8 g, 40.84 mmol) in toluene (200 ml). The reaction mixture was cooled to 0° C. and aqueous 35% NaOH (250 ml) was then added, followed by dropwise addition of tert-butyl 3-bromopropionate (4, 8.2 ml, 49.01 mmol) in toluene (50 ml). The mixture was stirred at room temperature overnight. The organic phase was separated and washed with water until this was neutral, dried over Na₂SO₄ and concentrated and the residue was co-evaporated with methylene chloride (3×). Purification via column chromatography (silica, heptane/ethyl acetate 4:1) gave 5 (11.2 g, 62%) as a yellow oil.

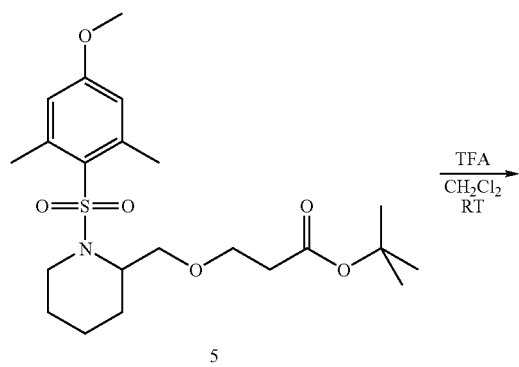

5

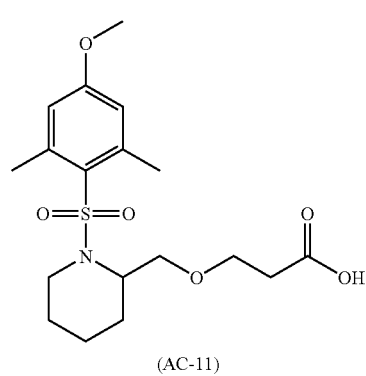

(AC-11)

tert-Butyl ester 5 (10.9 g, 24.68 mmol) was dissolved in CH₂Cl₂ (150 ml). TFA (75 ml) was added and the mixture was stirred at room temperature overnight. The reaction mixture was concentrated under reduced pressure and the residue was co-evaporated with toluene (3×) and CH₂Cl₂ (3×). AC-11 was obtained.

Synthesis of the Acid Unit AC-12: 2-[2-[1-[(4-Methoxy-2,6-dimethyl-phenyl)sulfonyl]-piperidin-2-yl]-ethoxy]-acetic Acid (S-12)

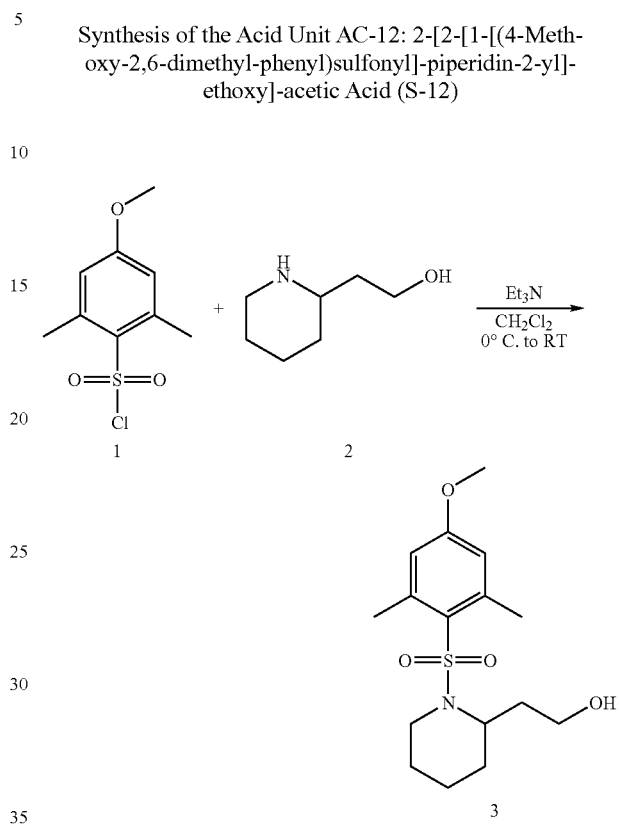

Et₃N (14.1 ml, 109 mmol) was added to a solution of 2-piperidine-ethanol (2, 5.63 g, 43.6 mmol) in CH₂Cl₂ (200 ml). 4-Methoxy-2,6-dimethylbenzenesulfonyl chloride (1, 10.23 g, 43.6 mmol) was added at 0° C. The mixture was stirred at 0° C. for 1 h and at room temperature overnight. Aqueous 1 M HCl (150 ml) was added, and after separation of the phases the organic phase was washed with sat. NaCl solution (150 ml), dried over Na₂SO₄ and concentrated to dryness to obtain compound 3 (14.85 g, '104%').

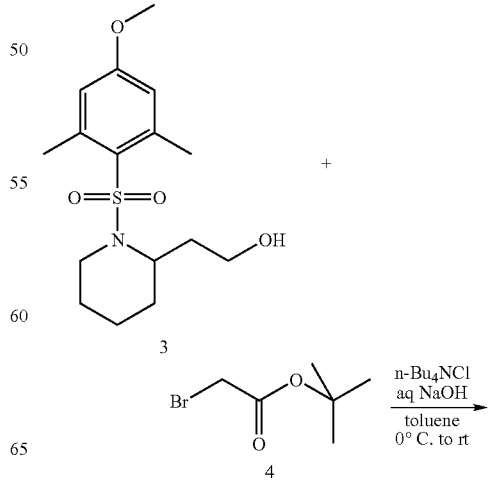

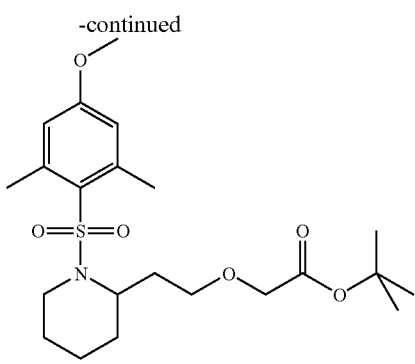

5

Bu₄NCl (4.04 g, 14.5 mmol) was added to a solution of the alcohol 3 (14.8 g, max. 43.6 mmol) in toluene (200 ml). After cooling to 0° C., aqueous 35% NaOH (200 ml) was added, followed by dropwise addition of tert-butyl 3-bromo-propionate (4, 9.53 ml, 65.4 mmol). The reaction mixture was stirred at room temperature for 3 h. The organic phase was separated, washed with water (3×200 ml), dried over Na₂SO₄ and concentrated to dryness. Purification via column chromatography (silica, heptane/ethyl acetate 4:1) gave compound 5 (12.90 g, 67%, 2 stages).

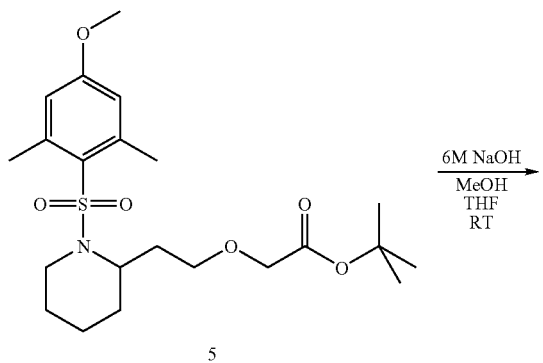

(AC-12)

Aqueous 6 M NaOH (95 ml) was added to a solution of the ester 5 (12.90 g, 29.2 mmol) in THF (95 ml) and MeOH (95 ml). After 1 h, the organic solvent was evaporated off and aqueous 6 M HCl (95 ml) was added at 0° C. The mixture was extracted with ethyl acetate (500 ml), dried over Na₂SO₄ and co-evaporated with diethyl ether (2×) to obtain the compound AC-12 (11.07 g, 98%).

Synthesis of the acid unit AC-13: 4-[Methyl-[[3-(trifluoromethyl)phenyl]sulfonyl]-amino]-butyric Acid (AC-13)

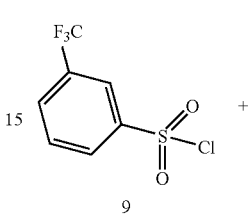

9

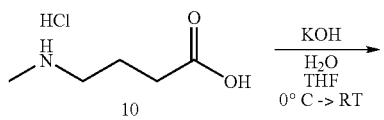

10

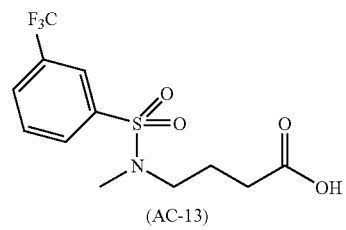

(AC-13)

4-(Methylamino)butanoic acid hydrochloride (10, 15.1 g, 98.1 mmol) was added to a solution of KOH (16.5 g, 294 mmol) in H₂O (75 ml) and the reaction mixture was cooled in an ice bath. A solution of 3-(trifluoromethyl)benzenesulfonyl chloride (9, 12.0 g, 49.1 mmol) in THF (75 ml) was added dropwise to the reaction mixture and the mixture was stirred at room temperature overnight. Aqueous 6 M HCl (75 ml) was added, while cooling with an ice bath, and the addition of CH₂Cl₂ then followed. The organic phase was separated, washed with sat. NaCl solution, dried over Na₂SO₄ and concentrated and the residue was co-evaporated with a minimal amount of diethyl ether. Recrystallization of the residue from ethyl acetate/heptane gave AC-13 (11.32 g, 71%).

Synthesis of the Acid Unit AC-14: 2-[4-[(2,4-Dichlorophenyl)sulfonyl]-3,4-dihydro-2H-[1,4]benzoxazin-3-yl]-acetic Acid (AC-14)

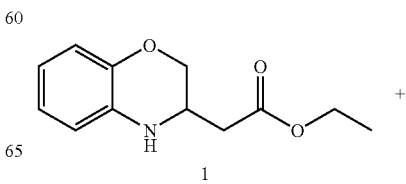

1

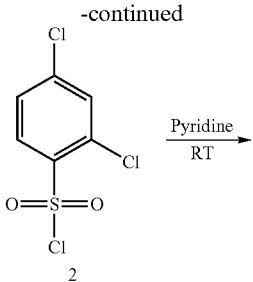

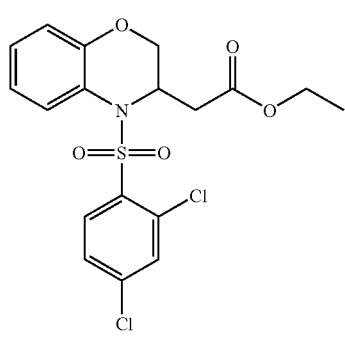

3. 2,4-Dichlorobenzenesulfonyl chloride (2, 10.67 g, 43.5 mmol) was added to a solution of 1 (8.74 g, 39.5 mmol) in pyridine (10 ml, 124 mmol). The reaction mixture was stirred at room temperature overnight and $CH_2Cl_2$ and aqueous 1 M HCl were then added. The organic phase was separated, washed with sat. NaCl solution, dried over $Na_2SO_4$ and concentrated. The residue was recrystallized (i-PrOH/$H_2O$) to obtain 3 (13.67 g, 80%).

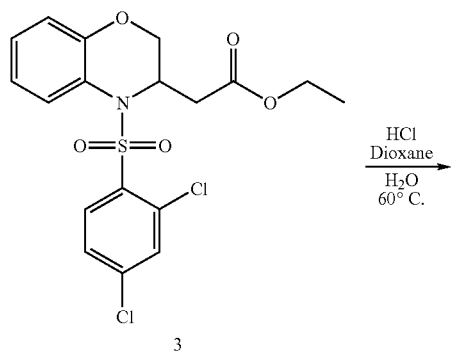

A suspension of the ester 3 (13.24 g, 30.8 mmol) in 4 M HCl in dioxane (77 ml, 308 mmol) and aqueous 6 M HCl (51.3 ml, 308 mmol) was stirred at 60° C. overnight. The reaction mixture was extracted with $CH_2Cl_2$ and the extract was washed with sat. NaCl solution, dried over $Na_2SO_4$ and concentrated. The residue was dissolved in 4 M HCl in dioxane (77 ml, 308 mmol), and aqueous 6 M HCl (51.3 ml, 308 mmol) was added. The reaction mixture was stirred at 60° C. overnight and extracted with $CH_2Cl_2$ and the extract was washed with sat. NaCl solution, dried over $Na_2SO_4$ and concentrated. The crude product was subjected to purification by column chromatography (silica, heptane/ethyl acetate 3:2→heptane/ethyl acetate/AcOH 1:1:0.01) and dissolved in ethyl acetate, the solution was washed with water and sat. NaCl solution, dried over $Na_2SO_4$ and concentrated and the residue was co-evaporated with $Et_2O$ (2×) to give AC-14 (11.39 g, 89%).

Synthesis of the Acid Unit AC-15: 2-[2-(N-[(4-Methoxy-2,6-dimethyl-phenyl)sulfonyl]-anilino)-ethoxy]-acetic Acid (AC-15)

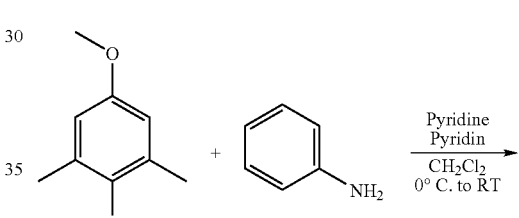

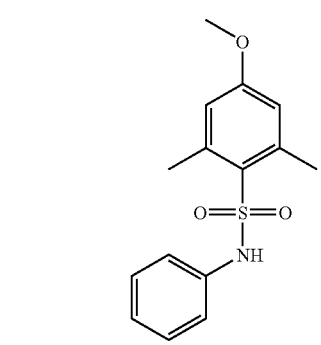

16. A solution of the sulfonyl chloride 8 (10.1 g, 43.0 mmol) in $CH_2Cl_2$ (100 ml) was added dropwise to a cooled (0° C.) solution of aniline (15, 3.92 ml, 43.0 mmol) and pyridine (10.4 ml, 129 mmol) in $CH_2Cl_2$ (250 ml) and the reaction mixture was stirred at room temperature for 3 h. The mixture was washed with aqueous 0.5 M $KHSO_4$ (100 ml) and sat. aqueous $NaHCO_3$ (100 ml), dried over $Na_2SO_4$ and concentrated to dryness to obtain the crude sulfonamide 16 (14.87 g, '119%').

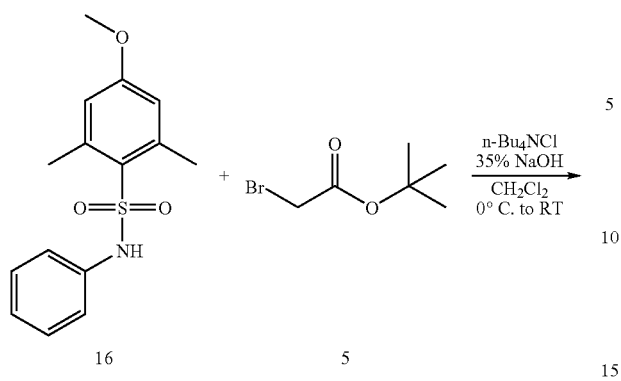

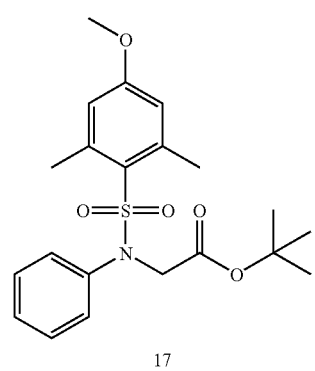

17. A solution of sulfonamide 16 (14.72 g, max. 43.0 mmol) and n-Bu₄NCl (1.50 g, 5.40 mmol) in CH₂Cl₂ (150 ml) was cooled to 0° C. and aqueous 35% NaOH (150 ml) was added. After 10 min, tert-butyl bromoacetate (5, 11.2 ml, 76.0 mmol) was added and the mixture was stirred at room temperature for 3 h. The phases were separated and the organic phase was washed with H₂O (3×200 ml). The organic phase was dried over Na₂SO₄ and concentrated to dryness to obtain the crude ester 17 (22.6 g, '130%').

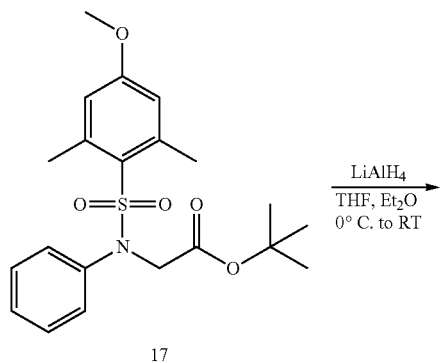

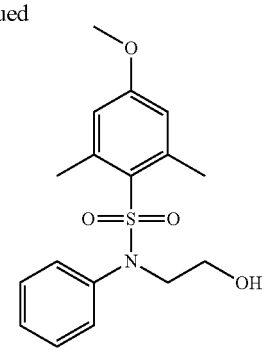

18. A solution of 4 M LiAlH₄ in Et₂O (20.9 ml, 84.0 mmol) was added dropwise to a stirred and cooled (0° C.) solution of the ester 17 (22.6 g, max. 43.0 mmol) in THF (225 ml). When the addition was complete, the reaction mixture was stirred at 0° C. for 15 min, Na₂SO₄*10H₂O was added until the evolution of gas had ended and the mixture was then stirred at room temperature overnight. The mixture was filtered over a small pad of Na₂SO₄ and the filtrate was concentrated to dryness. The crude product was purified by column chromatography (silica, heptane/ethyl acetate 2:1) to obtain the alcohol 18 (11.25 g, 78% over 3 stages).

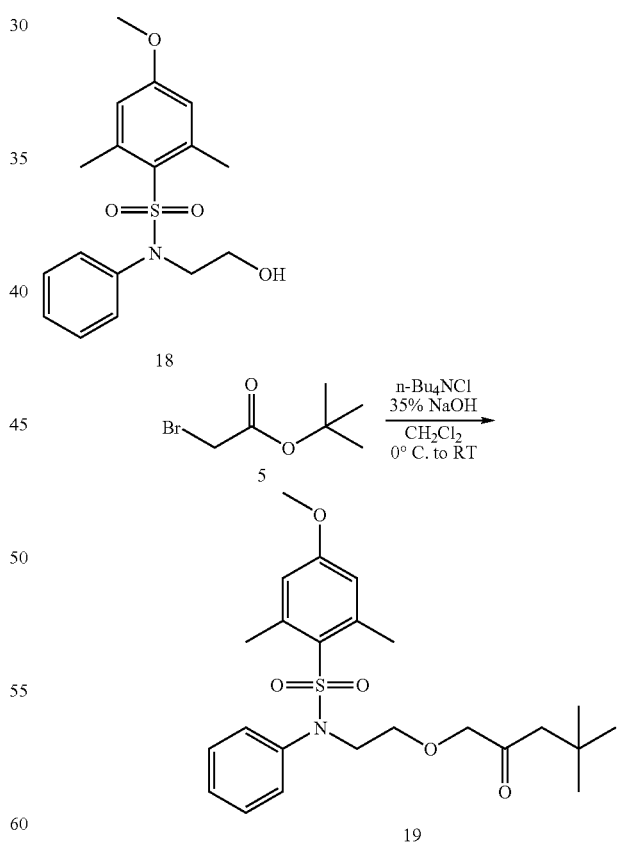

19. Aqueous 35% NaOH (120 ml) was added to a solution of the alcohol 18 (11.24 g, 33.5 mmol) and n-Bu₄NCl (992 mg, 3.57 mmol) in CH₂Cl₂ (120 ml) at 0° C., followed by tert-butyl bromoacetate (5, 7.43 ml, 50.3 mmol), and the reaction mixture was then stirred at room temperature. After 3 h, the phases were separated and the organic phase was washed with H₂O (3×250 ml). The organic phase was dried over Na₂SO₄ and concentrated to dryness. The ester 19 (12.00 g, 80%) was obtained as a yellow oil by purification by column chromatography (silica, heptane/ethyl acetate 3:1).

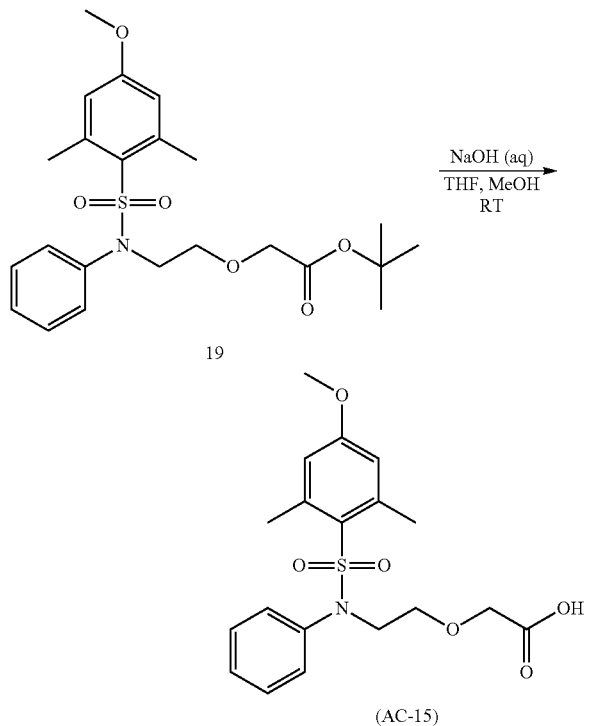

Aqueous 4 M NaOH (200 ml, 800 mmol) was added to a solution of the ester 19 (12.00 g, 26.70 mmol) in MeOH (200 ml) and THF (200 ml) and the reaction mixture was stirred at room temperature. After 3 h, the organic solvent was evaporated off and the aqueous phase was acidified with aqueous 6 M HCl (250 ml). The aqueous phase was extracted with CH₂Cl₂ (200 ml) and the combined organic phases were dried over Na₂SO₄ and concentrated to dryness to obtain the unit AC-15 (11.27 g, '107%').

Synthesis of the Acid Unit AC-16: 2-[[1-(Naphthalen-2-ylsulfonyl)-1,2,3,4-tetrahydro-quinolin-2-yl]-methoxy]-acetic Acid (AC-16)

The synthesis of the acid unit AC-16 was carried out analogously to the synthesis of the acid unit (AC-17) with naphthalene-2-sulfonyl chloride instead of 4-methoxy-2,6-dimethylbenzene-1-sulfonyl chloride.

Synthesis of the Acid Unit AC-17: 2-[[1-[(4-Methoxy-2,6-dimethyl-phenyl)-sulfonyl]-1,2,3,4-tetrahydro-quinolin-2-yl]-methoxy]-acetic Acid (AC-17)

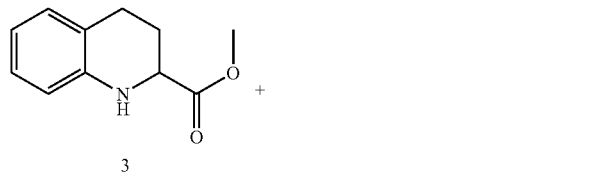

4. Sulfonyl chloride 2 (20.23 g, 86 mmol) was added to ester 3 (8.24 g, 43.1 mmol) in abs. pyridine (10.5 ml, 129 mmol) and the mixture was stirred at 40° C. overnight. CH₂Cl₂ (100 ml) was added and the reaction mixture was washed with aqueous 1 M HCl (100 ml), dried over Na₂SO₄ and concentrated to dryness under reduced pressure. Purification via column chromatography (silica, toluene/ethyl acetate 24:1) gave the sulfonamide 4 (14.39 g, 86%).

5. The sulfonamide 4 (14.29 g, 36.7 mmol) was dissolved in abs. THF (100 ml). After cooling to 0° C., a solution of 2 M LiBH₄ in THF (33.0 ml, 66.0 mmol) was slowly added dropwise and the reaction mixture was stirred at room temperature overnight. Since according to TLC (silica, heptane/ethyl acetate 1:1) the reaction had not proceeded to completion, 2 M LiBH₄ in THF (18.35 ml, 36.7 mmol) was again added and the reaction mixture was stirred at room temperature overnight. According to TLC, the reaction was complete. The reaction mixture was quenched by addition of Na₂SO₄.10H₂O, Na₂SO₄ was then added in order to remove residual water, the mixture was filtered and the filtrate was dried over Na₂SO₄ and concentrated to dryness under reduced pressure. The residue was dissolved in CH₂Cl₂ (100 ml) and the solution was washed with H₂O (100 ml) and concentrated to dryness under reduced pressure to obtain the alcohol 5 (14.01 g, '106%').

NaOH (84 ml) was then added, followed by addition of tert-butyl 2-bromoacetate (6, 6.40 ml, 43.9 mmol). After stirring at room temperature for 4 h, no starting material was detectable on the TLC (silica, heptane/ethyl acetate 1:1). The organic phase was separated and washed with H₂O (3×150 ml) and sat. NaCl solution (150 ml) until this was neutral, dried over Na₂SO₄ and concentrated under reduced pressure. Purification was carried out in that the crude product had to be subjected to column chromatography (silica, heptane/ethyl acetate 4:1) 2×. This gave the ester 7 (14.90 g, 90% over 2 stages).

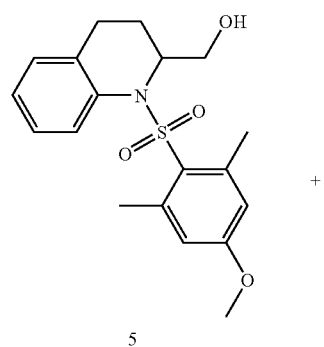

5

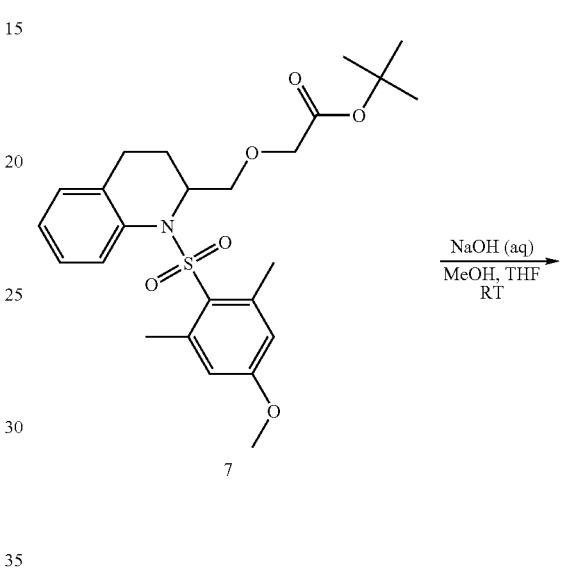

7

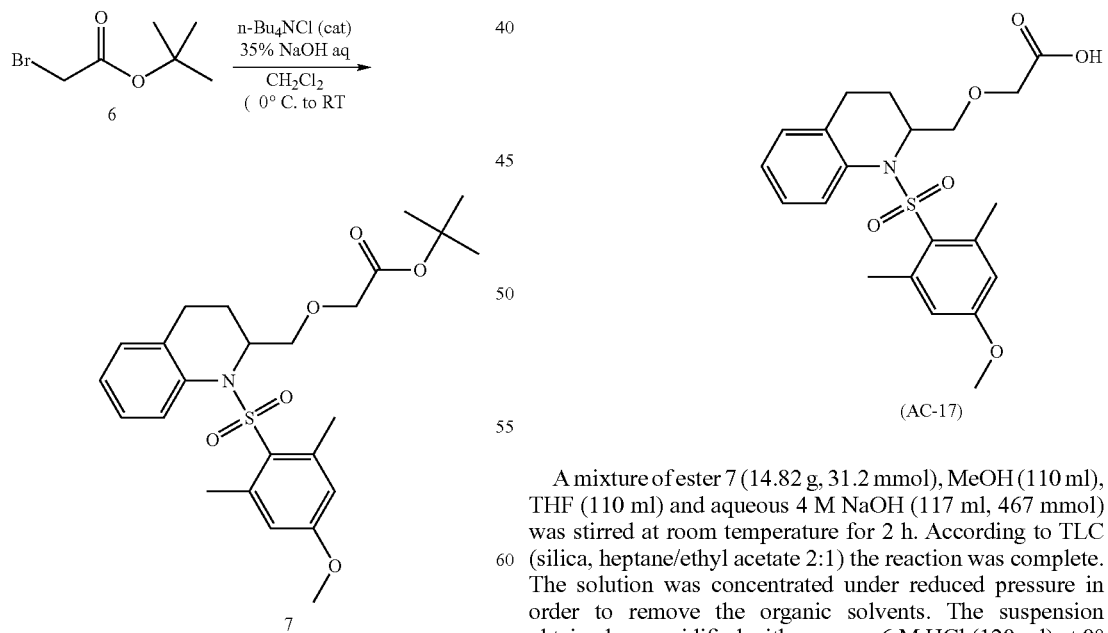

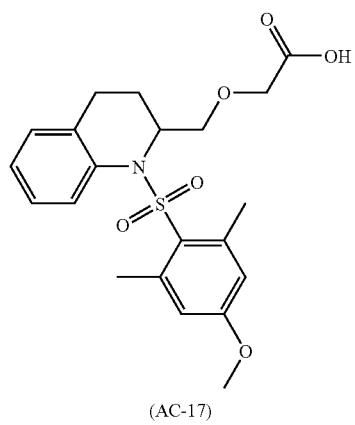

7. n-Bu₄NCl (3.36 g, 12.1 mmol) was added to a solution of the alcohol 5 (13.23 g, max. 34.7 mmol) in CH₂Cl₂ (80 ml). The reaction mixture was cooled to 0° C. and an aqueous 35% NaOH (84 ml) was then added, followed by addition of tert-butyl 2-bromoacetate A mixture of ester 7 (14.82 g, 31.2 mmol), MeOH (110 ml), THF (110 ml) and aqueous 4 M NaOH (117 ml, 467 mmol) was stirred at room temperature for 2 h. According to TLC (silica, heptane/ethyl acetate 2:1) the reaction was complete. The solution was concentrated under reduced pressure in order to remove the organic solvents. The suspension obtained was acidified with aqueous 6 M HCl (120 ml) at 0° C. CH₂Cl₂ (250 ml) was added and, after separation of the phases, the organic phase was dried over Na₂SO₄ and concentrated to dryness under reduced pressure to obtain the carboxylic acid AC-17 (12.64 g, 97%).

Synthesis of the Acid Units AC-18, AC-19, AC-20, AC-22: 4-[1-[(2-Chloro-6-methyl-phenyl)sulfonyl]-piperidin-2-yl]-butyric Acid (AC-18), 4-[1-[[2-(trifluoromethyl)-phenyl]sulfonyl]-piperidin-2-yl]-butyric Acid (AC-19), 4-[1-[(4-methoxy-2,6-dimethyl-phenyl)sulfonyl]-piperidin-2-yl]-butyric Acid (AC-20) and 4-[1-(naphthalen-2-ylsulfonyl)-piperidin-2-yl]-butyric Acid (AC-22)

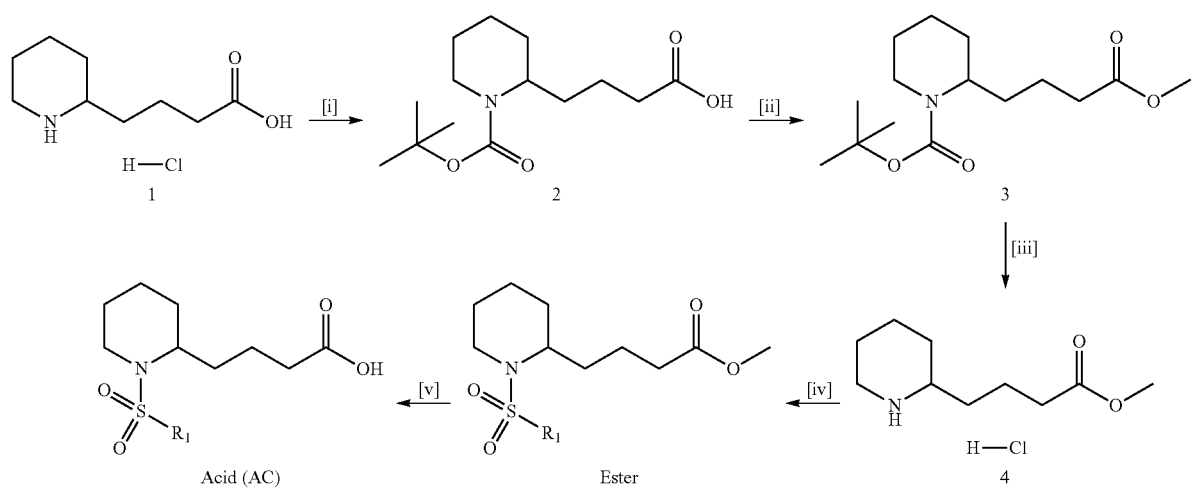

Stage (i): 4-(1-(tert-Butoxycarbonyl)piperidin-2-yl) butanoic Acid (2)

4-Piperidin-2-ylbutanoic acid hydrochloride (10.0 g, 48.3 mmol) and $K_2CO_3$ (26.6 g, 193.1 mmol) were dissolved in dist. water (70 ml) and dioxane (124 ml). The reaction mixture was cooled to 0° C. and di-tert-butyl dicarbonate (11.4 g, 53.1 mmol) was slowly added at this temperature. The reaction mixture was stirred at room temperature for 24 h. When the reaction was complete, water and ethyl acetate were added and the two phases were separated. The aqueous phase was extracted once with ethyl acetate. Thereafter, 2 M HCl (aqueous) was added to the aqueous phase in order to achieve a pH of 2. The aqueous phase was extracted 4× with methylene chloride at this pH. The combined organic phases were dried over $MgSO_4$, filtered and concentrated to dryness to obtain (2) (13.13 g, 100%).

Stage (ii): tert-Butyl 2-(4-methoxy-4-oxobutyl)piperidine-1-carboxylate (3)

1,1'-Carbonyldiimidazole (23.3 g, 143.7 mmol) was added to a solution of 4-(1-tert-butoxycarbonyl)piperidin-2-yl)butanoic acid (2) (26 g, 95.8 mmol) in methylene chloride. The reaction mixture was stirred at room temperature for 1 h. Methanol (19.4 ml, 479 mmol) was then added and the reaction mixture was stirred overnight. The complete reaction was checked by means of TLC. When the reaction was complete, the reaction mixture was washed 3× with sat. $NH_4Cl$ solution (aqueous) and 2× with sat. NaCl solution. The organic phase was dried over $MgSO_4$, filtered and concentrated under reduced pressure to obtain tert-butyl 2-(4-methoxy-4-oxobutyl)piperidine-1-carboxylate (3) (25.67 g, 94%).

Stage (iii): Methyl 4-(piperidin-2-yl)butanoate Hydrochloride (4)

Acetyl chloride was slowly added dropwise to a solution of tert-butyl 2-(4-methoxy-4-oxobutyl)piperidine-1-carboxylate (3) (25.67 g, 89.9 mmol) in methanol. The reaction mixture was stirred at room temperature for 5 h. The complete reaction was checked by means of TLC. When the reaction was complete, the reaction mixture was concentrated under reduced pressure to obtain methyl 4-(piperidine-2-yl)butanoate hydrochloride (4) (20.14 g, 100%).

General Working Instructions GWI 1-Sulfonylation (Esters 18, 19, 20 & 22)

Stage (iv): The sulfonyl chloride (3 eq.) was added to a solution of methyl 4-(piperidine-2-yl)butanoate hydrochloride (4) (1 eq.) in methylene chloride. N-Ethyl-diisopropylamine (3 eq.) was then added dropwise. The reaction mixture was stirred overnight at room temperature. The complete conversion of the reaction was monitored by means of TLC. When the reaction was complete, the reaction mixture was acidified with 1 M HCl (aqueous) and the aqueous phase was saturated with NaCl solution and then extracted 3× with methylene chloride. The combined organic phases were dried over $MgSO_4$, filtered and concentrated under reduced pressure. Purification via column chromatography (aluminium oxide; hexane/ethyl acetate) gave the desired product.

TABLE 1

Synthesis of the sulfonylated amino acid esters

| Ester no. | Structure | Name | Amino acid ester (4) |
|---|---|---|---|
| Ester 22 | 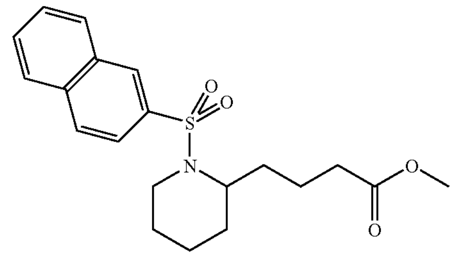 | methyl 4-(1-(naphthalen-2-ylsulfonyl)piperidin-2-yl)butanoate | methyl 4-(piperidin-2-yl)butanoate hydrochloride (4) |
| Ester 20 | 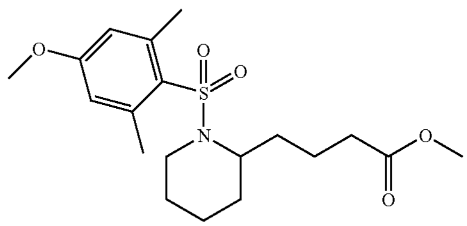 | methyl 4-(1-(4-methoxy-2,6-dimethylphenyl-sulfonyl)piperidin-2-yl)butanoate | methyl 4-(piperidin-2-yl)butanoate hydrochloride (4) |
| Ester 18 | 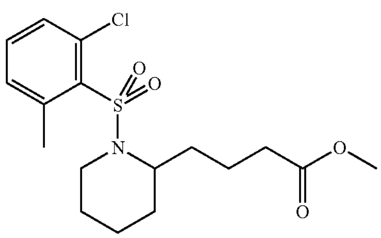 | methyl 4-(1-(2-chloro-6-methylphenylsulfonyl)-piperidin-2-yl)butanoate | methyl 4-(piperidin-2-yl)butanoate hydrochloride (4) |
| Ester 19 | 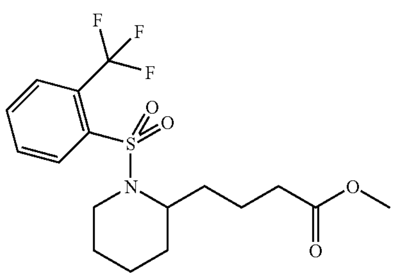 | Methyl 4-(1-(2-(trifluoromethyl)phenyl-sulfonyl)piperidin-2-yl)butanoate | methyl 4-(piperidin-2-yl)butanoate hydrochloride (4) |

| Ester no. | Sulfonyl chloride | Synthesis | Yield | Comments |
|---|---|---|---|---|
| Ester 22 | naphthalene-2-sulfonyl chloride | GWI 1 | 80% (18.1 mmol) | column chromatography: aluminum oxide; hexane/ethyl acetate 5.1 → 4:1 |
| Ester 20 | 4-methoxy-2,6-dimethylphenyl-1-sulfonyl chloride | GWI 1 | 63% (14.3 mmol) | column chromatography: aluminum oxide; hexane/ethyl acetate 98.2 → 8:2 |
| Ester 18 | 2-chloro-6-methylbenzene-1-sulfonyl chloride | GWI 1 | 93% (10.4 mmol) | column chromatography: aluminum oxide; hexane/ethyl acetate 98.2 → 8:2 |
| Ester 19 | 2-(trifluoromethyl)benzene-1-sulfonyl chloride | GWI 1 | 61% (11.5 mmol) | column chromatography: aluminum oxide; hexane/ethyl acetate 95.5 → 8:2 |

General Working Instructions GWI 2-Hydrolysis (AC-18, AC-19, AC-20 & AC-22)

Stage (v): Lithium hydroxide was added to a solution of the corresponding ester eq.) in methanol/water and the reaction mixture was stirred at room temperature overnight. The complete conversion of the reaction was monitored by means of TLC. When the reaction was complete, the methanol was evaporated off under reduced pressure and ethyl acetate was added to the residue. The mixture was acidified with dilute HCl. The aqueous phase was extracted 2× with ethyl acetate and the combined organic phases were dried over $Na_2SO_4$ and concentrated under reduced pressure to obtain the desired product (AC-18, AC-19, AC-20 & AC-22).

TABLE 2

Synthesis of the sulfonic acid esters

| Acid unit no. | Structure | Name | Ester | Synthesis | Yield | Comments |
|---|---|---|---|---|---|---|
| AC-22 | 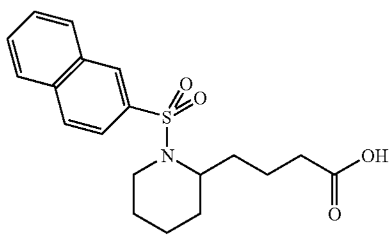 | 4-(1-naphthalen-2-ylsulfonyl)piperidin-2-yl)butanoic acid | methyl 4-(1-(naphthalen-2-ylsulfonyl)piperidin-2-yl)butanoate | GWI 2 | 102% (23.2 mmol) | |
| AC-20 | 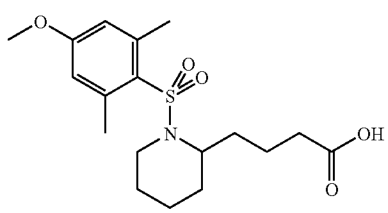 | 4-(1-(4-methoxy-2,6-dimethylphenylsulfonyl)-piperidin-2-yl)butanoic acid | methyl 4-(1-(4-methoxy-2,6-dimethylphenylsulfonyl)-piperidin-2-yl)butanoate | GWI 2 | 90% (14.6 mmol) | |
| AC-18 | 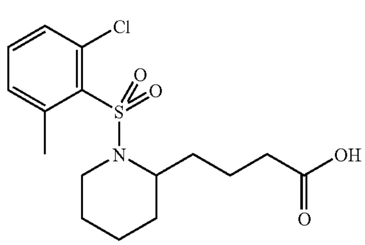 | 4-(1-(2-chloro-6-methylphenylsulfonyl)-piperidin-2-yl)butanoic acid | methyl 4-(1-(2-chloro-6-methylphenylsulfonyl)-piperidin-2-yl)butanoate | GWI 2 | 112% (8.22 mmol) | |
| AC-19 | 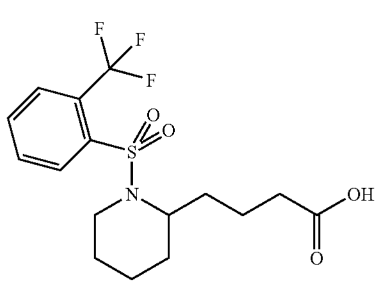 | 4-(1-(2-(trifluoromethyl)phenyl-sulfonyl)piperidin-2-yl)butanoic acid | methyl 4-(1-(2-(trifluoromethyl)phenyl-sulfonyl)piperidin-2-yl)butanoate | GWI 2 | 125% (11.1 mmol) | |

Synthesis of the Acid Unit AC-21: 4-[1-(Naphthalen-1-ylsulfonyl)-piperidin-2-yl]-butyric Acid (AC-21)

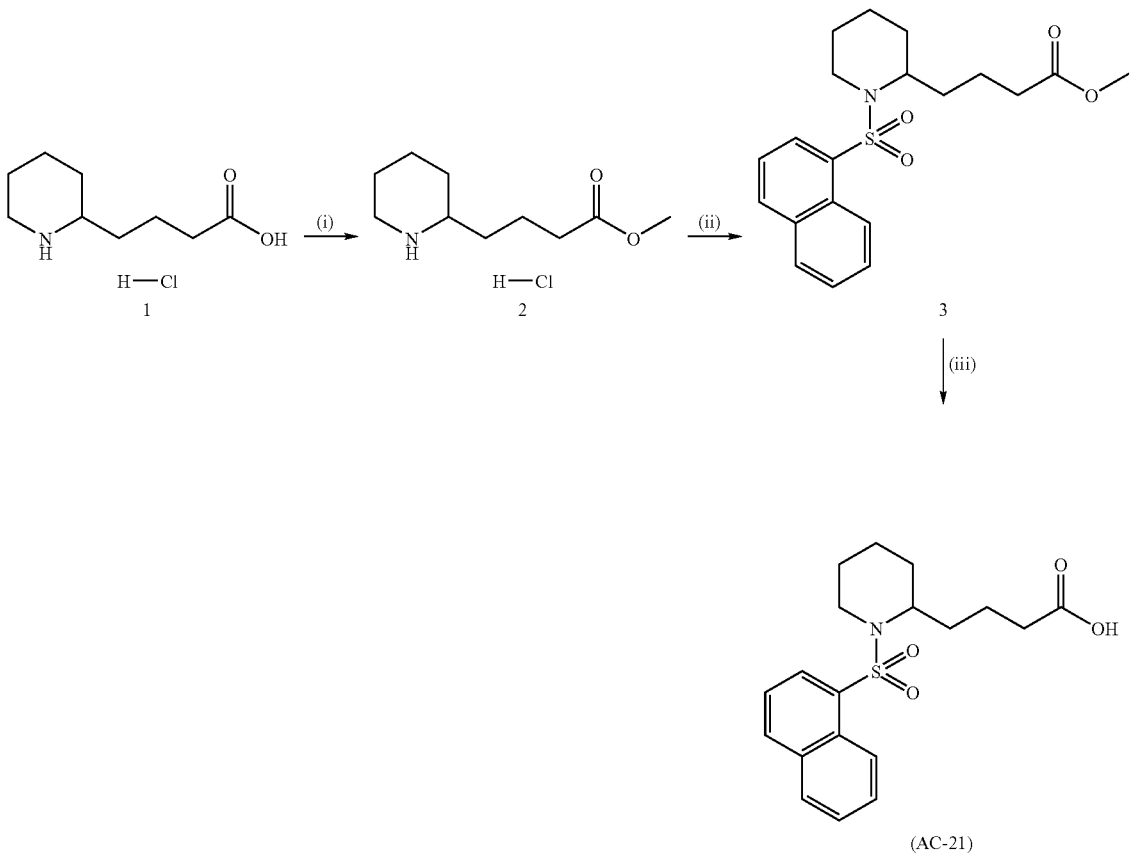

Stage (i): Methyl 4-(piperidin-2-yl)butanoate Hydrochloride (2)

A solution of 4-(2-piperidinyl)butanoic acid hydrochloride (5.95 g, 34.8 mmol) in methanol (104 ml) was cooled to 0° C. Thionyl chloride (7.54 ml, 104.3 mmol) was slowly added at this temperature. The reaction mixture was heated under reflux for 12 h. The solvent was evaporated off under reduced pressure. The residue was suspended in ethyl acetate and the suspension was heated under reflux. The suspension was filtered hot. A white precipitate precipitates out in the filtrate, and was filtered out and dried under reduced pressure to give the product methyl 4-(piperidine-2-yl)butanoate hydrochloride (2) (3.49 g, 45%).

Stage (ii): Methyl 4-(1-(naphthalen-1-ylsulfonyl)piperidin-2-yl)butanoate (3)

Naphthalene-1-sulfonyl chloride (13.7 g, 60.55 mmol) was added to a solution of methyl 4-(piperidine-2-yl)butanoate hydrochloride (2) (3.74 g, 20.2 mmol) in methylene chloride (143 ml). N-Ethyl-diisopropylamine (10.2 ml, 60.55 mmol) was then added dropwise. The reaction mixture was stirred overnight at room temperature. The completeness of the reaction was checked by means of TLC. When the reaction was complete, the reaction mixture was acidified with 1 M HCl (aqueous) and the aqueous phase was saturated with NaCl solution and then extracted 4× with methylene chloride. The combined organic phases were dried over $MgSO_4$, filtered and concentrated under reduced pressure. Purification via column chromatography (aluminium oxide; hexane/ethyl acetate 97.3→9:1) gave the desired product methyl 4-(1-(naphthalen-1-ylsulfonyl)piperidin-2-yl)butanoate 3 (4.95 g, 65%).

Stage (iii): 4-(1-(Naphthalen-1-ylsulfonyl)piperidin-2-yl)butanoic Acid (AC-21)

Lithium hydroxide (1.58 g, 65.9 mmol) was added to a solution of methyl 4-(1-(naphthalene-1-ylsulfonyl)piperidine-2-yl)butanoate 3 (4.95 g, 13.18 mmol) in methanol/water (54 ml/36 ml) and the reaction mixture was stirred at room temperature overnight. The completeness of the reaction was checked by means of TLC. When the reaction was complete, the methanol was distilled off under reduced pressure and ethyl acetate was added to the residue. The mixture was acidified with dilute HCl. The aqueous phase was extracted 2× with ethyl acetate and the combined organic phases were dried over $Na_2SO_4$ and concentrated under reduced pressure to obtain the desired product 4-(1-(naphthalene-1-ylsulfonyl)piperidine-2-yl)butanoic acid (AC-21) (4.38 g, 91%).

Synthesis of the Acid Unit AC-23: 2-[2-(Benzhydryl-methylsulfonyl-amino)-ethoxy]-acetic Acid (AC-23)

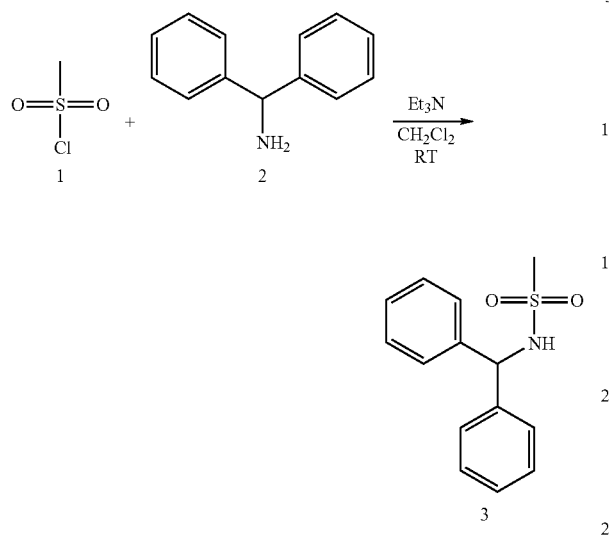

3. The sulfonyl chloride 1 (9.76 g, 85.2 mmol) and Et$_3$N (11.8 ml, 85.2 mmol) were dissolved in CH$_2$Cl$_2$ (100 ml), and a solution of diphenylmethanamine (2, 15.61 g, 85.2 mmol) in CH$_2$Cl$_2$ (40 ml) was added dropwise in the course of 10 min. The reaction mixture was stirred at room temperature for 18 h. The reaction mixture was washed with aqueous 0.5 M KHSO$_4$ (2×200 ml) and sat. NaCl solution (100 ml), dried over Na$_2$SO$_4$ and concentrated to dryness. Recrystallization from CH$_2$Cl$_2$ at 0-5° C. gave 17.63 g (79%) of the sulfonamide 3.

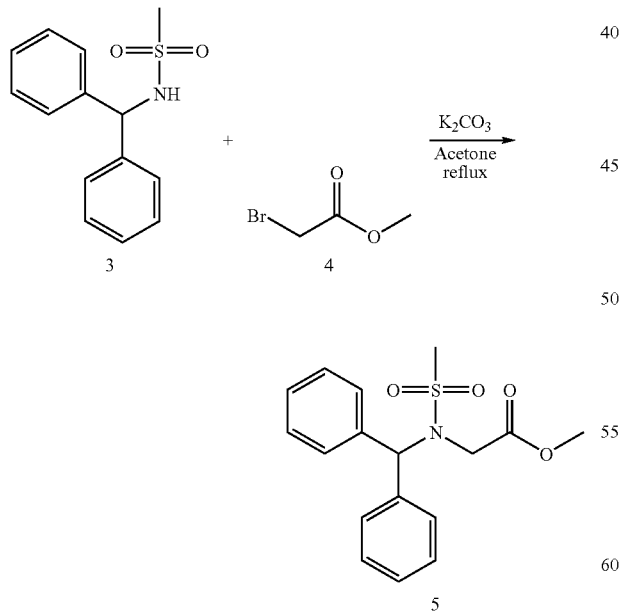

5. A suspension of the sulfonamide 3 (17.50 g, 66.96 mmol), K$_2$CO$_3$ (18.51 g, 133.9 mmol) and methyl bromoacetate (4, 31.8 ml, 355 mmol) in acetone (500 ml) was refluxed for 4 h. According to TLC (silica, heptane/ethyl acetate 2:1), the reaction was complete. The reaction mixture was filtered and the filtrate was concentrated to dryness. Purification by column chromatography (silica, toluene/THF 14:1) gave 11.95 g (54%) of the methyl ester 5.

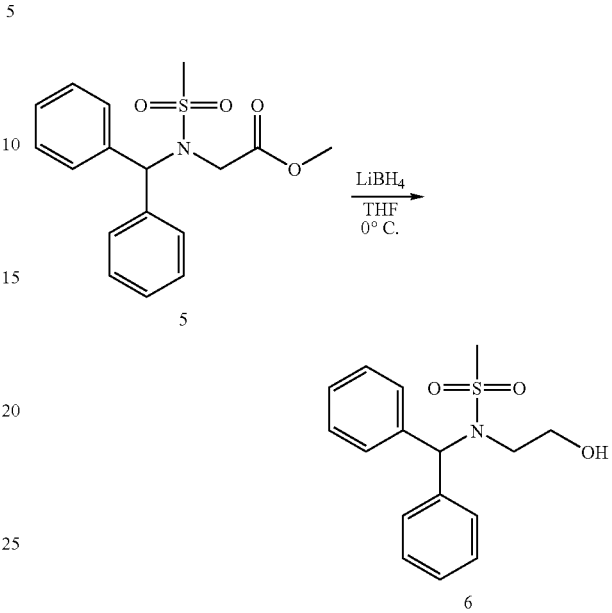

6. A solution of 2 M LiBH$_4$ in THF (26.6 ml, 53.2 mmol) was added dropwise to a stirred and cooled (0° C.) solution of the ester 5 (11.83 g, max. 35.48 mmol) in THF (100 ml). The reaction mixture was stirred at room temperature for 5 h. According to TLC (silica, heptane/ethyl acetate 1:1), the conversion is incomplete, and a further amount of 2 M LiBH$_4$ in THF (26.6 ml, 53.2 mmol) was added. After further stirring at room temperature overnight, according to TLC (silica, heptane/ethyl acetate 1:1) the reaction was complete. Na$_2$SO$_4$.10H$_2$O was added until the evolution of gas had ended, and H$_2$O was then added, followed by Na$_2$SO$_4$. The mixture was filtered over a small bed of Na$_2$SO$_4$ and the filtrate was concentrated to dryness. The product was dissolved in CH$_2$Cl$_2$ and the solution was dried again over Na$_2$SO$_4$. The product was purified by column chromatography (silica, heptane/ethyl acetate 1:1) to obtain the alcohol 6 (7.87 g, 73%).

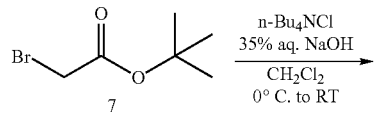

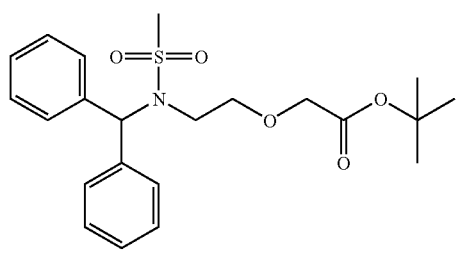

8

8. An aqueous 35% NaOH (100 ml) was added to a solution of the alcohol 6 (7.80 g, 25.5 mmol) and n-Bu$_4$NCl (710 mg, 2.55 mmol) in CH$_2$Cl$_2$ (100 ml) at 0° C., followed by tert-butyl bromoacetate (7, 11.3 ml, 76.6 mmol), and the reaction mixture was stirred at room temperature. After 3 h, the phases were separated and the organic phase was washed with H$_2$O (3×150 ml). The organic phase was dried over Na$_2$SO$_4$ and concentrated to dryness. Purification via column chromatography (silica, heptane/ethyl acetate 3:1) gave the ester 8 (9.06 g, 85%).

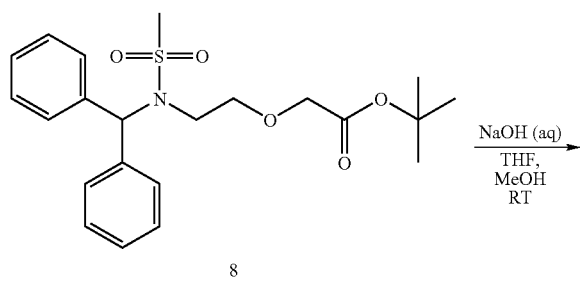

8

(AC-23)

An aqueous 4 M NaOH (162 ml, 647 mmol) was added to a solution of the ester 8 (9.05 g, 21.6 mmol) in MeOH (160 ml) and THF (160 ml) and the reaction mixture was stirred at room temperature. After 3 h, the organic phase was concentrated and the aqueous phase was acidified with aqueous 6 M HCl (200 ml). The aqueous phase was extracted with CH$_2$Cl$_2$ (200 ml) and the combined organic phases were dried over Na$_2$SO$_4$ and concentrated to dryness to obtain the unit AC-23 (7.87 g, 100%).

Synthesis of the Acid Unit AC-24: 2-[[4-[(4-Methoxy-2,6-dimethyl-phenyl)sulfonyl]-3,4-dihydro-2H-[1,4]benzoxazin-3-yl]-methoxy]-acetic Acid (AC-24)

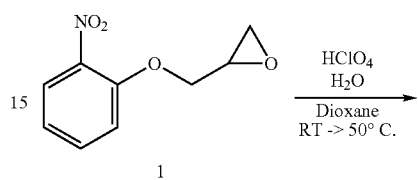

1

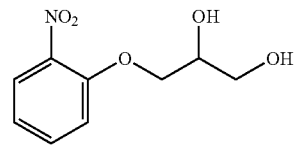

2

2. Perchloric acid (3.30 ml, 38.2 mmol) was added to a solution of 1 (37.3 g, 191 mmol) in dioxane (746 ml) and H$_2$O (568 ml) and the reaction mixture was stirred at 50° C. overnight. The reaction mixture was concentrated to half its volume and sat. NaHCO$_3$ solution was added. The H$_2$O phase was extracted with CH$_2$Cl$_2$ (2×) and the combined organic phases were washed with sat. NaCl solution, dried over Na$_2$SO$_4$ and concentrated. Purification by column chromatography (silica, heptane/ethyl acetate 2:3) gave 2 (30.6 g, 75%).

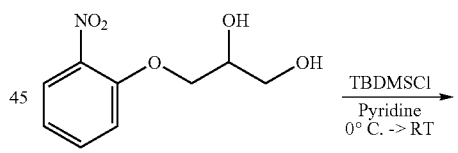

2

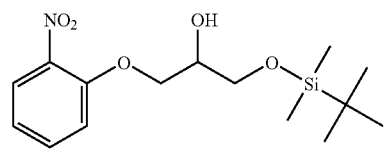

3

3. tert-Butyldimethylsilyl chloride (23.8 g, 158 mmol) was added to a solution of 2 (30.6 g, 143 mmol) in pyridine (75 ml), while cooling with an ice bath. The reaction mixture was stirred at room temperature for 2 h and then concentrated and the residue was co-evaporated with toluene. The residue was dissolved in ethyl acetate and the solution was washed with water and sat. NaCl solution, dried over Na$_2$SO$_4$ and concentrated to obtain 3 (46.7 g, 99%).

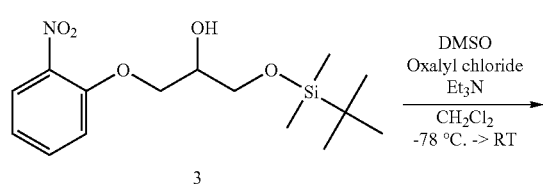

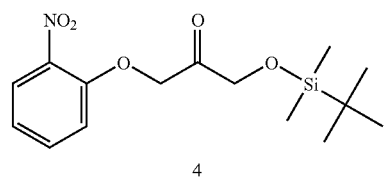

4. A solution of DMSO (21.24 ml, 299 mmol) in CH$_2$Cl$_2$ (600 ml) was added dropwise to a solution of oxalyl chloride (15.0 ml, 171 mmol) in CH$_2$Cl$_2$ (300 ml) at an internal temperature below −65° C. in the course of 30 min. A solution of 3 (46.7 g, 142 mmol) in CH$_2$Cl$_2$ (300 ml) was added dropwise in the course of 15 min, the temperature remaining below −65° C. The reaction mixture was stirred at −78° C. for a further 45 min and Et$_3$N (99.0 ml, 712 mmol) was then added. After the reaction mixture had been stirred at −78° C. for 45 min, the reaction mixture was warmed to room temperature, while stirring, and was then stirred for a further hour. The reaction mixture was washed with H$_2$O and sat. NaCl solution, dried over Na$_2$SO$_4$ and concentrated. The residue was dissolved in ether, the solution was filtered, the filtrate was concentrated and the residue was recrystallized (Et$_2$O/heptane) to obtain 4 (30.9 g, 67%). The mother liquor was concentrated and the residue was recrystallized (Et$_2$O/heptane) and gave additional product 4 (2.27 g, 5%).

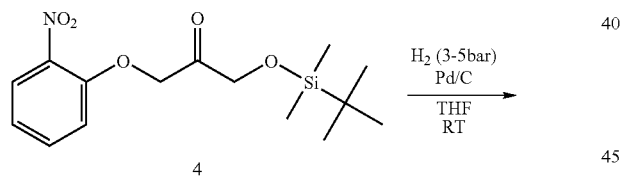

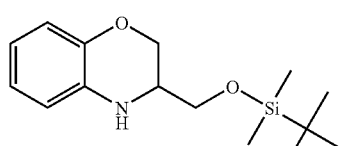

5. A mixture of 4 (18 g, 55.3 mmol) and 10% Pd/C (1.8 g, 1.7 mmol) in abs. THF (150 ml) was stirred under a hydrogen atmosphere (3 bar) for 2 days and then under a hydrogen atmosphere of 5 bar for a further day. The reaction mixture was filtered over Celite and eluted with THF. The filtrate was concentrated and the residue was dissolved in abs. THF (150 ml), 10% Pd/C (1.8 g, 1.7 mmol) was added and the reaction mixture obtained was stirred under a hydrogen atmosphere (~5 bar) for 2 days. The reaction mixture was filtered over Celite and eluted with THF. The filtrate was concentrated and purified by column chromatography (silica, heptane/Et$_2$O 9:1) to obtain 5 (7.11 g, 46%).

A further batch of 4 (15.06 g, 46.3 mmol) and 10% Pd/C (1.5 g, 1.4 mmol) in abs. THF (150 ml) was stirred under a hydrogen atmosphere (~5 bar) for 2 days. The reaction mixture was filtered over Celite and eluted with THF. The filtrate was concentrated and the residue was purified by column chromatography (silica, heptane/Et$_2$O 9:1) to obtain further product 5 (3.20 g, 25%).

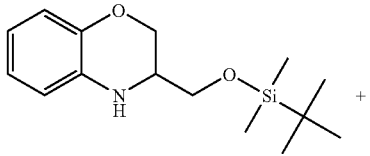

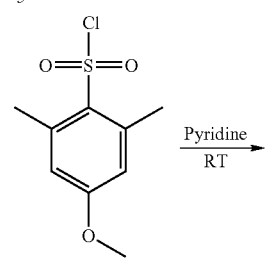

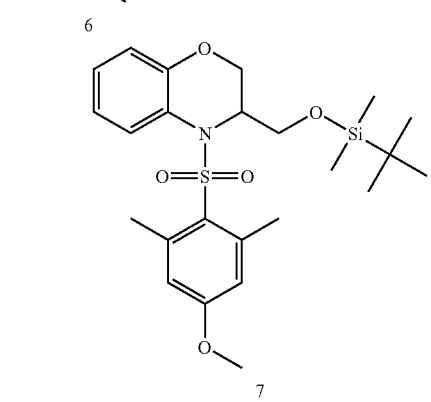

7. Sulfonyl chloride 6 (8.96 g, 38.2 mmol) was added to a solution of 5 (9.70 g, 34.7 mmol) in pyridine (8.42 ml) and the reaction mixture was stirred at room temperature for 2 d. The reaction mixture was concentrated, the residue was dissolved in CH$_2$Cl$_2$ and the solution was washed with H$_2$O and sat. NaCl solution and dried over Na$_2$SO$_4$ to obtain the crude product 7, which was employed directly in the next stage.

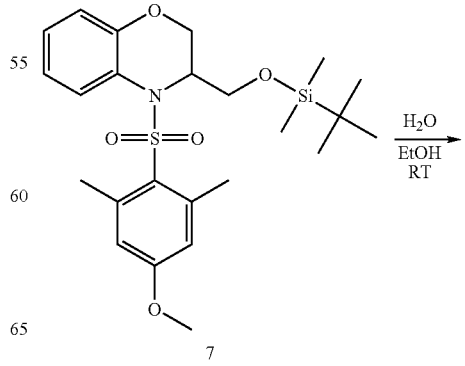

-continued

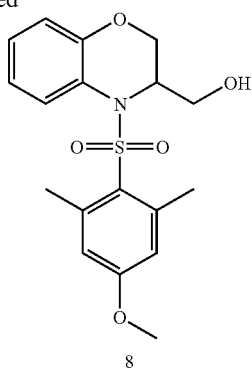

8

8. The crude product 7 was dissolved in EtOH (~100 ml) and H₂O (~100 ml), while heating, and the solution was left to stand overnight. The reaction mixture was concentrated, the residue was dissolved in CH₂Cl₂ and the solution was washed with sat. NaHCO₃ solution and sat. NaCl solution, dried over Na₂SO₄ and concentrated. The residue became solid by addition of ethyl acetate/heptane (2:1) and a little CH₂Cl₂. The precipitate obtained was washed with ethyl acetate/heptane (2:1) and dried to obtain 8 (9.68 g, 77% over 2 stages).

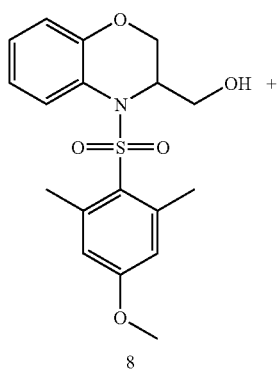

8

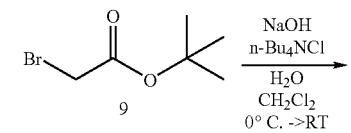

9

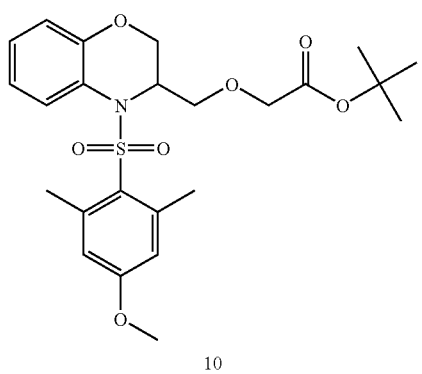

10

10. Aqueous 35% NaOH solution (130 ml) and tert-butyl bromoacetate (9, 11.6 ml, 80.0 mmol) were added in succession to an ice-cold solution of 8 (9.68 g, 26.6 mmol) and n-Bu₄NCl (2.44 g, 8.79 mmol) in CH₂Cl₂ (130 ml). The reaction mixture was stirred at room temperature for 4.5 h and water was then added. The organic phase was separated, washed with H₂O (2×), dried over Na₂SO₄ and concentrated. The residue was purified by column chromatography (silica, heptane/ethyl acetate 4:1→3:1) to obtain 10 (11.9 g, 94%).

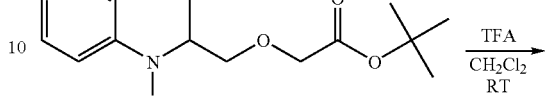

10

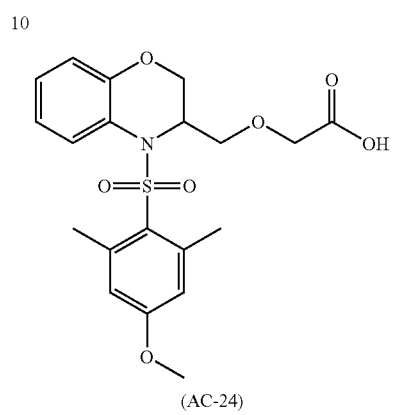

(AC-24)

A solution of 10 (11.80 g, 24.7 mmol) and TFA (25 ml, 324 mmol) in CH₂Cl₂ (125 ml) was stirred at room temperature for 2.5 h. The reaction mixture was concentrated and the residue was co-evaporated with toluene (2×) and CH₂Cl₂ (2×). The residue was dried under reduced pressure for 1 day to obtain AC-24 (10.26 g, 99%).

Synthesis of the Acid Unit AC-26: 2-[[4-[(2-Chloro-6-methyl-phenyl)sulfonyl]-3,4-dihydro-2H-[1,4]benzoxazin-3-yl]-methoxy]-acetic Acid (AC-26)

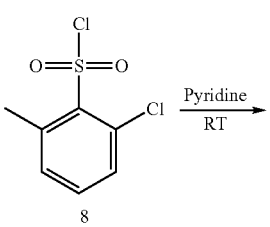

8

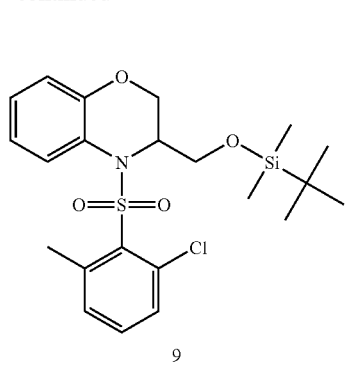

7. 2-Chloro-6-methylbenzenesulfonyl chloride (8, 7.82 g, 34.8 mmol) was added to a solution of 7 (8.83 g, 31.6 mmol) in pyridine (7.67 ml, 95.0 mmol) and the reaction mixture was stirred at room temperature overnight. CH$_2$Cl$_2$ and H$_2$O were added to the reaction mixture and the organic phase was separated, washed with water and sat. NaCl solution, dried over Na$_2$SO$_4$ and concentrated to obtain the product 9, which was employed directly as such in the next stage.

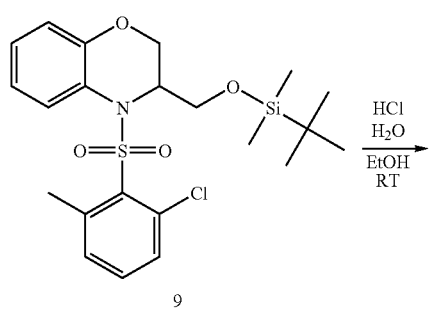

10. Aqueous 1 M HCl (50 ml, 50 mmol) was added to the crude product 9 in EtOH (200 ml) and the reaction mixture was stirred at room temperature overnight. The reaction mixture was concentrated, the residue was dissolved in CH$_2$Cl$_2$ and the solution was washed with sat. NaHCO$_3$ solution, dried over Na$_2$SO$_4$ and concentrated. The residue was purified by means of column chromatography (silica, heptane/ethyl acetate 2:1) to obtain 10 (7.75 g, 69%, 2 stages).

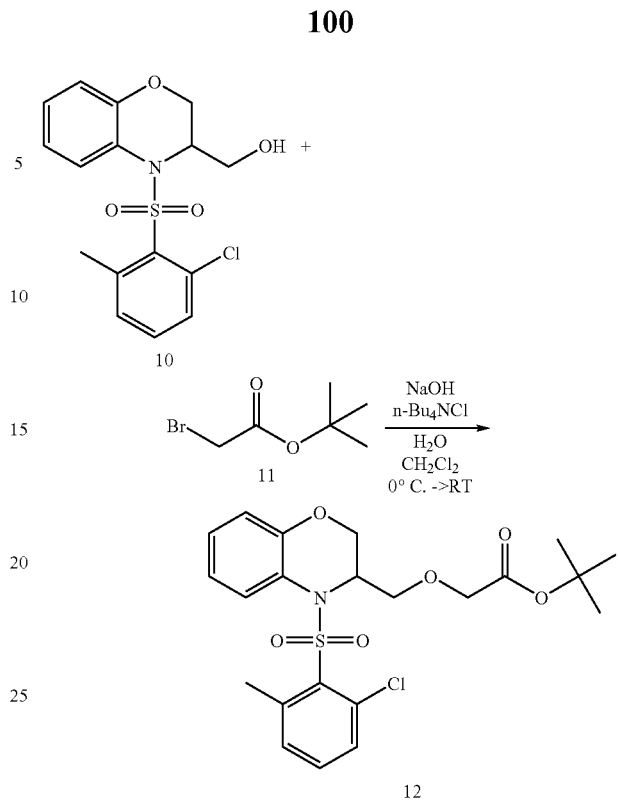

12. Aqueous 35% NaOH solution (110 ml) and tert-butyl bromoacetate (11, 9.57 ml, 65.7 mmol) were added in succession to an ice-cold solution of 10 (7.75 g, 21.9 mmol) and n-Bu$_4$NCl (2.00 g, 7.23 mmol) in CH$_2$Cl$_2$ (110 ml). The reaction mixture was stirred at room temperature for 4 h and H$_2$O was then added. The organic phase was separated, washed with water and sat. NaCl solution, dried over Na$_2$SO$_4$ and concentrated. The residue was purified by column chromatography (silica, heptane/ethyl acetate 4:1) to provide 12 (9.98 g, 92%).

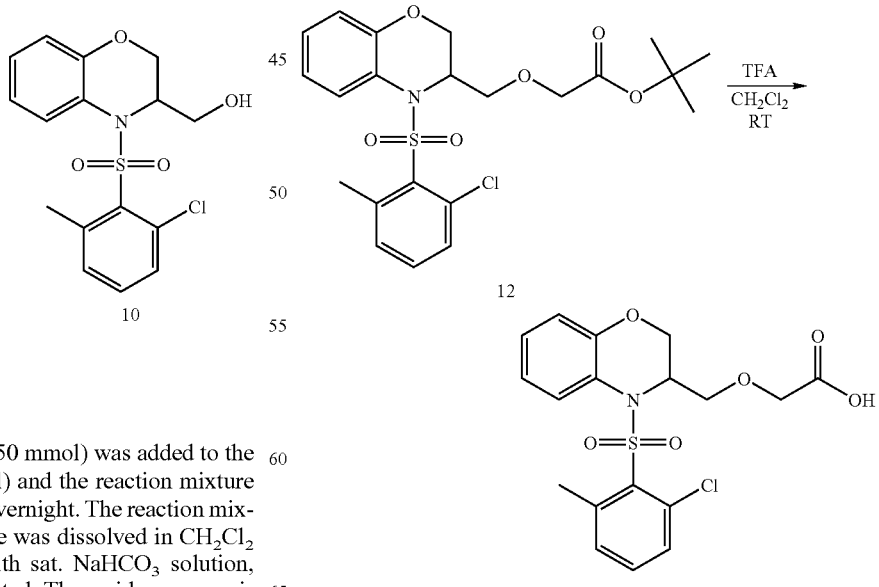

A solution of 12 (9.88 g, 20.1 mmol) and TFA (20 ml, 260 mmol) in CH$_2$Cl$_2$ (100 ml) was stirred at room temperature for 2 h. The reaction mixture was concentrated and the residue was co-evaporated with toluene (2×) and CH$_2$Cl$_2$ (2×). The residue was transferred into a vessel with CH$_2$Cl$_2$, the mixture was concentrated and the residue was dried under reduced pressure overnight to obtain product AC-26 (8.50 g, '103'%).

Synthesis of the Acid Unit AC-27: 2-[[4-[[2-(Trifluoromethyl)-phenyl]sulfonyl]-3,4-dihydro-2H-[1,4]benzoxazin-3-yl]-methoxy]-acetic Acid (AC-27)

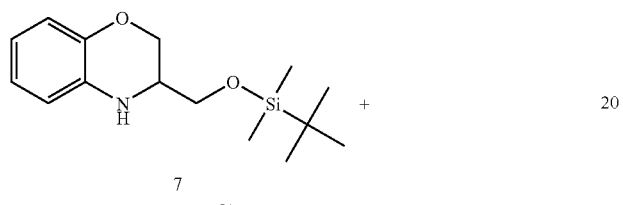

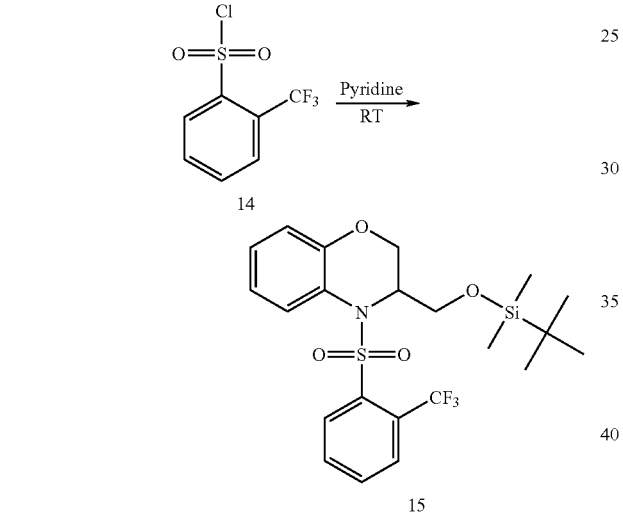

15. 2-(Trifluoromethyl)benzenesulfonyl chloride (14, 8.50 g, 34.8 mmol) was added to a solution of 7 (8.83 g, 31.6 mmol) in pyridine (7.67 ml, 95.0 mmol) and the reaction mixture was stirred at room temperature overnight. CH$_2$Cl$_2$ and H$_2$O were added and the organic phase was separated, washed with sat. NaCl solution and concentrated to obtain the crude produce 15, which was employed in this form in the next stage.

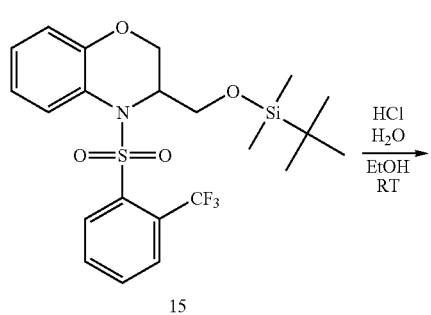

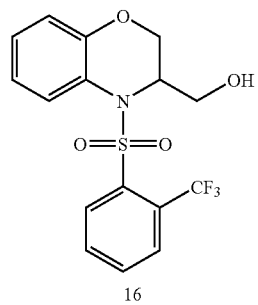

16. Aqueous 1 M HCl (50 ml, 50 mmol) was added to the crude product 15 in EtOH (200 ml) and the reaction mixture was stirred at room temperature overnight. The reaction mixture was concentrated, the residue was dissolved in CH$_2$Cl$_2$ and the solution was washed with aqueous sat. NaHCO$_3$ solution, dried over Na$_2$SO$_4$ and concentrated. The residue was purified by column chromatography (silica, heptane/ethyl acetate 2:1) to obtain product 16 (10.29 g, 78%, 2 stages).

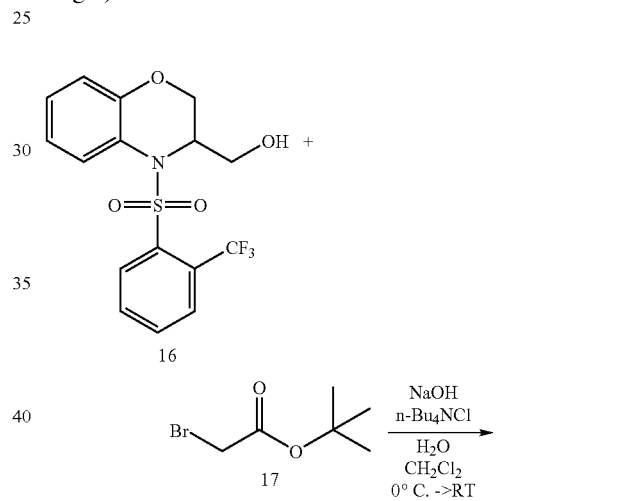

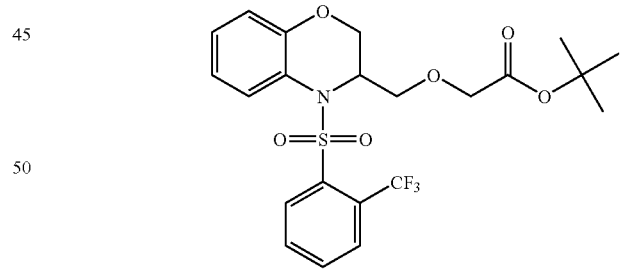

18. Aqueous 35% NaOH solution (125 ml) and tert-butyl bromoacetate (17, 10.83 ml, 74.4 mmol) were added in succession to an ice-cold solution of 16 (10.29 g, 24.81 mmol) and n-Bu$_4$NCl (2.28 g, 8.19 mmol) in CH$_2$Cl$_2$ (125 ml). The reaction mixture was stirred at room temperature for 4 h and H$_2$O was then added. The organic phase was separated, washed with water and sat. NaCl solution, dried over Na$_2$SO$_4$ and concentrated. The residue was purified by column chromatography (silica, heptane/ethyl acetate 4:1) to obtain purified product 18 (11.65 g, 93%).

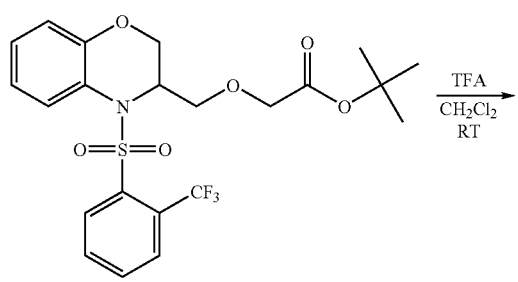

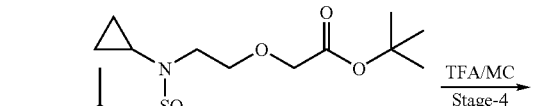

18

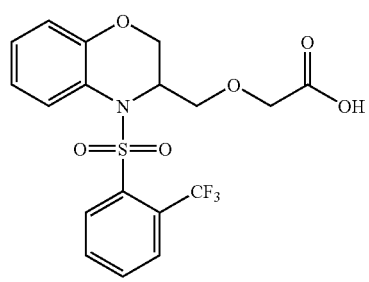

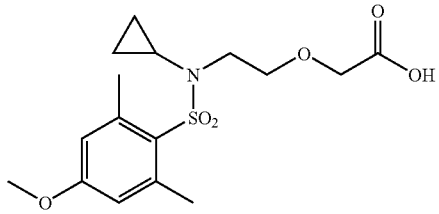

(AC-28)

(AC-27)

A solution of 18 (11.55 g, 22.98 mmol) and TFA (20 ml, 260 mmol) in CH$_2$Cl$_2$ (100 ml) was stirred at room temperature for 2 h. The reaction mixture was concentrated and the residue was co-evaporated with toluene (2×) and CH$_2$Cl$_2$ (2×). The residue was transferred into a vessel with CH$_2$Cl$_2$, the mixture was concentrated and the residue was dried under reduced pressure overnight to obtain AC-27 (10.18 g, '103'%).

Synthesis of the Acid Unit AC-28: 2-[2-[Cyclopropyl-[(4-methoxy-2,6-dimethyl-phenyl)sulfonyl]-amino]-ethoxy]-acetic Acid (AC-28)

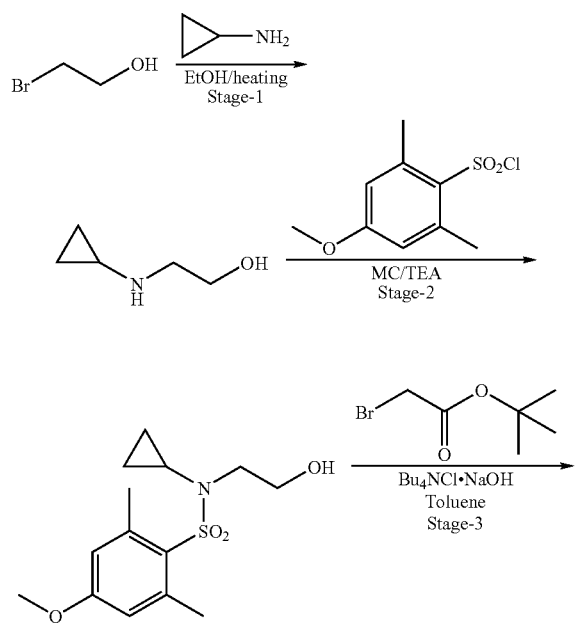

Stage-1: Cyclopropylamine (5 g, 1 eq.) was taken up in ethanol (60 ml), and 2-bromoethanol (0.5 eq.) was added. The reaction mixture obtained was heated at 60° C. for 16 h. The reaction mixture was concentrated in vacuo and the residue was employed in the next stage without further purification. Yield: 70%

Stage-2: A solution of 4-methoxy-2,6-dimethylbenzenesulfonyl chloride (1 eq.) in methylene chloride (65 ml) was added dropwise to a cold (0° C.) solution of 2-(cyclopropylamino)ethanol (40 mmol, 1.1 eq.) in methylene chloride (160 ml) and triethylamine (2.5 eq.) at a temperature of 0° C. When the addition was complete, the reaction mixture was stirred at room temperature for 90 min. After this time, the reaction was complete (TLC). 75 ml of a 0.5 M HCl were added to the reaction mixture and the mixture was stirred for 15 min. The organic phase was separated, washed with water, dried over Na$_2$SO$_4$ and concentrated to dryness to obtain the pure product. Yield: 90%

Stage-3: Tetrabutylammonium chloride (0.33 eq.) and 35% NaOH solution (100 ml) were added to a 0° C. cold solution of the sulfonamide just prepared (17.16 mmol) in toluene (100 ml) at 0° C. tert-Butyl bromoacetate (1.5 eq.) was added to this cold reaction mixture at a constant temperature. When the addition was complete, the reaction mixture was stirred at room temperature for 90 min. After this time, the reaction was complete (TLC). The organic phase was separated, washed with water until the pH was neutral, dried over Na$_2$SO$_4$ and concentrated to dryness to obtain the pure product. Yield: 90%

Stage-4: TFA (13 eq.) was added to an MC solution (10 ml/mmol) of the tert-butyl ester (1 eq.) at 0° C. and the reaction mixture obtained was stirred at room temperature for 2 h. The solvent was distilled off and the residue was dried under reduced pressure in order to remove TFA residues. The crude acid was employed directly in the synthesis library without further purification.

Synthesis of the Acid Unit AC-29: 2-[[1-[(2-Chloro-6-methyl-phenyl)sulfonyl]-piperidin-2-yl]-methoxy]-acetic Acid (AC-29)

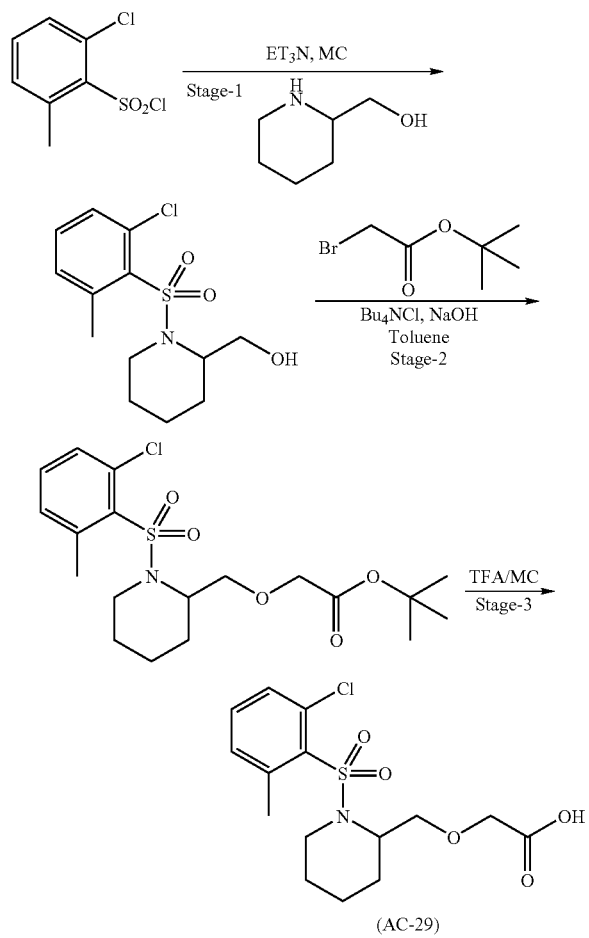

The synthesis of the unit AC-29 was carried out analogously to the synthesis of the unit AC-28.

Synthesis of the Acid Unit AC-30: 2-[2-[[(2-Chloro-6-methyl-phenyl)sulfonyl]-cyclopropyl-amino]-ethoxy]-acetic Acid (AC-30)

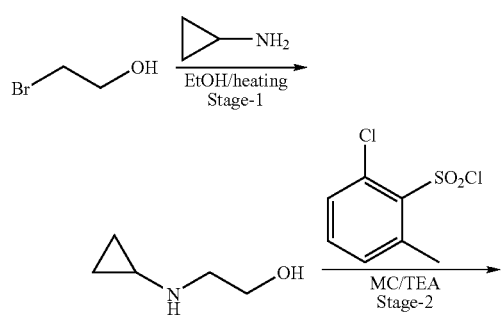

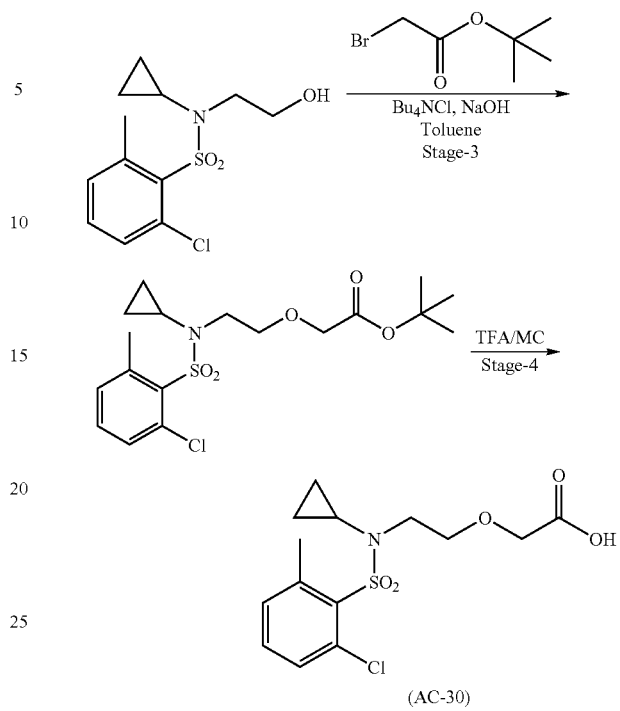

The synthesis of the unit AC-30 was carried out analogously to the synthesis of the unit AC-28.

Synthesis of the Acid Unit AC-31: 2-[1-[[3-(Trifluoromethyl)phenyl]sulfonyl]-piperidin-2-yl]-acetic Acid (AC-31)

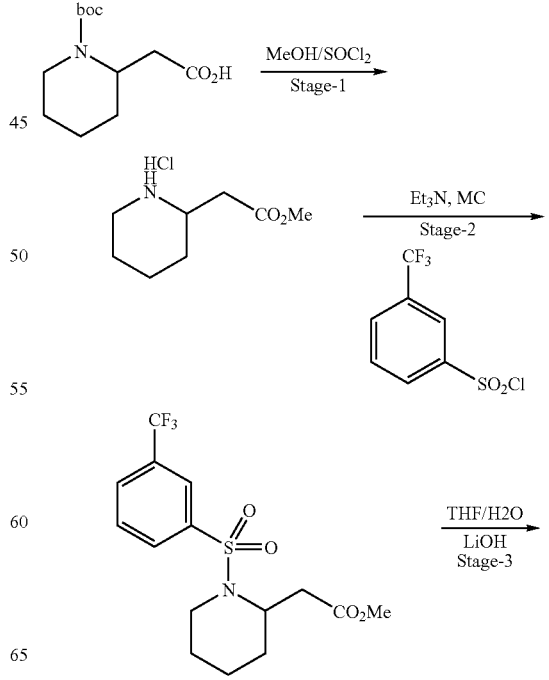

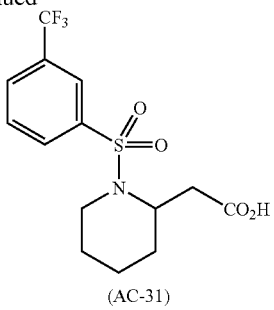

(AC-31)

Stage-1: Thionyl chloride (3 eq.) was added to a cold (0° C.) methanolic solution (60 ml) of 2-carboxymethylpiperidine-1-carboxylic acid tert-butyl ester (25 mmol) and the reaction mixture obtained was refluxed for 16 h. The solvent was concentrated to dryness and the crude solid was employed directly in the next stage. Yield: 90%

Stage-2: A solution of 3-trifluoromethylbenzenesulfonyl chloride (1 eq.) in methylene chloride (70 ml) was added dropwise to a cold (0° C.) solution of the ester just prepared (12 mmol, 1 eq.) in methylene chloride (100 ml) and triethylamine (2.5 eq.) at a constant temperature of 0° C. When the addition was complete, the reaction mixture was stirred at room temperature for 90 min. The organic phase was separated, washed with water and sat. NaCl solution, dried over $Na_2SO_4$ and concentrated in vacuo to obtain the crude product, which was pure enough for this to be employed in the next stage. Yield: 80%

Stage-3: A mixture of $THF/H_2O$ (8:2, 220 ml) was added at room temperature to the ester just obtained (12 mmol) and the reaction mixture was cooled to 0° C. LiOH (2 eq.) was added to this cold reaction mixture and the mixture was stirred at room temperature for 16 h. The solvent was concentrated to dryness in vacuo, the residue was dissolved in water, the solution was washed with methylene chloride and the aqueous phase was acidified cautiously with 1 (N)HCl. The mixture was extracted with ethyl acetate and the extract was washed successively with water and sat. NaCl solution and finally dried over $Na_2SO_4$. Concentration of the organic phase gave the pure acid.

Yield: 90%

Synthesis of the Acid Unit AC-32: 3-[1-[(4-Chloro-2,5-dimethyl-phenyl)sulfonyl]-piperidin-2-yl]-propionic Acid (AC-32)

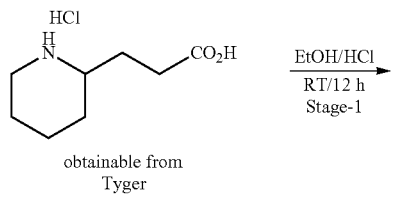

obtainable from Tyger

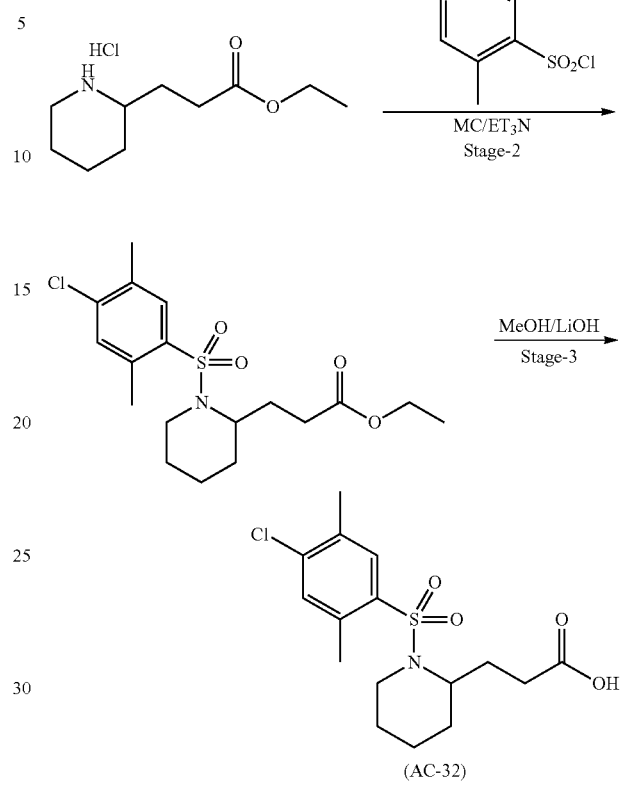

(AC-32)

Stage-1: Ethanol (200 ml) was added to 3-piperidin-2-yl-propionic acid hydrochloride (5 g), the mixture was saturated with HCl gas at 0° C. and the reaction mixture obtained was stirred at room temperature for 16 h (TLC control). The solvent was stripped off completely in vacuo and the crude product was employed in the next stage without further purification. Yield: 90%

Stage-2: 4-Chloro-2,5-dimethylbenzenesulfonyl chloride (25 mmol) was added to a methylene chloride solution (60 ml) of the ester just obtained (20 mmol) and the mixture was cooled to 0° C. Triethylamine (60 mmol) was added dropwise to this cold reaction mixture in the course of 15 min. The reaction was stirred at this temperature for 4 h (TLC control). When the consumption of the starting material was complete, the reaction mixture was diluted with MC, washed successively with water and sat. NaCl solution and finally dried over $Na_2SO_4$. Concentration of the organic phase in vacuo gave the crude sulfonamide, which was purified by column:chromatography (9:1 ethyl acetate in hexane).

Yield: 80%

Stage-3: A mixture of methanol/$H_2O$ (3:1, 90 ml) was added at room temperature to the sulfonamide just obtained (9 mmol) and the mixture was cooled to 0° C. LiOH (2 eq.) was added to this cold reaction mixture and the solution obtained was stirred at room temperature for 16 h. The solvent was concentrated to dryness in vacuo, the residue was dissolved in water, the solution was washed with methylene chloride and the aqueous phase was acidified cautiously with 1 (N)HCl. The mixture was extracted with ethyl acetate and the extract was washed successively with water and sat. NaCl solution and finally dried over Na$_2$SO$_4$. Concentration of the organic phase gave the pure acid. Yield: 80%

Synthesis of the Acid Unit AC-33: 3-[(Naphthalen-2-ylsulfonyl)amino]-3-phenyl-propionic Acid (AC-33)

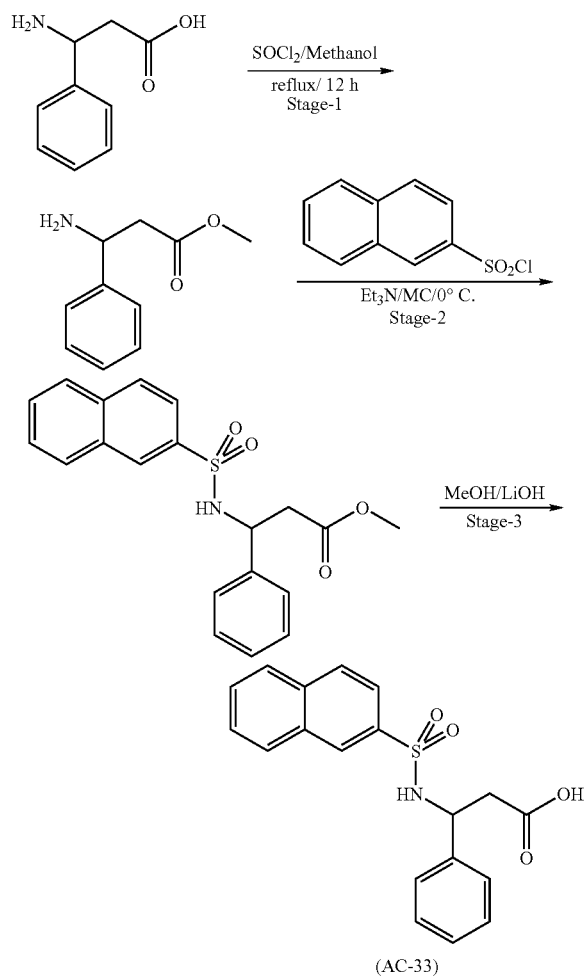

(AC-33)

Stage-1: Thionyl chloride (3 eq.) was added dropwise to a cold (0° C.) solution of 3-amino-3-phenylpropionic acid (54 mmol) in methanol (3 ml/mmol) and the reaction mixture obtained was refluxed for 12 h (TLC control). The solvent was concentrated to dryness and the residue was dried under reduced pressure. This was employed directly in the next stage without further purification. Yield: 90%

Stage-2: Triethylamine (3 eq.) was added to a cold (0° C.) suspension of the ester just obtained (32 mmol) in methylene chloride (200 ml), and a solution of naphthalene-2-sulfonyl chloride (1.2 eq.) in MC (50 ml) was added to the reaction mixture obtained. The reaction mixture obtained was stirred at room temperature for 3 h (TLC control). The mixture was diluted with MC, washed with water and sat. NaCl solution and finally dried over Na$_2$SO$_4$. Concentration of the organic phase gave the crude product, which was purified by column chromatography (3:7 ethyl acetate in hexane). Yield: 80%

Stage-3: A mixture of methanol/H$_2$O (3:1, 90 ml) was added at room temperature to the sulfonamide just obtained and the mixture was cooled to 0° C. LiOH.H$_2$O (2 eq.) was added to this cold reaction mixture and the solution obtained was stirred at room temperature for 16 h. The solvent was concentrated to dryness in vacuo, the residue was dissolved in water, the solution was washed with methylene chloride and the aqueous phase was acidified cautiously with 1 (N)HCl. The mixture was extracted with ethyl acetate and the extract was washed successively with water and sat. NaCl solution and finally dried over Na$_2$SO$_4$. Concentration of the organic phase gave the pure acid. Yield: 80%

Synthesis of the Amine Units for the Parallel Synthesis

The following amine units were used in the context of the parallel synthesis described below:

| | Structure | Name |
|---|---|---|
| AM-01 | 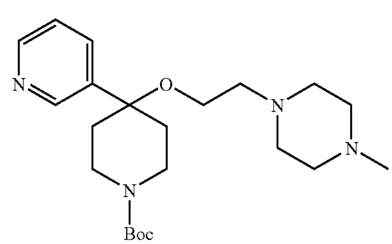 | tert-butyl 4-(2-(4-methylpiperazin-1-yl)ethoxy)-4-(pyridin-3-yl)piperidine-1-carboxylate (AM-01) |

| | Structure | Name |
|---|---|---|
| AM-02 | 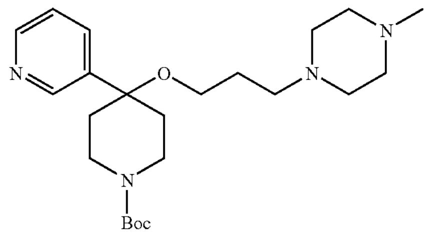 | tert-butyl 4-(3-(4-methylpiperazin-1-yl)propoxy)-4-(pyridin-3-yl)piperidine-1-carboxylate (AM-02) |
| AM-03 | 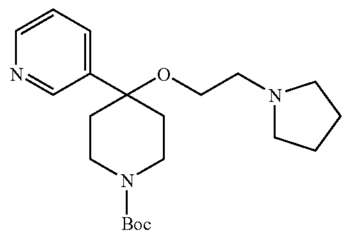 | tert-butyl 4-(pyridin-3-yl)-4-(2-(pyrrolidin-1-yl)ethoxy)piperidine-1-carboxylate (AM-03) |
| AM-04 | 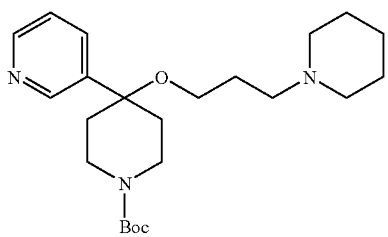 | tert-butyl 4-(3-(piperidin-1-yl)propoxy)-4-(pyridin-3-yl)piperidine-1-carboxylate (AM-04) |
| AM-05 | 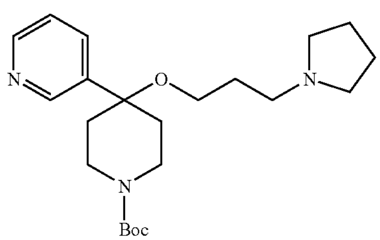 | tert-butyl 4-(pyridin-3-yl)-4-(3-(pyrrolidin-1-yl)propoxy)piperidine-1-carboxylate (AM-05) |
| AM-06 | 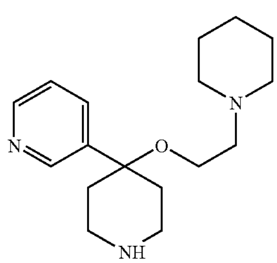 | 3-(4-(2-(piperidin-1-yl)ethoxy)piperidin-4-yl)pyridine (AM-06) |
| AM-07 | 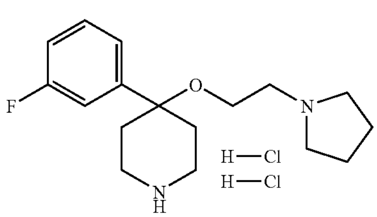 | 4-(3-fluorophenyl)-4-(2-pyrrolidin-1-yl-ethoxy)-piperidine dihydrochloride (AM-07) |

-continued

| | Structure | Name |
|---|---|---|
| AM-08 | 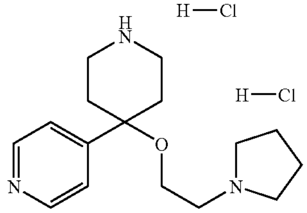 | 4-[4-(2-pyrrolidin-1-yl-ethoxy)-piperidin-4-yl]-pyridine dihydrochloride (AM-08) |
| AM-09 | 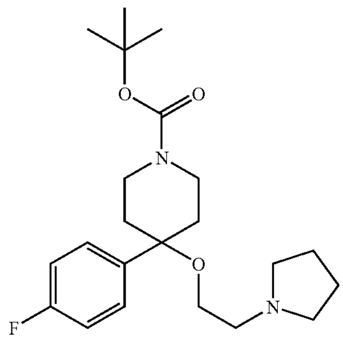 | 4-(4-fluorophenyl)-4-(2-pyrrolidin-1-yl-ethoxy)-piperidine-1-carboxylic acid tert-butyl ester (AM-09) |
| AM-10 | 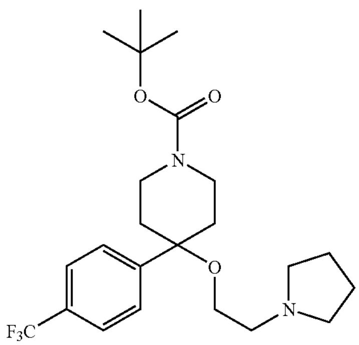 | 4-(2-pyrrolidin-1-yl-ethoxy)-4-[4-(trifluoromethyl)-phenyl]-piperidine-1-carboxylic acid tert-butyl ester (AM-10) |
| AM-11 | 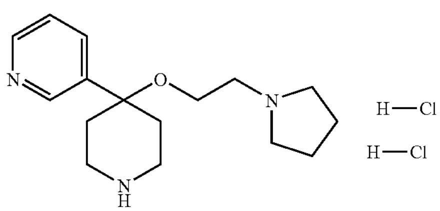 | 4-(2-pyrrolidin-1-yl-ethoxy)-4-[4-(trifluoromethyl)-phenyl]-piperidine-1-carboxylic acid tert-butyl ester (AM-11) |

Synthesis of the Amines AM-01-AM-04

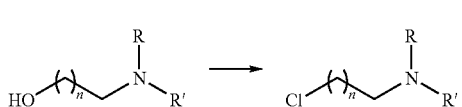

Thionyl chloride (1.5 eq.) was added to a solution of the corresponding alcohol (2 g, 1 eq.) in benzene (5 ml/mmol) at 0° C. The reaction mixture was then heated under reflux for 4 h. The solvent was removed completely and the solid formed was employed further without further purification.

The following compounds were used for the further synthesis.

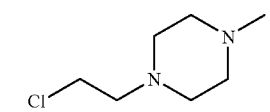

1-(2-chloroethyl)-4-ethylpiperazine according to the instructions

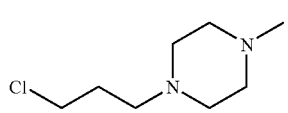

1-(3-chloropropyl)-4-ethylpiperazine according to the instructions

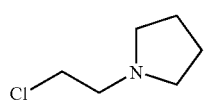

1-(2-chloroethyl)pyrrolidine obtainable commercially

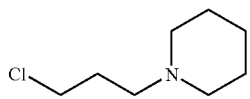

1-(2-chloroethyl)piperidine obtainable commercially

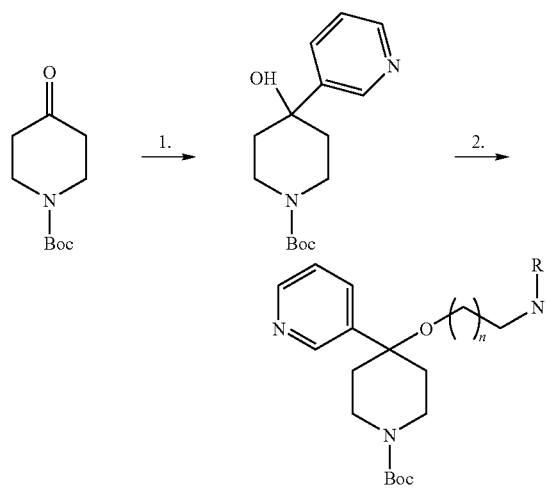

Stage 1. n-Butyllithium (2 eq.) was added to a solution of 3-bromopyridine (7.94 g, 1 eq.) in dry THF (1,600 ml) at −70° C. and the mixture was stirred at this temperature for 1 h. A solution of N-Boc-piperidone (10 g, 1 eq.) in THF (400 ml) was then added at −70° C. and the mixture was stirred at this temperature for 2 h (TLC control). When the reaction had ended, hydrolysis was first carried out with saturated ammonium chloride solution and the mixture was then warmed slowly to RT. It was diluted with ethyl acetate. The organic phase was washed with sodium chloride solution and dried over $Na_2SO_4$. The solvent was removed on a rotary evaporator and the crude product obtained was purified by column chromatography (silica gel, MC/methanol, 9:1).

Stage 2. The alcohol (2 g) was dissolved in benzene (20 ml), sodium amide (10 eq.) was added at 25° C. and the mixture was stirred at this temperature for 15 min. The corresponding chlorine compound (1.2 eq.) was then added and the mixture was heated under reflux for 16 h. When the reaction had ended (TLC control), the mixture was cooled to 0° C. and hydrolysis was carried out with ice. The aqueous phase was extracted with ethyl acetate. The organic phase was then washed successively with water and saturated NaCl solution and dried over $Na_2SO_4$. The solvent was removed on a rotary evaporator and the crude product obtained was purified by column chromatography (silica gel, MC/methanol, 95: 5).

| | Structure | Name |
|---|---|---|
| AM-01 | 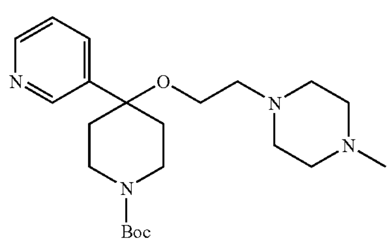 | tert-butyl 4-(2-(4-methylpiperazin-1-yl)ethoxy)-4-(pyridin-3-yl)piperidine-1-carboxylate |
| AM-02 | 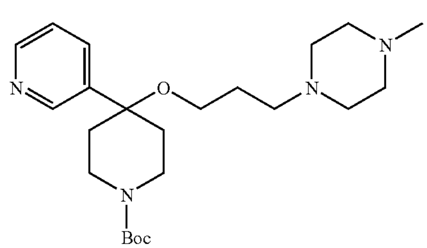 | tert-butyl 4-(3-(4-methylpiperazin-1-yl)propoxy)-4-(pyridin-3-yl)piperidine-1-carboxylate |

| | Structure | Name |
|---|---|---|
| AM-03 | 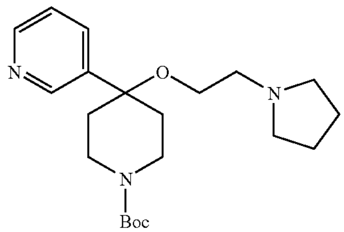 | tert-butyl 4-(pyridin-3-yl)-4-(2-(pyrrolidin-1-yl)ethoxy)piperidine-1-carboxylate |
| AM-04 | | tert-butyl 4-(3-(piperidin-1-yl)propoxy)-4-(pyridin-3-yl)piperidine-1-carboxylate | tert-Butyl 4-(pyridin-3-yl)-4-(3-(pyrrolidin-1-yl)propoxy)piperidine-1-carboxylate AM-05

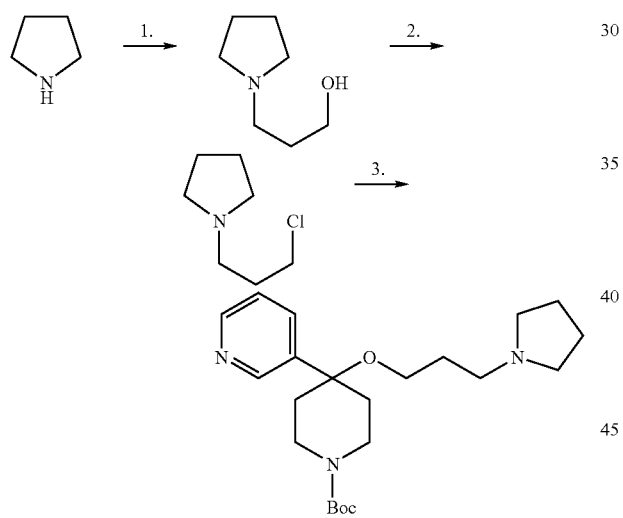

Stage 1. First pyrrolidine (6.95 ml) and then 3-chloropropanol (10 g, 106.3 mmol) were slowly added to a solution, heated to 50° C., of NaOH (5.06 g, 126.5 mmol) in water (4.55 ml) such that the solution did not heat up to above 70° C. After the complete addition, the mixture was first stirred at this temperature for a further 90 min and then cooled to 25° C. and stirred for a further 16 h. When the reaction had ended, the mixture was saturated with NaOH and extracted with benzene and the solvent was then stripped off on a rotary evaporator. The crude product was purified by distillation (98° C., 18 mm).

Stage 2. Thionyl chloride (1.5 eq.) was added to a solution of 3-(pyrrolidin-1-yl)propan-1-ol (2 g, 1 eq.) in benzene (5 ml/mmol) at 0° C. The reaction mixture was then heated under reflux for 4 h. The solvent was removed completely and the solid formed was employed further without further purification.

Stage 3. tert-Butyl 4-hydroxy-4-(pyridin-3-yl)piperidine-1-carboxylate (2 g) was dissolved in benzene (20 ml), sodium amide (10 eq.) was added at 25° C. and the mixture was stirred at this temperature for 15 min. The corresponding chlorine compound (1.2 eq.) was then added and the mixture was heated under reflux for 16 h. When the reaction had ended (TLC control), the mixture was cooled to 0° C. and hydrolysis was carried out with ice. The aqueous phase was extracted with ethyl acetate. The organic phase was then washed successively with water and saturated NaCl solution and dried over $Na_2SO_4$. The solvent was removed on a rotary evaporator and the crude product obtained was purified by column chromatography (silica gel, MC/methanol, 95:5).

3-(4-(2-(Piperidin-1-yl)ethoxy)piperidin-4-yl)pyridine AM-06

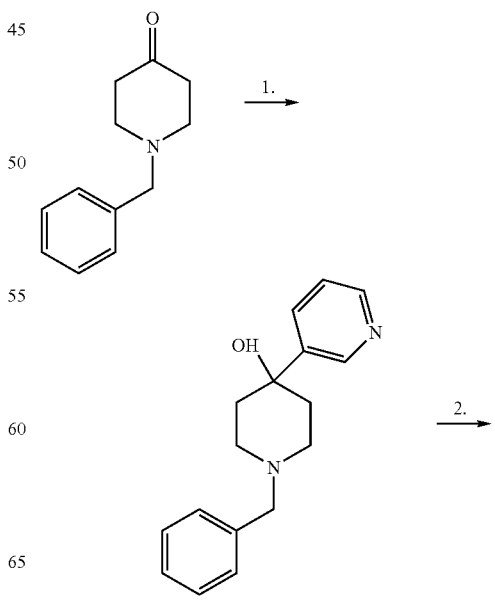

-continued

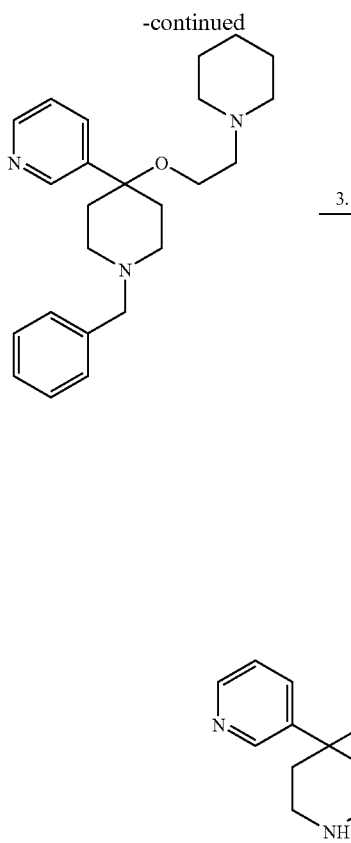

Stage 1. n-Butyllithium (2 eq.) was added to a solution of 3-bromopyridine (6.0 g, 1 eq.) in dry THF (600 ml) at −70° C. and the mixture was stirred at this temperature for 1 h. A solution of N-benzylpiperidone (7.1 g, 1 eq.) in THF (100 ml) was then added at −70° C. and the mixture was stirred at this temperature for 2 h (TLC control). When the reaction had ended, hydrolysis was first carried out with saturated ammonium chloride solution and the mixture was then heated slowly to 25° C. It was diluted with ethyl acetate. The organic phase was washed with sodium chloride solution and dried over Na$_2$SO$_4$. The solvent was removed on a rotary evaporator and the crude product obtained was purified by column chromatography (silica gel, MC/methanol, 9:1).

Stage 2. 1-Benzyl-4-(pyridin-3-yl)piperidin-4-ol (2 g) was dissolved in benzene (20 ml), sodium amide (10 eq.) was added at 25° C. and the mixture was stirred at this temperature for 15 min. 1-(2-Chloroethyl)piperidine hydrochloride (1.2 eq.) was then added and the mixture was heated under reflux for 16 h. When the reaction had ended (TLC control), the mixture was cooled to 0° C. and hydrolysis was carried out with ice. The aqueous phase was extracted with ethyl acetate. The organic phase was then washed successively with water and saturated NaCl solution and dried over Na$_2$SO$_4$. The solvent was removed on a rotary evaporator and the crude product obtained was purified by column chromatography (silica gel, MC/methanol, 95:5).

Stage 3. Pd(OH)$_2$ (50 wt. %) was added to a solution of the benzylated compound (1.9 g) in methanol (3 ml/mmol). The mixture was hydrogenolyzed under atmospheric pressure for 1 h (LCMS control). It was filtered over filtering earth and rinsing was carried out with methanol. The solvent was removed and the crude product obtained was employed further without further purification.

Synthesis of the Amine Unit AM-07: 4-(3-Fluorophenyl)-4-(2-pyrrolidin-1-yl-ethoxy)-piperidine Dihydrochloride (AM-07)

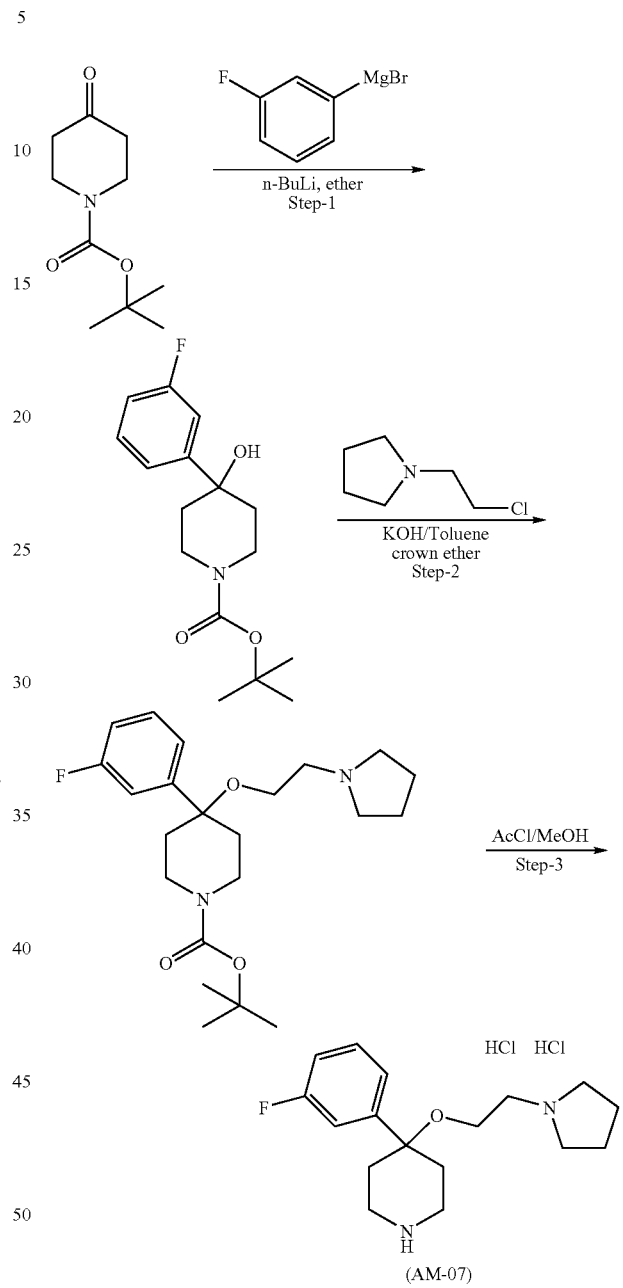

Stage-1: A solution of N-Boc-piperidone (10.05 mmol) in THF (10 mmol) was added to a solution of 3-fluorophenyl-magnesium bromide (15.075 mmol, 0.5 M) in THF at 0° C. When the addition was complete, the reaction was stirred at the same temperature for 2 h (TLC control). The reaction was then quenched with sat. NH$_4$Cl solution, the reaction mixture was diluted with ethyl acetate and the organic phase was washed successively with water and sat. NaCl solution. The organic phase was dried over Na$_2$SO$_4$ and finally concentrated under reduced pressure to obtain the crude product, which was purified by column chromatography (50% ethyl acetate in hexane). Yield: 40%

Stage-2: Dry, powdered KOH (9.9 g), 18-crown-6 (1.06 g) and 2-chloroethylpyrrolidine hydrochloride (1.5 eq.) were added to a benzene solution (200 ml) of the pyridine compound from stage-1 (9.84 g, 35.3 mmol) and the resulting mixture was refluxed for 16 h. The mixture was then cooled to 25° C. and diluted with ethyl acetate and the organic phase was washed successively with water and sat. NaCl solution and finally dried over $Na_2SO_4$. Concentration of the organic phase under reduced pressure gave the crude product, which was purified by column chromatography (5% methanol in methylene chloride). Yield: 50%

Stage-3: The Boc-protected amine just obtained (1 eq., 25.7 mmol) was dissolved in methanol/THF (2:1) and the solution was cooled to 0° C. Acetyl chloride (5 eq., 128.7 mmol) was added at this temperature. The reaction mixture was stirred at room temperature for 3 h (TLC control). When the reaction was complete, the reaction mixture was concentrated under reduced pressure to obtain the product AM-07 (26.6 mmol, 103%) as the HCl salt.

Synthesis of the Amine Unit AM-08: 4-[4-(2-Pyrrolidin-1-yl-ethoxy)-piperidin-4-yl]-pyridine Dihydrochloride (AM-08)

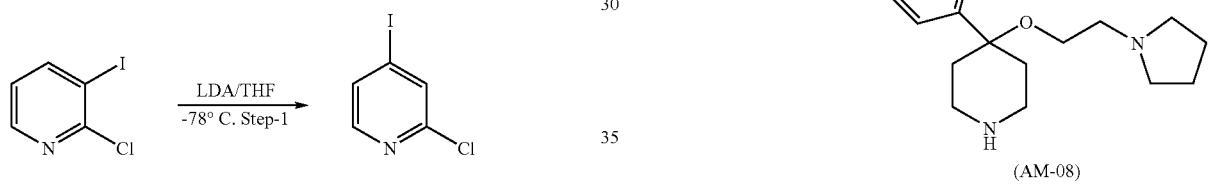

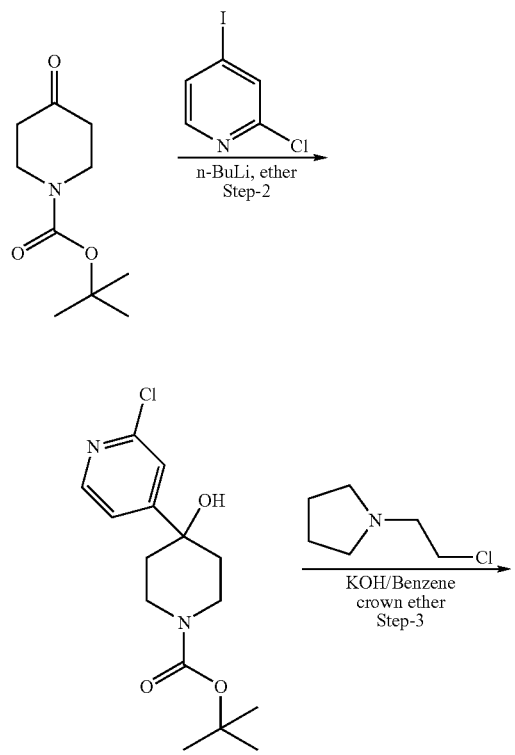

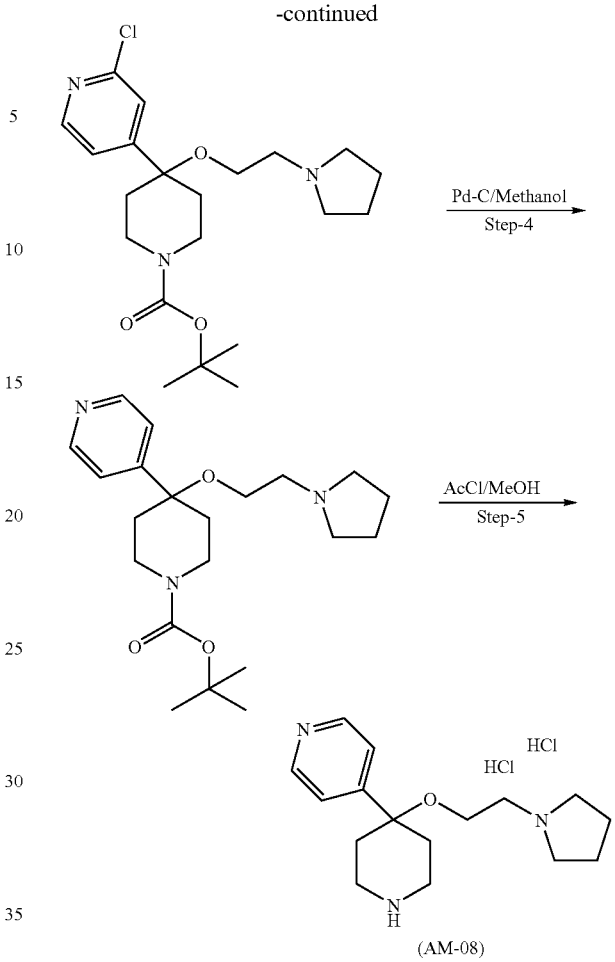

Stage-1: n-Butyllithium (31.38 mmol) was added to a cold (−15° C.) solution of diisopropylamine (31.38 mmol) in THF (50 ml) and the mixture was stirred at this temperature for 30 min. It was then cooled to −78° C., 2-chloro-3-iodopyridine (5 g, 20.9 mmol) in THF (10 ml) was added dropwise and the reaction mixture obtained was stirred at this temperature for a further hour (TLC control). The reaction was quenched with water (10 ml), the mixture was diluted with ethyl acetate and the organic phase was washed successively with water and sat. NaCl solution. Finally, this was dried over $Na_2SO_4$ and concentrated under reduced pressure to obtain the crude product, which was employed directly in the next stage. Yield: quantitative (crude)

Stage-2: n-BuLi (26 mmol) was added to diethyl ether (17.5 ml) and a solution of 2-chloro-4-iodopyridine (21.7 mmol) in 17.5 ml of diethyl ether was slowly added to this at −78° C. The resulting mixture was stirred at this temperature for 15 min and N-Boc-piperidone (3.5 g, 17.5 mmol) in 35 ml of diethyl ether was then added dropwise at −78° C. The mixture was stirred at this temperature for a further 45 min and the reaction was then quenched with water (50 ml) and brought to room temperature. The reaction mixture was diluted with ethyl acetate and the organic phase was washed with sat. NaCl solution and finally dried over $Na_2SO_4$. Concentration of the organic phase under reduced pressure gave the crude product, which was purified via a column chromatography (20% ethyl acetate in hexane). Yield: 32%

Stage-3: Dry, powdered KOH (11.74 g), 18-crown-6 (1.65 g) and N-2-chloroethylpyrrolidine hydrochloride (65 mmol)

were added to a benzene solution (260 ml) of the pyridine compound just obtained (13 g, 41.98 mmol) and the resulting mixture was refluxed for 16 h. The mixture was then cooled to 25° C. and diluted with ethyl acetate and the organic phase was washed successively with water and sat. NaCl solution and finally dried over Na₂SO₄. Concentration of the organic phase under reduced pressure gave the crude product, which was purified by column chromatography (5% methanol in methylene chloride). Yield: 75%

Stage-4: A solution of the chlorine compound just obtained (5 g) (12.2 mmol) in methanol (150 ml) was degassed with argon. 10% Pd—C (1 g) was added to this and the resulting reaction mixture was hydrogenated under atmospheric pressure for 16 h (TLC and LCMS control). The mixture was filtered over Celite, the residue was washed with methanol and the combined organic phases were concentrated to dryness to obtain the crude product, which was purified by column chromatography. Yield: 70%

Stage-5: The Boc-protected amine just obtained (1 eq., 26.9 mmol) was dissolved in methanol and the solution was cooled to 0° C. Acetyl chloride (5 eq., 134.5 mmol) was added at this temperature. The reaction mixture was stirred overnight at room temperature (TLC control). When the reaction was complete, the reaction mixture was concentrated to dryness under reduced pressure to obtain the product AM-08 (25.6 mmol, 95%) as the HCl salt.

Synthesis of the Amine Unit AM-09: 4-(4-Fluorophenyl)-4-(2-pyrrolidin-1-yl-ethoxy)-piperidine-1-carboxylic Acid tert-butyl Ester (AM-09)

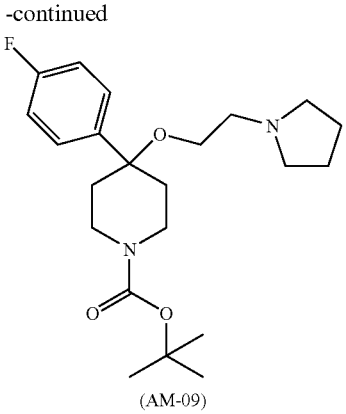

(AM-09)

Stage-1: A solution of N-Boc-piperidone (10 g, 50.188 mmol) in THF (100 ml) was added to a THF solution of 4-fluorophenylmagnesium bromide (100.376 mmol, 0.5 M) at 0° C. When the addition was complete, the reaction mixture was stirred at room temperature for 16 h (TLC control). The reaction was quenched with sat. NH₄Cl solution, the reaction mixture was diluted with ethyl acetate and the organic phase was washed successively with H₂O and sat. NaCl solution. The organic phase was dried over Na₂SO₄ and finally concentrated in vacuo to obtain the crude product, which was purified by column chromatography (2% methanol in methylene chloride). Yield: 75.6%

Stage-2: Dry, powdered KOH (10.44 g), 18-crown-6 (9.855 g) and 2-chloroethylpyrrolidine hydrochloride (1.5 eq.) were added to a toluene solution (187 ml) of the product just obtained (11.0 g, 37.288 mmol) and the mixture obtained was refluxed for 16 h. The mixture was cooled to 25° C. and diluted with ethyl acetate and the organic phase was washed successively with H₂O and sat. NaCl solution and finally dried over Na₂SO₄. Concentration of the organic phase in vacuo gave the crude product, which was purified by column chromatography (5% methanol in methylene chloride). Yield: 58.15%

Synthesis of the Amine Unit AM-10: 4-(2-Pyrrolidin-1-yl-ethoxy)-4-[4-(trifluoromethyl)-phenyl]-piperidine-1-carboxylic Acid tert-butyl Ester (AM-10)

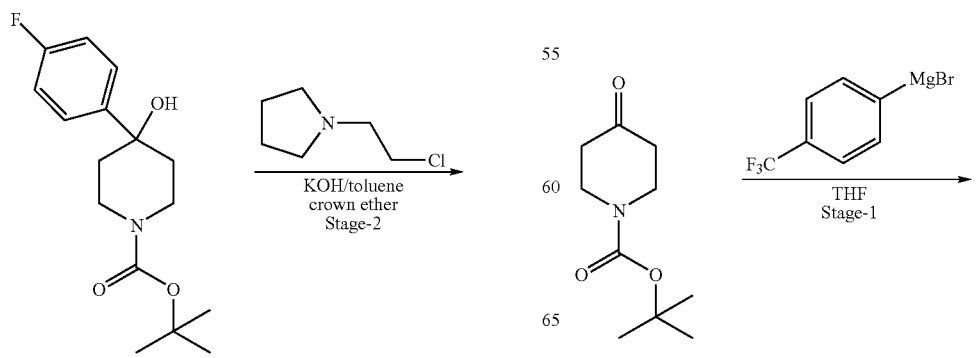

-continued

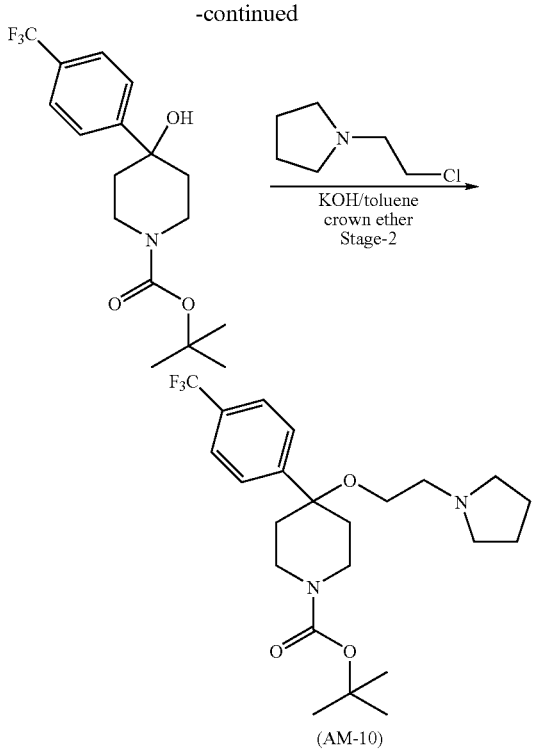

(AM-10)

Stage-1: A solution of N-Boc-piperidone (10 g, 50.188 mmol) in THF (100 ml) was added to a THF solution of 4-trifluoromethyl-phenylmagnesium bromide (100.376 mmol, 0.5 M) at 0° C. When the addition was complete, the reaction mixture was stirred at room temperature for 16 h (TLC control). The reaction was quenched with sat. aqueous NH₄Cl solution, the reaction mixture was diluted with ethyl acetate and the organic phase was washed successively with H₂O and sat. NaCl solution. The organic phase was dried over Na₂SO₄ and finally concentrated in vacuo to obtain the crude product, which was purified by column chromatography (2% methanol in methylene chloride). Yield: 54.8%

Stage-2: Dry, powdered KOH (5.23 g), 18-crown-6 (4.94 g) and 2-chloroethylpyrrolidine hydrochloride (1.5 eq.) were added to a toluene solution (94 ml) of the product just obtained (6.45 g, 18.69 mmol) and the reaction mixture obtained was refluxed for 16 h. The mixture was cooled to 25° C. and diluted with ethyl acetate and the organic phase was washed successively with H₂O and sat. NaCl solution and finally dried over Na₂SO₄. Concentration of the organic phase in vacuo gave the crude product, which was purified by column chromatography (5% methanol in methylene chloride). Yield: 52%

Synthesis of the Amine Unit AM-11: 3-[4-(2-Pyrrolidin-1-yl-ethoxy)-piperidin-4-yl]-pyridine Dihydrochloride (AM-11)

The Boc-protected amine AM-03 (1 eq., 12.7 mmol) was dissolved in methanol and the solution was cooled to 0° C. Acetyl chloride (5 eq., 63.5 mmol) was added at this temperature. The reaction mixture was stirred overnight at room temperature (TLC control). When the reaction was complete, the reaction mixture was concentrated to dryness under reduced pressure to obtain the product AM-11 (140 mmol, 110%) as the HCl salt.

Parallel Synthesis

Method A

Stage 1. TFA (20% in MC, 5 ml/mmol) was added to the Boc-protected amine unit (1 eq.) at 0° C. and the mixture was then stirred at 25° C. for 3 h (TLC control). When the reaction had ended, the solvent was removed thoroughly and the product was further employed directly without further purification.

Stage 2. EDCl (1.0 eq.), HOBt (0.7 eq.) and DIPEA (2 eq.) were added to a solution of the corresponding acid unit (0.7 eq.) in MC (3 ml/mmol) and the reaction mixture was stirred at 25° C. for 15 min.

In another reaction vessel, the Boc-deprotected amine unit (1.0 eq.) was dissolved in MC (2 ml/mmol), the solution was cooled in an ice bath and DIPEA (2.5 eq.) was added. This mixture was added to the mixture of the acid unit. The reaction mixture was stirred at 25° C. for 16 h and then diluted with MC. The organic phase was washed successively with aqueous ammonium chloride solution, sodium bicarbonate solution and sodium chloride solution and finally dried over Na₂SO₄. Purification was carried out on a purification system from Biotage operating in parallel.

Method B

EDCl (1.0 eq.), HOBt (0.7 eq.) and DIPEA (2 eq.) were added to a solution of the corresponding acid unit (0.7 eq.) in MC (3 ml/mmol) and the reaction mixture was stirred at 25° C. for 15 min. The corresponding amine unit (1 eq.), dissolved in MC (2 ml/mmol), was added to this mixture and the mixture was stirred at 25° C. for 16 h and then diluted with MC. The organic phase was washed successively with ammonium chloride solution, sodium bicarbonate solution and sodium chloride solution and finally dried over Na₂SO₄. Purification was carried out on a purification system from Biotage operating in parallel.

The example compounds listed in the following table, which were prepared by the parallel syntheses described above, were analyzed, inter alia, with the aid of their molecular weight. The particular method used for the synthesis and the molecular weights measured by means of ESI-MS are summarized in the following table.

| Example | Method | Name | Mass (ESI-MS) |
|---|---|---|---|
| 10 | A | 1-(4-(2-(piperidin-1-yl)ethoxy)-4-(pyridin-3-yl)piperidin-1-yl)-2-(1-(3-(trifluoromethyl)phenylsulfonyl)piperidin-2-yl)ethanone | 622.3 |
| 11 | A | N-(3-oxo-1-phenyl-3-(4-(2-(piperidin-1-yl)ethoxy)-4-(pyridin-3-yl)piperidin-1-yl)propyl)naphthalene-2-sulfonamide | 626.3 |
| 12 | B | 3-(1-(4-chloro-2,5-dimethylphenylsulfonyl)piperidin-2-yl)-1-(4-(3-(piperidin-1-yl)propoxy)-4-(pyridin-3-yl)piperidin-1-yl)propan-1-one | 644.3 |

-continued

| Example | Method | Name | Mass (ESI-MS) |
|---|---|---|---|
| 13 | A | 3-(1-(4-chloro-2,5-dimethylphenylsulfonyl)piperidin-2-yl)-1-(4-(2-(piperidin-1-yl)ethoxy)-4-(pyridin-3-yl)piperidin-1-yl)propan-1-one | 630.3 |
| 14 | A | 2-((1-(4-methoxy-2,6-dimethylphenylsulfonyl)piperidin-2-yl)methoxy)-1-(4-(2-(piperidin-1-yl)ethoxy)-4-(pyridin-3-yl)piperidin-1-yl)ethanone | 642.4 |
| 15 | A | 4-methoxy-N,2,6-trimethyl-N-(2-(2-oxo-2-(4-(2-(piperidin-1-yl)ethoxy)-4-(pyridin-3-yl)piperidin-1-yl)ethoxy)ethyl)benzenesulfonamide | 602.3 |
| 16 | A | 2-((1-(3,4-dichlorophenylsulfonyl)-1,2,3,4-tetrahydroquinolin-2-yl)methoxy)-1-(4-(2-(piperidin-1-yl)ethoxy)-4-(pyridin-3-yl)piperidin-1-yl)ethanone | 700.2 |
| 17 | B | 2-((1-(4-methoxy-2,6-dimethylphenylsulfonyl)piperidin-2-yl)methoxy)-1-(4-(3-(piperidin-1-yl)propoxy)-4-(pyridin-3-yl)piperidin-1-yl)ethanone | 656.4 |
| 18 | B | 4-methoxy-N,2,6-trimethyl-N-(2-(2-oxo-2-(4-(3-(piperidin-1-yl)propoxy)-4-(pyridin-3-yl)piperidin-1-yl)ethoxy)ethyl)benzenesulfonamide | 616.3 |
| 19 | B | 2-((1-(3,4-dichlorophenylsulfonyl)-1,2,3,4-tetrahydroquinolin-2-yl)methoxy)-1-(4-(3-(piperidin-1-yl)propoxy)-4-(pyridin-3-yl)piperidin-1-yl)ethanone | 714.2 |
| 20 | B | 2-((1-(4-methoxy-2,6-dimethylphenylsulfonyl)piperidin-2-yl)methoxy)-1-(4-(pyridin-3-yl)-4-(2-(pyrrolidin-1-yl)ethoxy)piperidin-1-yl)ethanone | 628.3 |
| 21 | B | 4-methoxy-N,2,6-trimethyl-N-(2-(2-oxo-2-(4-(pyridin-3-yl)-4-(2-(pyrrolidin-1-yl)ethoxy)piperidin-1-yl)ethoxy)ethyl)benzenesulfonamide | 588.3 |
| 22 | B | 1-(4-(pyridin-3-yl)-4-(2-(pyrrolidin-1-yl)ethoxy)piperidin-1-yl)-2-(1-(3-(trifluoromethyl)phenylsulfonyl)piperidin-2-yl)ethanone | 608.3 |
| 23 | B | 1-(4-(3-(piperidin-1-yl)propoxy)-4-(pyridin-3-yl)piperidin-1-yl)-2-(1-(3-(trifluoromethyl)phenylsulfonyl)piperidin-2-yl)ethanone | 636.3 |
| 24 | B | 2-((1-(3,4-dichlorophenylsulfonyl)-1,2,3,4-tetrahydroquinolin-2-yl)methoxy)-1-(4-(pyridin-3-yl)-4-(2-(pyrrolidin-1-yl)ethoxy)piperidin-1-yl)ethanone | 686.2 |
| 25 | B | 3-(1-(4-chloro-2,5-dimethylphenylsulfonyl)piperidin-2-yl)-1-(4-(pyridin-3-yl)-4-(2-(pyrrolidin-1-yl)ethoxy)piperidin-1-yl)propan-1-one | 616.3 |
| 26 | B | N-(3-oxo-1-phenyl-3-(4-(pyridin-3-yl)-4-(2-(pyrrolidin-1-yl)ethoxy)piperidin-1-yl)propyl)naphthalene-2-sulfonamide | 612.3 |
| 27 | B | N-(3-oxo-1-phenyl-3-(4-(3-(piperidin-1-yl)propoxy)-4-(pyridin-3-yl)piperidin-1-yl)propyl)naphthalene-2-sulfonamide | 640.3 |
| 28 | B | 2-((1-(4-methoxy-2,6-dimethylphenylsulfonyl)piperidin-2-yl)methoxy)-1-(4-(2-(4-methylpiperazin-1-yl)ethoxy)-4-(pyridin-3-yl)piperidin-1-yl)ethanone | 657.4 |
| 29 | B | 4-methoxy-N,2,6-trimethyl-N-(2-(2-(4-(2-(4-methylpiperazin-1-yl)ethoxy)-4-(pyridin-3-yl)piperidin-1-yl)-2-oxoethoxy)ethyl)benzenesulfonamide | 617.3 |
| 30 | B | 1-(4-(2-(4-methylpiperazin-1-yl)ethoxy)-4-(pyridin-3-yl)piperidin-1-yl)-2-(1-(3-(trifluoromethyl)phenylsulfonyl)piperidin-2-yl)ethanone | 637.3 |
| 31 | B | 3-(1-(4-chloro-2,5-dimethylphenylsulfonyl)piperidin-2-yl)-1-(4-(2-(4-methylpiperazin-1-yl)ethoxy)-4-(pyridin-3-yl)piperidin-1-yl)propan-1-one | 645.3 |
| 32 | B | N-(3-(4-(2-(4-methylpiperazin-1-yl)ethoxy)-4-(pyridin-3-yl)piperidin-1-yl)-3-oxo-1-phenylpropyl)naphthalene-2-sulfonamide | 641.3 |
| 33 | B | 2-((1-(4-methoxy-2,6-dimethylphenylsulfonyl)piperidin-2-yl)methoxy)-1-(4-(3-(4-methylpiperazin-1-yl)propoxy)-4-(pyridin-3-yl)piperidin-1-yl)ethanone | 671.4 |
| 34 | B | 4-methoxy-N,2,6-trimethyl-N-(2-(2-(4-(3-(4-methylpiperazin-1-yl)propoxy)-4-(pyridin-3-yl)piperidin-1-yl)-2-oxoethoxy)ethyl)benzenesulfonamide | 631.3 |
| 35 | B | 1-(4-(3-(4-methylpiperazin-1-yl)propoxy)-4-(pyridin-3-yl)piperidin-1-yl)-2-(1-(3- | 651.3 |

| Example | Method | Name | Mass (ESI-MS) |
|---|---|---|---|
| | | (trifluoromethyl)phenylsulfonyl)piperidin-2-yl)ethanone | |
| 36 | B | 3-(1-(4-chloro-2,5-dimethylphenylsulfonyl)piperidin-2-yl)-1-(4-(3-(4-methylpiperazin-1-yl)propoxy)-4-(pyridin-3-yl)piperidin-1-yl)propan-1-one | 659.3 |
| 37 | B | 2-((1-(3,4-dichlorophenylsulfonyl)-1,2,3,4-tetrahydroquinolin-2-yl)methoxy)-1-(4-(3-(4-methylpiperazin-1-yl)propoxy)-4-(pyridin-3-yl)piperidin-1-yl)ethanone | 729.3 |
| 38 | B | 2-((1-(3,4-dichlorophenylsulfonyl)-1,2,3,4-tetrahydroquinolin-2-yl)methoxy)-1-(4-(2-(4-methylpiperazin-1-yl)ethoxy)-4-(pyridin-3-yl)piperidin-1-yl)ethanone | 715.2 |
| 39 | B | N-(3-(4-(3-(4-methylpiperazin-1-yl)propoxy)-4-(pyridin-3-yl)piperidin-1-yl)-3-oxo-1-phenylpropyl)naphthalene-2-sulfonamide | 655.3 |
| 40 | B | 2-((1-(4-methoxy-2,6-dimethylphenylsulfonyl)piperidin-2-yl)methoxy)-1-(4-(pyridin-3-yl)-4-(3-(pyrrolidin-1-yl)propoxy)piperidin-1-yl)ethanone | 642.4 |
| 41 | B | 4-methoxy-N,2,6-trimethyl-N-(2-(2-oxo-2-(4-(pyridin-3-yl)-4-(3-(pyrrolidin-1-yl)propoxy)piperidin-1-yl)ethoxy)ethyl)benzenesulfonamide | 602.3 |
| 42 | B | 1-(4-(pyridin-3-yl)-4-(3-(pyrrolidin-1-yl)propoxy)piperidin-1-yl)-2-(1-(3-(trifluoromethyl)phenylsulfonyl)piperidin-2-yl)ethanone | 622.3 |
| 43 | B | 3-(1-(4-chloro-2,5-dimethylphenylsulfonyl)piperidin-2-yl)-1-(4-(pyridin-3-yl)-4-(3-(pyrrolidin-1-yl)propoxy)piperidin-1-yl)propan-1-one | 630.3 |
| 44 | B | N-(3-oxo-1-phenyl-3-(4-(pyridin-3-yl)-4-(3-(pyrrolidin-1-yl)propoxy)piperidin-1-yl)propyl)naphthalene-2-sulfonamide | 626.3 |
| 45 | B | 2-((1-(3,4-dichlorophenylsulfonyl)-1,2,3,4-tetrahydroquinolin-2-yl)methoxy)-1-(4-(pyridin-3-yl)-4-(3-(pyrrolidin-1-yl)propoxy)piperidin-1-yl)ethanone | 700.2 |
| 46 | A | 1-(4-(2-(piperidin-1-yl)ethoxy)-4-(pyridin-3-yl)piperidin-1-yl)-2-(1-(3-(trifluoromethyl)phenylsulfonyl)piperidin-2-yl)ethanone | 622.3 |

Parallel Synthesis of Examples 64 to 131

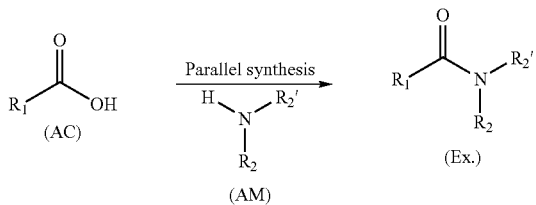

FIG. 1

Parallel Synthesis of Examples 64-131

According to the above figure, the acid units (AC) were reacted with the amine (AM) in a parallel synthesis to give the example compounds (Ex.) The correlation of product to reagent, unit and method can be seen from the synthesis matrix shown in the following.

The crude products of the parallel synthesis were analysed by HPLC-MS and then purified by means of reverse phase HPLC-MS. It was possible to demonstrate the identity of the products by analytical HPLC-MS measurements.

Apparatus and Methods for the HPLC-MS Analysis:

Parallel synthesis method: HPLC: Waters Alliance 2795 with PDA Waters 2996; MS: ZQ 2000 MassLynx Single Quadrupol MS detector; column: Atlantis dC18 30×2.1 mm, 3 μm; column temperature: 40° C., eluent A: water+0.1% formic acid; eluent B: methanol+0.1% formic acid; gradient: 0% B to 100% B in 2.3 min, 100% B for 0.4 min, 100% B to 0% B in 0.01 min, 0% B for 0.8 min; flow rate: 1.0 ml/min; ionization: ES+, 25 V; make up: 100 μl/min 70% methanol+ 0.2% formic acid; UV: 200-400 nm Apparatus and Methods for the HPLC-MS Purification:

Prep pump: Waters 2525; make-up pump: Waters 515; auxiliary detector: Waters DAD 2487; MS detector: Waters Micromass ZQ; injector/fraction collector: Waters Sample Manager 2767; gradient: initial: 60% water 40% methanol->12-14.5 min: 0% water 100% methanol->14.5-15 min: 60% water 40% methanol; flow rate: 35 ml/min column: Macherey-Nagel, C18 Gravity, 100×21 mm, 5μ. Individual examples were separated by means of a slightly modified variant of this method.

Parallel Synthesis Compounds 64-131: Method 1:

A solution of 1,1'-carbonyldiimidazole (150 μM) in 1 ml of methylene chloride is added to a solution of the acid (AC) (100 μM) in 1 ml of methylene chloride and the mixture is shaken at room temperature for 1.5 hours. A solution of the amine (AM) (150 μM) in Hünig's base (500 μM) and 1 ml of methylene chloride is then added. The reaction mixture was shaken at room temperature for 18 hours and finally concentrated. The solvent was removed under reduced pressure in a vacuum centrifuge (GeneVac). The final purification was carried out via HPLC-MS. The final analysis was carried out by means of LC-MS.

Parallel Synthesis Compounds 64-131: Method 2

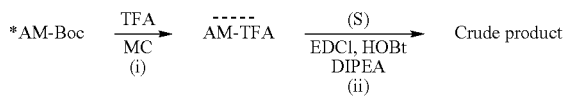

(i): 20% TFA in MC (10 ml/mmol) was added to the Boc-protected amine unit (*AM-Boc; 1 eq.) at 0° C. and the reaction mixture obtained was stirred at 25° C. for 4 h (TLC control). The solvent was evaporated completely and the residue was dried thoroughly to remove traces of TFA. The residue was employed directly in the next synthesis library.

(ii): EDCl (1.5 eq.), HOBt (1 eq.) and DIPEA (2.5 eq.) were added to a solution of the acid unit (AC, 1 eq.) in methylene chloride (3 ml/mmol) and the reaction mixture obtained was stirred at 25° C. for 15 min. In another round-bottomed flask, the Boc-deprotected amine unit (AM TFA, 1.0 eq.) in methylene chloride (1 ml/mmol) was cooled in an ice bath, DIPEA (4 eq.) was added and the mixture was then added to the reaction mixture. The reaction mixture was stirred at 25° C. for 16 h and then diluted with methylene chloride. The organic phase was washed successively with aqueous $NH_4Cl$ solution, $NaHCO_3$ solution and sat. NaCl solution and finally dried over $Na_2SO_4$. Concentration of the organic phase in vacuo gave the crude product of the particular example compound, which was purified via the Biotage parallel purification system.

Synthesis Matrix

Examples 64-131

| Ex. | Name | Acid (AC) | Amide (AM) | Method |
|---|---|---|---|---|
| 64 | 1-[4-(4-fluorophenyl)-4-(2-pyrrolidin-1-yl-ethoxy)-piperidin-1-yl]-2-[[1-[(4-methoxy-2,6-dimethyl-phenyl)sulfonyl]-piperidin-2-yl]-methoxy]-ethanone (64) | (AC-03) | (AM-09) | 2 |
| 65 | 2-[[1-[(4-methoxy-2,6-dimethyl-phenyl)sulfonyl]-piperidin-2-yl]-methoxy]-1-[4-(2-pyrrolidin-1-yl-ethoxy)-4-[4-(trifluoromethyl)-phenyl]-piperidin-1-yl]-ethanone (65) | (AC-03) | (AM-10) | 2 |
| 66 | N-cyclopropyl-N-[2-[2-[4-(4-fluorophenyl)-4-(2-pyrrolidin-1-yl-ethoxy)-piperidin-1-yl]-2-oxo-ethoxy]-ethyl]-4-methoxy-2,6-dimethyl-benzenesulfonic acid amide (66) | (AC-28) | (AM-09) | 2 |
| 67 | N-cyclopropyl-4-methoxy-2,6-dimethyl-N-[2-[2-oxo-2-[4-(2-pyrrolidin-1-yl-ethoxy)-4-[4-(trifluoromethyl)-phenyl]-piperidin-1-yl]-ethoxy]-ethyl]-benzenesulfonic acid amide (67) | (AC-28) | (AM-10) | 2 |
| 68 | 2-[[1-[(2-chloro-6-methyl-phenyl)sulfonyl]-piperidin-2-yl]-methoxy]-1-[4-(4-fluorophenyl)-4-(2-pyrrolidin-1-yl-ethoxy)-piperidin-1-yl]-ethanone (68) | (AC-29) | (AM-09) | 2 |
| 69 | 2-[[1-[(2-chloro-6-methyl-phenyl)sulfonyl]-piperidin-2-yl]-methoxy]-1-[4-(2-pyrrolidin-1-yl-ethoxy)-4-[4-(trifluoromethyl)-phenyl]-piperidin-1-yl]-ethanone (69) | (AC-29) | (AM-10) | 2 |
| 70 | 2-chloro-N-cyclopropyl-N-[2-[2-[4-(4-fluorophenyl)-4-(2-pyrrolidin-1-yl-ethoxy)-piperidin-1-yl]-2-oxo-ethoxy]-ethyl]-6-methyl-benzenesulfonic acid amide (70) | (AC-30) | (AM-09) | 2 |
| 71 | 2-chloro-N-cyclopropyl-6-methyl-N-[2-[2-oxo-2-[4-(2-pyrrolidin-1-yl-ethoxy)-4-[4-(trifluoromethyl)-phenyl]-piperidin-1-yl]-ethoxy]-ethyl]-benzenesulfonic acid amide (71) | (AC-30) | (AM-10) | 2 |
| 72 | 1-[4-(4-fluorophenyl)-4-(2-pyrrolidin-1-yl-ethoxy)-piperidin-1-yl]-2-[1-[[3-(trifluoromethyl)phenyl]sulfonyl]-piperidin-2-yl]-ethanone (72) | (AC-31) | (AM-09) | 2 |
| 73 | 1-[4-(2-pyrrolidin-1-yl-ethoxy)-4-[4-(trifluoromethyl)-phenyl]-piperidin-1-yl]-2-[1-[[3-(trifluoromethyl)phenyl]sulfonyl]-piperidin-2-yl]-ethanone (73) | (AC-31) | (AM-10) | 2 |
| 74 | 3-[1-[(4-chloro-2,5-dimethyl-phenyl)sulfonyl]-piperidin-2-yl]-1-[4-(4-fluorophenyl)-4-(2-pyrrolidin-1-yl-ethoxy)-piperidin-1-yl]-propan-1-one (74) | (AC-32) | (AM-09) | 2 |

-continued

| Ex. | Name | Acid (AC) | Amide (AM) | Method |
|---|---|---|---|---|
| 75 | 3-[1-[(4-chloro-2,5-dimethyl-phenyl)sulfonyl]-piperidin-2-yl]-1-[4-(2-pyrrolidin-1-yl-ethoxy)-4-[4-(trifluoromethyl)-phenyl]-piperidin-1-yl]-propan-1-one (75) | (AC-32) | (AM-10) | 2 |
| 76 | N-3-[4-(4-fluorophenyl)-4-(2-pyrrolidin-1-yl-ethoxy)-piperidin-1-yl]-3-oxo-1-phenyl-propyl]-naphthalene-2-sulfonic acid amide (76) | (AC-33) | (AM-09) | 2 |
| 77 | N-[3-oxo-1-phenyl-3-[4-(2-pyrrolidin-1-yl-ethoxy)-4-[4-(trifluoromethyl)-phenyl]-piperidin-1-yl]-propyl]-naphthalene-2-sulfonic acid amide (77) | (AC-33) | (AM-10) | 2 |
| 78 | 1-[4-(4-fluorophenyl)-4-(2-pyrrolidin-1-yl-ethoxy)-piperidin-1-yl]-4-[1-[(4-methoxy-2,6-dimethyl-phenyl)sulfonyl]-piperidin-2-yl]-butan-1-one (78) | (AC-20) | (AM-09) | 2 |
| 79 | 4-[1-[(4-methoxy-2,6-dimethyl-phenyl)sulfonyl]-piperidin-2-yl]-1-[4-(2-pyrrolidin-1-yl-ethoxy)-4-[4-(trifluoromethyl)-phenyl]-piperidin-1-yl]-butan-1-one (79) | (AC-20) | (AM-10) | 2 |
| 80 | 4-methoxy-N,2,6-trimethyl-N-[2-[2-oxo-2-[4-pyridin-3-yl-4-(2-pyrrolidin-1-yl-ethoxy)-piperidin-1-yl]-ethoxy]-ethyl]-benzenesulfonic acid amide (80) | (AC-05) | (AM-11) | 1 |
| 81 | N-[2-[2-[4-(3-fluorophenyl)-4-(2-pyrrolidin-1-yl-ethoxy)-piperidin-1-yl]-2-oxo-ethoxy]-ethyl]-4-methoxy-N,2,6-trimethyl-benzenesulfonic acid amide (81) | (AC-05) | (AM-07) | 1 |
| 82 | 2-[[1-[(4-methoxy-2,6-dimethyl-phenyl)sulfonyl]-piperidin-2-yl]-methoxy]-1-[4-pyridin-3-yl-4-(2-pyrrolidin-1-yl-ethoxy)-piperidin-1-yl]-ethanone (82) | (AC-03) | (AM-11) | 1 |
| 83 | 1-[4-(3-fluorophenyl)-4-(2-pyrrolidin-1-yl-ethoxy)-piperidin-1-yl]-2-[[1-[(4-methoxy-2,6-dimethyl-phenyl)sulfonyl]-piperidin-2-yl]-methoxy]-ethanone (83) | (AC-03) | (AM-07) | 1 |
| 84 | 2-[[1-[(4-methoxy-2,6-dimethyl-phenyl)sulfonyl]-piperidin-2-yl]-methoxy]-1-[4-pyridin-4-yl-4-(2-pyrrolidin-1-yl-ethoxy)-piperidin-1-yl]-ethanone (84) | (AC-03) | (AM-08) | 1 |
| 85 | 4-[1-[(2-chloro-6-methyl-phenyl)sulfonyl]-piperidin-2-yl]-1-[4-(3-fluorophenyl)-4-(2-pyrrolidin-1-yl-ethoxy)-piperidin-1-yl]-butan-1-one (85) | (AC-18) | (AM-07) | 1 |
| 86 | 1-[4-(3-fluorophenyl)-4-(2-pyrrolidin-1-yl-ethoxy)-piperidin-1-yl]-4-[1-[[2-(trifluoromethyl)-phenyl]sulfonyl]-piperidin-2-yl]-butan-1-one (86) | (AC-19) | (AM-07) | 1 |
| 87 | 4-[1-[(4-methoxy-2,6-dimethyl-phenyl)sulfonyl]-piperidin-2-yl]-1-[4-pyridin-3-yl-4-(2-pyrrolidin-1-yl-ethoxy)-piperidin-1-yl]-butan-1-one (87) | (AC-20) | (AM-11) | 1 |
| 88 | 4-[1-[(4-methoxy-2,6-dimethyl-phenyl)sulfonyl]-piperidin-2-yl]-1-[4-pyridin-3-yl-4-(2-pyrrolidin-1-yl-ethoxy)-piperidin-1-yl]-butan-1-one (88) | (AC-20) | (AM-11) | 1 |
| 89 | 1-[4-(3-fluorophenyl)-4-(2-pyrrolidin-1-yl-ethoxy)-piperidin-1-yl]-4-[1-[(4-methoxy-2,6-dimethyl-phenyl)sulfonyl]-piperidin-2-yl]-butan-1-one (89) | (AC-20) | (AM-07) | 1 |
| 90 | 4-[1-[(4-methoxy-2,6-dimethyl-phenyl)sulfonyl]-piperidin-2-yl]-1-[4-pyridin-4-yl-4-(2-pyrrolidin-1-yl-ethoxy)-piperidin-1-yl]-butan-1-one (90) | (AC-20) | (AM-08) | 1 |

-continued

| Ex. | Name | Acid (AC) | Amide (AM) | Method |
|---|---|---|---|---|
| 91 | 4-[1-[(4-methoxy-2,6-dimethyl-phenyl)sulfonyl]-piperidin-2-yl]-1-[4-pyridin-4-yl-4-(2-pyrrolidin-1-yl-ethoxy)-piperidin-1-yl]-butan-1-one (91) | (AC-20) | (AM-08) | 1 |
| 92 | 4-[1-(naphthalen-1-ylsulfonyl)-piperidin-2-yl]-1-[4-pyridin-3-yl-4-(2-pyrrolidin-1-yl-ethoxy)-piperidin-1-yl]-butan-1-one (92) | (AC-21) | (AM-11) | 1 |
| 93 | 1-[4-(3-fluorophenyl)-4-(2-pyrrolidin-1-yl-ethoxy)-piperidin-1-yl]-4-[1-(naphthalen-1-ylsulfonyl)-piperidin-2-yl]-butan-1-one (93) | (AC-21) | (AM-07) | 1 |
| 94 | 4-[1-(naphthalen-1-ylsulfonyl)-piperidin-2-yl]-1-[4-pyridin-4-yl-4-(2-pyrrolidin-1-yl-ethoxy)-piperidin-1-yl]-butan-1-one (94) | (AC-21) | (AM-08) | 1 |
| 95 | 4-[1-(naphthalen-2-ylsulfonyl)-piperidin-2-yl]-1-[4-pyridin-3-yl-4-(2-pyrrolidin-1-yl-ethoxy)-piperidin-1-yl]-butan-1-one (95) | (AC-22) | (AM-11) | 1 |
| 96 | 1-[4-(3-fluorophenyl)-4-(2-pyrrolidin-1-yl-ethoxy)-piperidin-1-yl]-4-[1-(naphthalen-2-ylsulfonyl)-piperidin-2-yl]-butan-1-one (96) | (AC-22) | (AM-07) | 1 |
| 98 | 4-methoxy-2,6-dimethyl-N-[2-[2-oxo-2-[4-pyridin-3-yl-4-(2-pyrrolidin-1-yl-ethoxy)-piperidin-1-yl]-ethoxy]-ethyl]-N-phenyl-benzenesulfonic acid amide (98) | (AC-15) | (AM-11) | 1 |
| 99 | N-[2-[2-[4-(3-fluorophenyl)-4-(2-pyrrolidin-1-yl-ethoxy)-piperidin-1-yl]-2-oxo-ethoxy]-ethyl]-4-methoxy-2,6-dimethyl-N-phenyl-benzenesulfonic acid amide (99) | (AC-15) | (AM-07) | 1 |
| 100 | 4-methoxy-2,6-dimethyl-N-[2-[2-oxo-2-[4-pyridin-4-yl-4-(2-pyrrolidin-1-yl-ethoxy)-piperidin-1-yl]-ethoxy]-ethyl]-N-phenyl-benzenesulfonic acid amide (100) | (AC-15) | (AM-08) | 1 |
| 101 | 2-[[1-[(4-methoxy-2,6-dimethyl-phenyl)sulfonyl]-1,2,3,4-tetrahydro-quinolin-2-yl]-methoxy]-1-[4-pyridin-3-yl-4-(2-pyrrolidin-1-yl-ethoxy)-piperidin-1-yl]-ethanone (101) | (AC-17) | (AM-11) | 1 |
| 102 | 1-[4-(3-fluorophenyl)-4-(2-pyrrolidin-1-yl-ethoxy)-piperidin-1-yl]-2-[[1-[(4-methoxy-2,6-dimethyl-phenyl)sulfonyl]-1,2,3,4-tetrahydro-quinolin-2-yl]-methoxy]-ethanone (102) | (AC-17) | (AM-07) | 1 |
| 103 | 2-[[1-[(4-methoxy-2,6-dimethyl-phenyl)sulfonyl]-1,2,3,4-tetrahydro-quinolin-2-yl]-methoxy]-1-[4-pyridin-4-yl-4-(2-pyrrolidin-1-yl-ethoxy)-piperidin-1-yl]-ethanone (103) | (AC-17) | (AM-08) | 1 |
| 104 | N-benzhydryl-N-[2-[2-oxo-2-[4-pyridin-3-yl-4-(2-pyrrolidin-1-yl-ethoxy)-piperidin-1-yl]-ethoxy]-ethyl]-methanesulfonic acid amide (104) | (AC-23) | (AM-11) | 1 |
| 105 | N-benzhydryl-N-[2-[2-[4-(3-fluorophenyl)-4-(2-pyrrolidin-1-yl-ethoxy)-piperidin-1-yl]-2-oxo-ethoxy]-ethyl]-methanesulfonic acid amide (105) | (AC-23) | (AM-07) | 1 |
| 106 | 2-[[4-[(4-methoxy-2,6-dimethyl-phenyl)sulfonyl]-3,4-dihydro-2H-[1,4]benzoxazin-3-yl]-methoxy]-1-[4-pyridin-3-yl-4-(2-pyrrolidin-1-yl-ethoxy)-piperidin-1-yl]-ethanone (106) | (AC-24) | (AM-11) | 1 |
| 107 | 1-[4-(3-fluorophenyl)-4-(2-pyrrolidin-1-yl-ethoxy)-piperidin-1-yl]-2-[[4-[(4-methoxy-2,6-dimethyl-phenyl)sulfonyl]-3,4-dihydro-2H-[1,4]benzoxazin-3-yl]-methoxy]-ethanone (107) | (AC-24) | (AM-07) | 1 |

-continued

| Ex. | Name | Acid (AC) | Amide (AM) | Method |
|---|---|---|---|---|
| 108 | 2-[[4-[(4-methoxy-2,6-dimethyl-phenyl)sulfonyl]-3,4-dihydro-2H-[1,4]benzoxazin-3-yl]-methoxy]-1-[4-pyridin-4-yl-4-(2-pyrrolidin-1-yl ethoxy)-piperidin-1-yl]-ethanone (108) | (AC-24) | (AM-08) | 1 |
| 109 | 2-[[4-[(2-chloro-6-methyl-phenyl)sulfonyl]-3,4-dihydro-2H-[1,4]benzoxazin-3-yl]-methoxy]-1-[4-(3-fluorophenyl)-4-(2-pyrrolidin-1-yl ethoxy)-piperidin-1-yl]-ethanone (109) | (AC-26) | (AM-07) | 1 |
| 110 | 1-[4-pyridin-3-yl-4-(2-pyrrolidin-1-yl-ethoxy)-piperidin-1-yl]-2-[[4-[[2-(trifluoromethyl)-phenyl]sulfonyl]-3,4-dihydro-2H-[1,4]benzoxazin-3-yl]-methoxy]-ethanone (110) | (AC-27) | (AM-11) | 1 |
| 111 | 1-[4-(3-fluorophenyl)-4-(2-pyrrolidin-1-yl-ethoxy)-piperidin-1-yl]-2-[[4-[[2-(trifluoromethyl)-phenyl]sulfonyl]-3,4-dihydro-2H-[1,4]benzoxazin-3-yl]-methoxy]-ethanone (111) | (AC-27) | (AM-07) | 1 |
| 112 | 1-[4-pyridin-4-yl-4-(2-pyrrolidin-1-yl-ethoxy)-piperidin-1-yl]-2-[[4-[[2-(trifluoromethyl)-phenyl]sulfonyl]-3,4-dihydro-2H-[1,4]benzoxazin-3-yl]-methoxy]-ethanone (112) | (AC-27) | (AM-08) | 1 |
| 113 | 4-methoxy-N,2,3,6-tetramethyl-N-[2-[2-oxo-2-[4-pyridin-3-yl-4-(2-pyrrolidin-1-yl-ethoxy)-piperidin-1-yl]-ethoxy]-ethyl]-benzenesulfonic acid amide (113) | (AC-07) | (AM-11) | 1 |
| 114 | N-[2-[2-[4-(3-fluorophenyl)-4-(2-pyrrolidin-1-yl-ethoxy)-piperidin-1-yl]-2-oxo-ethoxy]-ethyl]-4-methoxy-N,2,3,6-tetramethyl-benzenesulfonic acid amide (114) | (AC-07) | (AM-07) | 1 |
| 115 | 4-methoxy-N,2,3,6-tetramethyl-N-[2-[2-oxo-2-[4-pyridin-4-yl-4-(2-pyrrolidin-1-yl-ethoxy)-piperidin-1-yl]-ethoxy]-ethyl]-benzenesulfonic acid amide (115) | (AC-07) | (AM-08) | 1 |
| 116 | 1-[4-pyridin-3-yl-4-(2-pyrrolidin-1-yl-ethoxy)-piperidin-1-yl]-2-[[1-[[2-(trifluoromethyl)-phenyl]sulfonyl]-piperidin-2-yl]-methoxy]-ethanone (116) | (AC-10) | (AM-11) | 1 |
| 117 | 1-[4-pyridin-3-yl-4-(2-pyrrolidin-1-yl-ethoxy)-piperidin-1-yl]-2-[[1-[[2-(trifluoromethyl)-phenyl]sulfonyl]-piperidin-2-yl]-methoxy]-ethanone (117) | (AC-10) | (AM-11) | 1 |
| 118 | 1-[4-(3-fluorophenyl)-4-(2-pyrrolidin-1-yl-ethoxy)-piperidin-1-yl]-2-[[1-[[2-(trifluoromethyl)-phenyl]sulfonyl]-piperidin-2-yl]-methoxy]-ethanone (118) | (AC-10) | (AM-07) | 1 |
| 119 | 3-[[1-[(4-methoxy-2,6-dimethyl-phenyl)sulfonyl]-piperidin-2-yl]-methoxy]-1-[4-pyridin-3-yl-4-(2-pyrrolidin-1-yl-ethoxy)-piperidin-1-yl]-propan-1-one (119) | (AC-11) | (AM-11) | 1 |
| 120 | 3-[[1-[(4-methoxy-2,6-dimethyl-phenyl)sulfonyl]-piperidin-2-yl]-methoxy]-1-[4-pyridin-3-yl-4-(2-pyrrolidin-1-yl-ethoxy)-piperidin-1-yl]-propan-1-one (120) | (AC-11) | (AM-11) | 1 |
| 121 | 1-[4-(3-fluorophenyl)-4-(2-pyrrolidin-1-yl-ethoxy)-piperidin-1-yl]-3-[[1-[(4-methoxy-2,6-dimethyl-phenyl)sulfonyl]-piperidin-2-yl]-methoxy]-propan-1-one (121) | (AC-11) | (AM-07) | 1 |
| 122 | 1-[4-(3-fluorophenyl)-4-(2-pyrrolidin-1-yl-ethoxy)-piperidin-1-yl]-3-[[1-[(4-methoxy-2,6-dimethyl-phenyl)sulfonyl]-piperidin-2-yl]-methoxy]-propan-1-one (122) | (AC-11) | (AM-07) | 1 |

-continued

| Ex. | Name | Acid (AC) | Amide (AM) | Method |
|---|---|---|---|---|
| 123 | 2-[2-[1-[(4-methoxy-2,6-dimethyl-phenyl)sulfonyl]-piperidin-2-yl]-ethoxy]-1-[4-pyridin-3-yl-4-(2-pyrrolidin-1-yl-ethoxy)-piperidin-1-yl]-ethanone (123) | (AC-12) | (AM-11) | 1 |
| 124 | 2-[2-[1-[(4-methoxy-2,6-dimethyl-phenyl)sulfonyl]-piperidin-2-yl]-ethoxy]-1-[4-pyridin-3-yl-4-(2-pyrrolidin-1-yl-ethoxy)-piperidin-1-yl]-ethanone (124) | (AC-12) | (AM-11) | 1 |
| 125 | 1-[4-(3-fluorophenyl)-4-(2-pyrrolidin-1-yl-ethoxy)-piperidin-1-yl]-2-[2-[1-[(4-methoxy-2,6-dimethyl-phenyl)sulfonyl]-piperidin-2-yl]-ethoxy]-ethanone (125) | (AC-12) | (AM-07) | 1 |
| 126 | 1-[4-(3-fluorophenyl)-4-(2-pyrrolidin-1-yl-ethoxy)-piperidin-1-yl]-2-[2-[1-[(4-methoxy-2,6-dimethyl-phenyl)sulfonyl]-piperidin-2-yl]-ethoxy]-ethanone (126) | (AC-12) | (AM-07) | 1 |
| 127 | N-[4-[4-(3-fluorophenyl)-4-(2-pyrrolidin-1-yl-ethoxy)-piperidin-1-yl]-4-oxo-butyl]-N-methyl-3-(trifluoromethyl)-benzenesulfonic acid amide (127) | (AC-13) | (AM-07) | 1 |
| 128 | 2-[4-[(2,4-dichlorophenyl)sulfonyl]-3,4-dihydro-2H-[1,4]benzoxazin-3-yl]-1-[4-(3-fluorophenyl)-4-(2-pyrrolidin-1-yl-ethoxy)-piperidin-1-yl]-ethanone (128) | (AC-14) | (AM-07) | 1 |
| 129 | 2-[[1-(naphthalen-2-ylsulfonyl)-1,2,3,4-tetrahydro-quinolin-2-yl]-methoxy]-1-[4-pyridin-3-yl-4-(2-pyrrolidin-1-yl-ethoxy)-piperidin-1-yl]-ethanone (129) | (AC-16) | (AM-11) | 1 |
| 130 | 2-[[1-(naphthalen-2-ylsulfonyl)-1,2,3,4-tetrahydro-quinolin-2-yl]-methoxy]-1-[4-pyridin-3-yl-4-(2-pyrrolidin-1-yl-ethoxy)-piperidin-1-yl]-ethanone (130) | (AC-16) | (AM-11) | 1 |
| 131 | 1-[4-(3-fluorophenyl)-4-(2-pyrrolidin-1-yl-ethoxy)-piperidin-1-yl]-2-[[1-(naphthalen-2-ylsulfonyl)-1,2,3,4-tetrahydro-quinolin-2-yl]-methoxy]-ethanone (131) | (AC-16) | (AM-07) | 1 |

Analytical Data of Examples 64 to 131

| Example | [M+] found | R.t. [min] |
|---|---|---|
| 64 | 646.3 | 2.97 |
| 65 | 696.2 | 3.07 |
| 66 | 632.4 | 2.94 |
| 67 | 682.4 | 3.02 |
| 68 | 636.4 | 2.97 |
| 69 | 686.4 | 3.06 |
| 70 | 622.2 | 2.94 |
| 71 | 672.3 | 3.05 |
| 72 | 626.2 | 3 |
| 73 | 676.2 | 3.06 |
| 74 | 634.3 | 3.12 |
| 75 | 684.5 | 3.23 |
| 76 | 630.3 | 2.99 |
| 77 | 680.4 | 3.07 |
| 78 | 644.3 | 3.02 |
| 79 | 694.6 | 3.09 |
| 80 | 589.4 | 1.25 |
| 81 | 606.4 | 1.52 |
| 82 | 629.4 | 1.35 |
| 83 | 646.4 | 1.58 |
| 84 | 629.4 | 1.33 |
| 85 | 634.3 | 1.65 |
| 86 | 654.4 | 1.63 |
| 87 | 627.4 | 1.41 |
| 88 | 627.4 | 1.41 |
| 89 | 644.4 | 1.64 |
| 90 | 627.4 | 1.38 |
| 91 | 627.4 | 1.39 |
| 92 | 619.4 | 1.42 |
| 93 | 636.4 | 1.66 |
| 94 | 619.4 | 1.41 |
| 95 | 619.4 | 1.44 |
| 96 | 636.4 | 1.68 |
| 98 | 651.4 | 1.4 |
| 99 | 668.4 | 1.65 |
| 100 | 651.4 | 1.37 |
| 101 | 677.5 | 1.44 |
| 102 | 694.4 | 1.7 |
| 103 | 677.5 | 1.43 |
| 104 | 621.4 | 1.34 |
| 105 | 638.4 | 1.61 |
| 106 | 679.4 | 1.46 |
| 107 | 696.4 | 1.67 |
| 108 | 679.4 | 1.43 |
| 109 | 686.3 | 1.67 |

141

-continued

| Example | [M+] found | R.t. [min] |
|---|---|---|
| 110 | 589.4 | 1.43 |
| 111 | 706.4 | 1.67 |
| 112 | 689.4 | 1.4 |
| 113 | 603.4 | 1.33 |
| 114 | 620.4 | 1.57 |
| 115 | 603.4 | 1.3 |
| 116 | 639.4 | 1.31 |
| 117 | 639.4 | 1.32 |
| 118 | 656.3 | 1.58 |
| 119 | 643.4 | 1.36 |
| 120 | 685.5 | 1.38 |
| 121 | 660.4 | 1.6 |
| 122 | 660.4 | 1.6 |
| 123 | 643.4 | 1.35 |
| 124 | 643.4 | 1.34 |
| 125 | 660.4 | 1.59 |
| 126 | 660.3 | 1.58 |
| 127 | 600.2 | 1.56 |
| 128 | 676.2 | 1.69 |
| 129 | 669.3 | 1.44 |
| 130 | 669.3 | 1.43 |
| 131 | 686.3 | 1.65 |

Individual Substances

Persons skilled in the art will understand that the acid and amine units used in the following in the context of the syntheses of individual substances can also be employed in an analogous manner in the parallel synthesis described above. The equivalent amounts of reagents employed and the amounts of solvent and reaction temperatures and times can vary slightly between different reactions carried out by the same method. The working up and purification methods were adapted where appropriate according to the characteristic properties of the compounds.

Analytical Method for Individual Substances:

Materials and methods for the HPLC-MS analysis: HPLC: Waters Alliance 2795 with PDA Waters 2998; MS: Micromass Quattro Micro™ API; column: Waters Atlantis® T3, 3 µm, 100 Å, 2.1×30 mm; column temperature: 40° C., eluent A: water+0.1% formic acid; eluent B: acetonitrile+0.1% formic acid; gradient: 0% B to 100% B in 8.8 min, 100% B for 0.4 min, 100% B to 0% B in 0.01 min, 0% B for 0.8 min; flow rate: 1.0 ml/min; ionization: ES+, 25 V; make up: 100 µl/min 70% methanol+0.2% formic acid; UV: 200-400 nm Preparation of Example Compounds by Coupling of 3-(4-(2-(pyrrolidin-1-yl)ethoxy)piperidin-4-yl)pyridine Dihydrochloride [Amine D] with Various Carboxylic Acids

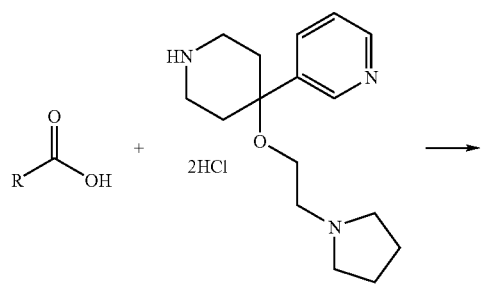

142

-continued

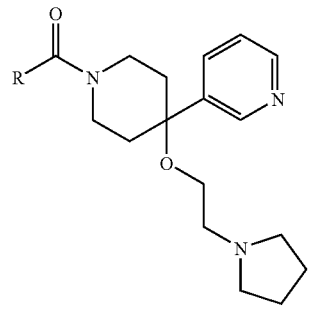

Method 1

Example 1

(S)-2-((1-(4-Methoxy-2,6-dimethylphenylsulfonyl)-1,2,3,4-tetrahydroquinolin-2-yl)methoxy)-1-(4-(pyridin-3-yl)-4-(2-(pyrrolidin-1-yl)ethoxy)piperidin-1-yl)ethanone 1,1'-Carbonyldiimidazole (49 mg, 0.3 mmol) and (S)-2-((1-(4-methoxy-2,6-dimethylphenylsulfonyl)-1,2,3,4-tetrahydroquinolin-2-yl)methoxy)acetic acid [acid AC1] (120 mg, 0.286 mmol) were dissolved in methylene chloride (4 ml) under an inert gas and the solution was stirred at room temperature for 30 min. 3-(4-(2-(Pyrrolidin-1-yl)ethoxy)piperidin-4-yl)pyridine dihydrochloride [amine D] (100 mg, 0.286 mmol), dissolved in methylene chloride (4 ml) and triethylamine (63 mg, 0.629 mmol), was added and the reaction mixture was stirred at room temperature for 15 h. Saturated sodium bicarbonate solution (20 ml) and methylene chloride (20 ml) were added, the phases were separated and the aqueous phase was extracted with methylene chloride (2×20 ml). The combined organic phases were washed with saturated sodium chloride solution (20 ml), dried over sodium sulfate and concentrated in vacuo. The crude product was purified by column chromatography (silica gel) with ethyl acetate/methanol/ammonia (25% eq.) 300/150/1. Yield: 130 mg, 67%, yellow, resin. MS, $R_t$=2.9 min, m/z=677.1 [MH]$^+$ The example compounds listed in the following table were prepared from 3-(4-(2-(pyrrolidin-1-yl)ethoxy)piperidin-4-yl)pyridine dihydrochloride [amine D] by reaction with the corresponding acid units analogously to the process described for Example 1.

| Example no. | Carboxylic acid (RCO₂H) (acid unit) | Yield (%) | HPLC-MS |
|---|---|---|---|
| 2 | 4-(1-(4-methoxy-2,6-dimethylphenyl-sulfonyl)piperidin-2-yl)butanoic acid [acid B] | 68 | MS, $R_t$ = 2.7 min, m/z = 627.1 $[MH]^+$ |
| 4 | 2-(2-(N-benzhydryl-2,4-dichlorophenyl-sulfonamido)ethoxy)acetic acid [acid G] | 82 | MS, $R_t$ = 3.6 min, m/z = 751.1 $[MH]^+$ |
| 5 | 2-(2-(4-methoxy-2,6-dimethyl-N-(pyridin-3-ylmethyl)phenylsulfonamido)ethoxy)acetic acid [acid I] | 91 | MS, $R_t$ = 2.0 min, m/z = 666.1 $[MH]^+$ |
| 6 | 2-(2-(N-benzhydryl-4-methoxy-2,6-dimethylphenylsulfonamido)ethoxy)acetic acid [acid H] | 65 | MS, $R_t$ = 3.4 min, m/z = 741.1 $[MH]^+$ |

Method 2

Example 3

N-Cyclopropyl-4-methoxy-2,6-dimethyl-N-(2-(2-oxo-2-(4-(pyridin-3-yl)-4-(2-(pyrrolidin-1-yl)ethoxy)piperidin-1-yl)ethoxy)ethyl)benzenesulfonamide 2-(2-(N-Cyclopropyl-4-methoxy-2,6-dimethylphenylsulfonamido)ethoxy)acetic acid [acid C] (150 mg, 0.42 mmol), O-(1H-benzotriazol-1-yl)-N,N,N',N'-tetramethyluronium tetrafluoroborate (135 mg, 0.42 mmol) and 1-hydroxybenzotriazole hydrate (57 mg, 0.42 mmol) were initially introduced into tetrahydrofuran (10 ml) under an inert gas and the mixture was stirred at room temperature for 30 min. A solution of 3-(4-(2-(pyrrolidin-1-yl)ethoxy)piperidin-4-yl)pyridine dihydrochloride [amine D] (146 mg, 0.42 mmol) and N-ethyl-diisopropylamine (81 mg, 0.63 mmol) in tetrahydrofuran (5 ml) was added and the mixture was stirred for 3 d. Tetrahydrofuran was removed in vacuo, the residue was taken up in ethyl acetate (50 ml) and saturated sodium bicarbonate solution (20 ml) and the phases were separated. The aqueous phase was extracted with ethyl acetate (2×50 ml) and the combined organic phases were washed with saturated sodium chloride solution (50 ml), dried over sodium sulfate and concentrated in vacuo. The crude product was purified by column chromatography (silica gel) with ethyl acetate/methylene chloride/methanol/ammonia (25% eq.) 300/100/50/1. The hydrochloride was precipitated from acetone/diethyl ether solution with 3 eq. of hydrogen chloride (solution in diethyl ether 2 mol/l).

Yield: 120 mg, 43%, white, finely crystalline. MS, $R_t$=2.5 min, m/z=615.2 $[MH]^+$ The example compounds listed in the following table were prepared from 3-(4-(2-(pyrrolidin-1-yl)ethoxy)piperidin-4-yl)pyridine dihydrochloride [amine D] by reaction with the corresponding acid units analogously to the process described for Example 3.

Method 3

Example 46

(S)-2-((1-(4-Methoxy-2,6-dimethylphenylsulfonyl)piperidin-2-yl)methoxy)-1-(4-(pyridin-3-yl)-4-(2-(pyrrolidin-1-yl)ethoxy)piperidin-1-yl)ethanone Hydrochloride (S)-2-((1-(4-Methoxy-2,6-dimethylphenylsulfonyl)piperidin-2-yl)methoxy)acetic acid [acid D] (1 eq.) was dissolved in methylene chloride (5 ml/mmol), the solution was cooled and diisopropylethylamine (2.5 eq.), 1-hydroxybenzotriazole hydrate (1 eq.) and EDCl (1.5 eq.) were added at 0° C. The cooling bath was removed and the reaction mixture was stirred at room temperature for 15 min. The reaction mixture was cooled again and 3-(4-(2-(pyrrolidin-1-yl)ethoxy)piperidin-4-yl)pyridine [amine D] (1.2 eq.) was added at 0° C. The ice bath was removed and the mixture was stirred at room temperature for 16 h. It was diluted with methylene chloride and washed with saturated ammonium chloride solution, saturated sodium chloride solution, saturated sodium bicarbonate solution and saturated sodium chloride solution again. The organic phase was dried over sodium sulfate and concentrated in vacuo. The crude product was purified by column chromatography (silica gel) with 2% methanol in methylene chloride and the hydrochloride was precipitated from dioxane solution with saturated hydrogen chloride in dioxane solution (not filtered with suction, but dioxane removed in vacuo and the residue dried).

Yield: 43%, pale yellow, finely crystalline. MS, $R_t$=3.1 min, m/z=629.3 $[MH]^+$ The example compounds listed in the following table were prepared from 3-(4-(2-(pyrrolidin-1-yl)ethoxy)piperidin-4-yl)pyridine dihydrochloride [amine D] by reaction with the corresponding carboxylic acids (acid unit) analogously to the process described for Example 46.

| Example no. | Carboxylic acid (RCO₂H) (acid unit) | Yield (%) | HCl precipitation | HPLC-MS |
|---|---|---|---|---|
| 7 | 2-(2-(2,4-dichloro-N-(2,3-dihydro-1H-inden-1-yl)phenylsulfonamido)ethoxy)acetic acid [acid J] | 67 | no | MS, $R_t$ = 3.3 min, m/z = 701.1 $[MH]^+$ |

| Example no. | Acid unit | Yield (%) | HCl precipitation | HPLC-MS) |
|---|---|---|---|---|
| 47 | (S)-2-((1-(2-(trifluoromethyl)phenyl-sulfonyl)piperidin-2-yl)methoxy)acetic acid [acid E] | 27 | no | MS, $R_t$ = 2.6 min, m/z = 639.1 $[MH]^+$ |
| 48 | (S)-2-((1-(2-chloro-6-methylphenyl-sulfonyl)piperidin-2-yl)methoxy)acetic acid [acid F] | 25 | no | MS, $R_t$ = 2.7 min, m/z = 619.1 $[MH]^+$ |

Preparation of Example Compounds by Coupling of (S)-2-((1-(4-methoxy-2,6-dimethylphenylsulfonyl)piperidin-2-yl)methoxy)acetic Acid [Acid D] with Various Amine Units

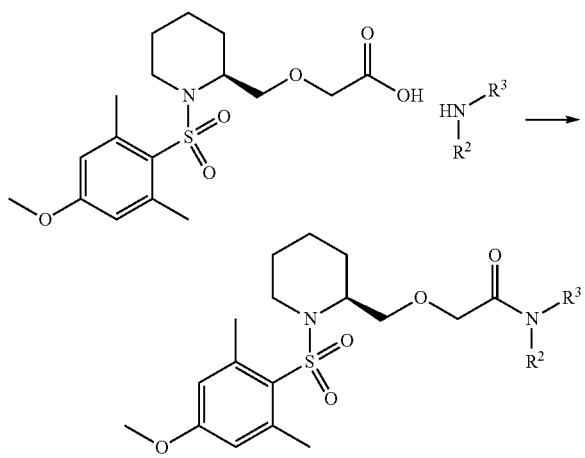

The example compounds listed in the following table were prepared from (S)-2-((1-(4-methoxy-2,6-dimethylphenylsulfonyl)piperidin-2-yl)methoxy)acetic acid [acid D] as the acid unit by reaction with the corresponding amines analogously to the process described Example 46 (Method 3).

| Example no. | Amine | Yield (%) | HCl-precipitation | HPLC-MS |
|---|---|---|---|---|
| 49 | 3-(4-((2-(pyrrolidin-1-yl)ethoxy)methyl)piperidin-4-yl)pyridine [amine A] | 19 | no | MS, $R_t$ = 2.5 min, m/z = 643.2 $[MH]^+$ |
| 50 | 3-(3-(2-(pyrrolidin-1-yl)ethoxy)pyrrolidin-3-yl)pyridine [amine B] | 29 | no | MS, $R_t$ = 2.8 min, m/z = 615.1 $[MH]^+$ |
| 51 | 4-(3-fluorophenyl)-4-(2-(pyrrolidin-1-yl)ethoxy)piperidine [amine C] | 26 | no | MS, $R_t$ = 3.7 min, m/z = 646.4 $[MH]^+$ |

Example 8

1-(4-(Pyridin-3-yl)-4-(2-(pyrrolidin-1-yl)ethoxy)piperidin-1-yl)-4-(1-(2-(trifluoromethyl)phenylsulfonyl)piperidin-2-yl)butan-1-one 4-(1-(tert-Butoxycarbonyl)piperidin-2-yl)butanoic Acid A solution of potassium carbonate (26.6 g, 193.1 mmol, 4 eq.) in water (70 ml) was added to a solution of 4-(piperidin-2-yl)butanoic acid hydrochloride (10 g, 48.3 mmol, 1 eq.) in 1,4-dioxane (125 ml). Di-tert-butyl dicarbonate (11.6 g, 53.1 mmol, 1.1 eq.) was added slowly at 0° C. The mixture was stirred at room temperature for 24 h.

For working up, water and ethyl acetate were added to the reaction mixture. The phases were separated and the aqueous phase was extracted with ethyl acetate (1×). The aqueous phase was adjusted to pH 2 with 2 M HCl solution and then extracted 4× with methylene chloride. The combined organic phases were dried over magnesium sulfate and concentrated under reduced pressure. The crude product was obtained as a colorless oil (13.1 g) and employed in the next stage without further working up.

4-(1-(tert-Butoxycarbonyl)piperidin-2-yl)butanoic Acid Methyl Ester 4-(1-tert-Butoxycarbonyl)piperidin-2-yl)butanoic acid (14.4 g, 53.06 mmol, 1 eq.) was dissolved in methylene chloride (100 ml) and 1,1-carbonyldiimidazole (12.9 g, 79.6 mmol, 1.5 eq.) was added. The mixture was stirred at room temperature for 1 h. Methanol (10.8 ml, 256.3 mmol, 5 eq.) was then added and the mixture was stirred at room temperature for 2 h.

For working up, the reaction mixture was washed 3× with sat. ammonium chloride solution and 2× with sodium chloride solution. The combined organic phases were dried over magnesium sulfate and concentrated under reduced pressure. The desired ester was obtained as a colorless solid (4.8 g) in a yield of 32% and was employed further without further purification.

4-(Piperidin-2-yl)butanoic Acid Methyl Ester Hydrochloride 4-(1-tert-Butoxycarbonyl)piperidin-2-yl)butanoic acid methyl ester (4.58 g, 16.05 mmol, 1 eq.) was dissolved in methanol (40 ml), and acetyl chloride (5.7 ml, 80.2 mmol, 5 eq.) was added at room temperature. The mixture was stirred at room temperature for 5 h.

The reaction mixture was then concentrated under reduced pressure and employed in the next stage without further working up. The desired product was obtained as a white solid (3.5 g) in a yield of 98%.

4-(1-(2-(Trifluoromethyl)phenylsulfonyl)piperidin-2-yl)butanoic Acid Methyl Ester 2-(Trifluoromethyl)benzene-1-sulfonic acid chloride (8.7 ml, 56.50 mmol, 3 eq.), dissolved in 50 ml of methylene chloride, was added to a suspension of 4-(piperidin-2-yl)butanoic acid methyl ester hydrochloride (3.49 g, 18.83 mmol, 1 eq.) in methylene chloride (85 ml). N-Ethyl-diisopropylamine (9.6 ml, 56.50 mmol, 3 eq.) was then slowly added dropwise. The mixture was stirred at room temperature for 24 h.

For working up, the reaction solution was acidified with 1 M aqueous HCl solution. The aqueous phase was saturated with sodium chloride and extracted 4× with methylene chloride. The combined organic phases were dried over magnesium sulfate and concentrated under reduced pressure. The residue (10.6 g) was purified by column chromatography [Alox Neutral (240 g) hexane/ethyl acetate 95:5→93:7→9:1→8:2]. The desired product was obtained as an orange-brown oil in a yield of 61% (4.5 g).

4-(1-(2-(Trifluoromethyl)phenylsulfonyl)piperidin-2-yl)butanoic Acid 4-(1-(2-(Trifluoromethyl)phenylsulfonyl)piperidin-2-yl)butanoic acid methyl ester (3.5 g, 8.9 mmol, 1 eq.) was dissolved in water (25 ml) and methanol (35 ml). Lithium hydroxide (1 g, 44.5 mmol, 5 eq.) was added, while stirring. The mixture was stirred at room temperature for 24 h.

For working up, the methanol was removed under reduced pressure. The residue was taken up in ethyl acetate and the mixture was acidified with dilute HCl solution. The aqueous phase was extracted 2× with ethyl acetate. The combined organic phases were dried over sodium sulfate and concentrated under reduced pressure. The crude product (4.2 g) was employed in the next stage without further purification.

1-(4-(Pyridin-3-yl)-4-(2-(pyrrolidin-1-yl)ethoxy)piperidin-1-yl)-4-(1-(2-(trifluoromethyl)phenylsulfonyl)piperidin-2-yl)butan-1-one 1-Hydroxybenzotriazole hydrate (HOBT) (0.021 g, 0.158 mmol, 0.3 eq.) and N-ethyl-diisopropylamine (0.269 ml, 1.59 mmol, 3 eq.) were added to a solution of 4-(1-(2-(trifluoromethyl)phenylsulfonyl)piperidin-2-yl)butanoic acid (0.251 g, 0.66 mmol, 1.25 eq.) in methylene chloride (7 ml). The mixture was cooled to 0° C., 1-(3-dimethylaminopropyl)-3-ethylcarbodiimide hydrochloride (EDCl) (0.152 g, 0.792 mmol, 1.5 eq.) was added and the mixture was stirred for approx. 15 min. 3-(4-(2-(Pyrrolidin-1-yl)ethoxy)piperidin-4-yl)pyridine dihydrochloride (0.184 g, 0.528 mmol, 1 eq.) was then added. The reaction mixture was stirred at room temperature for 72 h.

For purification, sat. sodium bicarbonate solution was added to the mixture and the mixture was diluted with ethyl acetate. The phases were separated and the aqueous phase was extracted 2× with ethyl acetate. The combined organic phases were dried over magnesium sulfate and concentrated under reduced pressure. The residue was purified by column chromatography [Alox Neutral (25 g), ethyl acetate 100%→ethyl acetate/methanol 95:5]. The desired product was obtained as a yellow-orange oil in a yield of 49% (0.164 g).

HPLC/MS analysis: $R_t$=2.8 min; purity (UV 200-400 nm) 98%; m/z=637.1

Example 9

4-(1-(2-Chloro-6-methylphenylsulfonyl)piperidin-2-yl)-1-(4-(pyridin-3-yl)-4-(2-(pyrrolidin-1-yl)ethoxy)piperidin-1-yl)butan-1-one

4-(1-(2-Chloro-6-methylphenylsulfonyl)piperidin-2-yl)butanoic Acid Methyl Ester 2-Chloro-6-methylbenzene-1-sulfonic acid chloride (7.6 ml, 33.83 mmol, 3 eq.), dissolved in 20 ml of methylene chloride, was added to a suspension of 4-(piperidin-2-yl)butanoic acid methyl ester hydrochloride (2.5 g, 11.3 mmol, 1 eq.) in methylene chloride (60 ml). N-Ethyl-diisopropylamine (5.7 ml, 33.8 mmol, 3 eq.) was then slowly added dropwise. The mixture was stirred at room temperature for 24 h.

For working up, the reaction solution was acidified with 1 M aqueous HCl solution. The aqueous phase was saturated with sodium chloride and extracted 3× with methylene chloride. The combined organic phases were dried with magnesium sulfate and concentrated under reduced pressure. The residue (10.6 g) was purified by column chromatography [Alox Neutral (240 g) hexane/ethyl acetate 98:2→92:8→9:1→8:2]. The desired product was obtained as a yellow oil in a yield of 93% (3.9 g).

4-(1-(2-Chloro-6-methylphenylsulfonyl)piperidin-2-yl)butanoic Acid 4-(1-(2-Chloro-6-methylphenylsulfonyl)piperidin-2-yl)butanoic acid methyl ester (2.7 g, 7.3 mmol, 1 eq.) was dissolved in water (20 ml) and methanol (30 ml). Lithium hydroxide (0.87 g, 36.5 mmol, 5 eq.) was added, while stirring. The mixture was stirred at room temperature for 24 h.

For working up, the methanol was removed under reduced pressure. The residue was taken up in ethyl acetate and the mixture was acidified with dilute HCl solution. The aqueous phase was extracted 2× with ethyl acetate. The combined organic phases were dried over sodium sulfate and concentrated under reduced pressure. The crude product (3 g) was employed in the next stage without further purification.

4-(1-(2-Chloro-6-methylphenylsulfonyl)piperidin-2-yl)-1-(4-(pyridin-3-yl)-4-(2-(pyrrolidin-1-yl)ethoxy)piperidin-1-yl)butan-1-one 1-Hydroxybenzotriazole hydrate (HOBT) (0.022 g, 0.168 mmol, 0.3 eq.) and N-ethyl-diisopropylamine (0.285 ml, 1.68 mmol, 3 eq.) were added to a solution of 4-(1-(2-chloro-6-methylphenylsulfonyl)piperidin-2-yl)butanoic acid (0.252 g, 0.7 mmol, 1.25 eq.) in methylene chloride (7 ml). The mixture was cooled to 0° C., 1-(3-dimethylaminopropyl)-3-ethylcarbodiimide hydrochloride (EDCl) (0.161 g, 0.84 mmol, 1.5 eq.) was added and the mixture was stirred for 15 min. 3-(4-(2-(Pyrrolidin-1-yl)ethoxy)piperidin-4-yl)pyridine dihydrochloride (0.195 g, 0.56 mmol, 1 eq.) was then added. The reaction mixture was stirred at room temperature for 72 h. For working up, sat. sodium bicarbonate solution was added to the mixture and the mixture was diluted with ethyl acetate. The phases were separated, and the aqueous phase was extracted 2× with ethyl acetate. The combined organic phases were dried over magnesium sulfate and concentrated under reduced pressure. The residue was purified by column chromatography [Alox Neutral (25 g), ethyl acetate 100%→ethyl acetate/methanol 95:5]. The desired product was obtained as a yellow-white solid in a yield of 61% (0.212 g).

HPLC/MS analysis: $R_t$=2.9 min; purity (UV 200-400 nm) 99%; m/z=617.1

Example 53

2-Chloro-N-cyclopropyl-N-[2-[2-[4-(3-fluorophenyl)-4-[2-(1-oxido-pyrrolidin-1-ium-1-yl)-ethoxy]-piperidin-1-yl]-2-oxo-ethoxy]-ethyl]-6-methyl-benzenesulfonic Acid Amide

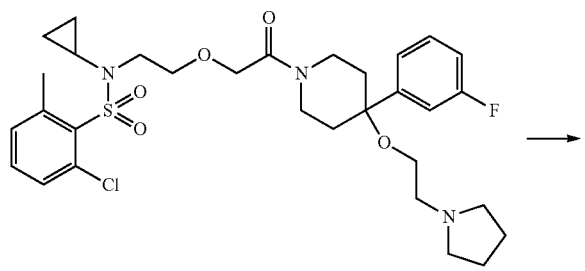

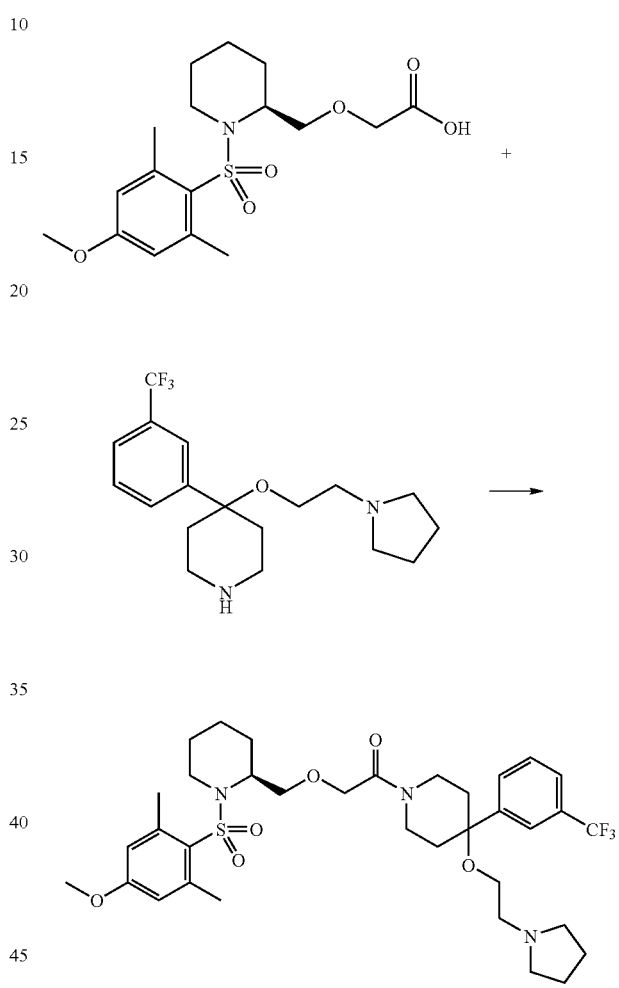

Example 54

2-[[(2S)-1-[(4-Methoxy-2,6-dimethyl-phenyl)sulfonyl]-piperidin-2-yl]-methoxy]-1-[4-(2-pyrrolidin-1-yl-ethoxy)-4-[3-(trifluoromethyl)phenyl]-piperidin-1-yl]-ethanone 1,2-Dibromoethane (6.8 ml) was added to mCPBA (112 mg, 2 eq.) and the mixture was cooled to 0° C. 2-Chloro-N-cyclopropyl-N-[2-[2-[4-(3-fluorophenyl)-4-(2-pyrrolidin-1-yl-ethoxy)-piperidin-1-yl]-2-oxo-ethoxy]-ethyl]-6-methyl-benzenesulfonic acid amide [Example 62] (200 mg, 1 eq.) was dissolved in methylene chloride (20 ml) and the solution was added dropwise to the reaction mixture. The reaction mixture was stirred at 0° C. for 1 h (TLC control) and then diluted with methylene chloride. The organic phase was washed twice with aqueous sodium bicarbonate solution and saturated sodium chloride solution, dried over sodium sulfate and concentrated to dryness on a rotary evaporator. The crude product was purified by means of column chromatography (Alox, 3% methanol in methylene chloride).

Yield: 40%. MS, $R_t$=3.8 min, m/z=638.3 [MH]$^+$

Diisopropylethylamine (4 eq.), EDCl HCl (1.2 eq.) and HOBt (1 eq.) were added to a mixture of (S)-2-((1-(4-methoxy-2,6-dimethylphenylsulfonyl)piperidin-2-yl)methoxy) acetic acid [acid D] (0.65 mmol) in methylene chloride (10 ml). A mixture of 4-(2-(pyrrolidin-1-yl)ethoxy)-4-(3-(trifluoromethyl)phenyl)piperidine [amine H] and DIPEA (2 eq.) in methylene chloride (3 ml) was added dropwise, while cooling with ice, and the reaction mixture was stirred at room temperature overnight. The reaction mixture was diluted with methylene chloride, washed with saturated ammonium chloride solution, saturated sodium chloride solution, saturated sodium bicarbonate solution and with sat. sodium chloride solution, dried over sodium sulfate and concentrated. The crude product was purified by means of column chromatography (silica gel, methanol/methylene chloride) to obtain the desired product. Yield: 78%. MS, $R_f$=3.9 min, m/z=696.4 [MH]$^+$

Example 55

2-[[(2S)-1-[(4-Methoxy-2,6-dimethyl-phenyl)sulfonyl]-piperidin-2-yl]-methoxy]-1-[4-pyridin-3-yl-4-(2-pyrrolidin-1-yl-ethoxy)-azepan-1-yl]-ethanone

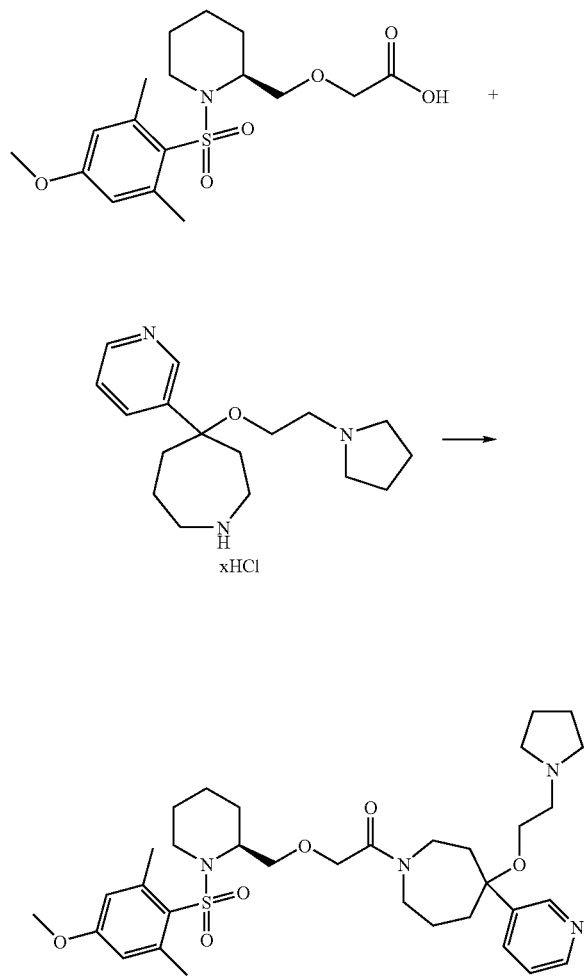

DIPEA (2.5 eq.) was added to a cooled solution (0° C.) of (S)-2-((1-(4-methoxy-2,6-dimethylphenylsulfonyl)piperidin-2-yl)methoxy)acetic acid [acid D] in methylene chloride (5 ml/mmol), followed by HOBt (1 eq.) and EDCl (1.5 eq.). The reaction mixture was stirred at room temperature for 10 min and cooled to 0° C. and 4-(pyridin-3-yl)-4-(2-(pyrrolidin-1-yl)ethoxy)azepan hydrochloride [amine K] (1.2 eq.) was added. The reaction mixture was then stirred at room temperature for 16 h. In this time, the educts reacted completely (TLC control). The reaction mixture was diluted with methylene chloride (20 ml) and washed with saturated ammonium chloride solution, saturated sodium chloride solution, saturated sodium bicarbonate solution and finally with sat. sodium chloride solution again. The organic phase was dried over sodium sulfate and concentrated to dryness on a rotary evaporator. The crude product was purified by means of column chromatography (silica gel, methanol/methylene chloride). Yield: 46%. MS, $R_f$=2.8 min, m/z=643.4 [MH]$^+$

Example 56

1-[4-(3-Chlorophenyl)-4-(2-pyrrolidin-1-yl-ethoxy)-piperidin-1-yl]-2-[[(2S)-1-[(4-methoxy-2,6-dimethyl-phenyl)sulfonyl]-piperidin-2-yl]-methoxy]-ethanone

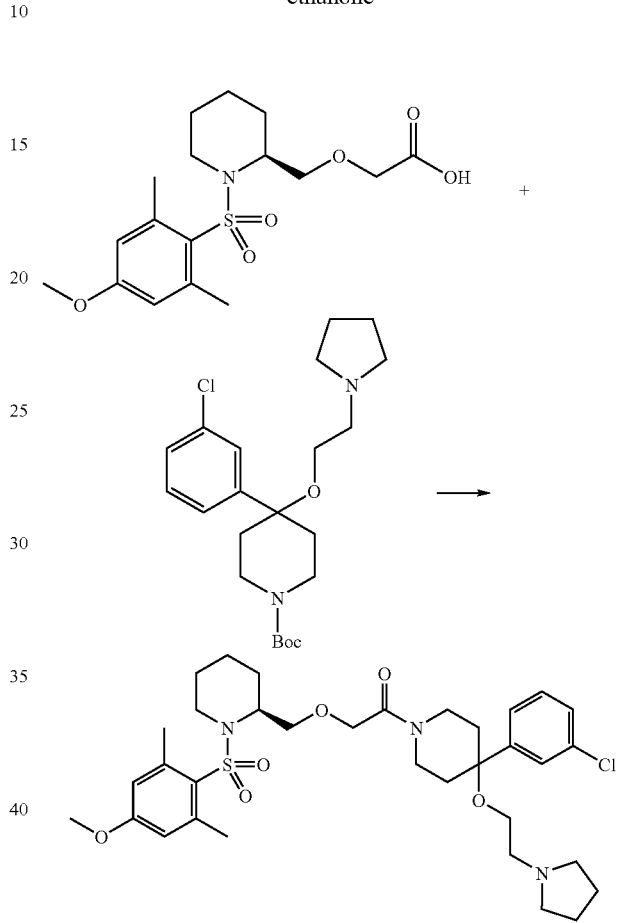

DIPEA (2.5 eq.) was added to a cooled solution (0° C.) of (S)-2-((1-(4-methoxy-2,6-dimethylphenylsulfonyl)piperidin-2-yl)methoxy)acetic acid [acid D] in methylene chloride (5 ml/mmol), followed by HOBt (1 eq.) and EDCl (1.5 eq.). The reaction mixture was stirred at room temperature for 10 min and cooled to 0° C. and a solution of Boc-deprotected tert-butyl 4-(3-chlorophenyl)-4-(2-(pyrrolidin-1-yl)ethoxy) piperidine-1-carboxylate [amine I] (1.2 eq.) [Boc-deprotected in the presence of TFA (10-13 eq.) in methylene chloride (see e.g. stage (iii)/amine H)] in methylene chloride was added. The reaction mixture was then stirred at room temperature for 16 h. In this time, the reaction reacted completely (TLC control). The reaction mixture was diluted with methylene chloride (20 ml) and washed with saturated ammonium chloride solution, saturated sodium chloride solution, saturated sodium bicarbonate solution and finally with sat. sodium chloride solution again. The organic phase was dried over sodium sulfate and concentrated to dryness on a rotary evaporator. The crude product was purified by means of column chromatography (silica gel, 2% methanol in methylene chloride)

Yield: 26%. MS, $R_f$=3.8 min, m/z=662.4 [MH]$^+$.

Example 57

2-[[(2S)-1-[(4-Methoxy-2,6-dimethyl-phenyl)sulfonyl]-piperidin-2-yl]-methoxy]-1-[4-pyridin-4-yl-4-(2-pyrrolidin-1-yl-ethoxy)-piperidin-1-yl]-ethanone

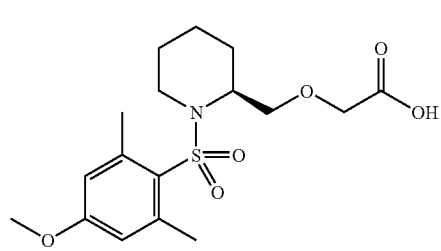

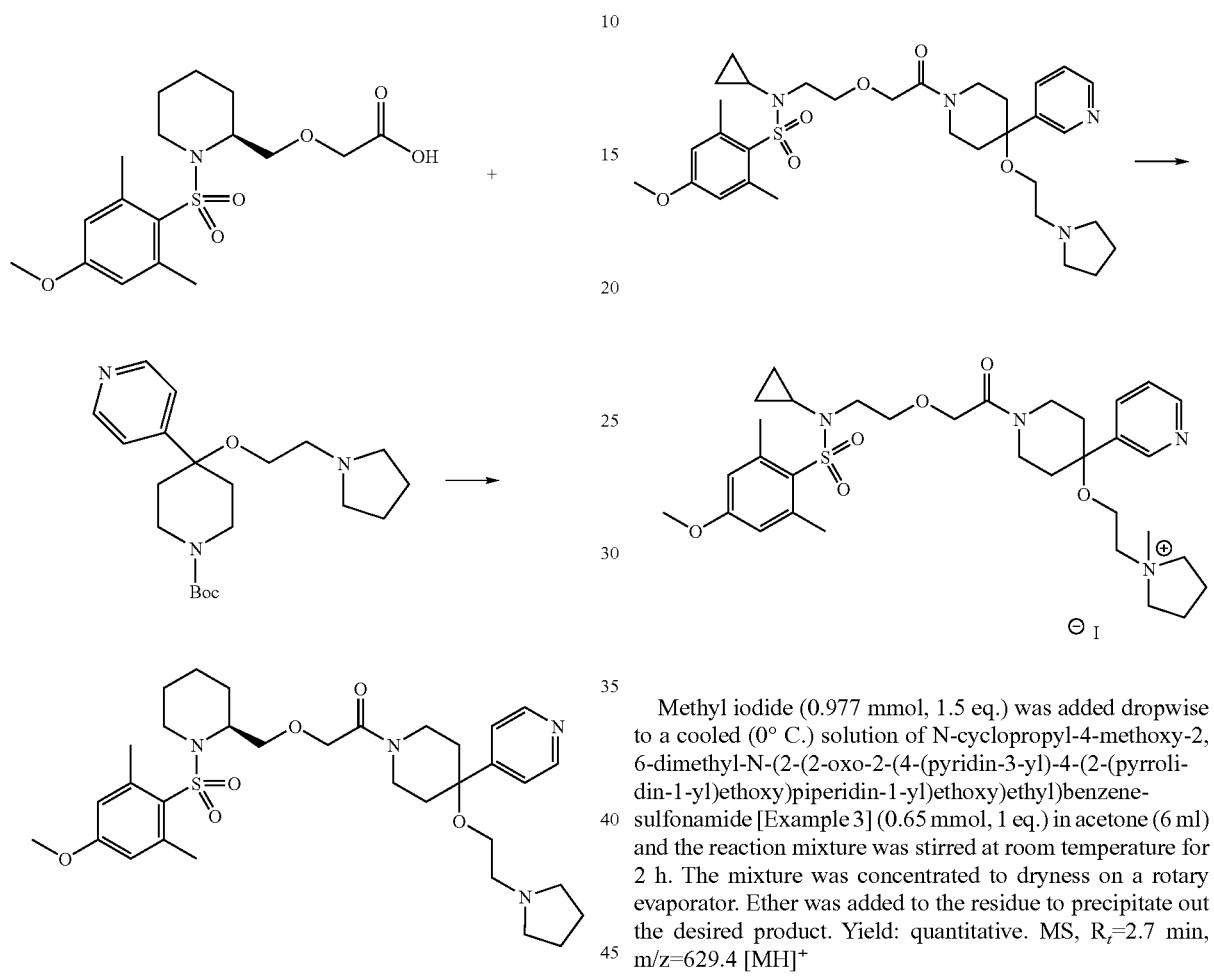

DIPEA (4 eq.), EDCl (1.2 eq.) and HOBt (1 eq.) were added to a solution of (S)-2-((1-(4-methoxy-2,6-dimethylphenylsulfonyl)piperidin-2-yl)methoxy)acetic acid [acid D] (0.65 mmol) in methylene chloride (5 ml). tert-Butyl 4-(pyridin-4-yl)-4-(2-(pyrrolidin-1-yl)ethoxy)piperidine-1-carboxylate [amine J] (0.78 mmol) [Boc-deprotected in the presence of TFA (10-13 eq.) in methylene chloride (see e.g. stage (iii)/amine H)] and DIPEA (2 eq.) were added dropwise in methylene chloride (3 ml) to the reaction mixture, while cooling with ice, and the mixture was stirred at room temperature overnight. The reaction mixture was diluted with methylene chloride and washed with saturated ammonium chloride solution, saturated sodium chloride solution, saturated sodium bicarbonate solution and finally with sat. sodium chloride solution again. The organic phase was dried over sodium sulfate and concentrated to dryness on a rotary evaporator. The crude product was purified by means of column chromatography (silica gel, methanol/methylene chloride) to obtain the desired product. Yield: 36%. MS, $R_t$=2.6 min, m/z=629.4 [MH]$^+$

Example 58

N-Cyclopropyl-4-methoxy-2,6-dimethyl-N-[2-[2-[4-[2-(1-methyl-pyrrolidin-1-ium-1-yl)-ethoxy]-4-pyridin-3-yl-piperidin-1-yl]-2-oxo-ethoxy]-ethyl]-benzenesulfonic Acid Amide Iodide Methyl iodide (0.977 mmol, 1.5 eq.) was added dropwise to a cooled (0° C.) solution of N-cyclopropyl-4-methoxy-2,6-dimethyl-N-(2-(2-oxo-2-(4-(pyridin-3-yl)-4-(2-(pyrrolidin-1-yl)ethoxy)piperidin-1-yl)ethoxy)ethyl)benzenesulfonamide [Example 3] (0.65 mmol, 1 eq.) in acetone (6 ml) and the reaction mixture was stirred at room temperature for 2 h. The mixture was concentrated to dryness on a rotary evaporator. Ether was added to the residue to precipitate out the desired product. Yield: quantitative. MS, $R_t$=2.7 min, m/z=629.4 [MH]$^+$

Example 59

2-[[(2S)-1-[(4-Methoxy-2,6-dimethyl-phenyl)sulfonyl]-piperidin-2-yl]-methoxy]-1-[4-pyridin-3-yl-4-[2-(1H-[1,2,4]triazol-1-yl)-ethoxy]-piperidin-1-yl]-ethanone

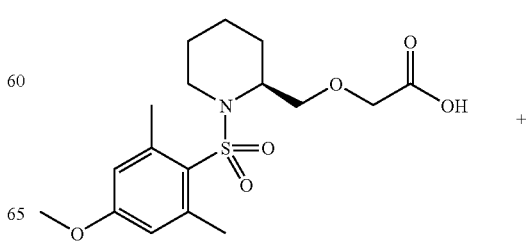

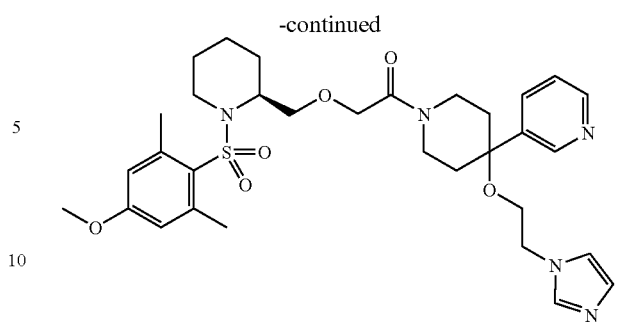

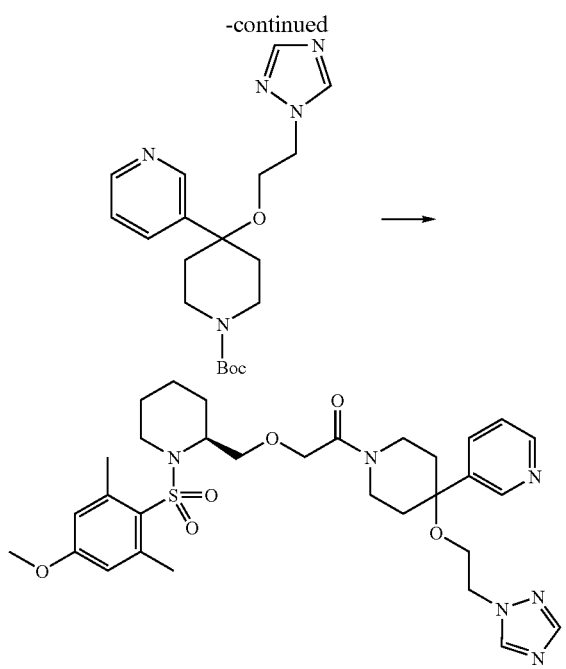

The desired target compound was synthesized under reaction conditions analogously to the process described for Example 61 (see below) from (S)-2-((1-(4-methoxy-2,6-dimethylphenylsulfonyl)piperidin-2-yl)methoxy)acetic acid [acid D] and tert-butyl 4-(2-(1H-1,2,4-triazol-1-yl)ethoxy)-4-(pyridin-3-yl)piperidine-1-carboxylate [amine G]. Yield: 24%. MS, R$_t$=3.3 min, m/z=627.4 [MH]$^+$ Example 60

1-[4-[2-(1H-Imidazol-1-yl)-ethoxy]-4-pyridin-3-yl-piperidin-1-yl]-2-[[(2S)-1-[(4-methoxy-2,6-dimethyl-phenyl)sulfonyl]-piperidin-2-yl]-methoxy]-ethanone

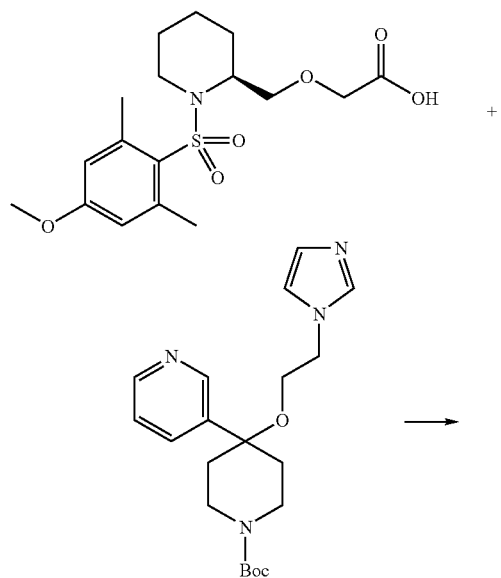

The desired target compound was synthesized under reaction conditions analogously to the process described for Example 61 (see below) from (S)-2-((1-(4-methoxy-2,6-dimethylphenylsulfonyl)piperidin-2-yl)methoxy)acetic acid [acid D] and tert-butyl 4-(2-(1H-imidazol-1-yl)ethoxy)-4-(pyridin-3-yl)piperidine-1-carboxylate [amine F]. Yield: 60%. MS, R$_t$=2.7 min, m/z=626.4 [MH]$^+$ Example 61

1-[4-[2-(Azetidin-1-yl)-ethoxy]-4-pyridin-3-yl-piperidin-1-yl]-2-[[(2S)-1-[(4-methoxy-2,6-dimethylphenyl)sulfonyl]-piperidin-2-yl]-methoxy]-ethanone

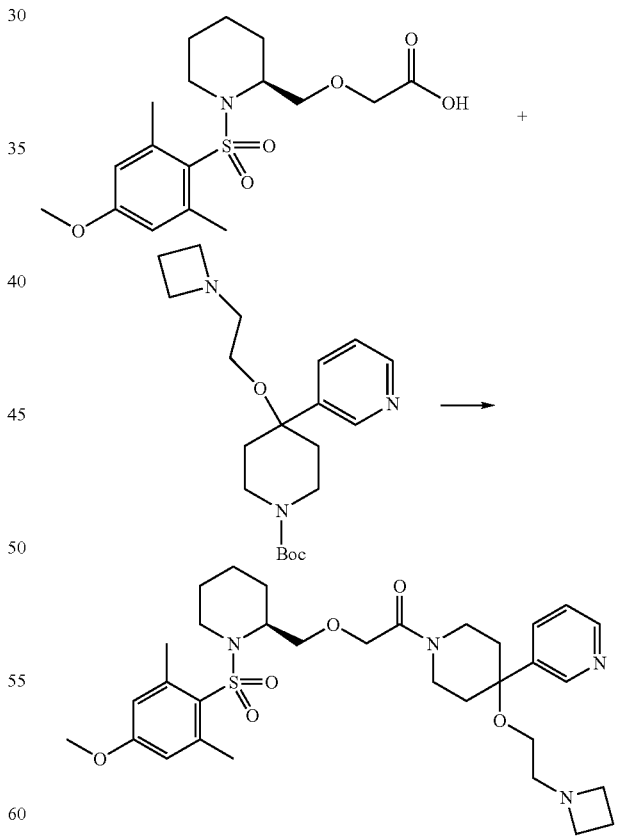

After the BOC deprotection of tert-butyl 4-(2-(azetidin-1-yl)ethoxy)-4-(pyridin-3-yl)piperidine-1-carboxylate [amine E] (0.15 g, 1.2 eq.) in the presence of TFA (10-13 eq.) in methylene chloride (see e.g. stage (iii)/amine H), the amine was added to a cooled (0° C.) solution comprising (S)-2-((1-

(4-methoxy-2,6-dimethylphenylsulfonyl)piperidin-2-yl)methoxy)acetic acid [acid D] (1 eq.), EDCl (1.5 eq.), HOBT (1 eq.) and DIPEA (3 eq.) in methylene chloride (10 ml). When the addition was complete, the reaction mixture was warmed to room temperature and stirred for 16 h. The reaction mixture was diluted with methylene chloride and washed with aqueous ammonium chloride solution and aqueous sodium bicarbonate solution. After concentration, the crude product was purified by means of column chromatography (Alox). Yield: 39%. MS, $R_t$=2.7 min, m/z=615.4 $[MH]^+$

Example 62

2-Chloro-N-cyclopropyl-N-[2-[2-[4-(3-fluorophenyl)-4-(2-pyrrolidin-1-yl-ethoxy)-piperidin-1-yl]-2-oxo-ethoxy]-ethyl]-6-methyl-benzenesulfonic Acid Amide

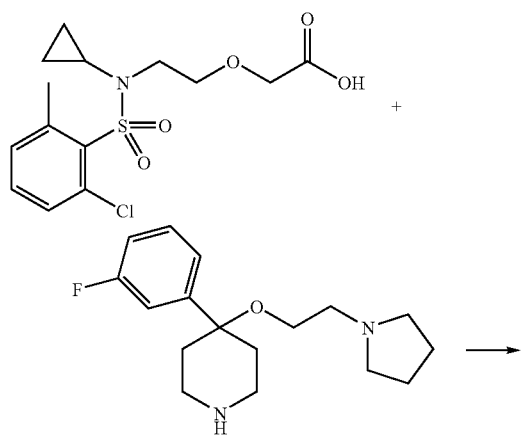

DIPEA (2 eq.) and HATU (1.2 eq.) were added to a solution of tetrahydrofuran and 2-(2-(2-chloro-N-cyclopropyl-6-methylphenylsulfonamido)ethoxy)acetic acid [acid K] (1 eq.) at 0° C. 4-(3-Fluorophenyl)-4-(2-(pyrrolidin-1-yl)ethoxy)piperidine [amine C] (1.2 eq.) was taken up in tetrahydrofuran (2 ml/mmol) and the solution was rendered basic with DIPEA (2 eq.) and added to the reaction mixture at 0° C. The reaction mixture was stirred at 25° C. for 16 h. The mixture was concentrated to dryness on a rotary evaporator, the residue was taken up in methylene chloride and the mixture was washed with water and sat. sodium chloride solution and dried over sodium sulfate. The organic phase was concentrated and the crude product was purified by means of column chromatography (5% methanol in methylene chloride). Yield: 60%. MS, $R_t$=3.6 min, m/z=622.4 $[MH]^+$ Syntheses of the Carboxylic Acids (Acid Units) for Individual Substance Syntheses (S)-2-((1-(4-Methoxy-2,6-dimethylphenylsulfonyl)-1,2,3,4-tetrahydroquinolin-2-yl)methoxy)acetic Acid [Acid A]

Employed in the Synthesis to Give Example 1

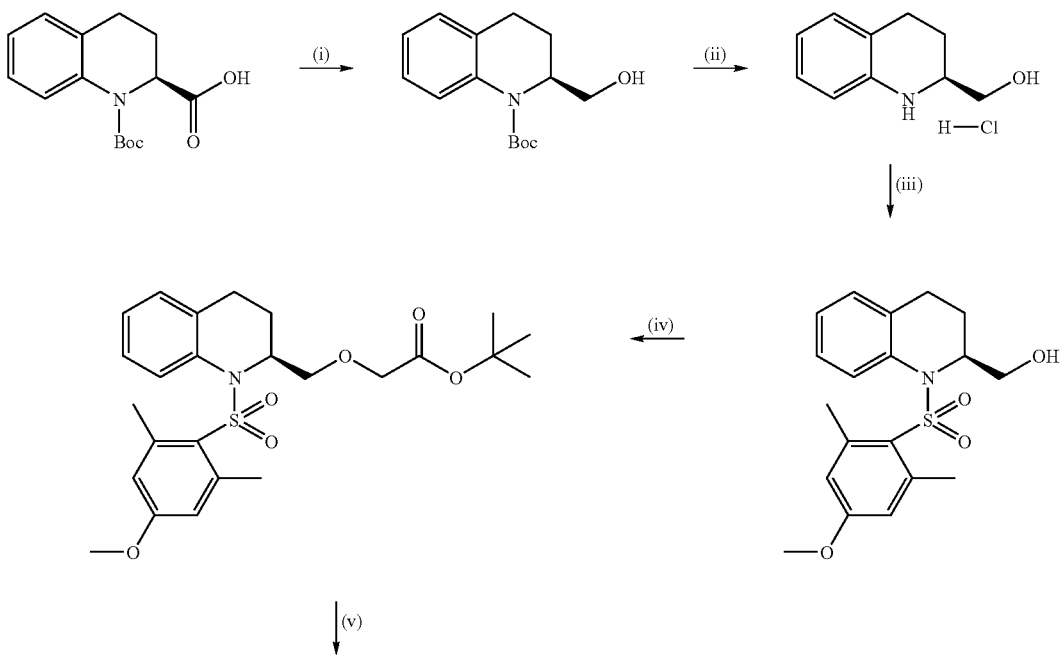

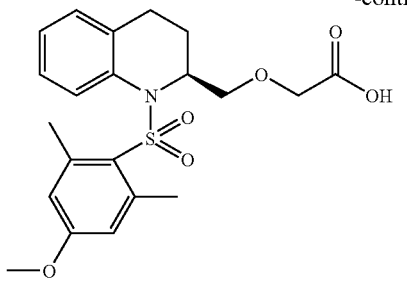

(i): (S)-1-(tert-Butoxycarbonyl)-1,2,3,4-tetrahydroquinoline-2-carboxylic acid (5 g, 18.03 mmol) was initially introduced into tetrahydrofuran (40 ml) and the mixture was cooled. Boron hydride-tetrahydrofuran complex (27 ml, 1 mol/l in THF) was cautiously added dropwise at 0° C. and the mixture was then stirred at room temperature for 15 h. The reaction mixture was cooled again, water (8 ml) was slowly added dropwise at 0° C., potassium carbonate (4.21 g, 30.65 mmol) was then added and the mixture was stirred for 30 min. After the phase separation the aqueous phase was extracted with diethyl ether (2×30 ml) and the combined organic phases were washed with saturated sodium chloride solution (30 ml), dried over sodium sulfate and concentrated in vacuo. The crude product was purified by column chromatography (silica gel) with hexane/ethyl acetate 2/1.

Yield: 3.98 g, 83%

(ii): Hydrogen chloride in methanol (1.25 mol/l, 60 ml) was added to (S)-tert-butyl 2-(hydroxymethyl)-3,4-dihydroquinoline-1(2H)-carboxylate (3.98 g, 15.1 mmol) and the mixture was refluxed for 2 h. The solvent was removed in vacuo, the residue was taken up in ethanol (5 ml) and the mixture was cooled. Diethyl ether (200 ml) was added and the mixture was stirred in an ice bath for 30 min. The precipitate was filtered out with suction, washed with diethyl ether and dried in vacuo.

Yield: 2.72 g, 90%

(iii): Pyridine (5.5 ml, 68.11 mmol) was added dropwise to a cooled solution of (S)-(1,2,3,4-tetrahydroquinolin-2-yl) methanol hydrochloride (2.72 g, 13.62 mmol) in methylene chloride (50 ml) and triethylamine (5.66 ml, 40.87 mmol) at 0° C., followed by 4-dimethylaminopyridine (16 mg, catalytic). 4-Methoxy-2,6-dimethylbenzenesulfonyl chloride (3.836 g, 16.35 mmol, synthesis see above), dissolved in methylene chloride (35 ml), was slowly added dropwise and the mixture was then warmed slowly to room temperature and stirred for 15 h. The reaction mixture was washed with saturated copper sulfate solution (20 ml) and saturated sodium chloride solution (20 ml), dried over sodium sulfate and concentrated in vacuo. The crude product was purified by column chromatography (silica gel) with hexane/ethyl acetate 2/1. Yield: 1.22 g, 24%

(iv): tert-Butyl 2-bromoacetate (1.358 g, 6.972 mmol) and tetra-n-butylammonium hydrogen sulfate (110 mg, 0.332 mmol) were stirred in sodium hydroxide solution (26 ml, 50% aq.) and toluene (20 ml). A solution of (S)-(1-(4-methoxy-2, 6-dimethylphenylsulfonyl)-1,2,3,4-tetrahydroquinolin-2-yl) methanol (1.2 g, 3.32 mmol) in toluene (10 ml) was added slowly. The addition was exothermic, cooling with an ice bath. After stirring at room temperature for 1 h, the phases were separated, the aqueous phase was extracted with diethyl ether (2×50 ml) and the combined organic phases were washed with saturated sodium chloride solution (30 ml), dried ($Na_2SO_4$) and concentrated in vacuo. The crude product was purified by column chromatography (silica gel) with hexane/ethyl acetate 5/1. Yield: 1.03 g, 65%.

(v): (S)-tert-butyl 2-((1-(4-Methoxy-2,6-dimethylphenylsulfonyl)-1,2,3,4-tetrahydroquinoline-2-yl)methoxy)acetate (1 g, 2.103 mmol) was dissolved in methylene chloride (15 ml) and trifluoroacetic acid (3.24 ml, 42.05 mmol) was added slowly. After stirring at room temperature for 2 h, the solvent was removed in vacuo and the residue was co-evaporated twice more with 20 ml of toluene each time. Yield: 0.84 g, 95%.

4-(1-(4-Methoxy-2,6-dimethylphenylsulfonyl)piperidin-2-yl)butanoic Acid [Acid B]

Employed in the Synthesis to Give Example 2

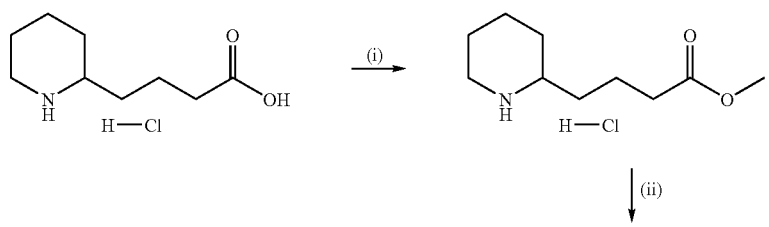

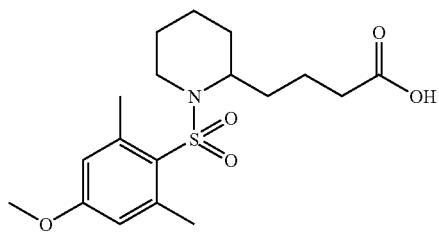
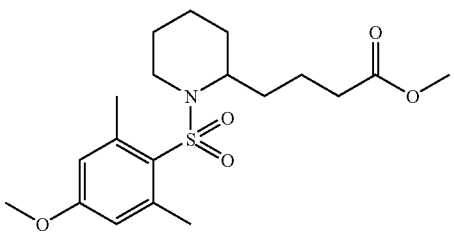

-continued (i): Hydrogen chloride in methanol 1.25 mol/l (58 ml, 72.43 mmol) was added to 4-piperidin-2-ylbutanoic acid hydrochloride (1.5 g, 7.243 mmol). The mixture was refluxed for 6 h, cooled to room temperature and stirred for 3 d. Thin layer chromatography control still showed educt, and the mixture was topped up with hydrogen chloride in methanol (4 ml) and refluxed for 3 h. The reaction mixture was concentrated in vacuo and the residue was taken up in ethanol/ether 1/1 (5 ml). The solution was slowly added dropwise to ice-cooled ether (300 ml), the resulting suspension was stirred in an ice bath for 1 h and the solid was filtered out with suction, washed with ether and dried in vacuo. Yield: 1.21 g (75%), white solid.

and lithium hydroxide was added (0.3 g, 12.9 mmol). The mixture was stirred at room temperature for 3 d, the methanol was then distilled off in vacuo and ethyl acetate (50 ml) and HCl solution (1 mol/l, 10 ml) were added to the residue. The phases were separated and the aqueous phase was extracted with ethyl acetate (2×50 ml). The combined organic phases were dried over sodium sulfate and concentrated in vacuo. Yield: 1.56 g (98%)

2-(2-(N-Cyclopropyl-4-methoxy-2,6-dimethylphenylsulfonamido)ethoxy)acetic Acid [Acid C]

Employed in the Synthesis to Give Example 3

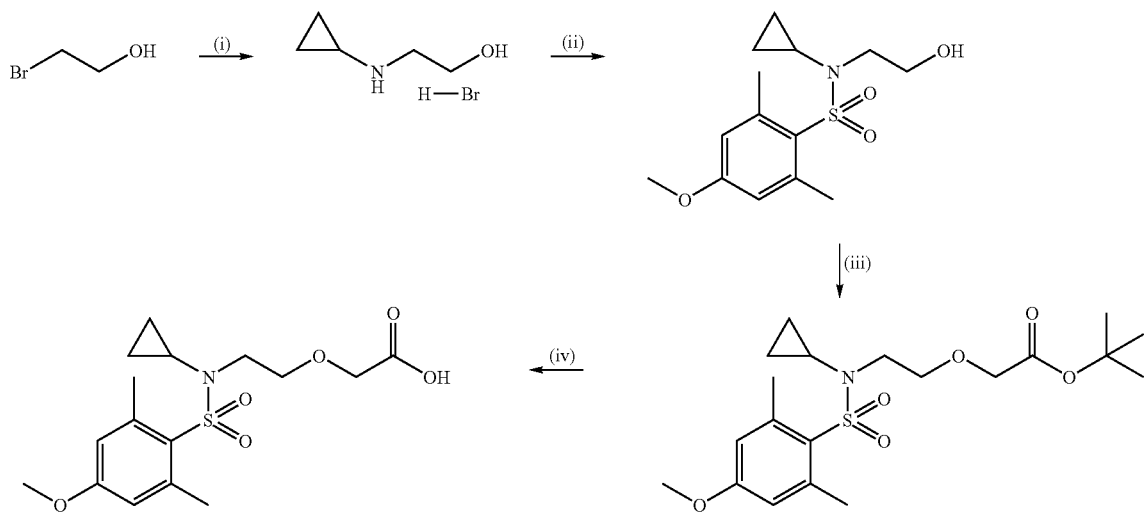

(ii): Methyl 4-(piperidin-2-yl)butanoic acid methyl ester hydrochloride (1.26 g, 5.683 mmol) was dissolved in methylene chloride (25 ml) and triethylamine (4 ml, 28.417 mmol) and a solution of 4-methoxy-2,6-dimethylbenzenesulfonic acid chloride (2.67 g, 11.37 mmol, synthesis in the following) in methylene chloride (10 ml) was added. The mixture was stirred at room temperature overnight. 1 mol/l of HCl solution (10 ml) was added to the reaction mixture, the phases were separated and the aqueous phase was extracted with methylene chloride (2×20 ml). The combined organic phases were washed with sat. sodium chloride solution (20 ml), dried over sodium sulfate and concentrated in vacuo. The crude product was purified by column chromatography (silica gel) with hexane/methylene chloride/ether (400/100/50). Yield: 1.65 g (75%)

(iii): Methyl 4-(1-(4-methoxy-2,6-dimethylphenylsulfonyl)piperidin-2-yl)butanoic acid methyl ester (1.65 g, 4.3 mmol) was dissolved in water (10 ml) and methanol (35 ml), (i): 2-Bromoethanol (5 g, 40.3 mmol) and cyclopropylamine (5.8 g, 100.8 mmol) were dissolved in ethanol (47 ml) and the mixture was stirred at 50° C. for 16 h. The solvent was removed in vacuo and the residue was co-evaporated three times with 30 ml of toluene each time and dried in vacuo. The crude product was reacted further without purification. Yield: 6.62 g, 90%

(ii): 2-(Cyclopropylamine)ethanol hydrobromide (5 g, 27.46 mmol) was dissolved in methylene chloride (20 ml), the solution was cooled and triethylamine (9.5 ml, 68.644 mmol) was added. A solution of 4-methoxy-2,6-dimethylbenzenesulfonyl chloride (6.44 g, 27.46 mmol, synthesis see below) in methylene chloride (20 ml) was added dropwise at 0° C. and the mixture was then stirred at room temperature for 15 h. Saturated sodium bicarbonate solution (20 ml) was added, the phases were separated, and the aqueous phase was extracted with methylene chloride (20 ml). The combined organic phases were washed with saturated sodium chloride solution (20 ml), dried over sodium sulfate and concentrated in vacuo. The crude product was purified by column chromatography (silica gel) with diethyl ether/hexane/methylene chloride 15/10/5. Yield: 4.74 g, 57%

(iii): tert-Butyl 2-bromoacetate (777 mg, 4 mmol) and tetra-n-butylammonium hydrogen sulfate (92 mg, 0.267 mmol) were stirred in sodium hydroxide solution (10 ml, 50% aq.) and toluene (10 ml). A solution of N-cyclopropyl-N-(2-hydroxyethyl)-4-methoxy-2,6-dimethylbenzenesulfonamide (0.8 g, 2.672 mmol) in toluene (5 ml) was added slowly. The addition was exothermic, cooling with an ice bath. After stirring at room temperature for 1.5 h, the phases were separated, the aqueous phase was extracted with diethyl ether (2×50 ml) and the combined organic phases were washed with saturated sodium chloride solution (30 ml), dried ($Na_2SO_4$) and concentrated in vacuo. The crude product was purified by column chromatography (silica gel) with hexane/diethyl ether/methylene chloride 2/1/1. Yield: 0.96 g, 86%.

(iv): tert-Butyl 2-(2-(N-cyclopropyl-4-methoxy-2,6-dimethylphenylsulfonamido)-ethoxy)acetate (0.95 g, 2.297 mmol) was dissolved in tetrahydrofuran (15 ml), sodium hydroxide (1.1 g, 13.784 mmol) was added and the reaction mixture was heated to 80° C. After 4 h, the mixture was cooled and water (10 ml) was added. The phases were separated and the aqueous phase was adjusted to pH=2 with hydrogen chloride solution (1 mol/l, aq.) and extracted with ethyl acetate (5×30 ml). These combined organic phases were dried over sodium sulfate and concentrated in vacuo. Yield: 0.81 g, 98%.

(S)-2-((1-(4-Methoxy-2,6-dimethylphenysulfonyl)piperidin-2-yl)methoxy)acetic Acid [Acid D]

Employed in the Synthesis to Give Examples 46, 54-57, 59-61 trifluoride etherate (2.1 ml, 117.1 mmol) was added, followed by boron dimethyl sulfide in tetrahydrofuran (dropwise, 3 ml, 30.9 mmol). The reaction mixture was then refluxed for 16 h. The mixture was quenched with ice-cooled methanol (10 ml), hydrogen chloride solution (conc. aq., 3 ml) was added dropwise and the mixture was refluxed for 30 min. After cooling, the mixture was rendered alkaline with dilute sodium hydroxide solution (4% aq.) and extracted with methylene chloride (3×50 ml). The combined organic phases were dried over sodium sulfate and concentrated in vacuo. The crude product was employed in the next stage without further purification. Yield: 44%.

(ii) (a) Chlorosulfonic acid (2 eq.) in methylene chloride (0.2 ml/mmol) was added dropwise to a cooled solution of 3,5-dimethylanisole (1 eq.) in methylene chloride (1.3 ml/mmol) at 0° C. When the reaction was complete (TLC control), ice-water was added and the organic phase was extracted with water and saturated sodium chloride solution. The organic phase was dried over sodium sulfate and concentrated in vacuo. The sulfonyl chloride obtained in this way was further reacted directly without further purification. Yield: 70%; (b) (S)-Piperidin-2-ylmethanol (1.1 eq.) was dissolved in methylene chloride (4 ml/mmol), the solution was cooled and triethylamine (2.5 eq.) was added. A solution of 4-methoxy-2,6-dimethylbenzenesulfonyl chloride (1 eq.) in methylene chloride (2 ml/mmol) was added dropwise at 0° C. and the mixture was then stirred at room temperature for 90 min. Hydrogen chloride solution (aq., 0.5 mol/l, 2 ml/mmol) was added, the mixture was stirred for 15 min and the phases were separated. The organic phase was washed with water, dried over sodium sulfate and concentrated in vacuo. The crude product was employed in the next stage without further purification.

Yield: 20%

(iii): Tetra-n-butylammonium chloride (0.33 eq.) and sodium hydroxide solution (5 ml/mmol, 35% aq.) were added

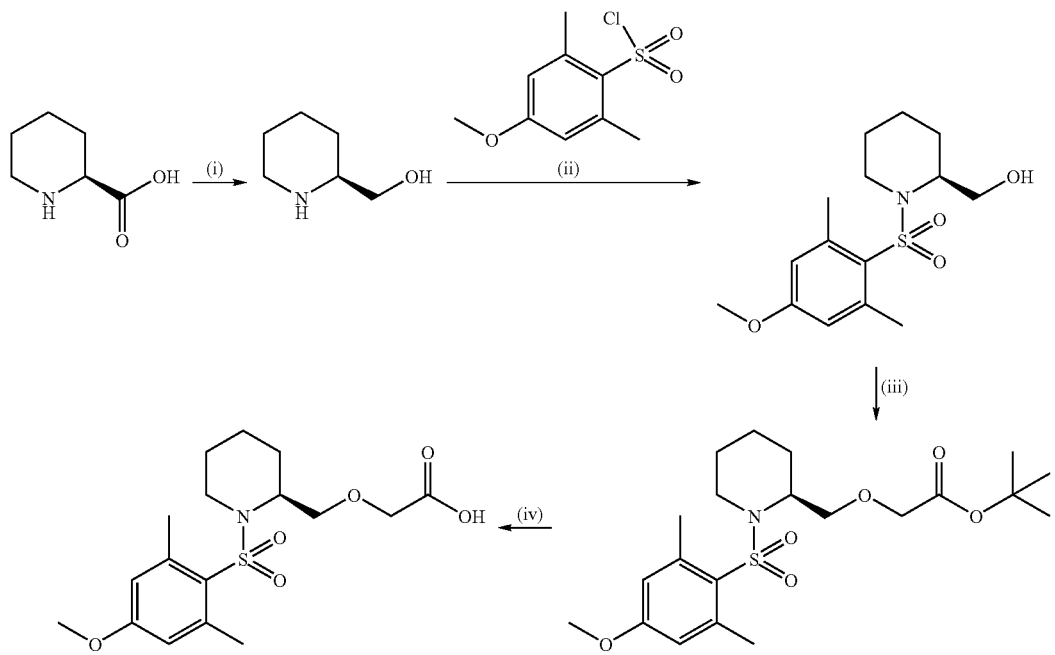

(i): (S)-Piperidine-2-carboxylic acid (2 g, 15.5 mmol) was initially introduced into tetrahydrofuran (20 ml), and boron to a cooled solution of (S)-(1-(4-methoxy-2,6-dimethylphenylsulfonyl)piperidin-2-yl)methanol (1 eq.) in toluene (5 ml/mmol) at 0° C.). tert-Butyl 2-bromoacetate (1.5 eq.) was then slowly added dropwise at 0° C. After stirring at room temperature for 90 min, the phases were separated and the organic phase was washed with water to pH neutrality, dried over sodium sulfate and concentrated in vacuo. The crude product was employed in the next stage without further purification. Yield: 64%

(iv): (S)-tert-Butyl 2-((1-(4-methoxy-2,6-dimethylphenylsulfonyl)piperidin-2-yl)methoxy)acetate (1 eq.) was dissolved in methylene chloride (10 ml/mmol), the solution was cooled and trifluoroacetic acid (13 eq.) was slowly added at 0° C. After stirring at room temperature for 2 h, the reaction mixture was concentrated in vacuo and the residue was dried. The crude product was employed in the next stage without further purification. [Alternatively, it is also possible to use 3 eq. of TFA.] Yield: quantitative, (S)-2-((1-(2-(Trifluoromethyl)phenylsulfonyl)piperidin-2-yl)methoxy)acetic Acid [Acid E]

Employed in the Synthesis to Give Example 47

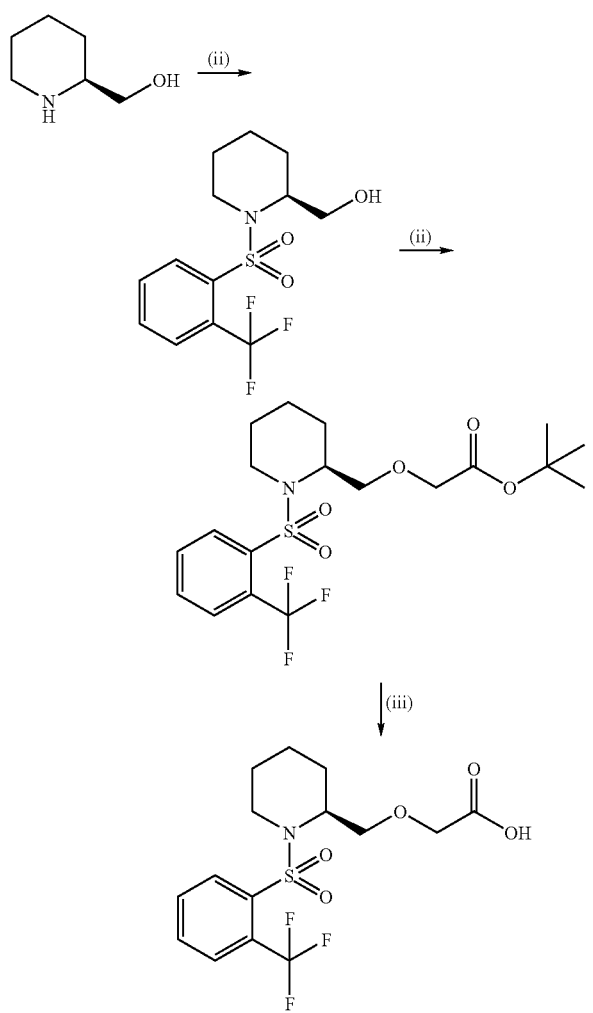

(i): (S)-Piperidin-2-ylmethanol (1.1 eq.) was dissolved in methylene chloride (4 ml/mmol), and triethylamine (2.5 eq.) was added. A solution of 2-(trifluoromethyl)benzenesulfonyl chloride (1 eq.) in methylene chloride (2 ml/mmol) was added dropwise at 0° C. and the mixture was then stirred at room temperature for 90 min. Hydrogen chloride solution (aq., 0.5 mol/l, 2 ml/mmol) was added, the mixture was stirred for 15 min and the phases were separated. The organic phase was washed with water, dried over sodium sulfate and concentrated in vacuo. The crude product was used in the next stage without further purification. Yield: 33%.

(ii): Tetra-n-butylammonium chloride (0.33 eq.) and sodium hydroxide solution (5 ml/mmol, 35% aq.) were added to a cooled solution of (S)-(1-(2-trifluoro-methyl)phenylsulfonyl)piperidin-2-yl)methanol (1 eq.) in toluene (5 ml/mmol) at 0° C. tert-Butyl 2-bromoacetate (1.5 eq.) was then slowly added dropwise at 0° C. After stirring at room temperature for 90 min, the phases were separated and the organic phase was washed with water to pH neutrality, dried over sodium sulfate and concentrated in vacuo. The crude product was employed in the next stage without further purification. Yield: 76%

(iii): (S)-tert-Butyl 2-((1-(2-(trifluoromethyl)phenylsulfonyl)piperidin-2-yl)methoxy)acetate (1 eq.) was dissolved in methylene chloride (10 ml/mmol), the solution was cooled and trifluoroacetic acid (13 eq.) was slowly added at 0° C. After stirring at room temperature for 2 h, the reaction mixture was concentrated in vacuo and the residue was dried. The crude product was employed in the next stage without further purification. Yield: quantitative.

(S)-2-((1-(2-Chloro-6-methylphenylsulfonyl)piperidin-2-yl)methoxy)acetic Acid [Acid F]

Employed in the Synthesis to Give Example 48

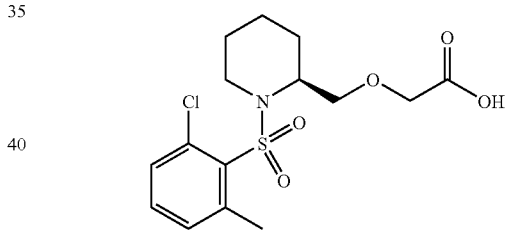

The synthesis was carried out analogously to the synthesis route described for (S)-2-((1-(2-(trifluoromethyl)phenylsulfonyl)piperidin-2-yl)methoxy)acetic acid [acid E], 2-chloro-6-methylbenzene-1-sulfonyl chloride being employed in stage (i).

2-(2-(N-Benzhydryl-2,4-dichlorophenylsulfonamido)ethoxy)acetic Acid [Acid G]

Employed in the Synthesis to Give Example 4

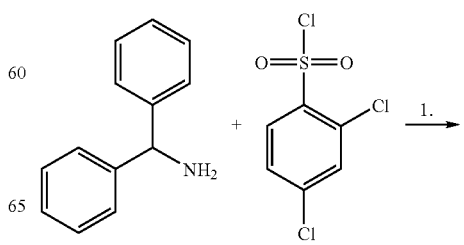

-continued

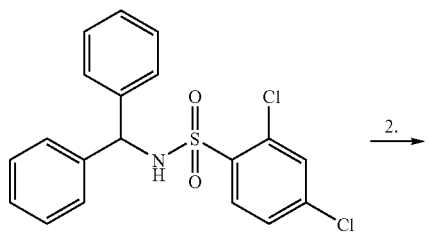

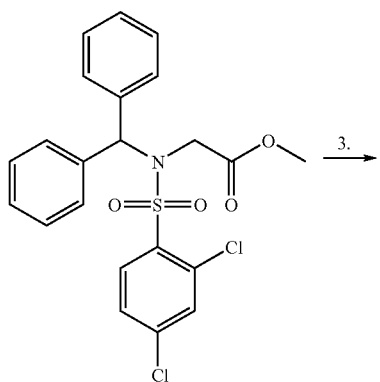

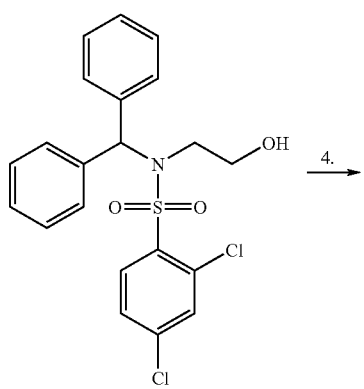

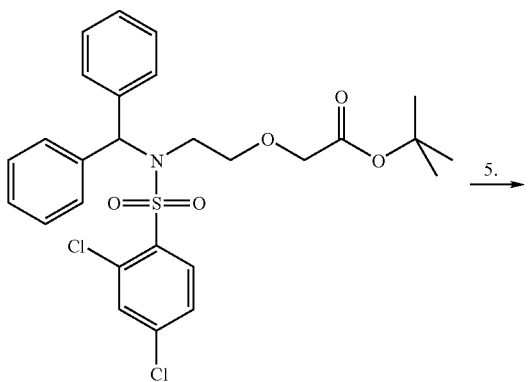

-continued

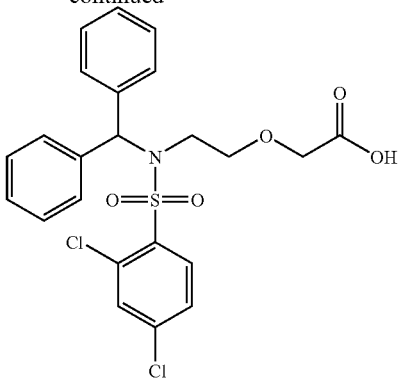

Stage 1. The reaction was carried out under an $N_2$ atmosphere. A solution of the 2,4-dichlorobenzenesulfonyl chloride (15.0 g, 61.1 mmol) in MC (40 ml) was added dropwise to a solution of diphenylmethanamine (11.2 g, 61.1 mmol) and triethylamine (8.49 ml, 61.1 mmol) in MC (100 ml) at 0° C. in the course of 10 min. The mixture was stirred at RT overnight and the organic phase was then washed with $KHSO_4$ solution (0.5 M, 2×100 ml) and sat. NaCl solution. The solid which had precipitated out was filtered out and the filtrate was concentrated. The residue was taken up in MC (25 ml) again. The solid which had formed was filtered out, washed with MC and dried on filter paper. Yield: 22.24 g, 93%.

Stage 2. The reaction was carried out under an $N_2$ atmosphere. A solution of the sulfonic acid amide (21.29 g, 54.3 mmol) in acetone (400 ml) was heated under reflux. $K_2CO_3$ (8.25 g, 59.7 mmol) was added and the mixture was stirred for 20 min. Bromoacetic acid ethyl ester (10.31 ml, 109 mmol) was then added and the mixture was stirred for 5 h. LCMS control showed that the reaction was not yet complete. The mixture was cooled to RT and stirred at this temperature over the weekend. Subsequent LCMS control showed complete conversion. The solids were filtered out and the filtrate was concentrated to dryness i. vac. The oil obtained was crystallized from diisopropyl ether/heptane. Yield: 20.45 g, 81%.

Stage 3. The reaction was carried out under an $N_2$ atmosphere. A solution of $LiBH_4$ in THF (2 M, 21.86 ml, 43.7 mmol) was added dropwise to a solution of the ester from stage 2 (20.3 g, 43.7 mmol) in dry THF (20 ml). The reaction mixture was stirred at RT overnight, subsequently heated at 40° C. for 3 h, cooled again to RT and stirred at RT over the weekend. Since the reaction had not yet ended, further $LiBH_4$ in THF (2 M, 4.0 ml, 8.0 mmol) was added dropwise. The mixture was heated again at 40° C. for 5 h, subsequently cooled to RT and stirred at RT overnight. According to LCMS control, the conversion was almost complete. Water (10 ml) was cautiously added and the mixture was stirred at RT for 30 min. The solid formed was filtered out, the filtrate was dried over $Na_2SO_4$ and the solvent was stripped off on a rotary evaporator. The crude product was purified by column chromatography (silica gel, heptane/ethyl acetate 1:1). Yield: 15.71 g, 82%.

Stage 4. Aqueous NaOH (35%, 200 ml) followed by tert-butyl bromoacetate (7.64 ml, 51.7 mmol) were added to a solution of the alcohol from stage 3 (15.05 g, 34.54 mmol) and $Bu_4NCl$ (2.7 g, 9.72 mmol) in MC (200 ml). The reaction mixture was stirred at RT for 2 h. Since the conversion was not complete (TLC control), further tert-butyl bromoacetate (3.82 ml, 25.9 mmol) was added and the mixture was stirred again at RT for 2 h. When the reaction had ended (TLC control), the phases were separated and the organic phase was washed with water and sat. NaCl solution, dried over Na₂SO₄ and concentrated. The crude product was purified by column chromatography (silica gel, heptane/ethyl acetate 95:5→9:1). Yield: 13.8 g, 73%

Stage 5. NaOH (10.0 g, 250.7 mmol) was added to a solution of the ester from stage 4 (13.8 g, 25.1 mmol) in a mixture of methanol (135 ml), THF (60 ml) and water (15 ml). The reaction mixture was stirred at RT for 2 h. The solvent was then removed on a rotary evaporator. MC (100 ml), water (50 ml) and then, at 0° C., KHSO₄ (0.5 M) were added and a pH of 2-3 was established. The phases were separated and the aqueous phase was then extracted with MC (2×100 ml). The combined organic phases were washed with water and sat. NaCl solution, dried over Na₂SO₄ and concentrated i. vac. The residue was taken up in MC and the mixture was concentrated again i. vac. The crude product (white foam) was employed further without further purification. Yield: 11.15 g, 90%.

The synthesis of 2-(2-(N-benzhydryl-4-methoxy-2,6-dimethylphenyl-sulfonamido)ethoxy)acetic acid [acid H] (employed in the synthesis to give Example 6) proceeds analogously to the synthesis of 2-(2-(N-benzhydryl-2,4-dichlorophenylsulfonamido)ethoxy)acetic acid [acid G].

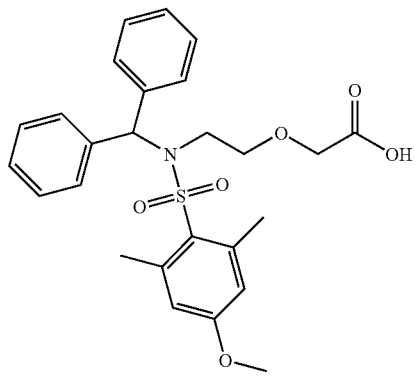

2-(2-(4-Methoxy-2,6-dimethyl-N-(pyridin-3-ylmethyl)phenylsulfonamido)-ethoxy)acetic Acid [Acid 1]

Employed in the Synthesis to Give Example 5

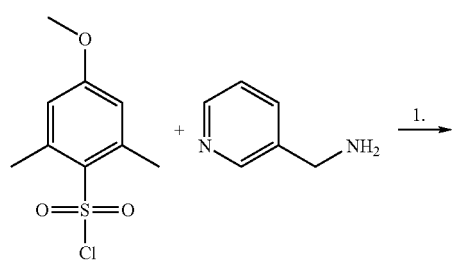

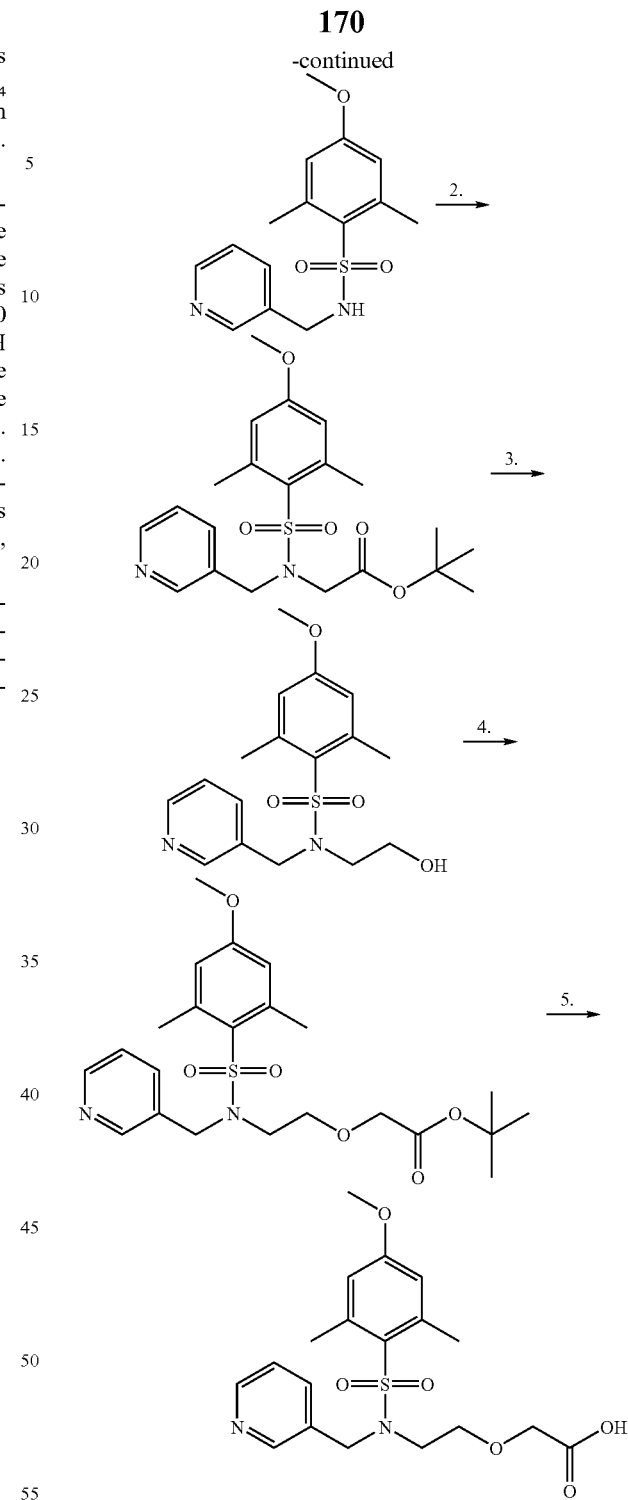

Stage 1. A solution of 4-methoxy-2,6-dimethylbenzene-1-sulfonyl chloride (8.0 g, 34.1 mmol) in MC (75 ml) was added dropwise to a solution of pyridin-3-ylmethanamine (3.48 ml, 34.1 mmol) and triethylamine (5.23 ml, 37.5 mmol) in MC (150 ml) at 0° C. The mixture was stirred at RT overnight and the organic phase was then washed with sat. NaCl solution (250 ml), dried over Na₂SO₄ and concentrated. The crude product was employed further without further purification.

Stage 2. Aqueous NaOH (35%, 78 ml) was added to a solution of the sulfonamide (11.85 g, max. 34.1 mmol) and Bu₄NCl (3.13 g, 11.25 mmol) in MC (100 ml) at 0° C., and after a reaction time of 10 min, tert-butyl bromoacetate (5.46 ml, 37.5 mmol) was added. The reaction mixture was stirred at RT for 2 h. When the reaction had ended (TLC control), the phases were separated and the organic phase was washed with water (3×200 ml), dried over Na₂SO₄ and concentrated. The crude product was purified by column chromatography (silica gel, MC/methanol 99:1). Yield: 12.02 g, 84% (two stages)

Stage 3. A solution of the ester from stage 2 (12.0 g, 28.5 mmol) in dry THF (100 ml) was added dropwise to a stirred and cooled solution of LAH (2 M in THF, 28.5 ml, 57.1 mmol) in dry THF (50 ml). The reaction mixture was stirred at 0° C. for 15 min. Na₂SO₄.10H₂O was then added until no further evolution of gas was observed. The reaction mixture was filtered over a narrow bed of Na₂SO₄ and the filtrate was concentrated to dryness. The crude product was employed further without further purification. Yield: 9.44 g, 94%

Stage 4. Aqueous NaOH (35%, 61.6 ml) was added to a solution of the alcohol from stage 3 (9.44 g, 26.9 mmol) and Bu₄NCl (2.47 g, 8.89 mmol) in MC (100 ml) at 0° C., and after a reaction time of 10 min, tert-butyl bromoacetate (4.12 ml, 28.3 mmol) was added. The reaction mixture was stirred at RT for 2 h. When the reaction had ended (TLC control), the phases were separated and the organic phase was washed with water (3×200 ml), dried over Na₂SO₄ and concentrated. The crude product was purified by column chromatography (silica gel, MC/methanol 99:1). Yield: 7.35 g, 59%.

Stage 5. NaOH (6 M, 77 ml, 465 mmol) was added to a solution of the ester from stage 4 (10.79 g, 23.23 mmol) in a mixture of methanol (80 ml), THF (80 ml) and water (15 ml). The reaction mixture was stirred at RT for 2 h. The solvent was then removed on a rotary evaporator. The residue was taken up in aqueous HCl solution (6 M, 82 ml) at 0° C. and the mixture was extracted with MC (2×150 ml). The combined organic phases were dried over Na₂SO₄ and concentrated. The crude product was employed further without further purification. Yield: 9.1 g, 96%.

2-(2-(2,4-Dichloro-N-(2,3-dihydro-1H-inden-1-yl) phenylsulfonamido)-ethoxy)acetic Acid [Acid J]

Employed in the Synthesis to Give Example 7

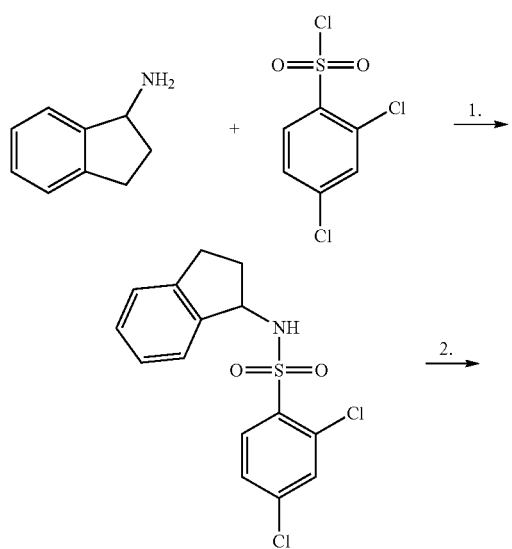

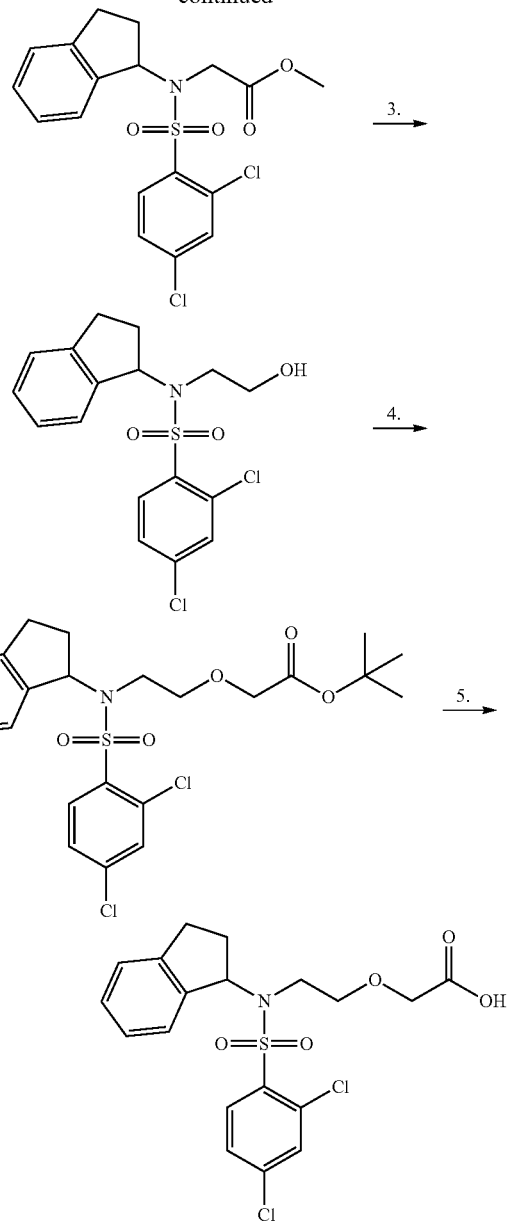

Stage 1. The reaction was carried out under an N₂ atmosphere. A solution of 2,4-dichlorobenzenesulfonyl chloride (18.4 g, 74.9 mmol) in MC (50 ml) was added dropwise to a solution of 1-aminoindane (10.0 g, 75 mmol) and triethylamine (15.7 ml, 113 mmol) in MC (50 ml) at 0° C. The mixture was then stirred at RT for 1 h. When the reaction had ended (TLC control), the organic phase was washed with KHSO₄ solution (0.5 M, 3×50 ml) and sat. NaCl solution, dried over Na₂SO₄ and concentrated. The crude product was employed further without further purification. Yield: 24.56 g, 96%

Stage 2. The reaction was carried out under an N₂ atmosphere. K₂CO₃ (5.42 g, 39.2 mmol) was added to a solution of the sulfonic acid amide (12.21 g, 35.7 mmol) and bromoacetic acid ethyl ester (10.92 g, 71.4 mmol) in acetone (100 ml). The reaction mixture was heated under reflux for 4 h. When the reaction had ended (TLC control), the solution was cooled to RT and filtered. The filtrate was concentrated to dryness i.

vac. The crude product was purified by column chromatography (silica gel, heptane/ethyl acetate, 4:1; the crude product was taken up in ethyl acetate and the mixture was introduced on to the column).

Stage 3. The reaction was carried out under an $N_2$ atmosphere. A solution of $LiBH_4$ in THF (2 M, 16.18 ml, 32.4 mmol) was added dropwise to a solution of the ester from stage 2 (12.19 g, 29.4 mmol) in dry THF (100 ml). The reaction mixture was stirred at RT overnight. Since the reaction had not yet ended (TLC control), further $LiBH_4$ in THF (2 M, 7.36 ml, 14.71 mmol) was added dropwise. After a reaction time of 1 d, $LiBH_4$ in THF (2 M, 7.36 ml, 14.71 mmol) was again added dropwise and the mixture was stirred for a further 7 h. For working up, $Na_2SO_4 \cdot 10H_2O$ was added and the mixture was stirred overnight. The suspension was filtered and the solvent was then removed on a rotary evaporator. The crude product was purified by column chromatography (silica gel, heptane/ethyl acetate 3:1). Yield: 10.12 g, 89%.

Stage 4. Aqueous NaOH (35%, 100 ml) followed by tert-butyl bromoacetate (11.51 ml, 78 mmol) were added to a solution of the alcohol from stage 3 (10.03 g, 26.0 mmol) and $Bu_4NCl$ (2.17 g, 7.81 mmol) in MC (100 ml). The reaction mixture was stirred at RT for 1 h. When the reaction had ended (TLC control), the phases were separated and the organic phase was washed with water (3×100 ml), dried over $Na_2SO_4$ and concentrated. The crude product was purified by column chromatography (silica gel, heptane/ethyl acetate 4:1). Yield: 11.53 g, 89%.

Stage 5. NaOH (9.22 g, 231 mmol) was added to a solution of the ester from stage 4 (11.53 g, 23.04 mmol) in a mixture of methanol (90 ml), THF (40 ml) and water (10 ml). The reaction mixture was stirred at RT for 1 h. The majority of the solvent was then removed. First MC (500 ml) and then, at 0° C., $KHSO_4$ (0.5 M, 500 ml) were added. To improve the phase separation, sat. NaCl solution was added. The aqueous phase was then extracted with ethyl acetate. The combined organic phases were dried over $Na_2SO_4$ and the cloudy solution was concentrated i. vac. The residue was taken up in ethyl acetate (300 ml) and the mixture was left to stand at RT for 1 h, during which a white powder separated out. $Na_2SO_4$ was added and, after 1 h, the suspension was filtered. The clear solution obtained was concentrated and the product was dried on a filter. Yield: 9.35 g, 91%.

2-(2-(2-Chloro-N-cyclopropyl-6-methylphenylsulfonamido)ethoxy)acetic Acid [Acid K]

Employed in the Synthesis to Give Example 62

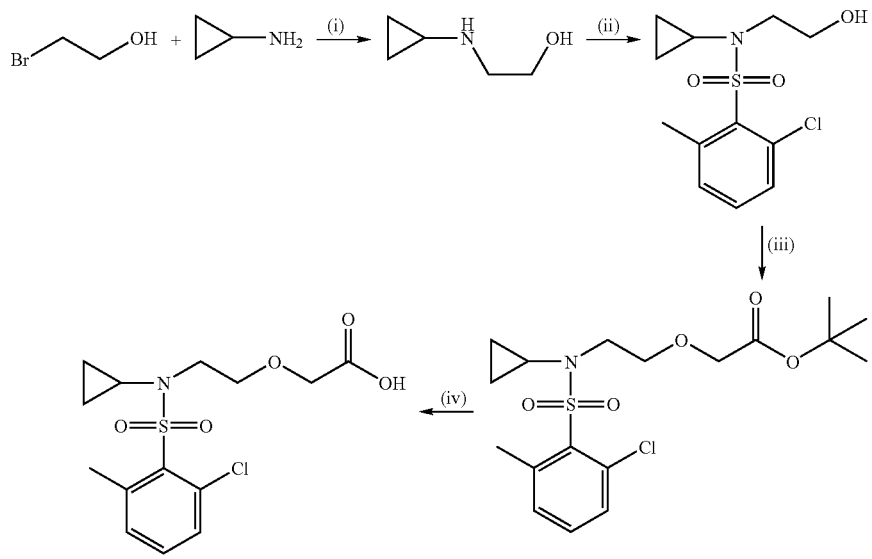

(i): Cyclopropylamine (5 g, 1 eq.) was dissolved in ethanol (60 ml), and 2-bromoethanol (0.5 eq.) was added. The reaction mixture was heated at 60° C. for 16 h. The reaction mixture was concentrated to dryness on a rotary evaporator and the residue was employed in the following stage without further purification. Yield: 70%

(ii): Triethylamine (2.5 eq.) was added to 2-(cyclopropylamino)ethanol (2 eq.) and the mixture was cooled to 0° C. 2-Chloro-6-methylbenzenesulfonyl chloride (1 eq.) was added to this cooled reaction mixture and the mixture was stirred at 25° C. for 2 h. The mixture was then diluted with methylene chloride and the organic phase was washed with water and sat. sodium chloride solution and dried over sodium sulfate. The solvent was removed on a rotary evaporator and the crude product was purified by column chromatography (10% ethyl acetate in hexane). Yield: 50%.

(iii): Tetrabutylammonium chloride (0.1 eq.) and 35% strength sodium hydroxide solution (15 ml) were added to a cooled solution of 2-chloro-N-cyclopropyl-N-(2-hydroxyethyl)-6-methylbenzenesulfonamide (1 eq.) in methylene chloride (15 ml) at 0° C. tert-Butyl 2-bromoacetate (1.2 eq.) was added dropwise at this temperature and the mixture was stirred at room temperature for 16 h (TLC control). The mixture was then diluted with methylene chloride and the organic phase was washed with water and sat. sodium chloride solution and dried over sodium sulfate. The solvent was removed on a rotary evaporator and the crude product was purified by column chromatography (20% ethyl acetate in hexane). Yield: 70%.

(iv): TFA (13 eq.) was added to a methylene chloride solution (10 ml/mmol) of tert-butyl 2-(2-(2-chloro-N-cyclopropyl-6-methylphenylsulfonamido)ethoxy)acetate (1 eq.) at 0° C. and the mixture was stirred at room temperature for 2 h.

The solvent was removed and the residue was dried in vacuo. The desired compound obtained in this way was employed in the next stage without further purification. Yield: quantitative.

Syntheses of the Amines (Amine Units) for Individual Substance Syntheses 3-(4-((2-(Pyrrolidin-1-yl)ethoxy)methyl)piperidin-4-yl)pyridine [Amine A]

Employed in the Synthesis to Give Example 49

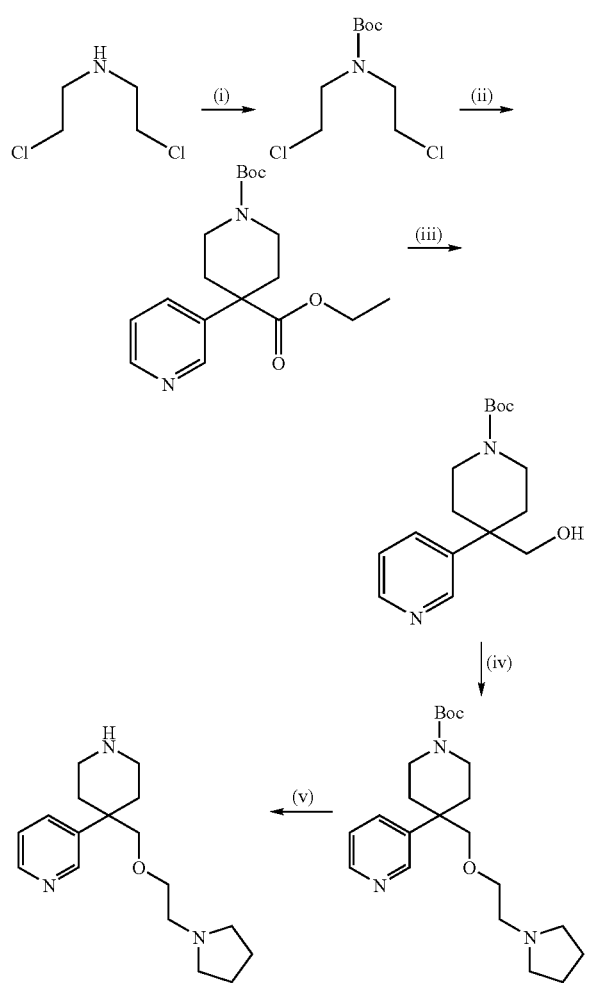

(i): Bis-(2-chloroethylamine (16.34 g, 91.5 mmol) was dissolved in methylene chloride (150 ml) and triethylamine (40 ml, 293 mmol), the solution was cooled and Boc anhydride (20 ml, 218 mmol) was added dropwise at 0° C. The reaction mixture warmed up to room temperature and was stirred for 16 h. Hydrolysis was carried out with ice and the mixture was extracted with methylene chloride (500 ml). The organic phase was washed with water and saturated sodium chloride solution, dried over sodium sulfate, filtered and concentrated in vacuo. The crude product was purified by column chromatography (silica gel) with 20% ethyl acetate in hexane. Yield: 49%

(ii): A solution of pyridin-3-ylacetic acid ethyl ester (5 g, 30 mmol) in dry N,N-dimethylformamide (20 ml) was added dropwise to a suspension of potassium tertiary butylate (7.54 g, 66.6 mmol) in dry N,N-dimethylformamide (30 ml) at 0° C. under argon. The reaction mixture was stirred at room temperature for 45 min and then cooled again to 0° C., and tert-butyl bis(2-chloroethyl)carbamate (7.23 g, 30 mmol), dissolved in N,N-dimethylformamide (20 ml), was added dropwise. The ice bath was removed and the mixture was stirred at room temperature for 16 h. The reaction mixture was extracted with ethyl acetate (300 ml). The organic phase was washed with water and saturated sodium chloride solution, dried over sodium sulfate, filtered and concentrated in vacuo. The crude product was purified by column chromatography (Alox neutral) with 5% ethyl acetate in hexane.

Yield: 24%.

(iii): A solution of 1-tert-butyl 4-ethyl 4-(pyridin-3-yl)piperidine-1,4-dicarboxylate (2.45 g, 7.3 mmol) in dry tetrahydrofuran (30 ml) was added in 2 portions to a suspension of lithium aluminium hydride (335 mg, 8.8 mmol) in dry tetrahydrofuran (25 ml) at 0° C. under argon. The mixture was stirred at the same temperature for 1 h, hydrolysis was then carried out with saturated sodium sulfate solution and the mixture was stirred at room temperature for 30 min. The reaction mixture was filtered over Celite, the residue was rinsed with ethyl acetate (3×50 ml) and the filtrate was concentrated in vacuo. The crude product was employed in the next synthesis step without further purification. Yield: quantitative (iv): Crushed potassium hydroxide (5 eq.) and 1-(2-chloroethyl)pyrrolidine hydrochloride (1.5 eq.) were added to a solution of tert-butyl 4-(hydroxymethyl)-4-pyridin-3-yl)piperidine-1-carboxylate (1 eq.) in benzene (5 ml/mmol). The reaction mixture was refluxed for 16 h and the benzene was then removed in vacuo. The residue was dissolved in methylene chloride and the solution was washed with water and saturated sodium chloride solution, dried over sodium sulfate and concentrated in vacuo. The crude product was purified by column chromatography (Alox neutral) with 2% methanol in methylene chloride. Yield: 67%.

(ii): tert-Butyl 4-(pyridin-3-yl)-4-((2-(pyrrolidin-1-yl)ethoxy)methyl)piperidine-1-carboxylate (1 eq.) was dissolved in methylene chloride (10 ml/mmol), the solution was cooled and trifluoroacetic acid (13 eq.) was added slowly. After stirring at room temperature for 2 h, the reaction mixture was concentrated in vacuo and the residue was dried. The crude product was employed in the next stage without further purification. Yield: quantitative.

3-(3-(2-(Pyrrolidin-1-yl)ethoxy)pyrrolidin-3-yl)pyridine [Amine B]

Employed in the Synthesis to Give Example 50

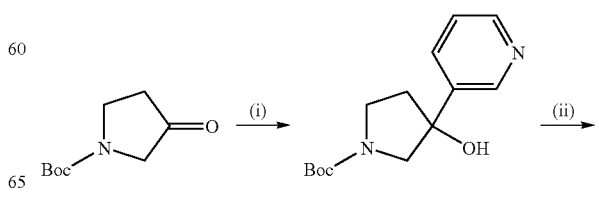

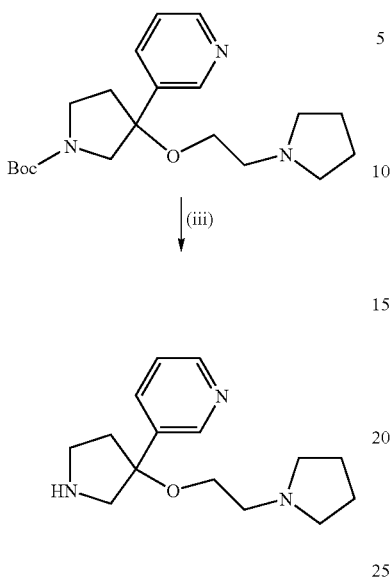

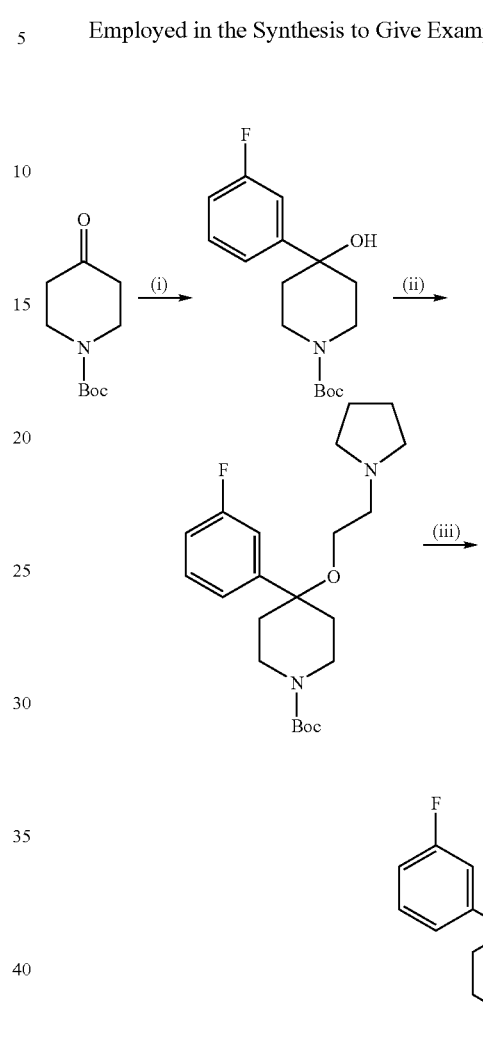

4-(3-Fluorophenyl)-4-(2-(pyrrolidin-1-yl)ethoxy)piperidine [Amine C]

Employed in the Synthesis to Give Example 51, 62

(i): N-Butyllithium in diethyl ether (1.57 mmol/l, 4 ml) was initially introduced into diethyl ether (dry, 12 ml) and the mixture was cooled to −78° C. 3-Bromopyridine (0.6 ml, 6.4 mmol), dissolved in diethyl ether (dry, 6 ml), was slowly added dropwise and the reaction mixture was stirred at this temperature for 20 min. tert-Butyl 3-oxopyrrolidine-1-carboxylate (1 g, 5.39 mmol), dissolved in diethyl ether (6 ml), was slowly added dropwise and the mixture was stirred under unchanged conditions for 1 h. The cooling bath was removed and the reaction mixture was hydrolyzed slowly with water (10 ml) at 0° C. The mixture was diluted with ethyl acetate, washed with saturated sodium chloride solution, dried over sodium sulfate and concentrated in vacuo. The crude product was purified by column chromatography (silica gel) with 4% methanol in methylene chloride. Yield: 38%.

(ii): Crushed potassium hydroxide (0.58 g, 10.41 mmol) and 1-(2-chloroethyl)-pyrrolidine hydrochloride (0.53 g, 3.12 mmol) were added to a solution of tert-butyl 3-hydroxy-3-(pyridin-3-yl)pyrrolidine-1-carboxylate (0.55 g, 2.98 mmol) in benzene (10 ml). The reaction mixture was refluxed for 16 h and the benzene was then removed in vacuo. The residue was dissolved in methylene chloride and the mixture was washed with water and saturated sodium chloride solution, dried over sodium sulfate and concentrated in vacuo. The crude product was purified by column chromatography (Alox neutral) with 2% methanol in methylene chloride. Yield: 67%

(iii): tert-Butyl 3-(pyridin-3-yl)-3-((2-(pyrrolidin-1-yl)ethoxy)pyrrolidine-1-carboxylate (1 eq.) was dissolved in methylene chloride (10 ml/mmol), the solution was cooled and trifluoroacetic acid (13 eq.) was added slowly. After stirring at room temperature for 2 h, the reaction mixture was concentrated in vacuo and the residue was dried. The crude product was employed in the next stage without further purification. Yield: quantitative.

(i) A solution of N-Boc piperidone (10 g, 50 mmol) in anhydrous tetrahydrofuran (50 ml) was added dropwise to 3-fluorophenylmagnesium bromide solution (1 mol/l in tetrahydrofuran, 200 ml, freshly prepared) at 0° C. The reaction mixture was heated slowly to 25° C. and stirred for 18 h. It was then cooled again to 0° C., hydrolysis was carried out with saturated ammonium chloride solution and the mixture was extracted with ethyl acetate (3×200 ml). The combined organic phases were washed with saturated sodium chloride solution, dried over sodium sulfate and concentrated in vacuo. The crude product was purified by column chromatography (silica gel) with 10% acetone in hexane. Yield: 60%.

(ii) A solution of tert-butyl 4-(3-fluorophenyl)-4-hydroxypiperidine-1-carboxylate (3 g, 10 mmol) in benzene (20 ml) followed by 1-(2-chloroethyl)pyrrolidine (2.58 g, 15 mmol) and 18-crown-6-(catalytic) were added to a suspension of anhydrous potassium hydroxide powder (2.8 g, 45 mmol) in anhydrous benzene (30 ml) at 25° C. under argon. The reaction mixture was refluxed for 18 h, cooled again, diluted with ethyl acetate and washed with water (twice) and saturated sodium chloride solution. The organic phase was dried over sodium sulfate, filtered and concentrated in vacuo. The crude product was purified by column chromatography (Alox neutral) with 1% methanol in methylene chloride and the desired compound 4 was present in a pure form. Yield: 62%.

(iii) Trifluoroacetic acid (13 eq.) was added to a solution of tert-butyl 4-(3-fluorophenyl)-4-(2-pyrrolidin-1-yl)ethoxy)piperidine-1-carboxylate in methylene chloride (10 ml/mmol, 1 eq.) at 0° C. The mixture was stirred at room temperature for 2 h, the solvent was then removed in vacuo and the residue was dried in vacuo, residues of trifluoroacetic acid being removed in this way. The crude product was employed in the next stage without further purification. Yield: quantitative.

3-(4-(2-(Pyrrolidin-1-yl)ethoxy)piperidin-4-yl)pyridine Dihydrochloride [Amine D]

Employed in the Synthesis of Example Compounds 1-7

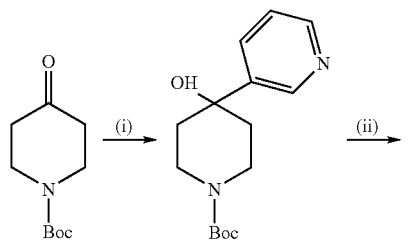

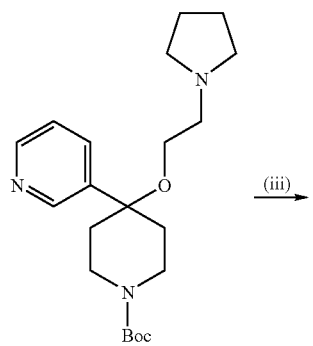

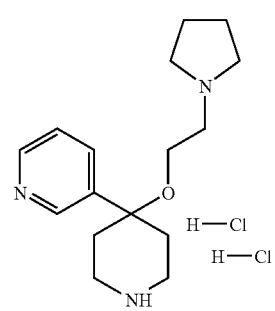

(i) n-Butyllithium (2 eq.) was added to a solution of 3-bromopyridine (7.94 g, 1 eq.) in dry tetrahydrofuran (1,600 ml) at −70° C. and the mixture was stirred at this temperature for 1 h. A solution of N-Boc-piperidone (10 g, 1 eq.) in THF (400 ml) was then added at −70° C. and the mixture was stirred at this temperature for 2 h (TLC control). When the reaction had ended, hydrolysis was carried out with saturated ammonium chloride solution and the mixture was then warmed slowly to RT. It was diluted with ethyl acetate. The organic phase was washed with sodium chloride solution and dried over sodium sulfate. The solvent was removed on a rotary evaporator and the crude product obtained was purified by column chromatography (silica gel, MC/methanol, 9:1).

(ii) tert-Butyl 4-hydroxy-4-pyridin-3-yl)piperidine-1-carboxylate (2 g) was dissolved in benzene (20 ml), sodium amide (10 eq.) was added at 25° C. and the mixture was stirred at this temperature for 15 min. 1-(2-Chloroethyl)pyrrolidine (1.2 eq.) was then added and the mixture was heated under reflux for 16 h. When the reaction had ended (TLC control), the mixture was cooled to 0° C. and hydrolysis was carried out with ice. The aqueous phase was extracted with ethyl acetate. The organic phase was washed with water and saturated NaCl solution and dried over $Na_2SO_4$. The solvent was removed on a rotary evaporator and the crude product obtained was purified by column chromatography (silica gel, MC/methanol, 95:5).

(iii) tert-Butyl 4-(pyridin-3-yl)-4-((2-(pyrrolidin-1-yl)ethoxy)methyl)piperidine-1-carboxylate (12.7 g, 33.82 mmol) was dissolved in methanol (80 ml), the solution was cooled in an ice bath and acetyl chloride (12 ml, 169.1 mmol) was added. After 3 h the reaction had ended according to TLC control (methylene chloride/methanol 9/1), the solvent was removed in vacuo and the residue was taken up in water/methylene chloride. The phases were separated and the aqueous phase was extracted with methylene chloride (2×) and dried by freeze drying.

Yield: quantitative tert-Butyl 4-(2-(azetidin-1-yl)ethoxy)-4-(pyridin-3-yl)piperidine-1-carboxylate [Amine E]

Employed in the Synthesis to Give Example 61

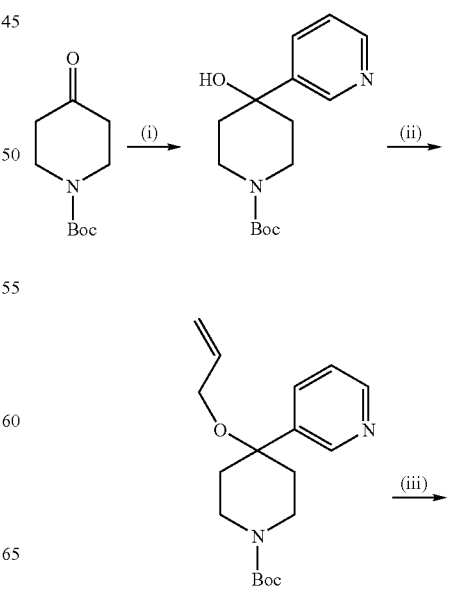

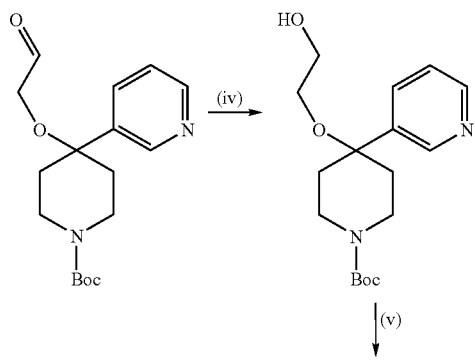

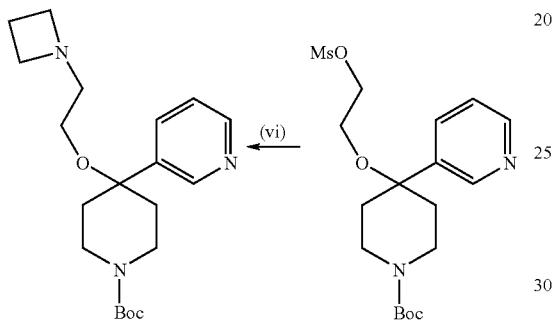

(i) A solution of 3-bromopyridine (9 ml, 93 mmol) in ether (50 ml) was added dropwise to a cooled (−78° C.) solution of n-BuLi (1.1 eq.) in ether (90 ml) and the reaction mixture was stirred for 20 min. tert-Butyl 4-oxopiperidine-1-carboxylate (15 g, 75 mmol) was dissolved in ether (90 ml) and the solution was added slowly to the reaction mixture. The reaction mixture was stirred at −78° C. for 1 h. Water was then added and the reaction mixture was warmed to room temperature. The phases were separated and the organic phase was washed with sat. sodium chloride solution and dried over sodium sulfate. After concentration, the crude product was dissolved in ethyl acetate and precipitated out with hexane. After filtration, the solid was dried in vacuo. Yield: 45%.

(ii) A suspension of tert-butyl 4-hydroxy-4-(pyridin-3-yl)piperidine-1-carboxylate (0.57 g, 2 mmol), allyl bromide (1.2 eq.) and KOH (21 eq.) in benzene (10 ml) was refluxed for 16 h. The reaction mixture was diluted with ethyl acetate and washed with water and sat. sodium chloride solution. The organic phase was dried over sodium sulfate, the solvent was removed in vacuo and the substance was purified by means of column chromatography. Yield: 15%.

(iii) Using ozonolysis conditions, tert-butyl 4-(allyloxy)-4-(pyridin-3-yl)piperidine-1-carboxylate (0.15 g, 0.47 mmol) was converted into tert-butyl 4-(2-oxoethoxy)-4-(pyridin-3-yl)piperidine-1-carboxylate. The crude product was employed in the next stage without purification.

(iv) Using NaBH$_4$ reduction conditions, tert-butyl 4-(2-oxoethoxy)-4-(pyridin-3-yl)piperidine-1-carboxylate (2 g, 6.3 mmol) was reduced to give tert-butyl 4-(2-hydroxyethoxy)-4-(pyridin-3-yl)piperidine-1-carboxylate. The crude product was filtered over silica gel. Yield: 70%.

(v) Triethylamine (2.5 eq.) and MsCl (1.5 eq.) were added to a solution of tert-butyl 4-(2-hydroxyethoxy)-(pyridin-3-yl)piperidine-1-carboxylate (0.4 g, 1.24 mmol) in methylene chloride (12 ml) at 0° C. and the mixture was stirred at room temperature for 3 h. The reaction mixture was diluted with methylene chloride, washed with water and sat. sodium chloride solution and dried over sodium sulfate. After concentration, the crude product [intermediate 1] was employed in the next stage without further purification.

(vi) A solution of tert-butyl 4-(2-(methylsulfonyloxy)ethoxy)-4-(pyridin-3-yl)piperidine-1-carboxylate (0.5 g, 1.25 mmol), azetidine (1.5 eq.) and DIPEA (2.5 eq.) in tetrahydrofuran was refluxed in a closed flask under complete evacuation for 24 h. The reaction mixture was diluted with ethyl acetate and washed successively with water and sat. sodium chloride solution. The organic phase was dried over sodium sulfate and concentrated. The crude product was purified by column chromatography (Alox). Yield: 11%.

tert-Butyl 4-(2-(1H-imidazol-1-yl)ethoxy)-4-(pyridin-3-yl)piperidine-1-carboxylate [Amine F]

Employed in the Synthesis to Give Example 60

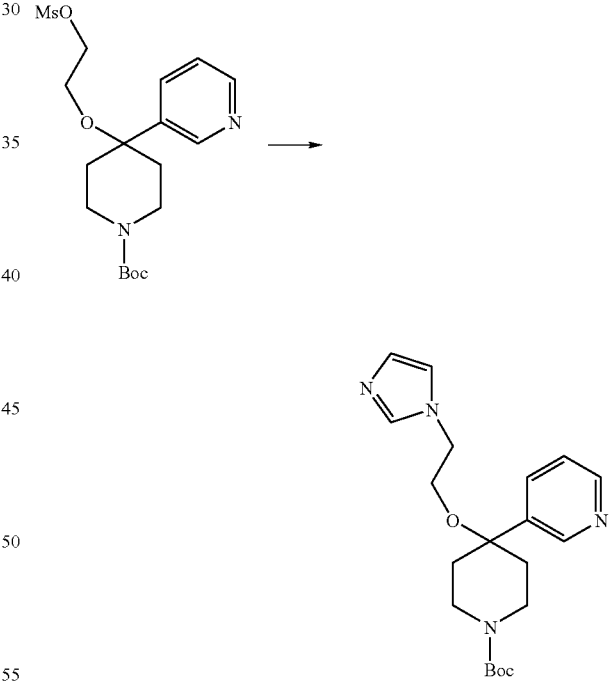

tert-Butyl 4-(2-(methylsulfonyloxy)ethoxy)-4-(pyridin-3-yl)piperidine-1-carboxylate [intermediate 1] (0.35 g, 0.87 mmol) was dissolved in DMF (2 ml) and the solution was added to a solution of sodium hydride (3 eq.) and imidazole (2 eq.) in DMF (5 ml) at 0° C. The reaction mixture was stirred at room temperature for 24 h. The mixture was then diluted with ethyl acetate and washed successively with water and sat. sodium chloride solution. After concentration, the crude product was purified by means of column chromatography (Alox). Yield: 37%.

tert-Butyl 4-(2-(1H-1,2,4-triazol-1-yl)ethoxy)-4-(pyridin-3-yl)piperidine-1-carboxylate [Amine G]

Employed in the Synthesis to Give Example 59

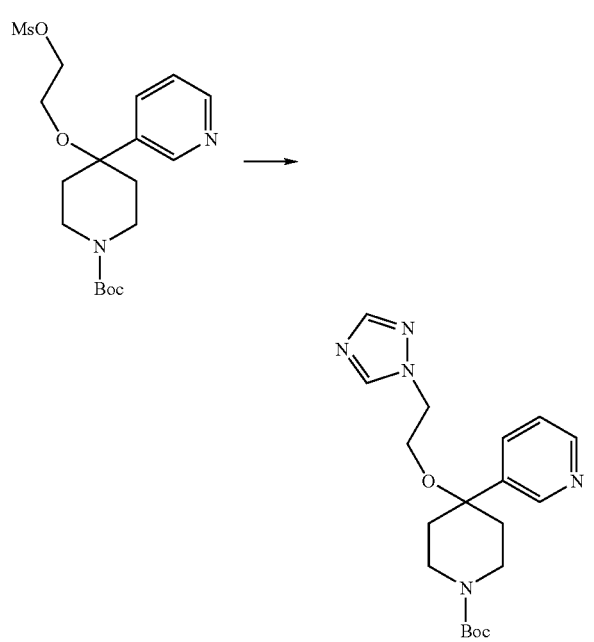

tert-Butyl 4-(2-(methylsulfonyloxy)ethoxy)-4-(pyridin-3-yl)piperidine-1-carboxylate [intermediate 1] (0.30 g, 0.75 mmol) was dissolved in DMF (2 ml) and the solution was added to a solution of sodium hydride (3 eq.) and triazole (2 eq.) in DMF (5 ml) at 0° C. The reaction mixture was stirred at room temperature for 24 h. The mixture was then diluted with ethyl acetate and washed successively with water and sat. sodium chloride solution. After concentration, the crude product was purified by means of column chromatography (Alox). Yield: 35%.

tert-Butyl 4-(2-(pyrrolidin-1-yl)ethoxy)-4-(3-(trifluoromethyl)phenyl)piperidine-1-carboxylate [Amine H]

Employed in the Synthesis to Give Example 54

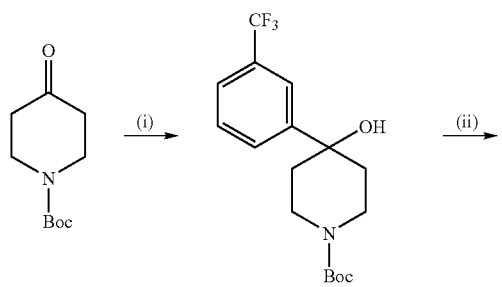

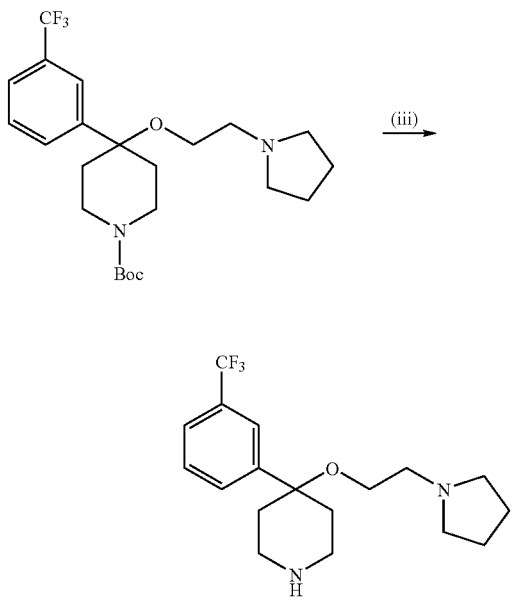

(i) N-Boc-Piperidone (10 mmol), dissolved in tetrahydrofuran, was added dropwise to a solution of 3-trifluoromethyl-phenyl-magnesium bromide (7 eq., prepared from 3-trifluoromethylbromobenzene (Mg, $I_2$)). The reaction mixture was stirred at room temperature for 16 h. After this time, the reaction mixture has reacted completely. Sat. ammonium chloride solution was then added and the mixture was extracted with ethyl acetate. The organic phase was washed with water and sat. sodium chloride solution, dried over sodium sulfate and concentrated to dryness on a rotary evaporator. The crude product was purified by means of column chromatography (methanol/methylene chloride). Yield: 66%.

(ii) tert-Butyl 4-hydroxy-4-(3-(trifluoromethyl)phenyl)piperidine-1-carboxylate (0.95 mmol) and 1-(2-chloroethyl)pyrrolidine (1.5 eq.) were added to a suspension of dry comminuted potassium hydroxide (10 eq.) in dry benzene (30 ml) at 25° C. under an argon atmosphere. The reaction mixture was evacuated completely and refluxed for 18 h. After this time, the reaction mixture was extracted with ethyl acetate. The organic phase was washed successively with water (2×) and sat. sodium chloride solution, dried over sodium sulfate, filtered and concentrated to dryness on a rotary evaporator. The crude product was purified by column chromatography (silica gel, 1% methanol in methylene chloride) to obtain the desired product. Yield: 21%.

(iii) TFA (10 eq.) was added to a solution of tert-butyl 4-(2-(pyrrolidin-1-yl)ethoxy)-4-(3-(trifluoromethyl)phenyl)piperidine-1-carboxylate (1 mmol) in methylene chloride (1 ml) at 0° C. The solution resulting from this was stirred at 25° C. for 1 h. The reaction mixture was concentrated to dryness on a rotary evaporator and the crude product was employed in the next stage without further purification.

tert-Butyl 4-(3-chlorophenyl)-4-(2-(pyrrolidin-1-yl)ethoxy)piperidine-1-carboxylate [Amine I]

Employed in the Synthesis to Give Example 56

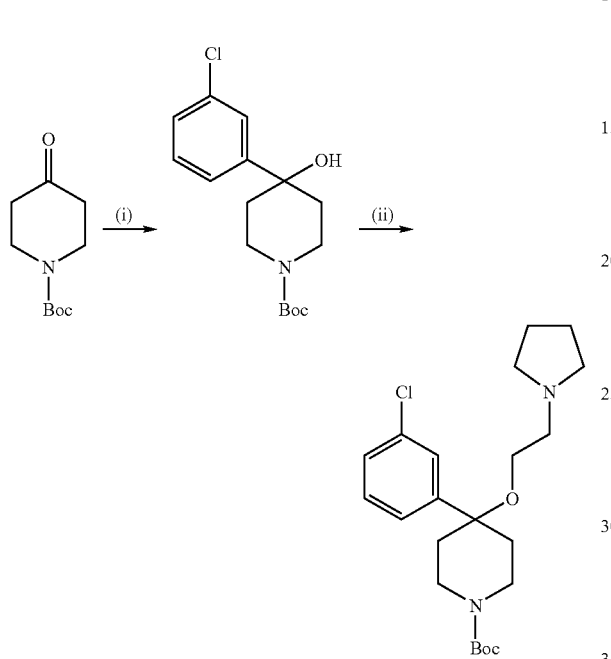

(i) Magnesium (7.2 eq.) was added to tetrahydrofuran (100 ml) under an inert gas atmosphere and a catalytic amount of iodine was added. 3-Bromochlorobenzene (6 eq.) was added in a catalytic amount and the reaction mixture was cooled to 0° C. The 3-bromochlorobenzene solution was added dropwise and the reaction mixture was stirred at room temperature for 3 h. N-Boc-Piperidone (1 eq.) was dissolved in tetrahydrofuran, the solution was added dropwise to the reaction mixture and the mixture was stirred at room temperature for 16 h. After this time, complete reaction of the educts had taken place, via TLC control. Saturated ammonium chloride solution was added to the reaction mixture and the mixture was extracted with ethyl acetate. The organic phase was washed with water and sat. sodium chloride solution, dried over sodium sulfate and concentrated to dryness on a rotary evaporator. The crude product was purified by column chromatography (silica gel, 2% methanol in methylene chloride) to obtain the desired product. Yield: 78%

(ii) Dry KOH powder (10 eq.) was initially introduced into benzene (10 ml), and tert-butyl 4-(3-chlorophenyl)-4-hydroxypiperidine-1-carboxylate (4.8 mmol), dissolved in benzene (40 ml) was added. 1-(2-Chloroethyl)pyrrolidine (1.5 eq.) and 18-crown-6 (catalytic amount) were added to the reaction mixture in succession. The mixture was refluxed under an inert gas for 16 h (complete reaction: TLC control). The reaction mixture was diluted with ethyl acetate, washed with water and sat. sodium chloride solution, dried over sodium sulfate and concentrated to dryness on a rotary evaporator. The crude product was purified by column chromatography (silica gel, 2% methanol in methylene chloride) to obtain the desired product. Yield: 9%.

tert-Butyl 4-(pyridin-4-yl)-4-(2-(pyrrolidin-1-yl)ethoxy)piperidine-1-carboxylate [Amine J]

Employed in the Synthesis of Example 57

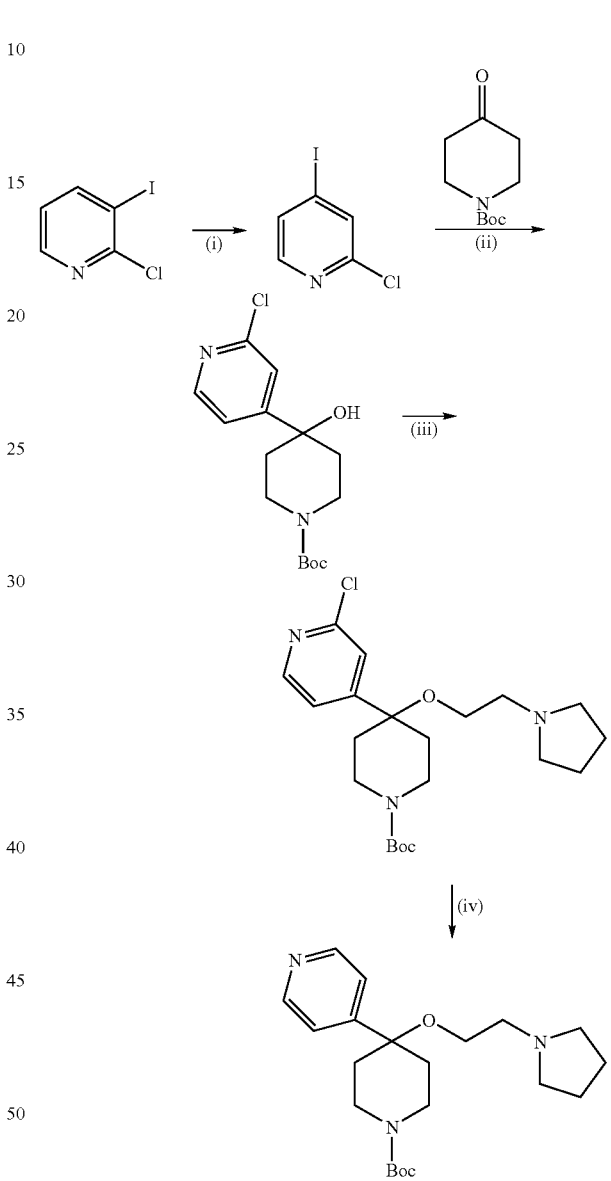

The amine unit [amine J] corresponds to the product of stage 4 of the synthesis of the amine unit AM-08 described above in connection with the parallel synthesis.

Functional Investigation on the Human Bradykinin Receptor 1 (B1R)

The agonistic or antagonistic action of substances can be determined on the bradykinin 1 receptor (B1R) of the human and rat species with the following assay. In accordance with this assay, the $Ca^{2+}$ inflow through the channel is quantified with the aid of a $Ca^{2+}$-sensitive dyestuff (type Fluo-4, Molecular Probes Europe BV, Leiden, Holland) in a fluorescent imaging plate reader (FLIPR, Molecular Devices, Sunnyvale, USA).

1 Method:

Chinese hamster ovary cells (CHO K1 cells) transfected stably with the human B1R gene (hB1R cells) or the B1R gene of the rat (rB1R cells) are used. For functional studies, these cells are plated out on black 96-well plates with a clear base (BD Biosciences, Heidelberg, Germany or Greiner, Frickenhausen, Germany) in a density of 20,000-35,000 cells/well. The cells are left overnight at 37° C. and 5% $CO_2$ in culture medium (hB1R cells: Nutrient Mixture Ham's F12, Gibco Invitrogen GmbH, Karlsruhe, Germany or DMEM, Sigma-Aldrich, Taufkirchen, Germany; rB1R cells: D-MEM/F12, Gibco Invitrogen GmbH, Karlsruhe, Germany) with 10 vol. % FBS (foetal bovine serum, Gibco Invitrogen GmbH, Karlsruhe, Germany or PAN Biotech GmbH, Aidenbach, Germany).

On the following day, the cells are loaded for 60 min at 37° C. with 2.13 µM Fluo-4 (Molecular Probes Europe BV, Leiden, Holland) in HBSS buffer (Hank's buffered saline solution, Gibco Invitrogen GmbH, Karlsruhe, Germany) with 2.5 mM probenecid (Sigma-Aldrich, Taufkirchen, Germany) and 10 mM HEPES (Sigma-Aldrich, Taufkirchen, Germany). The plates are then washed 2× with HBSS buffer, and HBSS buffer which additionally contains 0.1% BSA (bovine serum albumin; Sigma-Aldrich, Taufkirchen, Germany), 5.6 mM glucose and 0.05% gelatine (Merck KGaA, Darmstadt, Germany) is added. After a further incubation of 20 minutes at room temperature, the plates are inserted into the FLIPR for the $Ca^{2+}$ measurement.

Alternatively, the plates are washed with buffer A (15 mM HEPES, 80 mM NaCl, 5 mM KCl, 1.2 mM $CaCl_2$, 0.7 mM $MgSO_4$, 2 g/l glucose, 2.5 mM probenecid), buffer A is added and the plates are loaded with 2.5 µM Fluo-4 and 0.025% Pluronic F127 (Sigma-Aldrich, Taufkirchen, Germany). Thereafter, the cells are washed 2× with buffer A and incubated for 30 minutes with buffer A, which additionally contains 0.05% BSA and 0.05% gelatine, at room temperature and thereafter inserted into the FLIPR for the $Ca^{2+}$ measurement.

The $Ca^{2+}$-dependent fluorescence is measured here before and after addition of substances ($\lambda_{ex}$=488 nm, $\lambda_{em}$=540 nm). Quantification is by measurement of the highest fluorescence intensity (FC, fluorescence counts) over time.

2 FLIPR Assay:

The FLIPR protocol consists of 2 additions of substance. Test substances (10 µM) are first pipetted on to the cells and the $Ca^{2+}$ inflow is compared with the control (hB1R: Lys-Des-Arg$^9$-bradykinin >=50 nM; rB1R: Des-Arg$^9$-bradykinin 10 µM). This gives the figure in % activation based on the $Ca^{2+}$ signal after addition of Lys-Des-Arg$^9$-bradykinin (>=50 nM) or Des-Arg$^9$-bradykinin (10 µM).

After incubation for 10-20 minutes, Lys-Des-Arg$^9$-bradykinin (hB1R) or Des-Arg$^9$-bradykinin (rB1R) in the concentration of the $EC_{80}$ is applied and the inflow of $Ca^{2+}$ is likewise determined. Antagonists lead to a suppression of the $Ca^{2+}$ inflow. % inhibition compared with the maximum achievable inhibition is calculated.

In order to determine the $IC_{50}$ value, the substances were added in various concentrations. Duplicate or triplicate determinations (n=2 or n=3) were carried out, and these were repeated in at least one further independent experiment (N>=2).

3. Results of the Pharmacological Studies

The agonistic and antagonistic action of the compounds according to the invention on the bradykinin 1 receptor (B1R) of the human and rat species were determined as described above. Antagonists lead to a suppression of the $Ca^{2+}$ inflow. % inhibition compared with the maximum achievable inhibition was calculated.

| Example | B1R antagonism, human [10 µM] % inhibition | B1R antagonism, rat [10 µM] % inhibition |
| --- | --- | --- |
| 1 | 99 | 100 |
| 2 | 97 | 99 |
| 3 | 100 | 101 |
| 4 | 99 | 98 |
| 5 | 100 | 102 |
| 6 | 98 | 100 |
| 7 | 99 | 94 |
| 8 | 70 | 60 |
| 9 | 100 | 102 |
| 10 | 104 | 44 |
| 11 | 103 | 52 |
| 12 | 103 | 46 |
| 13 | 101 | 50 |
| 14 | 103 | 102 |
| 15 | 104 | 102 |
| 16 | 103 | 87 |
| 17 | 102 | 102 |
| 18 | 102 | 103 |
| 19 | 103 | 94 |
| 20 | 104 | 102 |
| 21 | 98 | 100 |
| 22 | 39 | 102 |
| 23 | 57 | 46 |
| 24 | 69 | 101 |
| 25 | 86 | 72 |
| 26 | 87 | 91 |
| 27 | 83 | 101 |
| 28 | 97 | 102 |
| 29 | 99 | 101 |
| 30 | 31 | 18 |
| 31 | 85 | 61 |
| 32 | 63 | 98 |
| 33 | 98 | 103 |
| 34 | 99 | 100 |
| 35 | 21 | 97 |
| 36 | 85 | 93 |
| 37 | 77 | 99 |
| 38 | 74 | 98 |
| 39 | 50 | 98 |
| 40 | 99 | 102 |
| 41 | 100 | 101 |
| 42 | 52 | 48 |
| 43 | 86 | 67 |
| 44 | 95 | 102 |
| 45 | 76 | 103 |
| 46 | 100 | 102 |
| 47 | 100 | 101 |
| 48 | 99 | 105 |
| 49 | 97 | 104 |
| 50 | 100 | 104 |
| 51 | 98 | 97 |
| 53 | 100 | 102 |
| 54 | 99 | 96 |
| 55 | 100 | 103 |
| 56 | 99 | 100 |
| 57 | 100 | 103 |
| 58 | 100 | 104 |
| 59 | 100 | 102 |
| 60 | 100 | 102 |
| 61 | 100 | 101 |
| 62 | 100 | 102 |
| 64 |  | 98 |
| 65 |  | 96 |
| 66 |  | 97 |
| 67 |  | 98 |
| 68 |  | 93 |
| 69 |  | 97 |
| 70 |  | 98 |
| 71 |  | 95 |
| 72 |  | 62 |
| 73 |  | 100 |

-continued

| Example | B1R antagonism, human [10 μM] % inhibition | B1R antagonism, rat [10 μM] % inhibition |
| --- | --- | --- |
| 74 |  | 92 |
| 75 |  | 96 |
| 76 |  | 90 |
| 77 |  | 94 |
| 78 |  | 95 |
| 79 |  | 100 |
| 80 | 100 | 102 |
| 81 | 100 | 97 |
| 82 | 100 | 102 |
| 83 | 100 | 99 |
| 84 | 100 | 103 |
| 85 | 100 | 98 |
| 86 |  | 102 |
| 87 | 100 | 102 |
| 88 | 100 | 102 |
| 89 | 100 | 99 |
| 90 | 100 | 102 |
| 91 | 100 | 103 |
| 92 |  | 95 |
| 93 |  | 101 |
| 94 |  | 59 |
| 95 | 95 | 101 |
| 96 |  | 79 |
| 97 | 100 | 99 |
| 98 | 100 | 103 |
| 99 | 99 | 97 |
| 100 | 100 | 102 |
| 101 | 100 | 102 |
| 102 | 99 | 98 |
| 103 | 100 | 103 |
| 104 |  | 100 |
| 105 |  | 99 |
| 106 | 100 | 101 |
| 107 | 98 | 97 |
| 108 | 100 | 103 |
| 109 | 91 | 99 |
| 110 |  | 75 |
| 111 |  | 101 |
| 112 | 100 | 81 |
| 113 | 100 | 103 |
| 114 | 100 | 99 |
| 115 | 100 | 102 |
| 116 | 100 | 101 |
| 117 | 100 | 103 |
| 118 | 100 | 97 |
| 119 | 100 | 102 |
| 120 | 100 | 103 |
| 121 | 100 | 99 |
| 122 | 100 | 100 |
| 123 |  | 96 |
| 124 |  | 98 |
| 125 |  | 99 |
| 126 |  | 98 |
| 127 |  | 49 |
| 128 |  | 41 |
| 129 |  | 92 |
| 130 |  | 83 |
| 131 |  | 44 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A substituted sulfonamide compound corresponding to formula I:

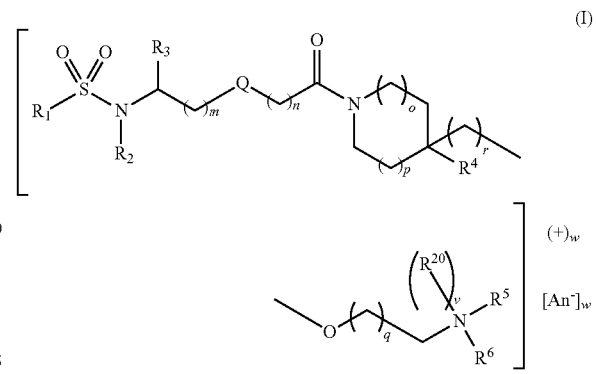

wherein
m represents 0, 1 or 2;
n represents 1 or 2;
o represents 0, 1 or 2;
p represents 0, 1 or 2;
q represents 0, 1, 2 or 3;
r represents 0, 1 or 2, with the proviso that q+r is not greater than 3;
v represents 0 or 1;
w represents 0 or 1, with the proviso that if v represents 0, w represents 0;
$An^-$ represents a halide anion;
Q represents a single bond, —O— or —$CH_2$—;
$R^1$ represents aryl or heteroaryl, or an aryl or heteroaryl bonded via a $C_{1-3}$-alkylene chain;
$R^2$ represents H, $C_{1-6}$-alkyl, $C_{3-8}$-cycloalkyl, bicyclic 8- to 12-membered carbocyclyl, CH(aryl)$_2$, aryl or heteroaryl; or denotes a $C_{3-8}$-cycloalkyl, bicyclic 8- to 12-membered carbocyclyl, CH(aryl)$_2$, aryl or heteroaryl bonded via a $C_{1-6}$-alkylene group, $C_{2-6}$-alkenylene group or $C_{2-6}$-alkynylene group; and
$R^3$ represents H, $C_{1-6}$-alkyl, aryl or heteroaryl; or denotes an aryl or heteroaryl bonded via a $C_{1-6}$-alkylene group, $C_{2-6}$-alkenylene group or $C_{2-6}$-alkynylene group; or
$R^2$ and $R^3$ together with the —N—(CH—)— group joining them form a 4-, 5-, 6- or 7-membered heterocyclic ring, which optionally may be fused with an aryl or heteroaryl group, wherein said heterocyclic ring may be saturated or mono- or polyunsaturated but not aromatic, and optionally may contain, in addition to the N hetero atom to which $R^2$ is bonded, one or more further hetero atoms or hetero atom groups selected from the group consisting of N, $NR^7$, O, S, S=O or S(=O)$_2$; wherein
$R^7$ represents H, $C_{1-6}$-alkyl, —C(=O)—$R^8$, $C_{3-8}$-cycloalkyl, aryl, heteroaryl, or a $C_{3-8}$-cycloalkyl, aryl or heteroaryl bonded via a $C_{1-3}$-alkylene group, and
$R^8$ denotes $C_{1-6}$-alkyl, $C_{3-8}$-cycloalkyl, aryl, heteroaryl, or a $C_{3-8}$-cycloalkyl, aryl or heteroaryl bonded via a $C_{1-3}$-alkylene group,
$R^4$ denotes aryl, heteroaryl or an aryl or heteroaryl bonded via a $C_{1-6}$-alkylene group;
$R^5$ and $R^6$ each independently represent H, $C_{1-6}$-alkyl, $C_{3-8}$-cycloalkyl or a $C_{3-8}$-cycloalkyl bonded via a $C_{1-3}$-alkylene group, wherein $R^5$ and $R^6$ are not simultaneously H; or
$R^5$ and $R^6$ together represent a substituted or unsubstituted 5- or 6-membered heteroaryl which optionally may contain, in addition to the N atom to which $R^5$ and $R^6$ are bonded, one or more further hetero atoms selected from the group consisting of N, O or S; or R$^5$ and R$^6$ together represent —(CH$_2$)$_d$— or —(CH$_2$)$_e$—X—(CH$_2$)$_f$—, wherein
d denotes 2, 3, 4, 5 or 6;
e and f each independently denote 1, 2 or 3, with the proviso that e+f is not greater than 5; and
X denotes NR$^{12}$, CF$_2$, O, S, S═O or S(═O)$_2$, wherein R$^{12}$ denotes H, C$_{1-6}$-alkyl, C$_{3-8}$-cycloalkyl, aryl, heteroaryl or a C$_{3-8}$-cycloalkyl, aryl or heteroaryl bonded via a C$_{1-3}$-alkylene group;
R$^{20}$ represents C$_{1-6}$-alkyl, cyclopropyl, a C$_{3-8}$-cycloalkyl, aryl or heteroaryl bonded via a C$_{1-3}$-alkylene group or ═O; with the proviso that if R$^{20}$ represents ═O, w represents 0; and
wherein said C$_{1-6}$-alkyl, C$_{1-6}$-alkylene, C$_{2-6}$-alkenylene, C$_{2-6}$-alkynylene, C$_{3-8}$-cycloalkyl, C$_{3-8}$-heterocycloalkyl, bicyclic 8- to 12-membered carbocyclyl, aryl and heteroaryl groups may each be unsubstituted or mono- or polysubstituted by identical or different substituents, and said C$_{1-6}$-alkyl, C$_{1-6}$-alkylene, C$_{2-6}$-alkenylene and C$_{2-6}$-alkynylene groups may each be branched or unbranched;
or a physiologically acceptable salt thereof.

2. A compound as claimed in claim 1, wherein said compound is in the form of a mixture of stereoisomers in any mixing ratio.

3. A compound as claimed in claim 2, wherein said compound is in the form of a racemic mixture.

4. A compound as claimed in claim 1, wherein said compound is in the form of an individual stereoisomer.

5. A compound as claimed in claim 1, wherein v, w and r each represent 0.

6. A compound as claimed in claim 1, wherein R$^1$ represents phenyl, naphthyl, Indolyl, benzofuranyl, benzothienyl, benzoxazolyl, benzoxadiazolyl, pyrrolyl, furanyl, thienyl, pyridinyl, pyridazinyl, pyrimidinyl, pyrazinyl, imidazothiazolyl, carbazolyl, dibenzofuranyl, dibenzothienyl, benzyl or 2-phenethyl.

7. A compound as claimed in claim 6, wherein R$^1$ represents phenyl, naphthyl, benzothienyl, benzoxadiazolyl, thiophenyl, pyridinyl, imidazothiazolyl or dibenzofuranyl.

8. A compound as claimed in claim 1, wherein
p and o each represent 1, or
p represents 1, and o represents 0.

9. A compound as claimed in claim 1, wherein
Q represents a single bond,
m represents 0 or 1, and
n represents 1 or 2;
or
Q represents —O—,
m represents 1 or 2, and
n represents 1.

10. A compound as claimed in claim 1, wherein R$^4$ represents phenyl, a phenyl group bonded via a C$_{1-3}$-alkylene group, or 2-, 3- or 4-pyridinyl, or a 2-, 3- or 4-pyridinyl bonded via a C$_{1-3}$-alkylene group; wherein the phenyl optionally may be substituted one or more times by F, Cl or CF$_3$.

11. A compound as claimed in claim 1, wherein q represents 1 or 2.

12. A compound as claimed in claim 1, wherein
R$^5$ and R$^6$ each independently represent C$_{1-6}$-alkyl which may be unsubstituted or mono- or polysubstituted; or
R$^5$ and R$^6$ together represent a group selected from the group consisting of —N═CH—CH═CH—, —CH═CH—N═CH—, —CH$_2$—CH$_2$—CH$_2$—, —CH$_2$—CH$_2$—CH$_2$—CH$_2$—, —CH$_2$—CH$_2$—CH$_2$—CH$_2$—CH$_2$— and —CH$_2$—CH$_2$—NR$^9$—CH$_2$—CH$_2$—; wherein R$^9$ denotes H or C$_{1-6}$-alkyl; or R$^5$ and R$^6$ together with the N atom to which they are bonded, represent a heteroaryl group selected from the group consisting of imidazolyl, triazolyl, pyrazolyl, benzimidazolyl, pyrrolyl and indolyl, wherein said heteroaryl group may be unsubstituted or mono- or polysubstituted by identical or different substituents independently selected from the group consisting of F, Cl, Br, CF$_3$, CH$_3$ and OCH$_3$.

13. A compound as claimed in claim 1, wherein R$^2$ represents H; C$_{1-6}$-alkyl; C$_{3-8}$-cycloalkyl; 8- to 10-membered benzo-fused cycloalkyl; CH(phenyl)$_2$; aryl; heteroaryl; a C$_{3-6}$-cycloalkyl, CH(phenyl)$_2$, aryl or heteroaryl group bonded via a C$_{1-6}$-alkylene group, C$_{2-6}$-alkenylene group or C$_{2-6}$-alkynylene group; wherein the C$_{1-6}$-alkyl, C$_{3-6}$-cycloalkyl, C$_{2-6}$-alkylene, C$_{2-6}$-alkenylene, C$_{2-6}$-alkynylene, 8- to 10-membered benzo-fused cycloalkyl, aryl and heteroaryl groups may each be unsubstituted or mono- or polysubstituted by identical or different substituents selected from the group consisting of C$_{1-6}$-alkyl, C$_{1-6}$-alkyl-O—, F, Cl, Br, I, CF$_3$, OCF$_3$, OH and SH.

14. A compound as claimed in claim 1, wherein R$^3$ represents H, C$_{1-6}$-alkyl, aryl, or aryl bonded via a C$_{1-6}$-alkylene group, C$_{2-6}$-alkenylene group or C$_{2-6}$-alkynylene group; wherein the C$_{1-6}$-alkyl, C$_{3-6}$-cycloalkyl, C$_{2-6}$-alkylene, C$_{2-6}$-alkenylene, C$_{2-6}$-alkynylene and aryl groups may each be unsubstituted or mono- or polysubstituted by identical or different substituents selected from the group consisting of C$_{1-6}$-alkyl, C$_{1-6}$-alkyl-O—, F, Cl, Br, I, CF$_3$, OCF$_3$, OH and SH.

15. A compound as claimed in claim 1, wherein R$^2$ and R$^3$ together with the —N—(CH—)— group joining them form a heterocyclic ring corresponding to formula II:

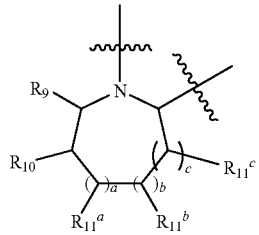

(II)

wherein
a, b and c each independently represent 0 or 1; and
R$^9$, R$^{10}$, R$^{11a}$, R$^{11b}$ and R$^{11c}$ each independently represent H, or two vicinal groups from R$^9$, R$^{10}$, R$^{11a}$, R$^{11b}$ and R$^{11c}$ form a 5- or 6-membered fused-on aryl or heteroaryl group, which may be unsubstituted or mono- or polysubstituted by identical or different substituents.

16. A compound as claimed in claim 1, selected from the group consisting of:

(1) (S)-2-((1-(4-methoxy-2,6-dimethylphenylsulfonyl)-1,2,3,4-tetrahydroquinolin-2-yl)methoxy)-1-(4-(pyridin-3-yl)-4-(2-(pyrrolidin-1-yl)ethoxy)piperidin-1-yl)ethanone (2) 4-(1-(4-methoxy-2,6-dimethylphenylsulfonyl)piperidin-2-yl)-1-(4-(pyridin-3-yl)-4-(2-(pyrrolidin-1-yl)ethoxy)piperidin-1-yl)butan-1-on (3) N-cyclopropyl-4-methoxy-2,6-dimethyl-N-(2-(2-oxo-2-(4-(pyridin-3-yl)-4-(2-(pyrrolidin-1-yl)ethoxy)piperidin-1-yl)ethoxy)ethyl)benzenesulfonamide (4) N-benzhydryl-2,4-dichloro-N-(2-(2-oxo-2-(4-(pyridin-3-yl)-4-(2-(pyrrolidin-1-yl)ethoxy)piperidin-1-yl)ethoxy)ethyl)benzenesulfonamide
(5) 4-methoxy-2,6-dimethyl-N-(2-(2-oxo-2-(4-(pyridin-3-yl)-4-(2-(pyrrolidin-1-yl)ethoxy)piperidin-1-yl)ethoxy)ethyl)-N-(pyridin-3-ylmethyl)benzenesulfonamide
(6) N-benzhydryl-4-methoxy-2,6-dimethyl-N-(2-(2-oxo-2-(4-(pyridin-3-yl)-4-(2-(pyrrolidin-1-yl)ethoxy)piperidin-1-yl)ethoxy)ethyl)benzenesulfonamide
(7) 2,4-dichloro-N-(2,3-dihydro-1H-inden-1-yl)-N-(2-(2-oxo-2-(4-(pyridin-3-yl)-4-(2-(pyrrolidin-1-yl)ethoxy)piperidin-1-yl)ethoxy)ethyl)benzenesulfonamide
(8) 1-(4-(pyridin-3-yl)-4-(2-(pyrrolidin-1-yl)ethoxy)piperidin-1-yl)-4-(1-(2-(trifluoromethyl)phenylsulfonyl)piperidin-2-yl)butan-1-one
(9) 4-(1-(2-chloro-6-methylphenylsulfonyl)piperidin-2-yl)-1-(4-(pyridin-3-yl)-4-(2-(pyrrolidin-1-yl)ethoxy)piperidin-1-yl)butan-1-one
(10) 1-(4-(2-(piperidin-1-yl)ethoxy)-4-(pyridin-3-yl)piperidin-1-yl)-2-(1-(3-(trifluoromethyl)phenylsulfonyl)piperidin-2-yl)ethanone
(11) N-(3-oxo-1-phenyl-3-(4-(2-(piperidin-1-yl)ethoxy)-4-(pyridin-3-yl)piperidin-1-yl)propyl)naphthalene-2-sulfonamide
(12) 3-(1-(4-chloro-2,5-dimethylphenylsulfonyl)piperidin-2-yl)-1-(4-(3-(piperidin-1-yl)propoxy)-4-(pyridin-3-yl)piperidin-1-yl)propan-1-one
(13) 3-(1-(4-chloro-2,5-dimethylphenylsulfonyl)piperidin-2-yl)-1-(4-(2-(piperidin-1-yl)ethoxy)-4-(pyridin-3-yl)piperidin-1-yl)propan-1-one
(14) 2-((1-(4-methoxy-2,6-dimethylphenylsulfonyl)piperidin-2-yl)methoxy)-1-(4-(2-(piperidin-1-yl)ethoxy)-4-(pyridin-3-yl)piperidin-1-yl)ethanone
(15) 4-methoxy-N,2,6-trimethyl-N-(2-(2-oxo-2-(4-(2-(piperidin-1-yl)ethoxy)-4-(pyridin-3-yl)piperidin-1-yl)ethoxy)ethyl)benzenesulfonamide
(16) 2-((1-(3,4-dichlorophenylsulfonyl)-1,2,3,4-tetrahydroquinolin-2-yl)methoxy)-1-(4-(2-(piperidin-1-yl)ethoxy)-4-(pyridin-3-yl)piperidin-1-yl)ethanone
(17) 2-((1-(4-methoxy-2,6-dimethylphenylsulfonyl)piperidin-2-yl)methoxy)-1-(4-(3-(piperidin-1-yl)propoxy)-4-(pyridin-3-yl)piperidin-1-yl)ethanone
(18) 4-methoxy-N,2,6-trimethyl-N-(2-(2-oxo-2-(4-(3-(piperidin-1-yl)propoxy)-4-(pyridin-3-yl)piperidin-1-yl)ethoxy)ethyl)benzenesulfonamide
(19) 2-((1-(3,4-dichlorophenylsulfonyl)-1,2,3,4-tetrahydroquinolin-2-yl)methoxy)-1-(4-(3-(piperidin-1-yl)propoxy)-4-(pyridin-3-yl)piperidin-1-yl)ethanone
(20) 2-((1-(4-methoxy-2,6-dimethylphenylsulfonyl)piperidin-2-yl)methoxy)-1-(4-(pyridin-3-yl)-4-(2-(pyrrolidin-1-yl)ethoxy)piperidin-1-yl)ethanone
(21) 4-methoxy-N,2,6-trimethyl-N-(2-(2-oxo-2-(4-(pyridin-3-yl)-4-(2-(pyrrolidin-1-yl)ethoxy)piperidin-1-yl)ethoxy)ethyl)benzenesulfonamide
(22) 1-(4-(pyridin-3-yl)-4-(2-(pyrrolidin-1-yl)ethoxy)piperidin-1-yl)-2-(1-(3-(trifluoromethyl)phenylsulfonyl)piperidin-2-yl)ethanone
(23) 1-(4-(3-(piperidin-1-yl)propoxy)-4-(pyridin-3-yl)piperidin-1-yl)-2-(1-(3-(trifluoromethyl)phenylsulfonyl)piperidin-2-yl)ethanone
(24) 2-((1-(3,4-dichlorophenylsulfonyl)-1,2,3,4-tetrahydroquinolin-2-yl)methoxy)-1-(4-(pyridin-3-yl)-4-(2-(pyrrolidin-1-yl)ethoxy)piperidin-1-yl)ethanone
(25) 3-(1-(4-chloro-2,5-dimethylphenylsulfonyl)piperidin-2-yl)-1-(4-(pyridin-3-yl)-4-(2-(pyrrolidin-1-yl)ethoxy)piperidin-1-yl)propan-1-one
(26) N-(3-oxo-1-phenyl-3-(4-(pyridin-3-yl)-4-(2-(pyrrolidin-1-yl)ethoxy)piperidin-1-yl)propyl)naphthalene-2-sulfonamide
(27) N-(3-oxo-1-phenyl-3-(4-(3-(piperidin-1-yl)propoxy)-4-(pyridin-3-yl)piperidin-1-yl)propyl)naphthalene-2-sulfonamide
(28) 2-((1-(4-methoxy-2,6-dimethylphenylsulfonyl)piperidin-2-yl)methoxy)-1-(4-(2-(4-methylpiperazin-1-yl)ethoxy)-4-(pyridin-3-yl)piperidin-1-yl)ethanone
(29) 4-methoxy-N,2,6-trimethyl-N-(2-(2-(4-(2-(4-methylpiperazin-1-yl)ethoxy)-4-(pyridin-3-yl)piperidin-1-yl)-2-oxoethoxy)ethyl)benzenesulfonamide
(30) 1-(4-(2-(4-methylpiperazin-1-yl)ethoxy)-4-(pyridin-3-yl)piperidin-1-yl)-2-(1-(3-(trifluoromethyl)phenylsulfonyl)piperidin-2-yl)ethanone
(31) 3-(1-(4-chloro-2,5-dimethylphenylsulfonyl)piperidin-2-yl)-1-(4-(2-(4-methylpiperazin-1-yl)ethoxy)-4-(pyridin-3-yl)piperidin-1-yl)propan-1-one
(32) N-(3-(4-(2-(4-methylpiperazin-1-yl)ethoxy)-4-(pyridin-3-yl)piperidin-1-yl)-3-oxo-1-phenylpropyl)naphthalene-2-sulfonamide
(33) 2-((1-(4-methoxy-2,6-dimethylphenylsulfonyl)piperidin-2-yl)methoxy)-1-(4-(3-(4-methylpiperazin-1-yl)propoxy)-4-(pyridin-3-yl)piperidin-1-yl)ethanone
(34) 4-methoxy-N,2,6-trimethyl-N-(2-(2-(4-(3-(4-methylpiperazin-1-yl)propoxy)-4-(pyridin-3-yl)piperidin-1-yl)-2-oxoethoxy)ethyl)benzenesulfonamide
(35) 1-(4-(3-(4-methylpiperazin-1-yl)propoxy)-4-(pyridin-3-yl)piperidin-1-yl)-2-(1-(3-(trifluoromethyl)phenylsulfonyl)piperidin-2-yl)ethanone
(36) 3-(1-(4-chloro-2,5-dimethylphenylsulfonyl)piperidin-2-yl)-1-(4-(3-(4-methylpiperazin-1-yl)propoxy)-4-(pyridin-3-yl)piperidin-1-yl)propan-1-one
(37) 2-((1-(3,4-dichlorophenylsulfonyl)-1,2,3,4-tetrahydroquinolin-2-yl)methoxy)-1-(4-(3-(4-methylpiperazin-1-yl)propoxy)-4-(pyridin-3-yl)piperidin-1-yl)ethanone
(38) 2-((1-(3,4-dichlorophenylsulfonyl)-1,2,3,4-tetrahydroquinolin-2-yl)methoxy)-1-(4-(2-(4-methylpiperazin-1-yl)ethoxy)-4-(pyridin-3-yl)piperidin-1-yl)ethanone
(39) N-(3-(4-(3-(4-methylpiperazin-1-yl)propoxy)-4-(pyridin-3-yl)piperidin-1-yl)-3-oxo-1-phenylpropyl)naphthalene-2-sulfonamide
(40) 2-((1-(4-methoxy-2,6-dimethylphenylsulfonyl)piperidin-2-yl)methoxy)-1-(4-(pyridin-3-yl)-4-(3-(pyrrolidin-1-yl)propoxy)piperidin-1-yl)ethanone
(41) 4-methoxy-N,2,6-trimethyl-N-(2-(2-oxo-2-(4-(pyridin-3-yl)-4-(3-(pyrrolidin-1-yl)propoxy)piperidin-1-yl)ethoxy)ethyl)benzenesulfonamide
(42) 1-(4-(pyridin-3-yl)-4-(3-(pyrrolidin-1-yl)propoxy)piperidin-1-yl)-2-(1-(3-(trifluoromethyl)phenylsulfonyl)piperidin-2-yl)ethanone
(43) 3-(1-(4-chloro-2,5-dimethylphenylsulfonyl)piperidin-2-yl)-1-(4-(pyridin-3-yl)-4-(3-(pyrrolidin-1-yl)propoxy)piperidin-1-yl)propan-1-one
(44) N-(3-oxo-1-phenyl-3-(4-(pyridin-3-yl)-4-(3-(pyrrolidin-1-yl)propoxy)piperidin-1-yl)propyl)naphthalene-2-sulfonamide
(45) 2-((1-(3,4-dichlorophenylsulfonyl)-1,2,3,4-tetrahydroquinolin-2-yl)methoxy)-1-(4-(pyridin-3-yl)-4-(3-(pyrrolidin-1-yl)propoxy)piperidin-1-yl)ethanone
(46) (S)-2-((1-(4-methoxy-2,6-dimethylphenylsulfonyl)piperidin-2-yl)methoxy)-1-(4-(pyridin-3-yl)-4-(2-(pyrrolidin-1-yl)ethoxy)piperidin-1-yl)ethanone hydrochloride

(47) (S)-1-(4-(pyridin-3-yl)-4-(2-(pyrrolidin-1-yl)ethoxy)piperidin-1-yl)-2-((1-(2-(trifluoromethyl)phenylsulfonyl)piperidin-2-yl)methoxy)ethanone
(48) (S)-2-((1-(2-chloro-6-methylphenylsulfonyl)piperidin-2-yl)methoxy)-1-(4-(pyridin-3-yl)-4-(2-(pyrrolidin-1-yl)ethoxy)piperidin-1-yl)ethanone
(49) (S)-2-((1-(4-methoxy-2,6-dimethylphenylsulfonyl)piperidin-2-yl)methoxy)-1-(4-(pyridin-3-yl)-4-((2-(pyrrolidin-1-yl)ethoxy)methyl)piperidin-1-yl)ethanone
(50) 2-(((S)-1-(4-methoxy-2,6-dimethylphenylsulfonyl)piperidin-2-yl)methoxy)-1-(3-(pyridin-3-yl)-3-(2-(pyrrolidin-1-yl)ethoxy)pyrrolidin-1-yl)ethanone
(51) (S)-1-(4-(3-fluorophenyl)-4-(2-(pyrrolidin-1-yl)ethoxy)piperidin-1-yl)-2-((1-(4-methoxy-2,6-dimethylphenylsulfonyl)piperidin-2-yl)methoxy)ethanone
(53) 2-chloro-N-cyclopropyl-N-[2-[2-[4-(3-fluorophenyl)-4-[2-(1-oxido-pyrrolidin-1-ium-1-yl)-ethoxy]-piperidin-1-yl]-2-oxo-ethoxy]-ethyl]-6-methyl-benzenesulfonic acid amide
(54) 2-[[(2S)-1-[(4-methoxy-2,6-dimethyl-phenyl)sulfonyl]-piperidin-2-yl]-methoxy]-1-[4-(2-pyrrolidin-1-yl-ethoxy)-4-[3-(trifluoromethyl)phenyl]-piperidin-1-yl]-ethanone
(55) 2-[[(2S)-1-[(4-methoxy-2,6-dimethyl-phenyl)sulfonyl]-piperidin-2-yl]-methoxy]-1-[4-pyridin-3-yl-4-(2-pyrrolidin-1-yl-ethoxy)-azepan-1-yl]-ethanone
(56) 1-[4-(3-chlorophenyl)-4-(2-pyrrolidin-1-yl-ethoxy)-piperidin-1-yl]-2-[[(2S)-1-[(4-methoxy-2,6-dimethyl-phenyl)sulfonyl]-piperidin-2-yl]-methoxy]-ethanone
(57) 2-[[(2S)-1-[(4-methoxy-2,6-dimethyl-phenyl)sulfonyl]-piperidin-2-yl]-methoxy]-1-[4-pyridin-4-yl-4-(2-pyrrolidin-1-yl-ethoxy)-piperidin-1-yl]-ethanone
(58) N-cyclopropyl-4-methoxy-2,6-dimethyl-N-[2-[2-[4-[2-(1-methyl-pyrrolidin-1-ium-1-yl)-ethoxy]-4-pyridin-3-yl-piperidin-1-yl]-2-oxo-ethoxy]-ethyl]-benzenesulfonic acid amide iodide
(59) 2-[[(2S)-1-[(4-methoxy-2,6-dimethyl-phenyl)sulfonyl]-piperidin-2-yl]-methoxy]-1-[4-pyridin-3-yl-4-[2-(1H-[1,2,4]triazol-1-yl)-ethoxy]-piperidin-1-yl]-ethanone
(60) 1-[4-[2-(1H-imidazol-1-yl)-ethoxy]-4-pyridin-3-yl-piperidin-1-yl]-2-[[(2S)-1-[(4-methoxy-2,6-dimethyl-phenyl)sulfonyl]-piperidin-2-yl]-methoxy]-ethanone
(61) 1-[4-[2-(azetidin-1-yl)-ethoxy]-4-pyridin-3-yl-piperidin-1-yl]-2-[[(2S)-1-[(4-methoxy-2,6-dimethyl-phenyl)sulfonyl]-piperidin-2-yl]-methoxy]-ethanone
(62) 2-chloro-N-cyclopropyl-N-[2-[2-[4-(3-fluorophenyl)-4-(2-pyrrolidin-1-yl-ethoxy)-piperidin-1-yl]-2-oxo-ethoxy]-ethyl]-6-methyl-benzenesulfonic acid amide
(64) 1-[4-(4-fluorophenyl)-4-(2-pyrrolidin-1-yl-ethoxy)-piperidin-1-yl]-2-[[1-[(4-methoxy-2,6-dimethyl-phenyl)sulfonyl]-piperidin-2-yl]-methoxy]-ethanone
(65) 2-[[1-[(4-methoxy-2,6-dimethyl-phenyl)sulfonyl]-piperidin-2-yl]-methoxy]-1-[4-(2-pyrrolidin-1-yl-ethoxy)-4-[4-(trifluoromethyl)-phenyl]-piperidin-1-yl]-ethanone
(66) N-cyclopropyl-N-[2-[2-[4-(4-fluorophenyl)-4-(2-pyrrolidin-1-yl-ethoxy)-piperidin-1-yl]-2-oxo-ethoxy]-ethyl]-4-methoxy-2,6-dimethyl-benzenesulfonic acid amide
(67) N-cyclopropyl-4-methoxy-2,6-dimethyl-N-[2-[2-oxo-2-[4-(2-pyrrolidin-1-yl-ethoxy)-4-[4-(trifluoromethyl)-phenyl]-piperidin-1-yl]-ethoxy]-ethyl]-benzenesulfonic acid amide
(68) 2-[[1-[(2-chloro-6-methyl-phenyl)sulfonyl]-piperidin-2-yl]-methoxy]-1-[4-(4-fluorophenyl)-4-(2-pyrrolidin-1-yl-ethoxy)-piperidin-1-yl]-ethanone
(69) 2-[[1-[(2-chloro-6-methyl-phenyl)sulfonyl]-piperidin-2-yl]-methoxy]-1-[4-(2-pyrrolidin-1-yl-ethoxy)-4-[4-(trifluoromethyl)-phenyl]-piperidin-1-yl]-ethanone
(70) 2-chloro-N-cyclopropyl-N-[2-[2-[4-(4-fluorophenyl)-4-(2-pyrrolidin-1-yl-ethoxy)-piperidin-1-yl]-2-oxo-ethoxy]-ethyl]-6-methyl-benzenesulfonic acid amide
(71) 2-chloro-N-cyclopropyl-6-methyl-N-[2-[2-oxo-2-[4-(2-pyrrolidin-1-yl-ethoxy)-4-[4-(trifluoromethyl)-phenyl]-piperidin-1-yl]-ethoxy]-ethyl]-benzenesulfonic acid amide
(72) 1-[4-(4-fluorophenyl)-4-(2-pyrrolidin-1-yl-ethoxy)-piperidin-1-yl]-2-[1-[[3-(trifluoromethyl)phenyl]sulfonyl]-piperidin-2-yl]-ethanone
(73) 1-[4-(2-pyrrolidin-1-yl-ethoxy)-4-[4-(trifluoromethyl)-phenyl]-piperidin-1-yl]-2-[1-[[3-(trifluoromethyl)phenyl]sulfonyl]-piperidin-2-yl]-ethanone
(74) 3-[1-[(4-chloro-2,5-dimethyl-phenyl)sulfonyl]-piperidin-2-yl]-1-[4-(4-fluorophenyl)-4-(2-pyrrolidin-1-yl-ethoxy)-piperidin-1-yl]-propan-1-one
(75) 3-[1-[(4-chloro-2,5-dimethyl-phenyl)sulfonyl]-piperidin-2-yl]-1-[4-(2-pyrrolidin-1-yl-ethoxy)-4-[4-(trifluoromethyl)-phenyl]-piperidin-1-yl]-propan-1-one
(76) N-[3-[4-(4-fluorophenyl)-4-(2-pyrrolidin-1-yl-ethoxy)-piperidin-1-yl]-3-oxo-1-phenyl-propyl]-naphthalene-2-sulfonic acid amide
(77) N-[3-oxo-1-phenyl-3-[4-(2-pyrrolidin-1-yl-ethoxy)-4-[4-(trifluoromethyl)-phenyl]-piperidin-1-yl]-propyl]-naphthalene-2-sulfonic acid amide
(78) 1-[4-(4-fluorophenyl)-4-(2-pyrrolidin-1-yl-ethoxy)-piperidin-1-yl]-4-[1-[(4-methoxy-2,6-dimethyl-phenyl)sulfonyl]-piperidin-2-yl]-butan-1-one
(79) 4-[1-[(4-methoxy-2,6-dimethyl-phenyl)sulfonyl]-piperidin-2-yl]-1-[4-(2-pyrrolidin-1-yl-ethoxy)-4-[4-(trifluoromethyl)-phenyl]-piperidin-1-yl]-butan-1-one
(80) 4-methoxy-N,2,6-trimethyl-N-[2-[2-oxo-2-[4-pyridin-3-yl-4-(2-pyrrolidin-1-yl-ethoxy)-piperidin-1-yl]-ethoxy]-ethyl]-benzenesulfonic acid amide
(81) N-[2-[2-[4-(3-fluorophenyl)-4-(2-pyrrolidin-1-yl-ethoxy)-piperidin-1-yl]-2-oxo-ethoxy]-ethyl]-4-methoxy-N,2,6-trimethyl-benzenesulfonic acid amide
(82) 2-[[1-[(4-methoxy-2,6-dimethyl-phenyl)sulfonyl]-piperidin-2-yl]-methoxy]-1-[4-pyridin-3-yl-4-(2-pyrrolidin-1-yl-ethoxy)-piperidin-1-yl]-ethanone
(83) 1-[4-(3-fluorophenyl)-4-(2-pyrrolidin-1-yl-ethoxy)-piperidin-1-yl]-2-[[1-[(4-methoxy-2,6-dimethyl-phenyl)sulfonyl]-piperidin-2-yl]-methoxy]-ethanone
(84) 2-[[1-[(4-methoxy-2,6-dimethyl-phenyl)sulfonyl]-piperidin-2-yl]-methoxy]-1-[4-pyridin-4-yl-4-(2-pyrrolidin-1-yl-ethoxy)-piperidin-1-yl]-ethanone
(85) 4-[1-[(2-chloro-6-methyl-phenyl)sulfonyl]-piperidin-2-yl]-1-[4-(3-fluorophenyl)-4-(2-pyrrolidin-1-yl-ethoxy)-piperidin-1-yl]-butan-1-one
(86) 1-[4-(3-fluorophenyl)-4-(2-pyrrolidin-1-yl-ethoxy)-piperidin-1-yl]-4-[1-[[2-(trifluoromethyl)-phenyl]sulfonyl]-piperidin-2-yl]-butan-1-one
(87) 4-[1-[(4-methoxy-2,6-dimethyl-phenyl)sulfonyl]-piperidin-2-yl]-1-[4-pyridin-3-yl-4-(2-pyrrolidin-1-yl-ethoxy)-piperidin-1-yl]-butan-1-one

(88) 4-[1-[(4-methoxy-2,6-dimethyl-phenyl)sulfonyl]-piperidin-2-yl]-1-[4-pyridin-3-yl-4-(2-pyrrolidin-1-yl-ethoxy)-piperidin-1-yl]-butan-1-one

(89) 1-[4-(3-fluorophenyl)-4-(2-pyrrolidin-1-yl-ethoxy)-piperidin-1-yl]-4-[1-[(4-methoxy-2,6-dimethyl-phenyl)sulfonyl]-piperidin-2-yl]-butan-1-one

(90) 4-[1-[(4-methoxy-2,6-dimethyl-phenyl)sulfonyl]-piperidin-2-yl]-1-[4-pyridin-4-yl-4-(2-pyrrolidin-1-yl-ethoxy)-piperidin-1-yl]-butan-1-one

(91) 4-[1-[(4-methoxy-2,6-dimethyl-phenyl)sulfonyl]-piperidin-2-yl]-1-[4-pyridin-4-yl-4-(2-pyrrolidin-1-yl-ethoxy)-piperidin-1-yl]-butan-1-one

(92) 4-[1-(naphthalen-1-ylsulfonyl)-piperidin-2-yl]-1-[4-pyridin-3-yl-4-(2-pyrrolidin-1-yl-ethoxy)-piperidin-1-yl]-butan-1-one

(93) 1-[4-(3-fluorophenyl)-4-(2-pyrrolidin-1-yl-ethoxy)-piperidin-1-yl]-4-[1-(naphthalen-1-ylsulfonyl)-piperidin-2-yl]-butan-1-one

(94) 4-[1-(naphthalen-1-ylsulfonyl)-piperidin-2-yl]-1-[4-pyridin-4-yl-4-(2-pyrrolidin-1-yl-ethoxy)-piperidin-1-yl]-butan-1-one

(95) 4-[1-(naphthalen-2-ylsulfonyl)-piperidin-2-yl]-1-[4-pyridin-3-yl-4-(2-pyrrolidin-1-yl-ethoxy)-piperidin-1-yl]-butan-1-one

(96) 1-[4-(3-fluorophenyl)-4-(2-pyrrolidin-1-yl-ethoxy)-piperidin-1-yl]-4-[1-(naphthalen-2-ylsulfonyl)-piperidin-2-yl]-butan-1-one

(98) 4-methoxy-2,6-dimethyl-N-[2-[2-oxo-2-[4-pyridin-3-yl-4-(2-pyrrolidin-1-yl-ethoxy)-piperidin-1-yl]-ethoxy]-ethyl]-N-phenyl-benzenesulfonic acid amide

(99) N-[2-[2-[4-(3-fluorophenyl)-4-(2-pyrrolidin-1-yl-ethoxy)-piperidin-1-yl]-2-oxo-ethoxy]-ethyl]-4-methoxy-2,6-dimethyl-N-phenyl-benzenesulfonic acid amide (100) 4-methoxy-2,6-dimethyl-N-[2-[2-oxo-2-[4-pyridin-4-yl-4-(2-pyrrolidin-1-yl-ethoxy)-piperidin-1-yl]-ethoxy]-ethyl]-N-phenyl-benzenesulfonic acid amide (101) 2-[[1-[(4-methoxy-2,6-dimethyl-phenyl)sulfonyl]-1,2,3,4-tetrahydro-quinolin-2-yl]-methoxy]-1-[4-pyridin-3-yl-4-(2-pyrrolidin-1-yl-ethoxy)-piperidin-1-yl]-ethanone (102) 1-[4-(3-fluorophenyl)-4-(2-pyrrolidin-1-yl-ethoxy)-piperidin-1-yl]-2-[[1-[(4-methoxy-2,6-dimethyl-phenyl)sulfonyl]-1,2,3,4-tetrahydro-quinolin-2-yl]-methoxy]-ethanone (103) 2-[[1-[(4-methoxy-2,6-dimethyl-phenyl)sulfonyl]-1,2,3,4-tetrahydro-quinolin-2-yl]-methoxy]-1-[4-pyridin-4-yl-4-(2-pyrrolidin-1-yl-ethoxy)-piperidin-1-yl]-ethanone (104) N-benzhydryl-N-[2-[2-oxo-2-[4-pyridin-3-yl-4-(2-pyrrolidin-1-yl-ethoxy)-piperidin-1-yl]-ethoxy]-ethyl]-methanesulfonic acid amide (105) N-benzhydryl-N-[2-[2-[4-(3-fluorophenyl)-4-(2-pyrrolidin-1-yl-ethoxy)-piperidin-1-yl]-2-oxo-ethoxy]-ethyl]-methanesulfonic acid amide (106) 2-[[4-[(4-methoxy-2,6-dimethyl-phenyl)sulfonyl]-3,4-dihydro-2H-[1,4]benzoxazin-3-yl]-methoxy]-1-[4-pyridin-3-yl-4-(2-pyrrolidin-1-yl-ethoxy)-piperidin-1-yl]-ethanone (107) 1-[4-(3-fluorophenyl)-4-(2-pyrrolidin-1-yl-ethoxy)-piperidin-1-yl]-2-[[4-[(4-methoxy-2,6-dimethyl-phenyl)sulfonyl]-3,4-dihydro-2H-[1,4]benzoxazin-3-yl]-methoxy]-ethanone (108) 2-[[4-[(4-methoxy-2,6-dimethyl-phenyl)sulfonyl]-3,4-dihydro-2H-[1,4]benzoxazin-3-yl]-methoxy]-1-[4-pyridin-4-yl-4-(2-pyrrolidin-1-yl-ethoxy)-piperidin-1-yl]-ethanone (109) 2-[[4-[(2-chloro-6-methyl-phenyl)sulfonyl]-3,4-dihydro-2H-[1,4]benzoxazin-3-yl]-methoxy]-1-[4-(3-fluorophenyl)-4-(2-pyrrolidin-1-yl-ethoxy)-piperidin-1-yl]-ethanone (110) 1-[4-pyridin-3-yl-4-(2-pyrrolidin-1-yl-ethoxy)-piperidin-1-yl]-2-[[4-[[2-(trifluoromethyl)-phenyl]sulfonyl]-3,4-dihydro-2H-[1,4]benzoxazin-3-yl]-methoxy]-ethanone (111) 1-[4-(3-fluorophenyl)-4-(2-pyrrolidin-1-yl-ethoxy)-piperidin-1-yl]-2-[[4-[[2-(trifluoromethyl)-phenyl]sulfonyl]-3,4-dihydro-2H-[1,4]benzoxazin-3-yl]-methoxy]-ethanone (112) 1-[4-pyridin-4-yl-4-(2-pyrrolidin-1-yl-ethoxy)-piperidin-1-yl]-2-[[4-[[2-(trifluoromethyl)-phenyl]sulfonyl]-3,4-dihydro-2H-[1,4]benzoxazin-3-yl]-methoxy]-ethanone (113) 4-methoxy-N,2,3,6-tetramethyl-N-[2-[2-oxo-2-[4-pyridin-3-yl-4-(2-pyrrolidin-1-yl-ethoxy)-piperidin-1-yl]-ethoxy]-ethyl]-benzenesulfonic acid amide (114) N-[2-[2-[4-(3-fluorophenyl)-4-(2-pyrrolidin-1-yl-ethoxy)-piperidin-1-yl]-2-oxo-ethoxy]-ethyl]-4-methoxy-N,2,3,6-tetramethyl-benzenesulfonic acid amide (115) 4-methoxy-N,2,3,6-tetramethyl-N-[2-[2-oxo-2-[4-pyridin-4-yl-4-(2-pyrrolidin-1-yl-ethoxy)-piperidin-1-yl]-ethoxy]-ethyl]-benzenesulfonic acid amide (116) 1-[4-pyridin-3-yl-4-(2-pyrrolidin-1-yl-ethoxy)-piperidin-1-yl]-2-[[1-[[2-(trifluoromethyl)-phenyl]sulfonyl]-piperidin-2-yl]-methoxy]-ethanone (117) 1-[4-pyridin-3-yl-4-(2-pyrrolidin-1-yl-ethoxy)-piperidin-1-yl]-2-[[1-[[2-(trifluoromethyl)-phenyl]sulfonyl]-piperidin-2-yl]-methoxy]-ethanone (118) 1-[4-(3-fluorophenyl)-4-(2-pyrrolidin-1-yl-ethoxy)-piperidin-1-yl]-2-[[1-[[2-(trifluoromethyl)-phenyl]sulfonyl]-piperidin-2-yl]-methoxy]-ethanone (119) 3-[[1-[(4-methoxy-2,6-dimethyl-phenyl)sulfonyl]-piperidin-2-yl]-methoxy]-1-[4-pyridin-3-yl-4-(2-pyrrolidin-1-yl-ethoxy)-piperidin-1-yl]-propan-1-one (120) 3-[[1-[(4-methoxy-2,6-dimethyl-phenyl)sulfonyl]-piperidin-2-yl]-methoxy]-1-[4-pyridin-3-yl-4-(2-pyrrolidin-1-yl-ethoxy)-piperidin-1-yl]-propan-1-one (121) 1-[4-(3-fluorophenyl)-4-(2-pyrrolidin-1-yl-ethoxy)-piperidin-1-yl]-3-[[1-[(4-methoxy-2,6-dimethyl-phenyl)sulfonyl]-piperidin-2-yl]-methoxy]-propan-1-one (122) 1-[4-(3-fluorophenyl)-4-(2-pyrrolidin-1-yl-ethoxy)-piperidin-1-yl]-3-[[1-[(4-methoxy-2,6-dimethyl-phenyl)sulfonyl]-piperidin-2-yl]-methoxy]-propan-1-one (123) 2-[2-[1-[(4-methoxy-2,6-dimethyl-phenyl)sulfonyl]-piperidin-2-yl]-ethoxy]-1-[4-pyridin-3-yl-4-(2-pyrrolidin-1-yl-ethoxy)-piperidin-1-yl]-ethanone (124) 2-[2-[1-[(4-methoxy-2,6-dimethyl-phenyl)sulfonyl]-piperidin-2-yl]-ethoxy]-1-[4-pyridin-3-yl-4-(2-pyrrolidin-1-yl-ethoxy)-piperidin-1-yl]-ethanone (125) 1-[4-(3-fluorophenyl)-4-(2-pyrrolidin-1-yl-ethoxy)-piperidin-1-yl]-2-[2-[1-[(4-methoxy-2,6-dimethyl-phenyl)sulfonyl]-piperidin-2-yl]-ethoxy]-ethanone (126) 1-[4-(3-fluorophenyl)-4-(2-pyrrolidin-1-yl-ethoxy)-piperidin-1-yl]-2-[2-[1-[(4-methoxy-2,6-dimethyl-phenyl)sulfonyl]-piperidin-2-yl]-ethoxy]-ethanone (127) N-[4-[4-(3-fluorophenyl)-4-(2-pyrrolidin-1-yl-ethoxy)-piperidin-1-yl]-4-oxo-butyl]-N-methyl-3-(trifluoromethyl)-benzenesulfonic acid amide (128) 2-[4-[(2,4-dichlorophenyl)sulfonyl]-3,4-dihydro-2H-[1,4]benzoxazin-3-yl]-1-[4-(3-fluorophenyl)-4-(2-pyrrolidin-1-yl-ethoxy)-piperidin-1-yl]-ethanone
(129) 2-[[1-(naphthalen-2-ylsulfonyl)-1,2,3,4-tetrahydro-quinolin-2-yl]-methoxy]-1-[4-pyridin-3-yl-4-(2-pyrrolidin-1-yl-ethoxy)-piperidin-1-yl]-ethanone
(130) 2-[[1-(naphthalen-2-ylsulfonyl)-1,2,3,4-tetrahydro-quinolin-2-yl]-methoxy]-1-[4-pyridin-3-yl-4-(2-pyrrolidin-1-yl-ethoxy)-piperidin-1-yl]-ethanone
(131) 1-[4-(3-fluorophenyl)-4-(2-pyrrolidin-1-yl-ethoxy)-piperidin-1-yl]-2-[[1-(naphthalen-2-ylsulfonyl)-1,2,3,4-tetrahydro-quinolin-2-yl]-methoxy]-ethanone or a physiologically acceptable salt thereof.

17. A pharmaceutical composition comprising a compound as claimed in claim 1, and at least one pharmaceutically acceptable carrier or auxiliary substance.

\* \* \* \* \*